(12) United States Patent
Schwoebel et al.

(10) Patent No.: US 9,291,549 B2
(45) Date of Patent: *Mar. 22, 2016

(54) PATHOGEN DETECTION BIOSENSOR

(75) Inventors: Eric Schwoebel, Woburn, MA (US);
James Harper, Jamaica Plain, MA (US);
Martha S. Petrovick, Barre, MA (US);
Frances Nargi, Littleton, MA (US);
Mark Hollis, Concord, MA (US);
Bernadette Johnson, Hollis, NH (US);
Joseph Lacirignola, Beverly, MA (US);
Richard Mathews, Chelmsford, MA (US); Kristine Hogan, Danvers, MA (US); Trina Vian, Groton, MA (US);
Allan Heff, Newton, MA (US); Mark Hennessy, Falls Church, VA (US);
Songeeta Palchaudhuri, Somerville, MA (US); Todd Rider, Littleton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 996 days.

This patent is subject to a terminal disclaimer.

(21) Appl. No.: 13/454,604

(22) Filed: Apr. 24, 2012

(65) Prior Publication Data

US 2012/0225423 A1 Sep. 6, 2012

Related U.S. Application Data

(63) Continuation of application No. 12/085,495, filed as application No. PCT/US2006/045691 on Nov. 30, 2006, now Pat. No. 8,216,797, which is a continuation-in-part of application No. 11/001,583, (Continued)

(51) Int. Cl.
*G01N 33/53* (2006.01)
*G01N 21/07* (2006.01)

(Continued)

(52) U.S. Cl.
CPC ............ *G01N 21/07* (2013.01); *G01N 21/6428* (2013.01); *G01N 33/582* (2013.01)

(58) Field of Classification Search
None
See application file for complete search history.

(56) References Cited

U.S. PATENT DOCUMENTS 3,880,592 A 4/1975 Kelley et al.
4,493,895 A 1/1985 Colaruotolo et al.
(Continued)

FOREIGN PATENT DOCUMENTS

CN 1526024 A 9/2004
CN 1595160 3/2005
(Continued)

OTHER PUBLICATIONS

D'Orazio, P., "Biosensors in clinical chemistry," *Clinica Chimica Acta*, 334:41-69 (2003).
(Continued)

*Primary Examiner* — Chris L Chin
(74) *Attorney, Agent, or Firm* — Hamilton, Brook, Smith & Reynolds P.C.

(57) ABSTRACT

The invention described herein provides methods for the detection of target particles, such as pathogens, soluble antigens, nucleic acids, toxins, chemicals, plant pathogens, blood borne pathogens, bacteria, viruses and the like. Also described is an emittor cell comprising a receptor, wherein the receptor can be an antibody or an Fc receptor, and an emittor molecule for the detection of a target particle in a sample wherein the target particle to be detected is bound by one or more receptors on the emittor cell. Also provided are optoelectronic sensor devices for detecting a target particle in a sample, including in a plurality of samples.

6 Claims, 130 Drawing Sheets

Related U.S. Application Data filed on Dec. 1, 2004, now Pat. No. 7,422,860, which is a continuation-in-part of application No. 10/467,242, filed as application No. PCT/US02/03606 on Feb. 6, 2002, now Pat. No. 7,214,346.

(60) Provisional application No. 60/266,977, filed on Feb. 7, 2001, provisional application No. 60/741,271, filed on Nov. 30, 2005.

(51) Int. Cl.
*G01N 21/64* (2006.01)
*G01N 33/58* (2006.01)

(56) References Cited

U.S. PATENT DOCUMENTS

| | | | |
|---|---|---|---|
| 4,499,052 | A | 2/1985 | Fulwyler |
| 4,632,761 | A | 12/1986 | Bowers et al. |
| 4,675,287 | A | 6/1987 | Reisfeld et al. |
| 4,946,778 | A | 8/1990 | Ladner et al. |
| 5,055,408 | A | 10/1991 | Higo et al. |
| 5,126,276 | A | 6/1992 | Fish et al. |
| 5,139,937 | A | 8/1992 | Inouye et al. |
| 5,162,227 | A | 11/1992 | Cormier |
| 5,223,409 | A | 6/1993 | Ladner et al. |
| 5,292,658 | A | 3/1994 | Cormier et al. |
| 5,360,728 | A | 11/1994 | Prasher |
| 5,418,155 | A | 5/1995 | Cormier et al. |
| 5,422,266 | A | 6/1995 | Cormier et al. |
| 5,541,309 | A | 7/1996 | Prasher |
| 5,552,064 | A | 9/1996 | Chachowski et al. |
| 5,578,269 | A | 11/1996 | Yaremko et al. |
| 5,585,266 | A * | 12/1996 | Plitt .................. C12M 23/52 210/150 |
| 5,698,450 | A | 12/1997 | Ringrose et al. |
| 5,701,012 | A | 12/1997 | Ho |
| 5,702,884 | A | 12/1997 | Ekeze et al. |
| 5,714,666 | A | 2/1998 | Pritchett et al. |
| 5,744,320 | A | 4/1998 | Sherf et al. |
| 5,744,579 | A | 4/1998 | Cormier et al. |
| 5,766,941 | A | 6/1998 | Cormier et al. |
| 5,798,441 | A | 8/1998 | Cormier et al. |
| 5,846,708 | A | 12/1998 | Hollis et al. |
| 5,932,795 | A | 8/1999 | Koutrakis et al. |
| 5,985,214 | A | 11/1999 | Stylli et al. |
| 6,007,778 | A | 12/1999 | Cholewa |
| 6,087,114 | A | 7/2000 | Rider |
| 6,103,479 | A | 8/2000 | Taylor |
| 6,228,610 | B1 | 5/2001 | Flor et al. |
| 6,239,453 | B1 | 5/2001 | Yamada et al. |
| 6,248,542 | B1 | 6/2001 | Rider et al. |
| 6,331,415 | B1 | 12/2001 | Cabilly et al. |
| 6,672,947 | B2 | 1/2004 | Tsao et al. |
| 6,800,448 | B2 | 10/2004 | Rider et al. |
| 6,872,538 | B1 | 3/2005 | Dupriez et al. |
| 7,090,988 | B2 | 8/2006 | Rider et al. |
| 7,214,346 | B2 | 5/2007 | Harper et al. |
| 7,422,860 | B2 | 9/2008 | Schwoebel et al. |
| 7,517,660 | B2 | 4/2009 | Rider et al. |
| 7,947,509 | B2 | 5/2011 | Harper et al. |
| 8,067,184 | B2 | 11/2011 | Schwoebel et al. |
| 8,216,797 | B2 | 7/2012 | Schwoebel et al. |
| 8,722,347 | B2 | 5/2014 | Rider et al. |
| 8,835,127 | B2 | 9/2014 | Schwoebel et al. |
| 9,005,989 | B2 * | 4/2015 | Harper .................. G01N 21/07 422/82.05 |
| 2001/0016328 | A1 | 8/2001 | Rider et al. |
| 2002/0045189 | A1 | 4/2002 | Imajo et al. |
| 2002/0106786 | A1 | 8/2002 | Carvalho et al. |
| 2003/0104390 | A1 | 6/2003 | Etienne et al. |
| 2007/0087391 | A1 | 4/2007 | Rider et al. |
| 2008/0009017 | A1 | 1/2008 | Harper et al. |
| 2010/0003700 | A1 | 1/2010 | Rider et al. |
| 2010/0041031 | A1 | 2/2010 | Schwoebel et al. |
| 2010/0062415 | A1 | 3/2010 | Schwoebel et al. |
| 2012/0135404 | A1 | 5/2012 | Schwoebel et al. |
| 2012/0190006 | A1 | 7/2012 | Harper et al. |
| 2015/0050723 | A1 | 2/2015 | Schwoebel et al. |
| 2015/0093745 | A1 * | 4/2015 | Harper .................. G01N 21/07 435/5 |

FOREIGN PATENT DOCUMENTS

| | | |
|---|---|---|
| EP | 0 301 583 A2 | 2/1989 |
| EP | 0 345 027 A2 | 12/1989 |
| EP | 0 372 352 A2 | 6/1990 |
| EP | 0 392 377 A2 | 10/1990 |
| EP | 0 722 087 A1 | 7/1996 |
| EP | 0 795 751 A2 | 9/1997 |
| EP | 0 823 633 A1 | 2/1998 |
| EP | 1 145 002 B2 | 10/2001 |
| EP | 1 364 070 B1 | 11/2006 |
| FR | 2 790 093 A1 | 8/2000 |
| JP | 64-035374 | 2/1989 |
| JP | 01-250065 | 10/1989 |
| JP | 02-031163 | 2/1990 |
| JP | 2253162 | 10/1990 |
| JP | 3153700 | 7/1991 |
| JP | 06-160387 | 6/1994 |
| JP | H 06-507078 | 8/1994 |
| JP | 63-35641 | 12/1994 |
| JP | 8-506661 | 7/1996 |
| JP | 9-509494 T | 9/1997 |
| JP | 10-2898 | 1/1998 |
| JP | 2000-329761 | 11/2000 |
| JP | 2001-510893 | 8/2001 |
| JP | 2004/121819 | 4/2004 |
| JP | 2004-527736 A | 9/2004 |
| JP | 2004-532108 | 10/2004 |
| JP | 2005-518553 | 6/2005 |
| JP | 2006-500562 | 1/2006 |
| JP | 5352237 | 8/2013 |
| WO | WO 86/07463 | 12/1986 |
| WO | WO 93/16201 | 8/1993 |
| WO | WO 94/18565 A1 | 8/1994 |
| WO | WO 95/23348 | 8/1995 |
| WO | WO 96/04558 A1 | 2/1996 |
| WO | WO 98/25146 | 6/1998 |
| WO | WO 99/04239 | 1/1999 |
| WO | WO 99/30156 | 6/1999 |
| WO | WO 99/58975 | 11/1999 |
| WO | WO 00/02045 A2 | 1/2000 |
| WO | WO 00/02045 A3 | 1/2000 |
| WO | WO 01/36965 A2 | 5/2001 |
| WO | WO 01/36965 A3 | 5/2001 |
| WO | WO 02/066683 A2 | 8/2002 |
| WO | WO 03/073817 A2 | 9/2003 |
| WO | WO 2004/027426 A2 | 4/2004 |
| WO | WO 2007/046825 A2 | 4/2007 |
| WO | WO 2008/048300 A2 | 4/2008 |

OTHER PUBLICATIONS

Page, D.L. and Pizziconi, V.B., "A cell-based immunobiosensor with engineered molecular recognition—Part III: engineering molecular recognition," *Biosensors & Bioelectronics*, 12(7):559-566 (1997).
Whelan, R.J. and Zare, R.N., "Single-cell immunosensors for protein detection," *Biosensors & Bioelectronics*, 19:331-336 (2003).
Wijesuriya, D.C. and Rechnitz, G.A., "Biosensors based on plant and animal tissues," *Biosensors & Bioelectronics*, 8:155-160 (1993).
Notice of Allowance, U.S. Appl. No. 13/039,780, Dated: Aug. 15, 2014.
Office Communications, Canadian Patent Application No. 2,631,615, Dated: Sep. 16, 2014.
Redacted English Translation of Office Action, Mexican Patent Application No. MX/a/2012/003854, Dated: Aug. 12, 2014.
English Translation of Office Action, Japanese Patent Application No. 2013-106326, Dated: Sep. 24, 2014.
English Translation of Office Action, Chinese Patent Application No. 201310191503.7, Dated: Jul. 30, 2014.
English Translation of Office Action, Japanese Patent Application No. 2014-108897, Dated: Feb. 9, 2015.

(56) References Cited

OTHER PUBLICATIONS

Redacted English Translation of Office Action, Brazilian Patent Application No. PI0619234-3, Dated: Mar. 11, 2015.
English Translation of Office Action, Japanese Patent Application No. 2013-106326, Dated: Jul. 21, 2015.
Office Action, Australian Application No. 2011265469, dated: Aug. 21, 2012.
English Translation of Office Action, Chinese Application No. 200580047362.5, dated: Sep. 24, 2012.
English Translation of Office Action, Chinese Application No. 200910137895.2; Dated: Sep. 7, 2012.
English Translation of Office Action, Chinese Application No. 200680051617.X, Dated: Sep. 13, 2012.
Office Action, Canadian Application No. 2,631,615, Dated: Nov. 19, 2012.
English Translation of Office Action, Japanese Application No. 2007-544468, Dated: Jan. 21, 2013.
English Translation of Office Action, Japanese Application No. 2008-543423, Dated: Jan. 21, 2013.
Office Action, European Application No. 11 171 720.3, Dated: Feb. 15, 2013.
Office Action, Canadian Application No. 2,588,787, Dated: Mar. 22, 2013.
Office Action, U.S. Appl. No. 12/380,603, Dated: Mar. 25, 2013.
English Translation of Office Action, Japanese Application No. 2012-133389, Dated: Jun. 21, 2013.
Redacted English Translation of Office Action, Mexican Application No. MX/a/2009/010113; Dated: Jul. 23, 2013.
Office Action, U.S. Appl. No. 13/267,276, Dated: Nov. 7, 2013.
Office Action, U.S. Appl. No. 13/039780, Dated: Sep. 30, 2013.
Notice of Grounds for Rejection (English Translation) for Japanese Application No. 5338877, Dated: Aug. 13, 2013.
Office Action, Canadian Application No. 2,588,787, Dated: May 21, 2014.
Notice of Allowance, U.S. Appl. No. 13/267,276, Dated: Jun. 2, 2014.
Requisition, Canadian Application No. 2,588,787; Dated: May 14, 2012.
English Translation of Office Action, Chinese Application No. 200580047362.5; Dated May 3, 2012.
Examination Report for Australian Application No. 2013201247, Dated: Oct. 29, 2013.
Non-Final Office Action, U.S. Appl. No. 13/039,780, Dated: Dec. 20, 2013.
Office Action, Canadian Application No. 2,799,371; Dated: Jan. 21, 2014.
Notice of Allowance, U.S. Appl. No. 12/380,603, Dated: Jan. 21, 2014.
Office Action English Translation, Brazilian Application No. PI0207084-7; Dated: Feb. 12, 2014.
Office Action, European Application No. 11 171 720.3; Dated: Mar. 12, 2014.
Baylor, D.A., "Photoreceptor Signals and Vision," *Investigative Ophthalmology*, 28(1):34-49 (1987).
Button, D., et al., "Aequorin-expressing Mammalian Cell Lines Used to Report $Ca^{2+}$ Mobilization," *Cell Calcium*, 14:663-671 (1993).
Chalfie, M., "Green Fluorescent Protein," *Photochemistry and Photobiology*, 62(4):651-656 (1995).
Davis, L.S., et al., "The Induction of T Cell Unresponsiveness by Rapidly Modulating CD3," *J. Immunol.* 142:1084-1094 (1989).
"Introducing BioFlash™, a Rapid Diagnostic System for the Ultra-Sensitive Detection of Pathogens." Innovative Biosensors, Inc. [online] (2006). XP002428493 [retrieved on Jun. 19, 2007]. Retrieved from the Internet URL: http://cc.msnscache.com/cache.aspx?q=8242421289075&lang=en-US&mkt=en-US&FORM=CVRE.
Kombrink, E. and Somssich, I.E., "Defense Responses of Plants to Pathogens," *Advances in Botanical Research*, 21:1-34 (1995).
Kostov, Y., et al., "All Solid-State GFP Sensor," Biotechnology and Bioengineering, Including: Symposium Biotechnology In Energy Production and Conservation, John Wiley & Sons. NY, vol. 70(4): 473-477 (2000).
Mosier, D.E. "Primary In Vitro Antibody Responses by Purified Murine B Lymphocytes in Serum-Free Defined Medium," *The Journal of Immunology*, 127(4):1490-1493 (1981).
Paddle, B.M. "Biosensors for Chemical and Biological Agents of Defence Interest," *Biosensors & Bioelectronics*, 11(11):1079-1113 (1996).
Page, D.L., et al., "A Cell-based Immunobiosensor with Engineered Molecular Recognition-Part II: Enzyme Amplification Systems," *Biosensors & Bioelectronics*, 12(6):457-466 (1997).
Pancrazio, J.J., et al., "Development and Application of Cell-Based Biosensors," *Annals of Biomedical Engineering*, 27(6):697-711 (1999).
Parikh, V.S., et al., "COOH Terminus of Membrane IgM is Essential for an Antigen-Specific Induction of Some But Not All Early Activation Events in Mature B Cells," *J. Exp. Med.*, 174:1103-1109 (1991).
Pizziconi, V.B., et al., "A Cell-based Immunobiosensor with Engineered Molecular Recognition-Part I: Design Feasibility," *Biosensors & Bioelectronics*, 12(4):287-299 (1997).
Rider, T.H., et al., "A B Cell-Based Sensor for Rapid Identification of Pathogens," *Science*, 301(5630):213-215 (2003).
Shimomura, O., et al., "Calcium Binding, Quantum Yield, and Emitting Molecule in Aequorin Bioluminescence," *Nature*, 227:1356-1357 (1970).
Shimomura, O., et al., "Light-emitting Properties of Recombinant Semi-Synthetic Aequorins and Recombinant Fluorescein-conjugated Aequorin for Measuring Cellular Calcium," *Cell Calcium*, 14:373-378 (1993).
Wilson, H.A., et al., "Crosslinkage of B Lymphocyte Surface Immunoglobulin by Anti-Ig or Antigen Induces Prolonged Oscillation of Intracellular Ionized Calcium," *Journal of Experimental Medicine*, 166:601-606 (1987).
Wilson, H.A., et al., "The B Lymphocyte Calcium Response to Anti-Ig Is Diminished by Membrane Immunoglobulin Cross-Linkage to the Fcγ Receptor," *The Journal of Immunology*, 138(6):1712-1718 (1987).
Restriction Requirement, U.S. Appl. No. 08/987,410; dated: Oct. 1, 1998.
Office Action, U.S. Appl. No. 08/987,410, dated: Feb. 4, 1999.
Notice of Allowance and Issue Fee Due, U.S. Appl. No. 08/987,410, dated: Sep. 21, 1999.
Restriction Requirement, U.S. Appl. No. 09/169,196; dated: Mar. 27, 2000.
Office Action, U.S. Appl. No. 09/169,196, dated: Aug. 22, 2000.
Notice of Allowance and Issue Fee Due, U.S. Appl. No. 09/169,196, dated: Feb. 12, 2001.
Notification of Transmittal of the International Search Report or the Declaration, International Application No. PCT/US98/25539, dated Mar. 23, 1999.
Notification of Transmittal of International Preliminary Examination Report, International Application No. PCT/US98/25539, dated: Sep. 2, 1999.
Office Action, U.S. Appl. No. 09/848,811, dated: Aug. 26, 2003.
Notice of Allowance and Fees Due, U.S. Appl. No. 09/848,811, dated: May 4, 2004.
Office Action, U.S. Appl. No. 10/910,554, dated: Sep. 29, 2005.
Notice of Allowance and Fees Due, U.S. Appl. No. 10/910,554, dated: Apr. 12, 2006.
Office Action, U.S. Appl. No. 11/471,275, dated: Jun. 27, 2008.
Notice of Allowance and Fees Due, U.S. Appl. No. 11/471,275, dated: Dec. 3, 2008.
Notification of Transmittal of the International Search Report or the Declaration, International Application No. PCT/US02/03606, dated: Aug. 9, 2002.
Notification of Transmittal of International Preliminary Examination Report, International Application No. PCT/US02/03606, dated: Nov. 12, 2002.
Office Action, Australian Application No. 2002256992, dated: Jun. 5, 2006.

(56) References Cited

OTHER PUBLICATIONS

Chinese First Office Action and English Translation, Chinese Application No. 02807911.6, dated: Mar. 4, 2005.
Chinese Second Office Action and English Translation, Chinese Application No. 02807911.6, dated: May 12, 2006.
Chinese Grounds of Rejection and English Translation, Chinese Application No. 02807911.6, dated: Apr. 6, 2007.
English Translation of Chinese Decision of Granting Patent Right for Invention, Chinese Application No. 02807911.6, dated: Feb. 20, 2009.
European Search Report, European Application No. 02726568.5, dated: Jan. 30, 2004.
Office Action, European Application No. 02726568.5, dated: May 14, 2004.
Office Action, European Application No. 02726568.5, dated: Dec. 1, 2004.
Office Action, European Application No. 02726568.5, dated: May 30, 2005.
Summons to Attend Oral Proceedings, European Application No. 02726568.5, Dated: Nov. 21, 2005.
Decision to Grant a European Patent, European Application No. 02726568.5, dated: Oct. 19, 2006.
English Translation of Notice of Reasons for Rejection, Japanese Application No. 2002-566387, dated: Feb. 8, 2008.
English Translation of Notice of Reasons for Rejection, Japanese Application No. 2002-566387, dated: Dec. 8, 2008.
English Translation of Mexican Office Action, Mexican Application No. PA/a/2003/007070, dated: Dec. 12, 2006.
English Translation of Mexican Office Action, Mexican Application No. PA/a/2003/007070, dated: Aug. 5, 2009.
Restriction Requirement, U.S. Appl. No. 10/467,242; dated: Apr. 28, 2005.
Office Action, U.S. Appl. No. 10/467,242, dated: Jul. 5, 2005.
Office Action, U.S. Appl. No. 10/467,242, dated: Apr. 10, 2006.
Notice of Allowance and Fees Due, U.S. Appl. No. 10/467,242, dated: Jan. 4, 2007.
Response to Rule 312 Communication, U.S. Appl. No. 10/467,242; dated: Feb. 21, 2007.
Restriction Requirement, U.S. Appl. No. 11/001,583; dated: Mar. 9, 2007.
Office Action, U.S. Appl. No. 11/001,583; dated: Oct. 3, 2007.
Office Communication, U.S. Appl. No. 11/001,583; dated: Mar. 21, 2008.
Notice of Allowance and Fees Due, U.S. Appl. No. 11/001,583, dated: Apr. 10, 2008.
Notification of Transmittal of the International Search Report and the Written Opinion of the International Searching Authority, or the Declaration, International Application No. PCT/US2005/043343, dated: May 7, 2007.
Notification Concerning Transmittal of Copy of International Preliminary Report on Patentability, International Application No. PCT/US2005/043343, dated: Jun. 14, 2007.
Extended European Search Report, European Application No. 06022907.7, dated: Jun. 19, 2007.
Office Communication, European Application No. 06022907.7, dated: Apr. 8, 2008.
Office Communication, European Application No. 06022907.7, dated: May 30, 2008.
Office Action, European Application No. 06022907.7, dated: Feb. 12, 2009.
Restriction Requirement, U.S. Appl. No. 11/800,607; dated: Apr. 29, 2009.
Office Action, U.S. Appl. No. 11/800,607, dated: Nov. 30, 2009.
Office Action, European Application No. 05858641.3, dated: Nov. 15, 2007.
Office Action, European Application No. 05858641.3, dated: Sep. 22, 2008.
Office Communication, European Application No. 05 858 641.3, dated: Apr. 20, 2009.

Notice of Intent to Grant, European Application No. 05 858 641.3, dated: Oct. 7, 2009.
Office Action, Australian Application No. 2005337484, dated: Mar. 24, 2009.
English Translation of Chinese Office Action, Chinese Application No. 2005800473625, dated: Aug. 7, 2009.
Notification of Transmittal of the International Search Report and the Written Opinion of the International Searching Authority, or the Declaration, International Application No. PCT/US2006/045691, dated: Aug. 19, 2008.
Notification Concerning Transmittal of Copy of International Preliminary Report on Patentability, International Application No. PCT/US2006/045691, dated: Sep. 12, 2008.
Office Action, Australian Application No. 2006350038, dated Feb. 5, 2010.
Office Action, European Application No. 06851774.7, dated: Jun. 29, 2009.
Office Action, Canadian Application 2,437,033, dated Feb. 19, 2010.
Restriction Requirement, U.S. Appl. No. 12/217,471, dated: Mar. 29, 2010.
Boie, Y., et al., "Molecular Cloning and Characterization of the Four Rat Prostaglandin $E_2$ Prostanoid Receptor Subtypes," *European Journal of Pharmacology*, 340: 227-241 (1997).
Brini, M., et al., "Transfected Aequorin in the Measurement of Cytosolic $Ca^{2+}$ Concentration $([Ca^{2+}]_c$ )," *Journal of Biological Chemistry*, 270(17): 9896-9903 (1995).
Murgia, M., et al., "Cytosolic Free Calcium Concentration in the Mitogenic Stimulation of T Lymphocytes by Anti-CD3 Monoclonal Antibodies," *Cell Calcium*, 16: 167-180 (1994).
Rizzuto, R., et al., "Microdomains with High $Ca^{2+}$ Close to $IP_3$-Sensitive Channels That Are Sensed by Neighboring Mitochondria," *Science*, 262: 744-747 (1993).
Rizzuto, R., et al., "Rapid Changes of Mitochondrial $Ca^{2+}$ Revealed by Specifically Targeted Recombinant Aequorin," *Nature*, 358: 325-327 (1992).
Sedlik, C., et al., "Recombinant Parvovirus-like Particles as an Antigen Carrier: A Novel Nonreplicative Exogenous Antigen to Elicit Protective Antiviral Cytotoxic T Cells," *Proc. Natl. Acad. Sci. USA*, 94: 7503-7508 (1997).
Stables, J., et al., "A Bioluminescent Assay for Agonist Activity at Potentially Any G-Protein-Coupled Receptor," *Analytical Biochemistry*, 252: 115-126 (1997).
Office Action, U.S. Appl. No. 11/800,607, dated Jun. 4, 2010.
Office Action, Canadian Application 2,437,033, dated: Sep. 16, 2010.
Office Action, U.S. Appl. No. 12/217,471, dated: Aug. 23, 2010.
English Translation of Chinese Office Action, Chinese Application No. 200910137895.2, dated: Sep. 30, 2010.
Office Action, U.S. Appl. No. 12/380,603; dated Mar. 2, 2011.
Office Action, European Application No. 06851774.7, dated Jan. 13, 2011.
Office Action, U.S. Appl. No. 12/217,471; dated Apr. 19, 2011.
Office Action, Australian Application No. 2006350038; dated Mar. 18, 2011.
Restriction Requirement, U.S. Appl. No. 12/085,495; dated Apr. 26, 2011.
Office Action, U.S. Appl. No. 12/380,603, dated Jun. 7, 2011.
English Translation of Japanese Office Action, Japanese Application No. 2008-543423, dated: Apr. 27, 2011.
Notice of Allowance, U.S. Appl. No. 12/217,471, dated: Jul. 6, 2011.
English Translation of Chinese Office Action, Chinese Application No. 200580047362.5, dated: Jun. 15, 2011.
Notice of Acceptance, Australian Application No. 2006350038, dated Aug. 31, 2011.
Final Office Action, U.S. Appl. No. 12/380,603, dated: Jan. 31, 2012.
Gutarra, L., et al. "Methods for Detection of *Ralstonia solanacearum* in potato crops," Integrated Management of Bacterial Wilt. Proceedings, Sec. 5-97: pp. 1-13 (1995).
Scott, R.M. et al., "Isolation of Dengue Viruses from Peripheral Blood Leukocytes of Patients with Hemorrhagic Fever," the *Journal of Infectious Diseases*, 141(1):1-6 (1980).
Office Action, U.S. Appl. No. 12/085,495, dated: Jun. 8, 2011.
Mexican Office Action with English Translation, MX Application No. 2008-006945, dated: Sep. 13, 2011.

(56) References Cited

OTHER PUBLICATIONS

English Translation of Japanese Office Action, Japanese Application No. 2007-544468, dated: Oct. 24, 2011.
Office Action, U.S. Appl. No. 12/085,495; dated Nov. 17, 2011.
Requisition, Canadian Application No. 2,437,033, dated: Nov. 24, 2011.
Office Action, Japanese Application No. 2008-543423, dated Dec. 13, 2011.
Office Action, European Application No. 06851774.7, dated: Dec. 15, 2011.
Office Action, Chinese Application No. 200680051617.X, dated: Dec. 21, 2011.
Extended European Search Report, European Application No. 11171720.3, dated: Dec. 27, 2011.
Notice of Allowance, U.S. Appl. No. 12/085,495, dated: Jan. 26, 2012.
English Translation of Chinese Office Action, Chinese Application No. 200910137895.2, dated Feb. 1, 2012.
Office Action, U.S. Appl. No. 14/540,273, entitled "Optoelectronic Detection System," Date Mailed: Sep. 25, 2015.

* cited by examiner

B-Cell Response to Foot-and-Mouth Disease Virus

- Tests done at Plum Island USDA BL-3 Facility

Legend:
- Background
- Clone 8; FMDV
- Clone 12; FMDV
- Clone 31; FMDV
- Mutant FMDV

FIG. 5

Automated Cell-Delivery Concept

- Sensor cells compatible with delivery using syringe pumps, automatic pipettors, etc.

- Different sensor-cell types in individual pre-loaded syringes

- Environmental control to maintain B-cell performance

- One B-cell droplet per test, added <u>after</u> aerosol collection

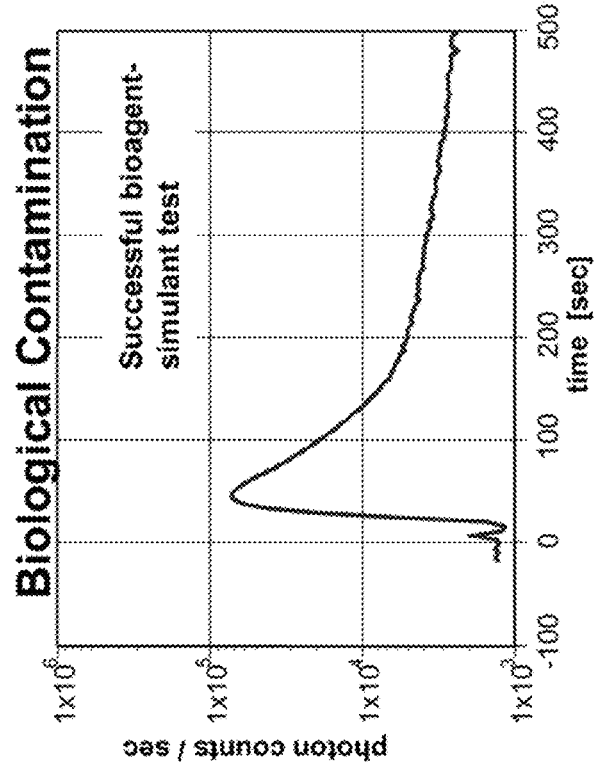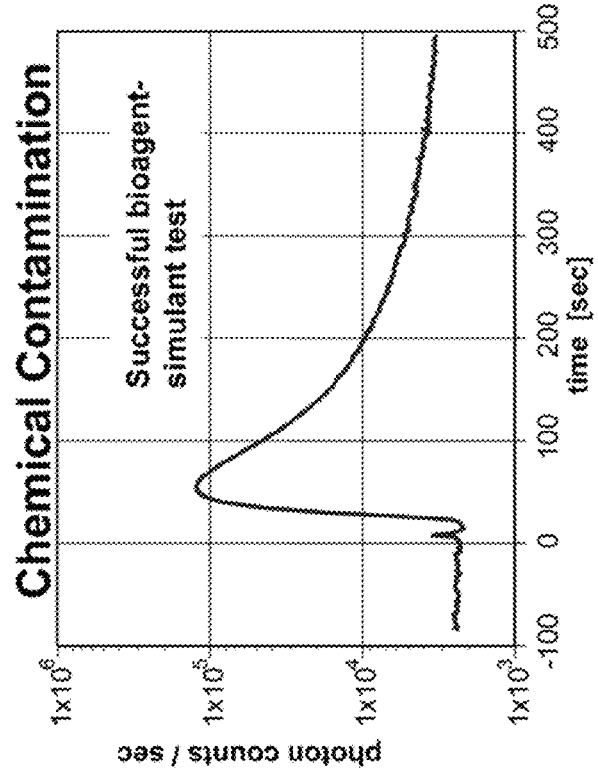
FIG. 11

FIG. 14

Optics/PMT-Module Concept

- Complementary shapes aid alignment and shield optics from stray light
- Integrated reflectors and lenses improve light collection
- 10 simultaneous tests using two of these modules per rotor
- Signal obtained less than one minute following collection of dry sample

Direct-Impaction Agent-Delivery System for Sensor Cell Identification Sensor

- Direct-air impaction deposits agents into multiple-well tapes or plates
- High sample concentration via air-to-air concentrator and small fluid volumes (µl)
- Rapid identification with low consumables usage

FIG. 16

Wet Centrifuge / Impactor Concept

Integrated Dry-Impactor/Sensor Concept

Effects of Cell Treatments on the Response of YP-specific B-cells to killed Yersenia pestis

FIG. 22

Background: CANARY-Sensor Strategy

Strategy: Detection of DNA by CANARY

Strategy for Sedimentation of DNA

Dose-Response to Bead-Bound ssDNA

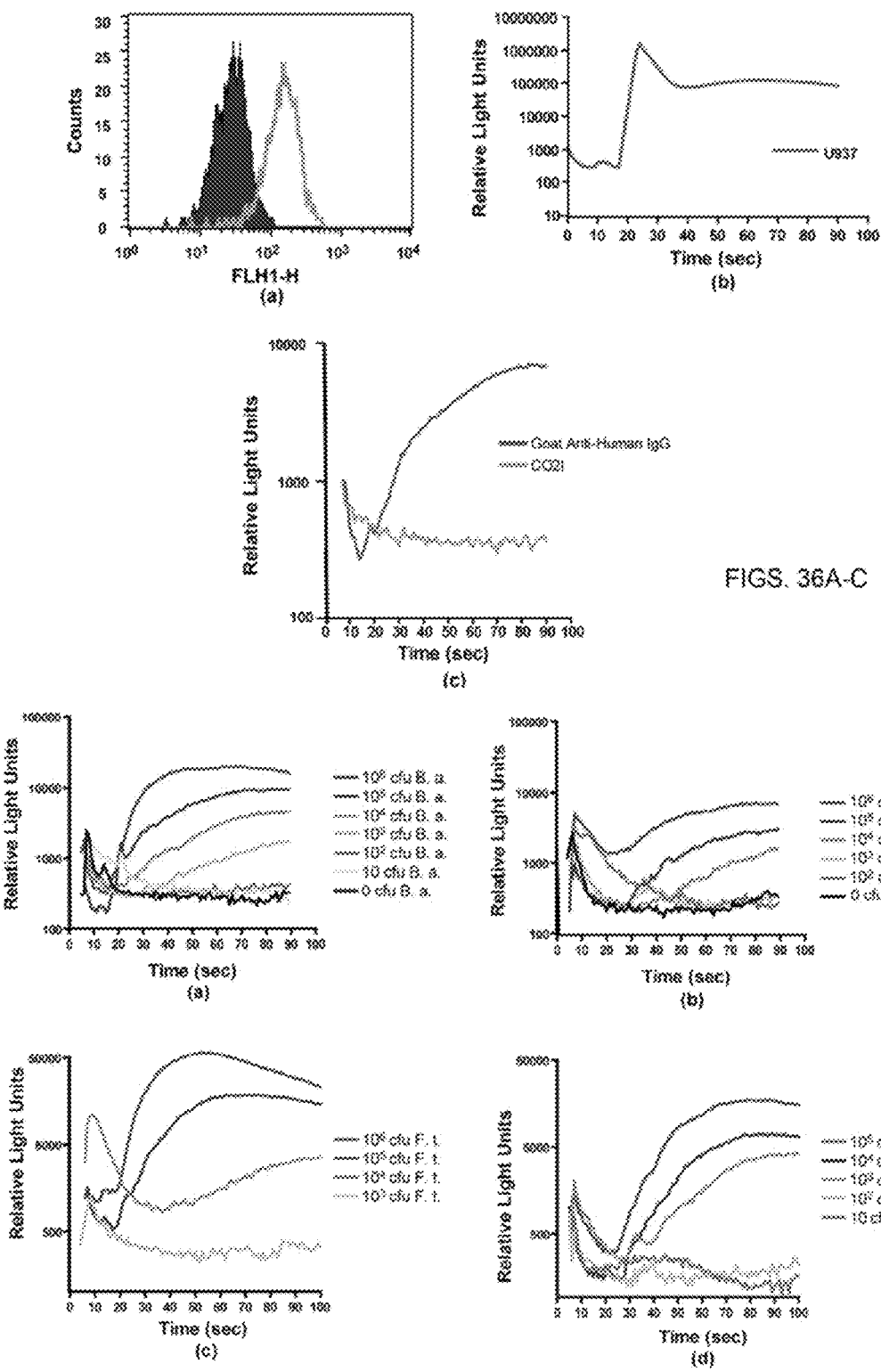
FIGS. 36A-C
FIGS. 37A-D

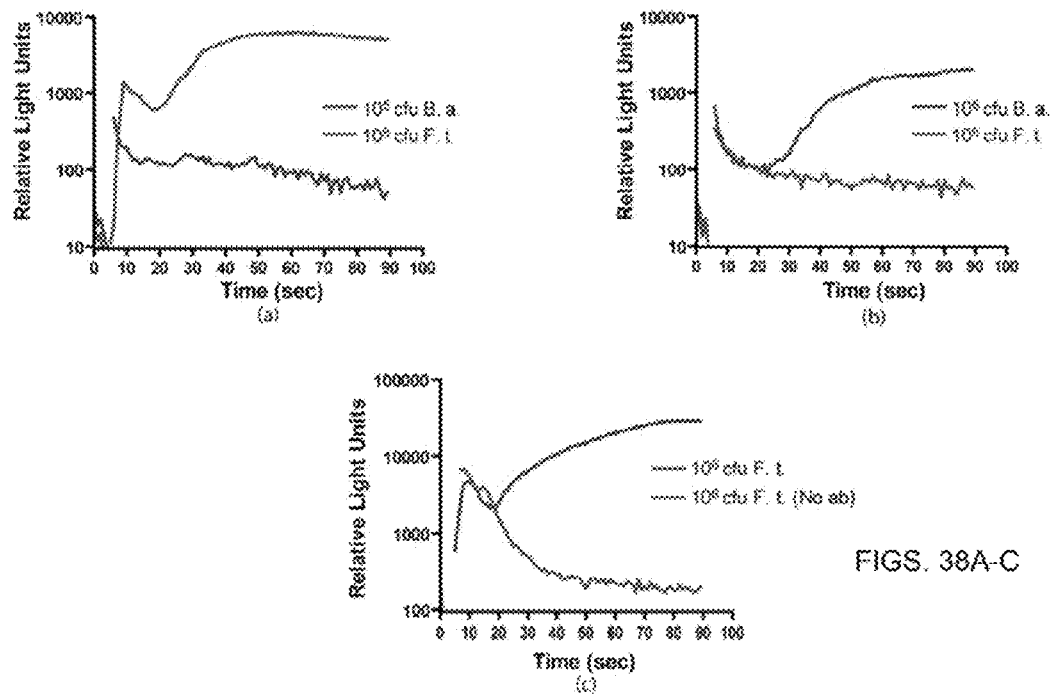
FIGS. 38A-C
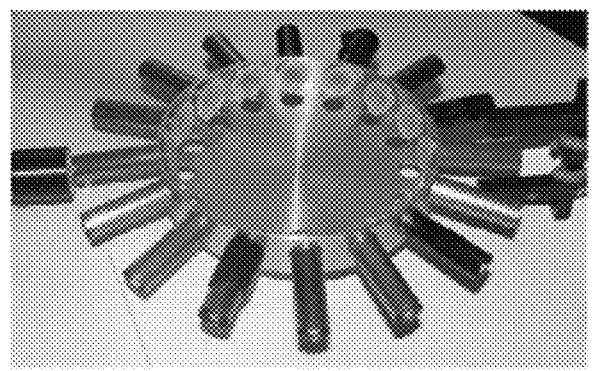
FIG. 39
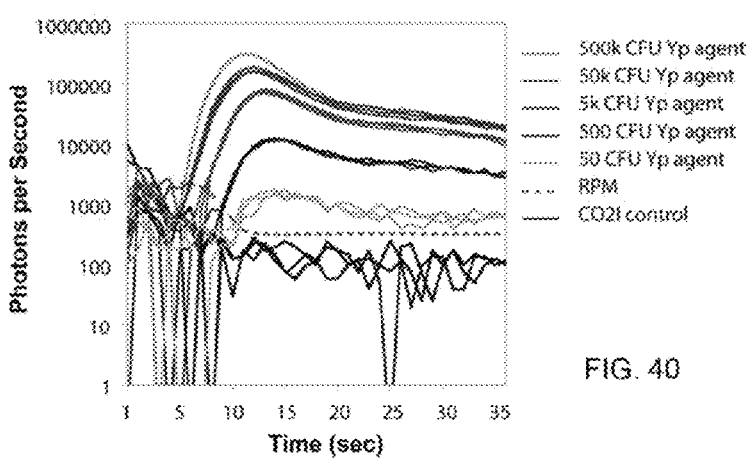
FIG. 40

CANARY Detection of Toxin Simulants

- Modification of CANARY assay to detect soluble, monomeric proteins
  - Speed: Currently ≥ 15 min
  - Sensitivity: 6 ng so far (0.01xLD50)
- Assay modifications under development to optimize speed and sensitivity

Soluble Toxin Simulant*

Antibody Site 1 → ← Antibody Site 2

*Heavy chain of botulinum toxin

FIG. 46

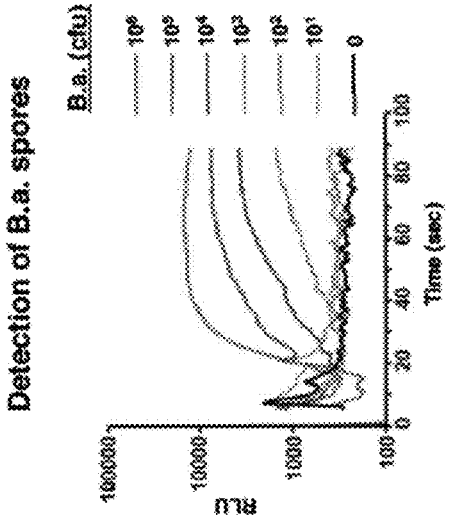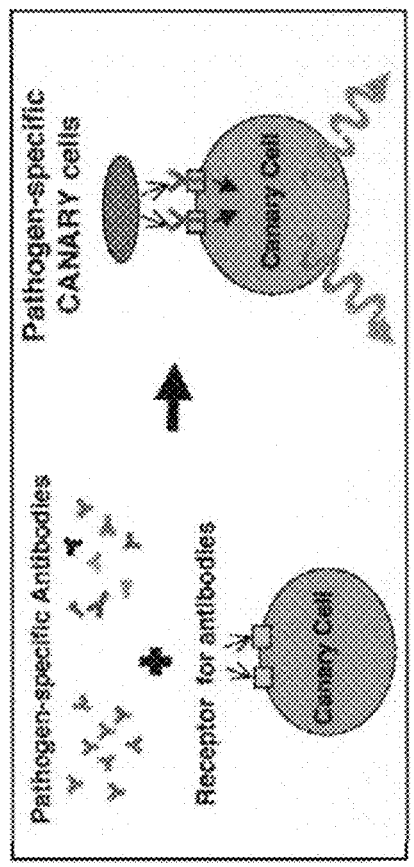
FIG. 47

Detection of Soluble, Monomeric Antigen by CANARY

Soluble Toxin Simulant (BoNT/A Heavy Chain)
6E10-10 Epitope ← → 6B2-2 Epitope

Antibody-Coated Bead
6E10-10 Antibody

Incubate, Wash

Add cells, spin

6B2-2 Antibody
6B2-2 CANARY cell

BoNT antibodies provided by S. Bavari and G. Ludwig, USAMRIID

FIG. 57

Detection of BoNT/A Hc by CANARY

- 400 ng/ml (4 ng)
- 400 ng/ml (4 ng)
- 80 ng/ml (800 pg)
- 80 ng/ml (800 pg)
- 16 ng/ml (160 pg)
- 16 ng/ml (160 pg)
- CO2I

Y-axis: RLU (10 – 10,000)
X-axis: Time (seconds) (0 – 120)

Nasal Swab Assay Protocol

FIG. 62

Detection of BoNT/A Hc in Nasal Swab Eluates

Toxin Detection: 5 Approaches

1) Bead-bound antigen: Current sensitivity and speed: 800 pg at 80 ng/ml (0.001 LD50 for BoNT/A by inhalation) in 5 minutes.

2) Two CANARY cells: Current sensitivity and speed : 50 ng at 1 µg/ml (0.07 LD50 for BoNT/A by inhalation) in 7 minutes. Optimal sensitivity and speed not yet determined.

3) Two antibodies, one CANARY cell: Antibodies to 2 different epitopes on one B cell. Simplest approach on paper. Not yet demonstrated.

4) CANARY cell plus soluble antibody: Soluble antibodies are used to crosslink antigen bound by the CANARY cell. Promising but preliminary.

5) Universal CANARY cell: Antibodies to 2 or more epitopes are captured in Fc receptors. Not yet demonstrated for toxins.

FIG. 72

FcR Project: Cell Lines

- Currently have good aequorin expressing cell line (U937#4) for Fc receptor assay
  – Aequorin gene is in pEF Blasticidin Vector
  – Cells are cultured in RPMI/10% FBS complete media plus 5 ug/ml Blasticidin

- also have 3 clones expressing EGFP-Aequorin Chimera.
  – EGFP-Aequorin gene is in pCDNA3.1 (CMV) G418 vector
  – Cells are cultured in RPMI/10% FBS complete media plus 0.8 mg/ml G418

FIG. 75

Protocol for Priming/Loading U937 Cells

Day 1:

U937 Aequorin or EGFP-Aequorin Cells at a concentration ~0.5 x10e6 cells/ml are primed with IFN gamma (200 ng/ml)

- No DMSO priming is required.
- Stock IFN gamma is at 100 ng/ul (So use 2 ul per ml of cultured cells).
- typically set up 5 mls of cells at 0.5x10e6 cells/ml. This gives 3-5 epi tubes for assay

Day 2

IFN gamma primed U937 cells are counted and desired number of cells are loaded with 4x coelenterazine

- For each epi tube set up 0.75x10e6 cells in 100 ul CO2I containing 4x Coel (200 uM final).
- Cells are incubated in dark for 2 hours at R.T.
- Cells are then washed 3x in CO2I and resuspended at 0. 5x10e6 cells/ml
- Cells are rotated overnight at RT and are ready to use the next day.

FIG. 76

Protocol for FC Assay

U937 cells charged with 4x coelenterazine are set up with desired antibody as follows:

1. Add appropriate antibody:
   - For purified (monoclonal or polyclonal) antibody typically use 10-100 ug/ml antibody.
   - For supernatant antibodies (α-BS) typically set up 1:1 ratio of supernatant to cells.
2. Incubate cells with antibody at 37°C for 5-30 mins
3. Cells can be used directly in traditional CANARY assay (washing cells is optional). Note: If using supernatant antibody and not washing cells prior to assay; adjust the volume of cells used in the assay to get 10,000 cells for assay

FIG. 77

1. Other Methods to Improve Sensitivity of U937 FC Receptor Assay

- Generate U937 cell line with Aequorin under control of CMV promoter

- Generate additional macrophage cell lines (i.e. HL60, THP-1, etc) expressing Aequorin Alternative cell lines may be explored i.e. mouse macrophage cell line.

- Generate Jurkat cells that express aequorin and FC receptor.

FIG. 78

2. Develop CANARY Cells (M12g3R and U937) with different color emissions using GFP variants -EGFP-Aequorin chimera.

-The Emission of aequorin at 488nm is absorbed by the EGFP and the wavelength of light emitted from the cells upon stimulation is shifted to 509nm

- EGFP-Aequorin Chimera Construct were generated by overlap-splicing PCR and Cloned into pCDNA3.1 (CMV/G418 vector)

- M12g3R and U937 Cells were transfected with EGFP-Aequorin.

-Characterization of the chimeric cell lines suggest they function as well as aequorin alone.

FIG. 79

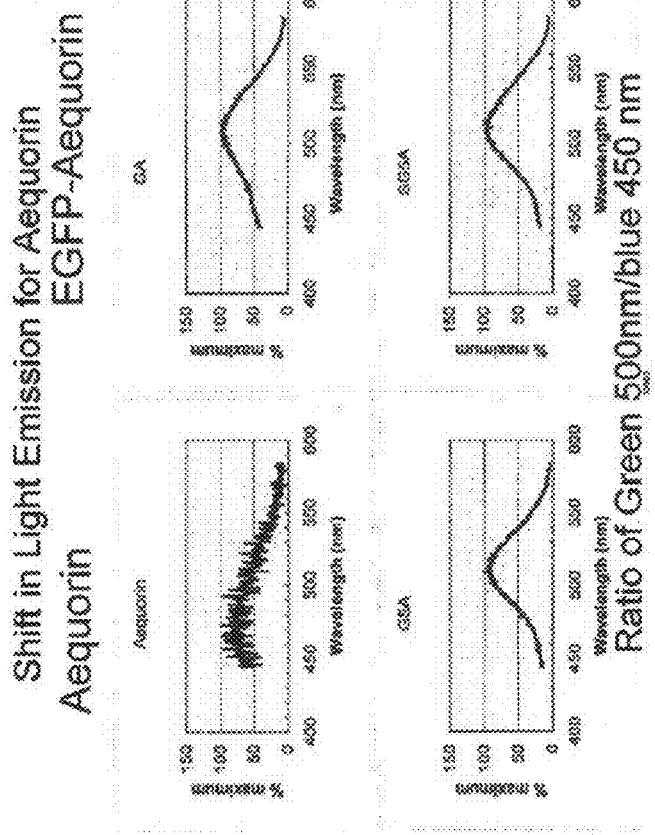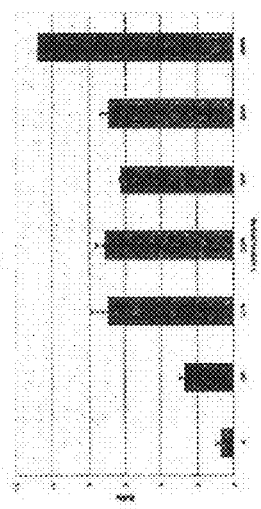
FIG. 80
Chimeric green fluorescent protein-aequorin as bioluminescent Ca2+ reporters at the single-cell level.
Baubet V, Le Mouellic H, Campbell AK, Lucas-Meunier E, Fossier P, Brulet P.

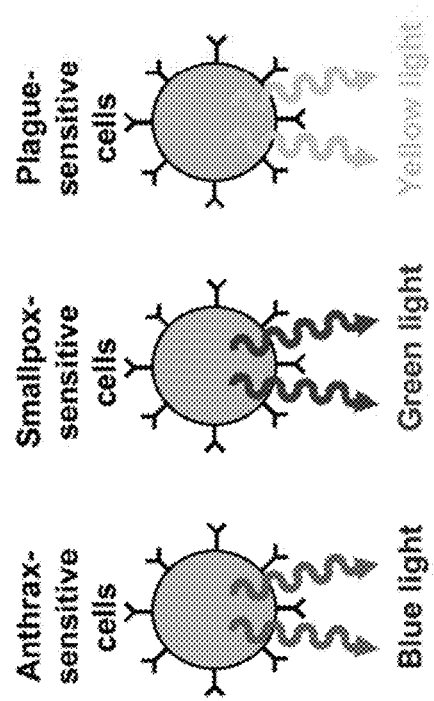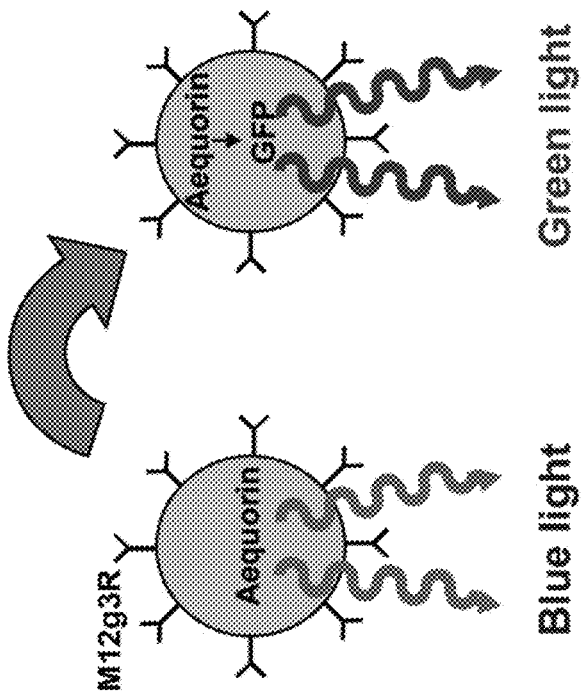
FIG. 86

Emission of Different Colors

| Natural light emission in *Aequorea victoria* jellyfish | Blue-emitting CANARY cells | Green-emitting CANARY cells | Yellow-emitting CANARY cells | CANARY cells with other colors |
|---|---|---|---|---|
| Aequorin → Blue light output; Green fluorescent protein (GFP) → Green light output | Aequorin → Blue light output | Aequorin → GFP → Green light output | Aequorin → Yellow-shifted GFP mutant → Yellow light output | Use:<br>• Mutant aequorins<br>• Aequorin homologs<br>• Other GFP mutants<br>• Etc. |

FIG. 87

EGFP-Aequorin

```
Kozak                                              EGFP
5' GCC-ACC-ATG-GTG-AGC-AAG-GGC 3' (SEQ ID NO: 12)
            48°C M   V   S   K   G   E  .....  M   D   E   L   Y   K   stop (SEQ ID NO: 13)
5' ATG-GTG-AGC-AAG-GGC-GAG......ATG-GAC-GAG-CTG-TAC-AAG-TAA 3' (SEQ ID NO: 14)
3' TAC-CAC-TCG-TTC-CCG-CTC......TAC-CTG-CTC-GAC-ATG-TTC-ATT 5'
                                        Linker
                                         50°C
                       3' C-CTG-CTC-GAC-ATG-TTC-AGA-CCG-CCA-CCT-AGT-CC 5' (SEQ ID NO: 15)
                                                    50°C
```

```
                              Linker                                Aequorin
                         5' T-GGC-GGT-GGA-TCA-AGA-ACC-AGC-GAA-CAA-TA 3' (SEQ ID NO: 16)
                                                    46°C
         M   T   S   E   E   Q   Y   .....  Y   G   G   A   V   P   stop
      5' ATG-ACC-AGC-GAA-CAA-TAC...TAC-GGT-GGA-GCT-GTC-CCC-TAA 3' (SEQ ID NO: 17)
      3' TAC-TGG-TCG-CTT-GTT-ATG....ATG-CCA-CCT-CGA-CAG-GGG-ATT 5' (SEQ ID NO: 18)
                                                    50°C
                       3' A-CCT-CGA-CAG-GGG-ATT 5' (SEQ ID NO: 19)
```

Splicing by overlap extension
(~10 rounds with EGFP & Aequorin PCR products,
then add primers for ends and do ~25 rounds)

```
       EGFP               Linker           Aequorin
Kozak  M   V  ..... Y   K   S   G   G   G   G   M   T  ..... V   P   stop (SEQ ID NO: 20)
5' GCC-ACC-ATG-GTG.....TAC-AAG-TCT-GGC-GGT-GGA-TCA-GGA-ATG-ACC.....GTC-CCC-TAA 3' (SEQ ID NO: 21)
3' CGG-TGG-TAC-CAC.....ATG-TTC-AGA-CCG-CCA-CCT-AGT-CCT-TAC-TGG.....CAG-GGG-ATT 5'
```

FIG. 88

Applications of Universal CANARY Cells

- Detection of toxins, cardiac troponin, or other monovalent antigens

- Rapid response to outbreaks of new clinical pathogens (e.g., HIV, Ebola, SARS, West Nile virus)

- Rapid response to genetically modified biowarfare agents

- Detection of pathogens for which antibodies but not hybridomas are available

- Initial tests to determine the effectiveness of CANARY with new antibodies or new pathogens

- Short-term or small-volume commercial applications that cannot justify engineering a whole new CANARY cell line

FIG. 91

Macrophage Approach

Macrophage cell lines
- J774: has Ca$^{2+}$ signaling

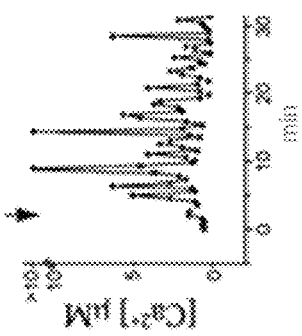

[D.J. Hackam (1997) *J. Exp. Med.* 186, 955; J.D. Young (1984) *PNAS* 81, 5430]

- U937: has Ca$^{2+}$ signaling
  [A. Melendez (1998) *Curr. Biol.* 8, 210; R.A. Floto (1997) *J. Biol. Chem.* 272, 4753]
- THP-1: has Ca$^{2+}$ signaling
  [C. Ebel (2001) *Immunobiol.* 203, 616; E. Garcia (2001) *J. Leuk. Biol.* 70, 649]
- HL-60: Ca$^{2+}$ signaling unknown
- Mn: Ca$^{2+}$ signaling unknown
- RAW 264.7: Ca$^{2+}$ signaling unknown

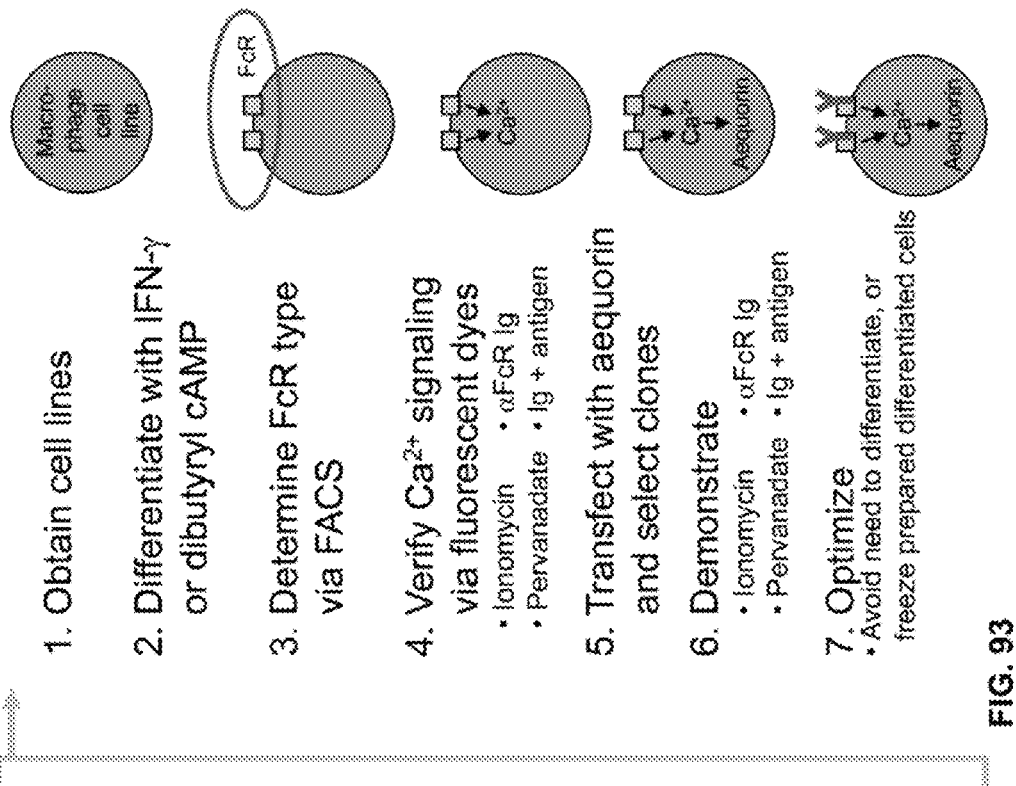

1. Obtain cell lines
2. Differentiate with IFN-γ or dibutyryl cAMP
3. Determine FcR type via FACS
4. Verify Ca$^{2+}$ signaling via fluorescent dyes
   - Ionomycin
   - αFcR Ig
   - Pervanadate
   - Ig + antigen
5. Transfect with aequorin and select clones
6. Demonstrate
   - Ionomycin
   - αFcR Ig
   - Pervanadate
   - Ig + antigen
7. Optimize
   - Avoid need to differentiate, or freeze prepared differentiated cells

FIG. 93

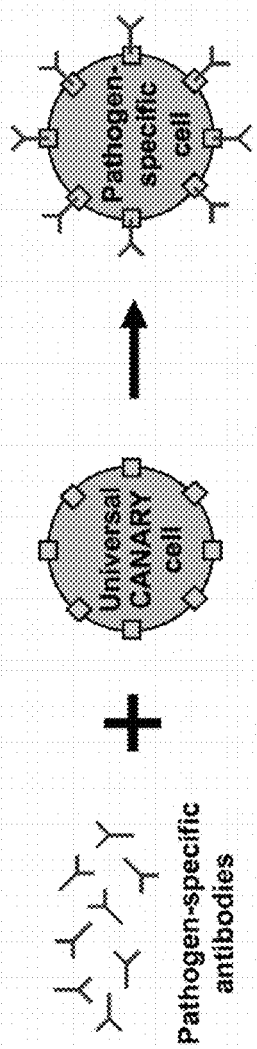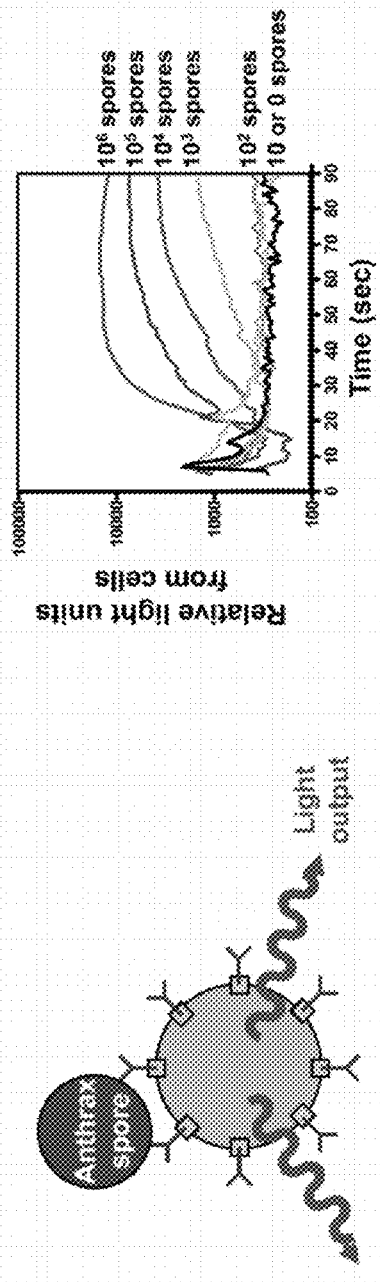
FIG. 97

FIG. 100

This graph demonstrates detection of 100 cfu/mL (5cfu/CANARY test) of Ralstonia solanacearum in geranium extract utilizing the protocol listed above and pictured below.

Geranium Tissue Processing

Slice stem at crown → Place in container, blow off residual soil → Slice ~1cm above base of stem Punch core sample → Extrude core sample from punch → Place core in extraction medium

FIG. 101

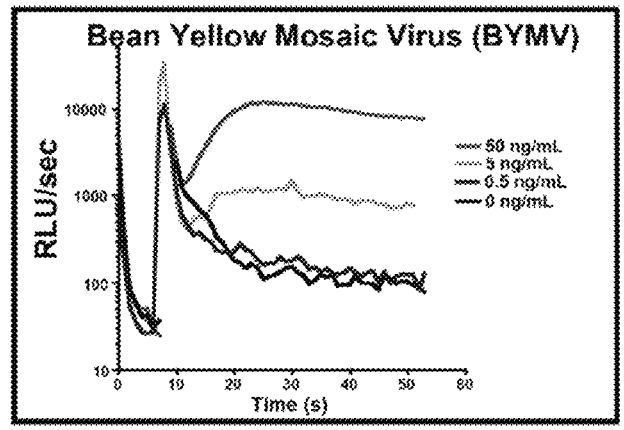
FIG. 102
This graph shows detection of 5 ng/mL (0.05 ng/CANARY test) of BYMV, a potyvirus, using the bead attachment process described above. The method allows for collection-to-detection in under 7 minutes.
Device and Protocol for CANARY Detection of Fluid-Phase Blood-Borne Pathogens:
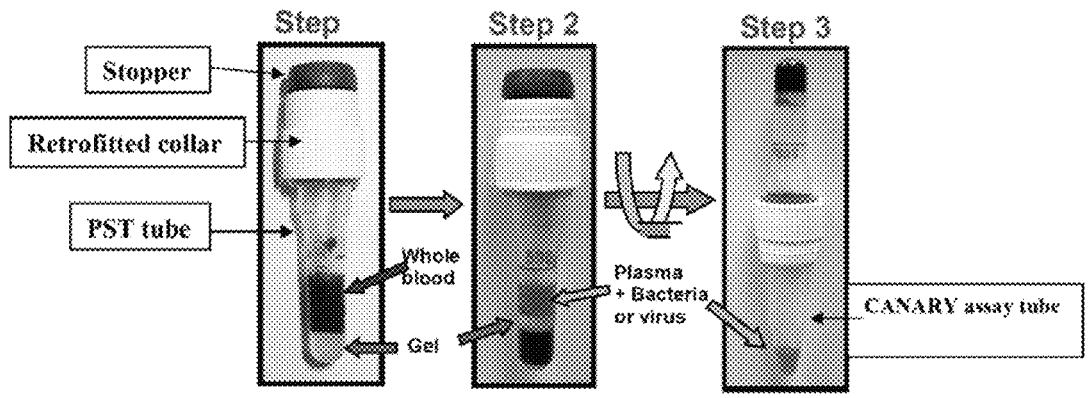
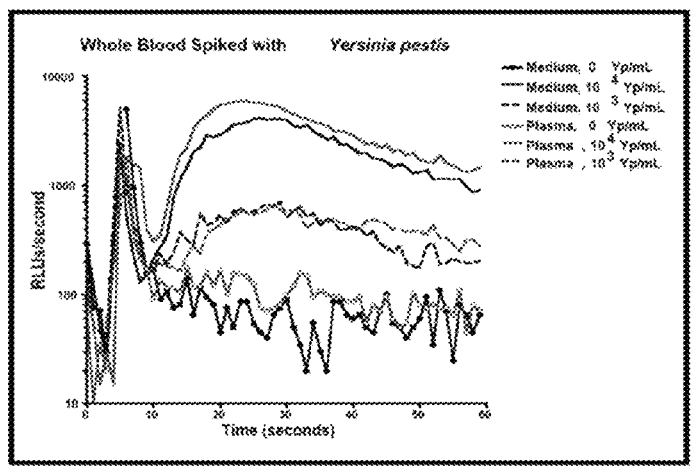
FIG. 103

Device and Protocol for CANARY Detection of Intracellular Blood-Borne Pathogens:

(tube diagram with layers labeled: Whole Blood, PBS, Gel, FD)

The following diagram indicates the position of the components post-centrifugation.

(tube diagram post-centrifugation with layers labeled: Plasma, PBS, Pathogens; White Blood Cells; Gel; Red Blood Cells; with FD extracted to the side)

FIG. 104

(graph titled "Y. pestis-spiked whole blood, processed for extraction of intracellular pathogens"; x-axis: Time (seconds); y-axis: RLU/second; legend: Medium only, 0 Yp, $10^4$ cfu Yp/mL, $10^3$ cfu Yp/mL)

FIG. 105

The limit of detection for Y. pestis in spiked whole blood is 1000 cfu/mL when the blood sample is processed by the method described above to obtain intracellular pathogens.

FIG. 106. Ba Standard with 20ul cell delivery. 50ul of Ba samples prepared in $CO_2$ (I) media and tested with 20ul B cells. Results indicate low background and an LOD of 50 cfu Ba (n=2).

FIG. 107. Ba B cell spray. 50ul of Ba samples prepared in $CO_2$ (I) media and tested with varying number of B cell sprays. Results indicate increased background with 2 sprays compared to 20ul cell delivery. Number of sprays did not affect peak intensity with 50,000 cfu Ba (n=1).

FIG. 108. Ba Standard with 1-spray cell delivery. 50ul of Ba samples prepared in $CO_2$ (I) media and tested with one spray of B cells. Results indicate similar backgrounds with 20ul cell delivery and LOD of 5,000 cfu. 50 and 500cfu Ba showed 50% chance of detection (n=2).

FIG. 109. Ba Standard: 500cfu Ba detection with 20ul B cells. 50ul of Ba samples with 500cfu Ba was prepared in $CO_2$ (I) media and tested with 20ul B cells. Results 100% detection of 500cfu even with higher background than normally seen (n=3).

FIG. 110. Ba B cell Spray: 500cfu Ba detection with 1-spray B cells. 50ul of Ba samples with 500cfu Ba was prepared in $CO_2$ (l) media and tested with 1 spray of B cells. Results indicate 50% detection of 500cfu and a 2-3x higher background (n=14).

FIG. 111. Ba B cell Spray: 500cfu Ba detection with 1-spray B cells and no spin. 50ul of Ba samples with 500cfu Ba was prepared in $CO_2$ (l) media and tested with 1 spray of B cells. Samples were not spun for 5 seconds before reading. Results indicate no cell to agent interaction resulting in 0% detection of 500cfu Ba (n=9).

FIG. 112. Yp B cell Spray: 500cfu Yp detection with 20ul B cells. 50ul of Yp samples with 500cfu Yp was prepared in $CO_2$ (l) media and tested with 20ul B cells. Results indicate a typical background and 100% detection of 500cfu Yp (n=4).

FIG. 113. Yp B cell Spray: 500cfu Yp detection with 1-spray B cells. 50ul of Yp samples with 500cfu Yp was prepared in $CO_2$ (l) media and tested with 1 spray of B cells. Results indicate a slightly increased background with 100% detection of 500cfu Yp (n=8).

FIG. 114. Yp Standard: 500cfu Ba detection with 20ul B cells. 50ul of Yp samples with 500cfu Yp was prepared in CO₂ (I) media and tested with 20ul B cells. Results 100% detection of 500cfu with a typical background (n=7).

FIG. 115. Yp B cell Spray: 500cfu dried Yp detection with 20ul B cells. 5ul of Yp samples with 500cfu Yp was prepared in dH2O, dried overnight, and tested with 20ul B cells. Results indicate 100% detection of 500cfu Yp (n=10).

FIG. 116. Yp B cell Spray: 500cfu dried Yp detection with 1-spray B cells. 5ul of Yp samples with 500cfu Yp was prepared in dH2O, dried overnight, and tested with 1-spray B cells. Results indicate a higher background, but 100% detection of 500cfu Yp (n=10).

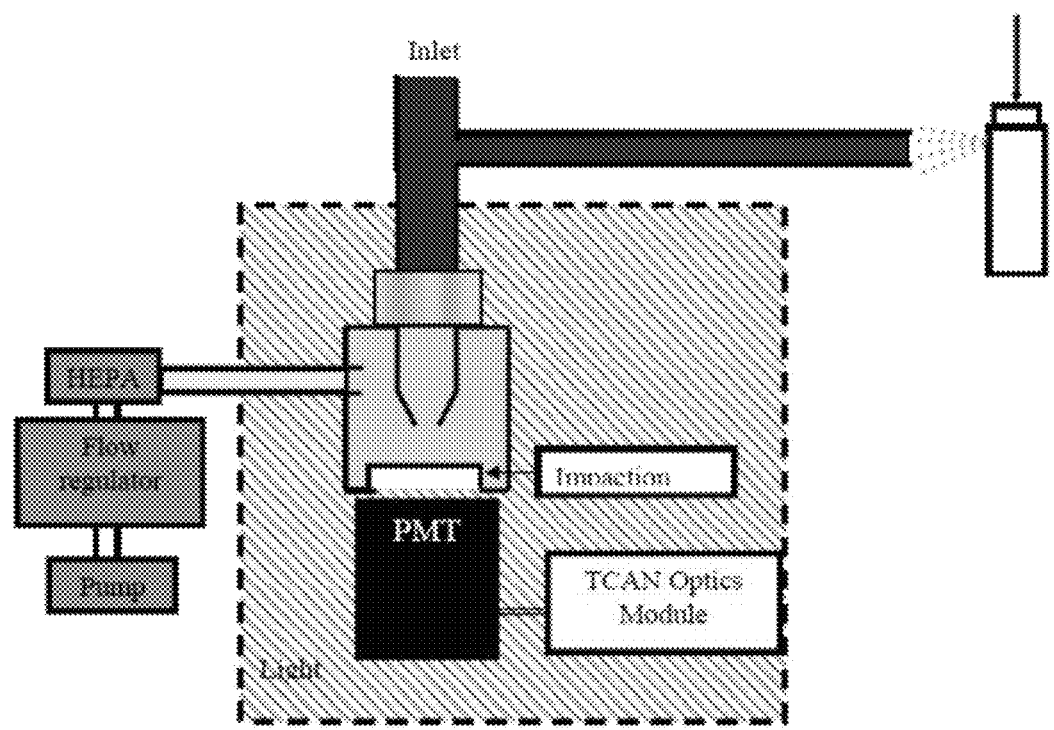
FIG. 117. Setup for B cell impaction experiment.

FIG. 118. Schematic representation of technique 4

FIG. 119. Technique 4 schematic representation.

Ideal Gas Law:

$$PV = nRT$$

FIG. 120. Technique 4 schematic representation.

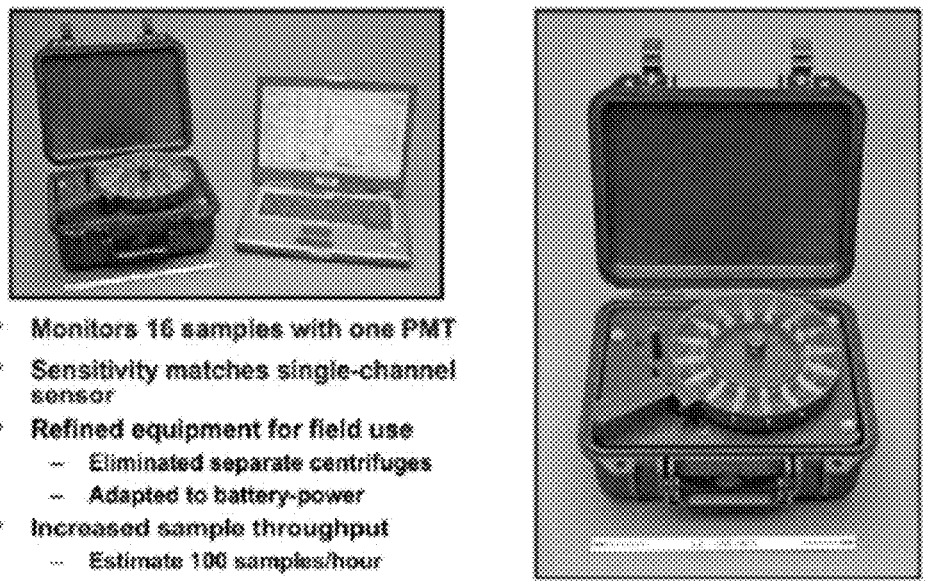
FIG. 121. *Portable 16-channel sensor.*
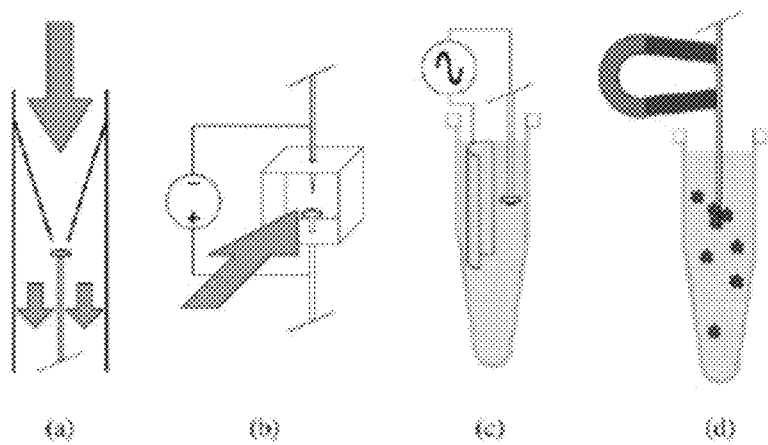
FIG. 122

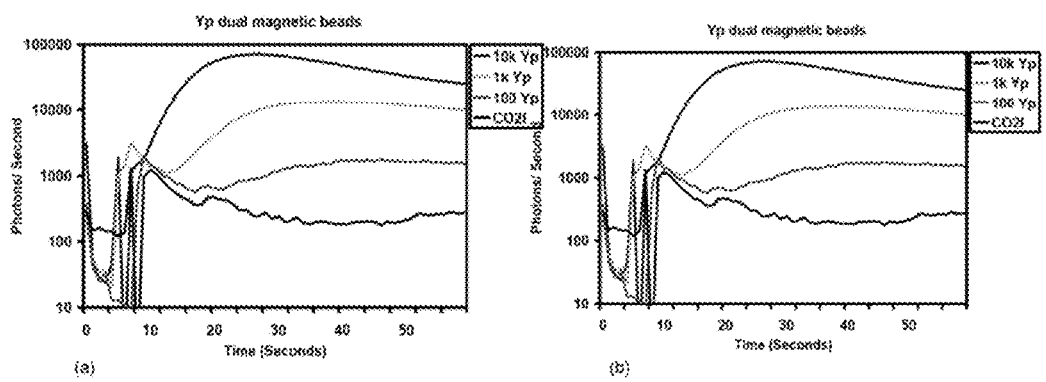
FIG. 127
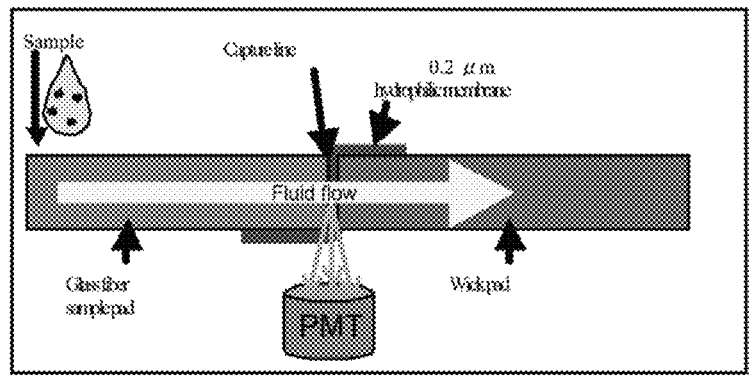
FIG. 128
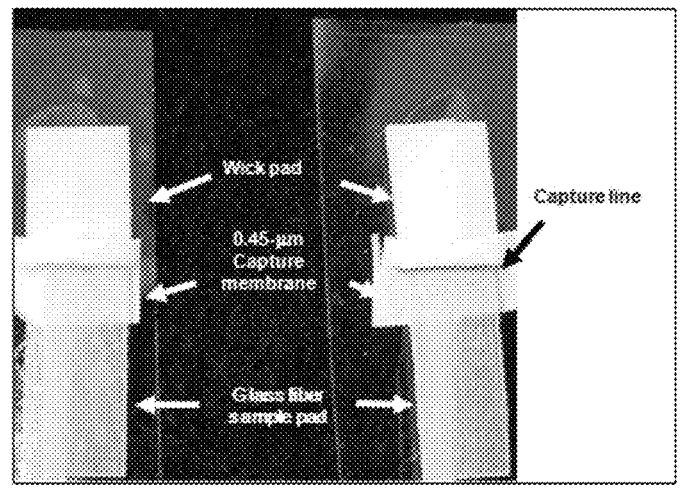
Top View    FIG. 129

Aerosol Collection Features

- Goal to eliminate need for concentrators by increasing sampling volume
  - If 10 ACPLA, 1 minute sampling at 25 Lpm with 50% efficiency would collect ~125 particles
- Air Flows >25 Lpm/channel measured using 250 watt blower Assembled Rapid Prototype — Air outlets, Aerosol inlet air flow profiles aerosol in — Particle-depleted air out

FIG. 133

Aerosol Collection Optimization

Impaction Geometry Modeling

3 Lpm

30 Lpm

1 μm particles, profile #14 fluorescent 1μm particles deposit in grooves

FIG. 134

Status of B-Cell Lines*

Can Be Detected

*Bacillus anthracis*, spores

*Bacillus anthracis*, 2 for vegetative

*Francisella tularensis*

*Yersinia pestis*

*Vibrio cholerae* (strains O139 and O1)

*Brucella spp.*

*Chlamydia spp.*

***Bacillus subtilis* spores (for use as simulant)**

DNA/RNA sequence

Botulinum Toxin

*Salmonella spp.*

*Shigella dysenteriae*

*E. coli* O157:H7

FMD virus

VEE virus

Dengue virus

Orthopoxviruses (smallpox)

*Ralstonia spp.*

Potyvirus

In Development

Ricin

SEB

*Phytophthora spp.*

Hybridomas, antibody sequences, and inactivated agents provided by: NMRC; USAMRIID; ATCC; Borstel Research Center, Germany; CDC-Ft. Collins; DPG; John Kearney, Univ. Alabama; USDA-ARS; and US Army-Natick

*CDC/USDA "A and B Lists"

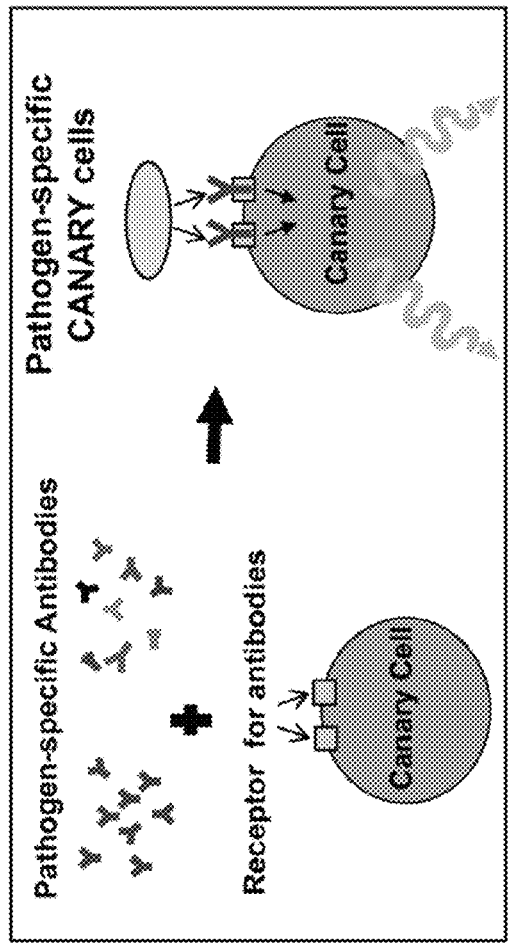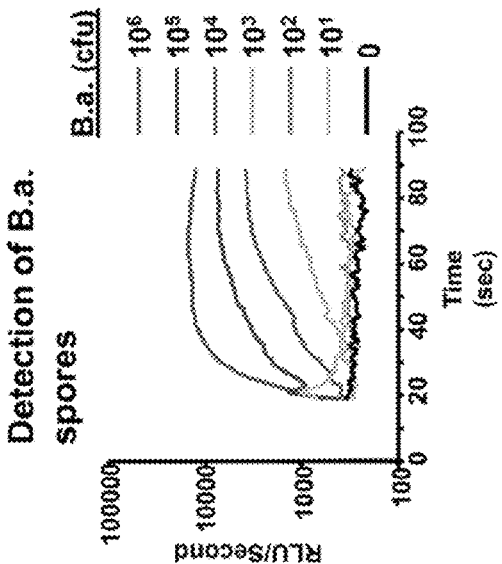
FIG. 140

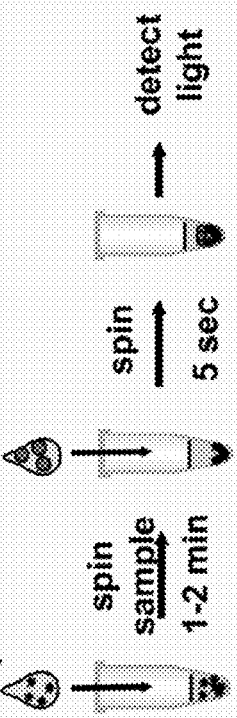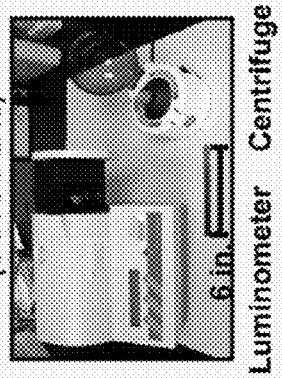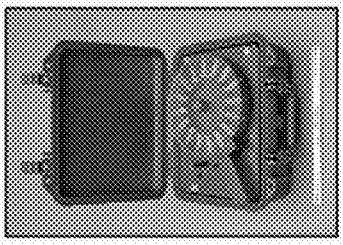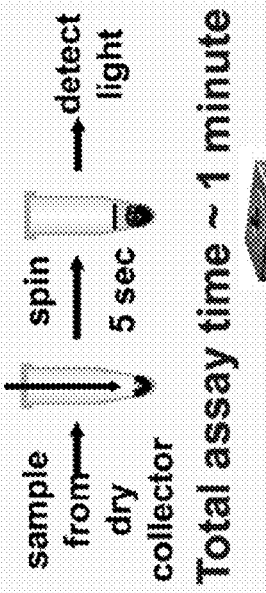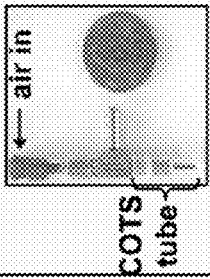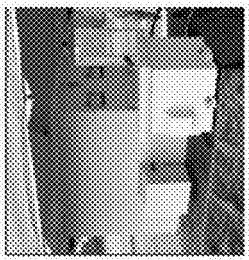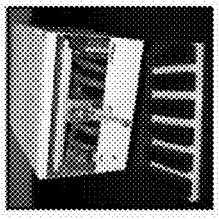
FIG. 141

CANARY Identification in Liquid

B. anthracis spore
Colony forming units (cfu)
- 50,000 ($10^6$ cfu/ml)
- 5,000 ($10^5$ cfu/ml)
- 500 ($10^4$ cfu/ml)
- 50 ($10^3$ cfu/ml)
- 0

Antibody sequence supplied by Prof. John Kearney
Inactivated Ba spores supplied by DPG

[Graph: RLU/second (10 to 100,000) vs Time (seconds, 0 to 60)]

- Best combination of speed and sensitivity for pathogen identification ($\leq$ 50 particles in < 3 min including pre-spin)
- Sensitivity is comparable for other bacteria and large viruses tested to date including *Y. pestis* and vaccinia virus (smallpox vaccine strain)

FIG. 142

Detection of Botulinum Toxin using Bead Capture

Approach

Results

Legend:
- 4 ng (800 ng/ml)
- 800 pg (80 ng/ml)
- 160 pg (16 ng/ml)
- 32 pg (3.2 ng/ml)
- 6 pg (0.6 ng/ml)
- no toxin Y-axis: RLU (10 to 100,000)
X-axis: Time (seconds), 0 to 120

Sensitivity: 32 pg total (0.000058 × LD$_{50}$) at 3.2 ng/ml

Speed: < 6 minutes total: 2-minute bead binding to BoNT Hc, wash (optional), cell addition and centrifugation, data acquisition

FIG. 144

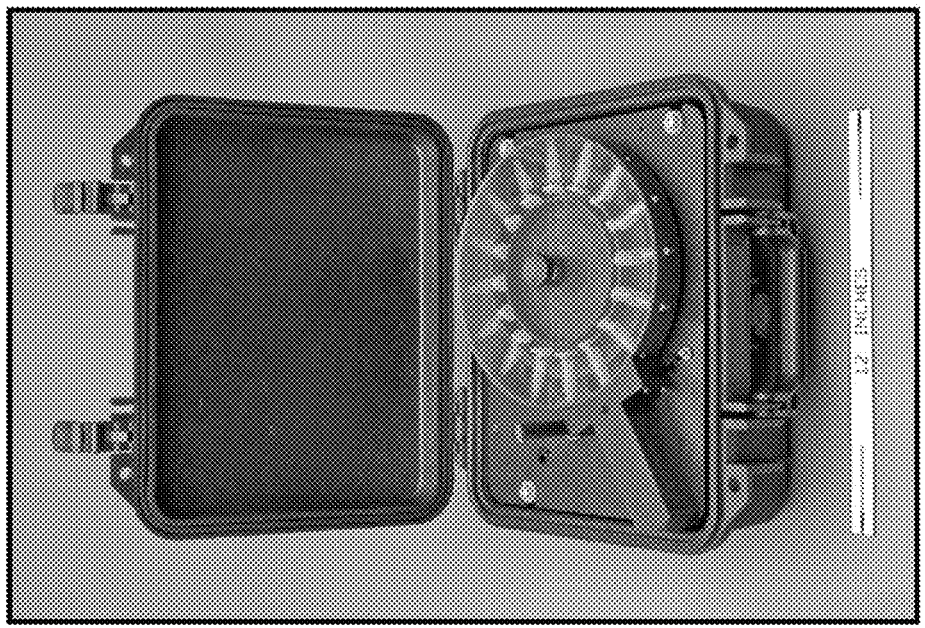
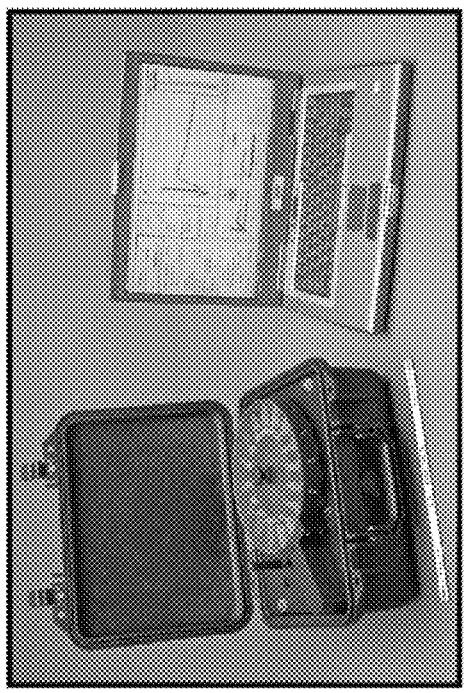
Portable 16-Channel CANARY Sensor
- Monitors 16 samples with one PMT
- Sensitivity matches single-channel sensor
- Refined equipment for field use
  – Eliminates separate centrifuges
  – Adapted to battery power
- Increased sample throughput
  – Estimate 100 samples/hour
FIG. 149

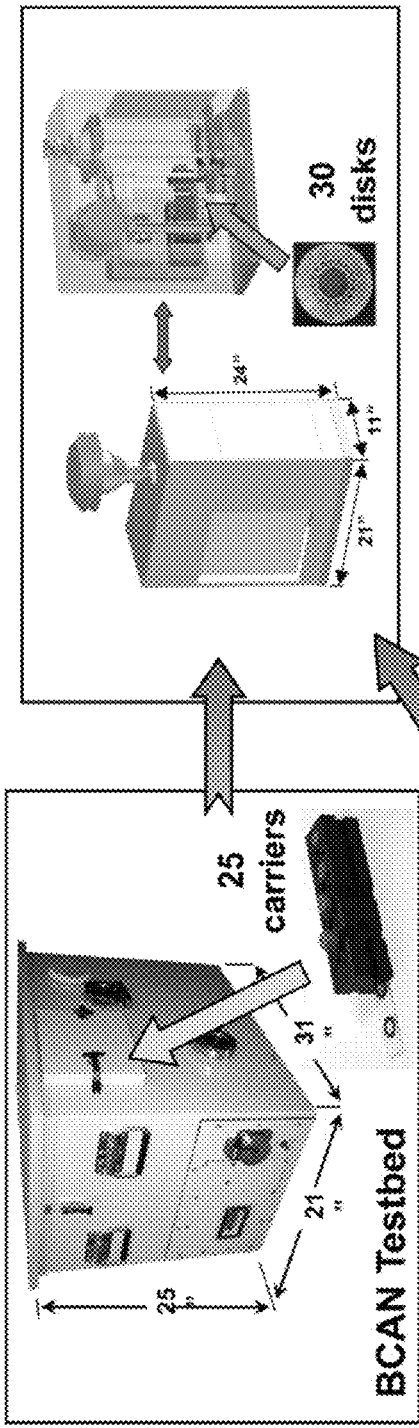
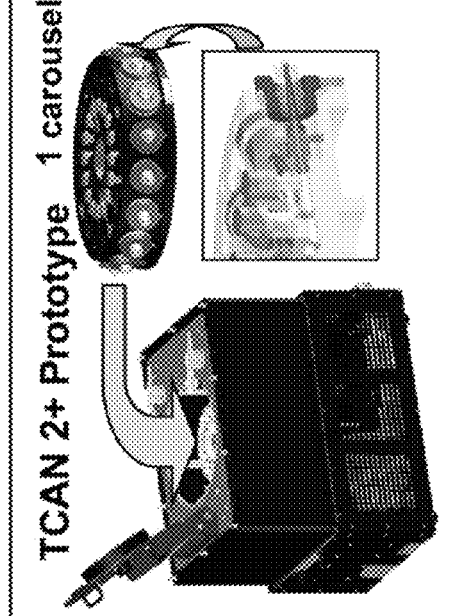
FIG. 151

Summary

- Best combination of speed and sensitivity for pathogen identification
  - ≤ 50 particles in < 3 min for liquid samples
  - ID within 1 minute following collection of aerosol samples
  - First Detect-to-Warn aerosol sensors: > 13,000 tests with excellent ROC performance

- Utility demonstrated for wide range of applications in complex samples
  - Bacteria
  - Viruses
  - Toxins
  - DNA/RNA sequence
  - Fungi

- Bioaerosol ID
  - Medical diagnostics
  - Agricultural monitoring
  - Environmental testing
  - Food safety tests
  - Rapid cell lines (emerging diseases)

- Developing fieldable sensors with advanced cell logistics

Extraction of Potyvirus from Infected Plant Tissue

Intact potyvirus with cryptotope    Capture bead    Bound virus with cryptotope exposed

Polystyrene beads are added to macerated plant tissue; Potyvirus binds almost instantaneously to the beads

Advantages of using bead capture:
- Binding event exposes the cryptotope recognized by the B cells
- Bead binding increases sensitivity of CANARY assay by allowing otherwise non-sedimentable virus to be concentrated into a pellet
- By using magnetic beads, the virus can be pulled away from potentially assay-interfering plant debris
- Bead-bound virus is readily detected in CANARY assay

FIG. 156

Sample Prep for Phytophthora-Infected Plant Tissue

- Incubate macerated plant-tissue test sample for 15 minutes with magnetic beads coated with anti-phytophthora-antibody

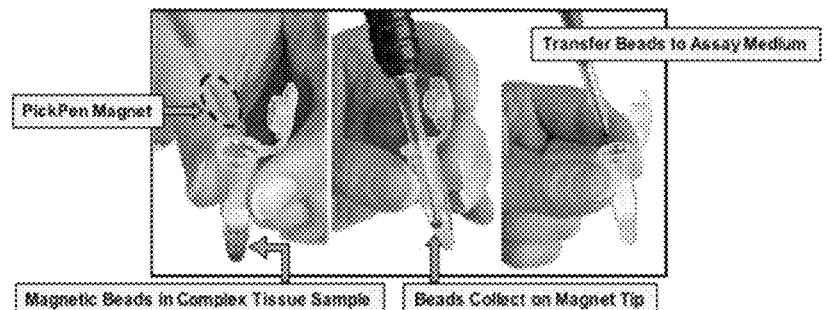

- Insert pickpen into sample to collect magnetic bead-bound phytophthora mycelia
- Transfer beads to clean tube containing CANARY assay medium
- Proceed with standard CANARY assay to test for presence of phytophthora in the test sample

FIG. 157A

Phytophthora Detection By CANARY

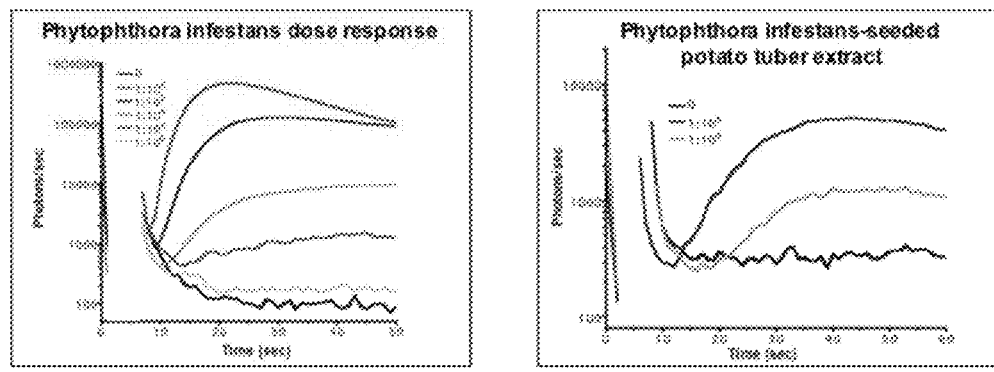

- CANARY cells exhibit a dose-dependent response to Phytophthora spp.* mycelia
- Magnetic bead capture of phytophthora from complex plant-tissue-sample extracts eliminates assay interference
- Total time of assay including sample prep and bead binding is 20 minutes

* Hybridomas provided by Neogen Corp.

FIG. 157B

BoNT/A in urine, 15 min binding, washed

FIG. 158

Detection of BoNT/A in blood, short binding step

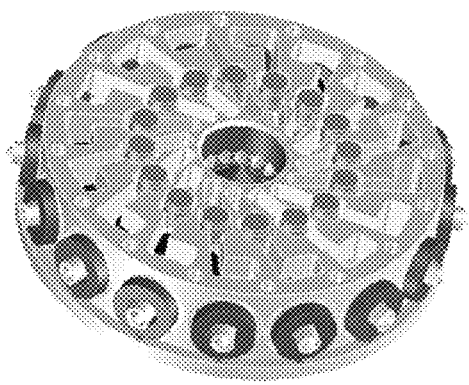
FIG. 168
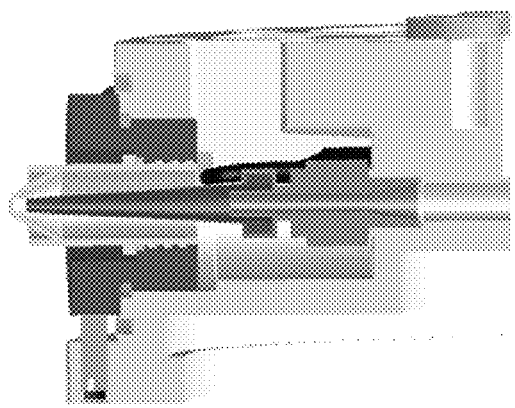
FIG. 169
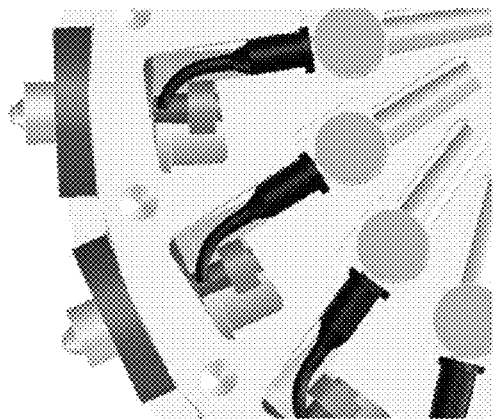
FIG. 170
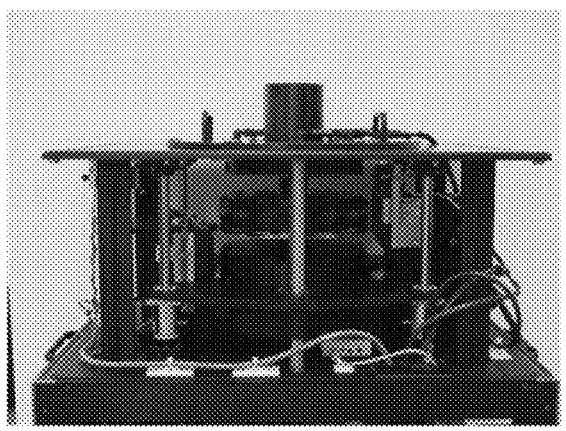
FIG. 171
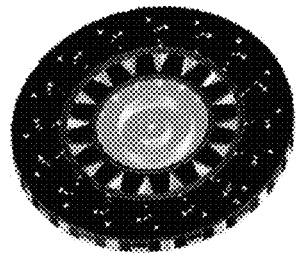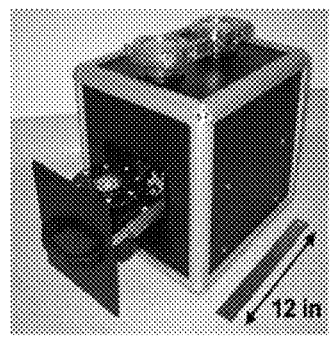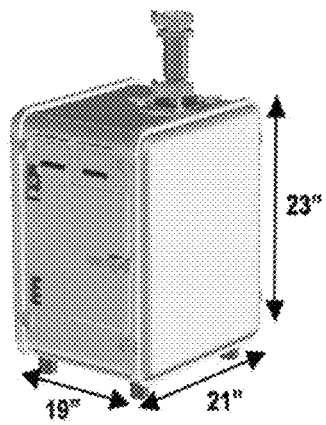
FIG. 172

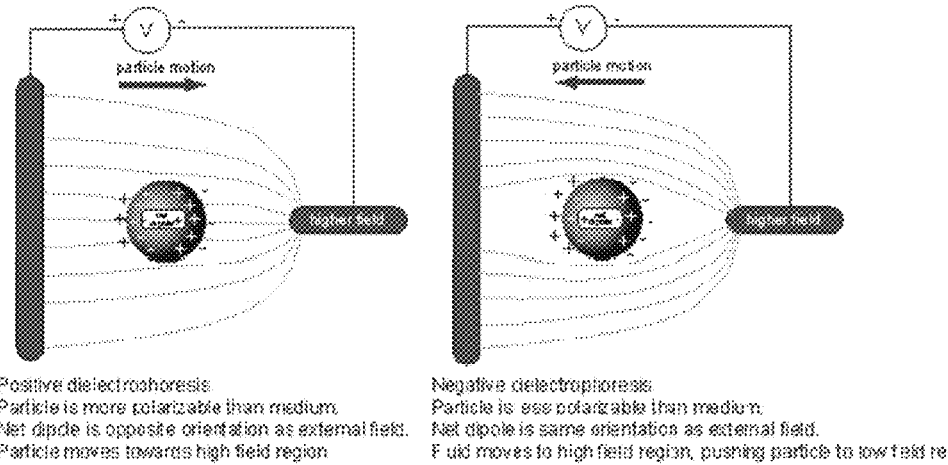
FIG. 181
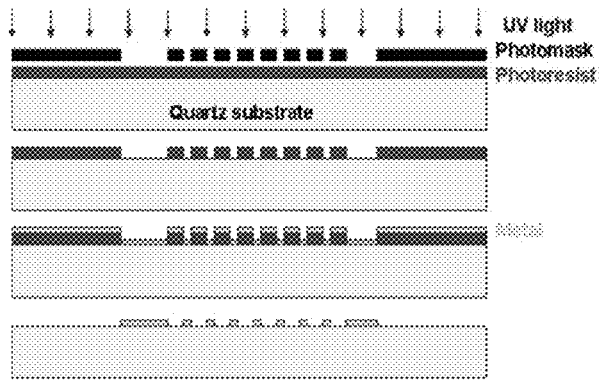
FIG. 182
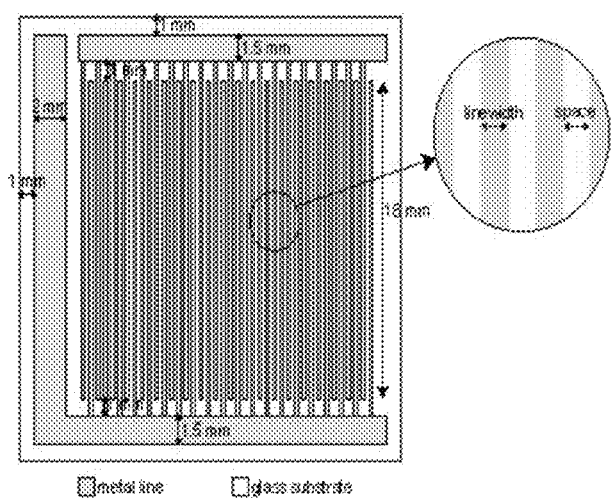 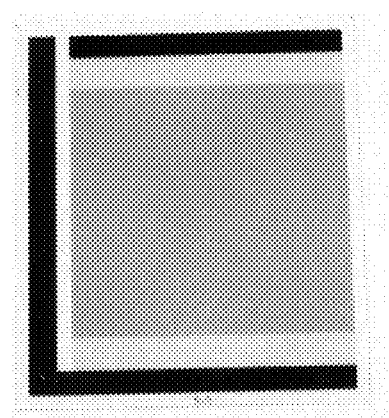
FIG. 183A  FIG. 183B

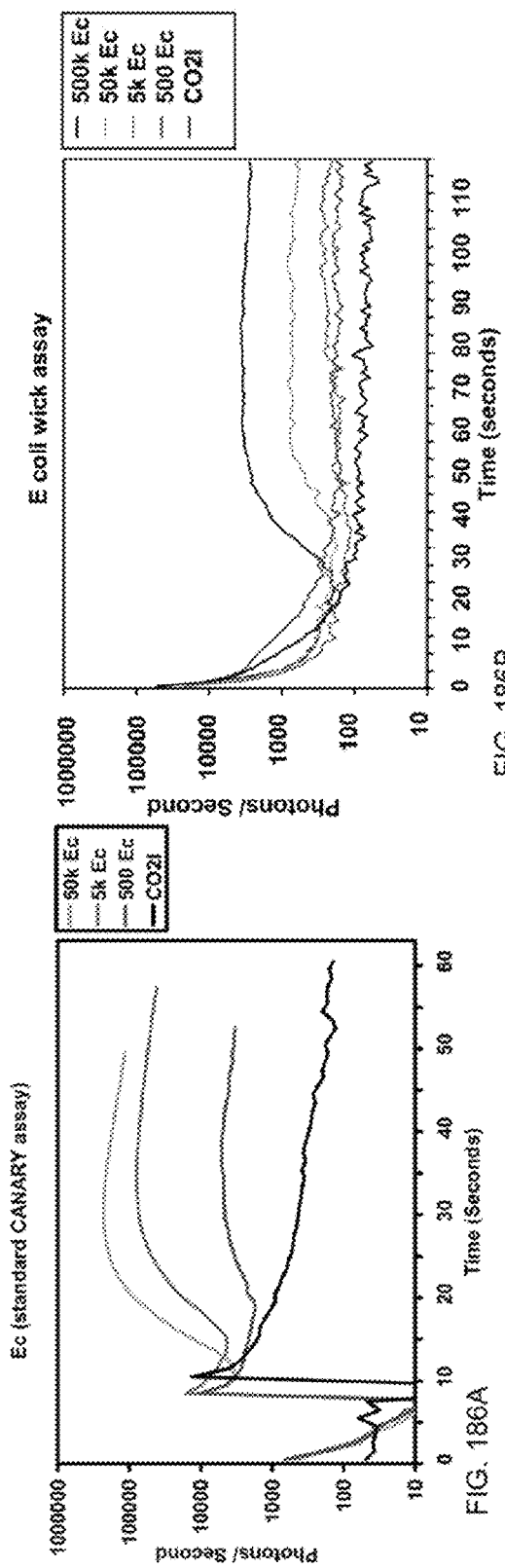
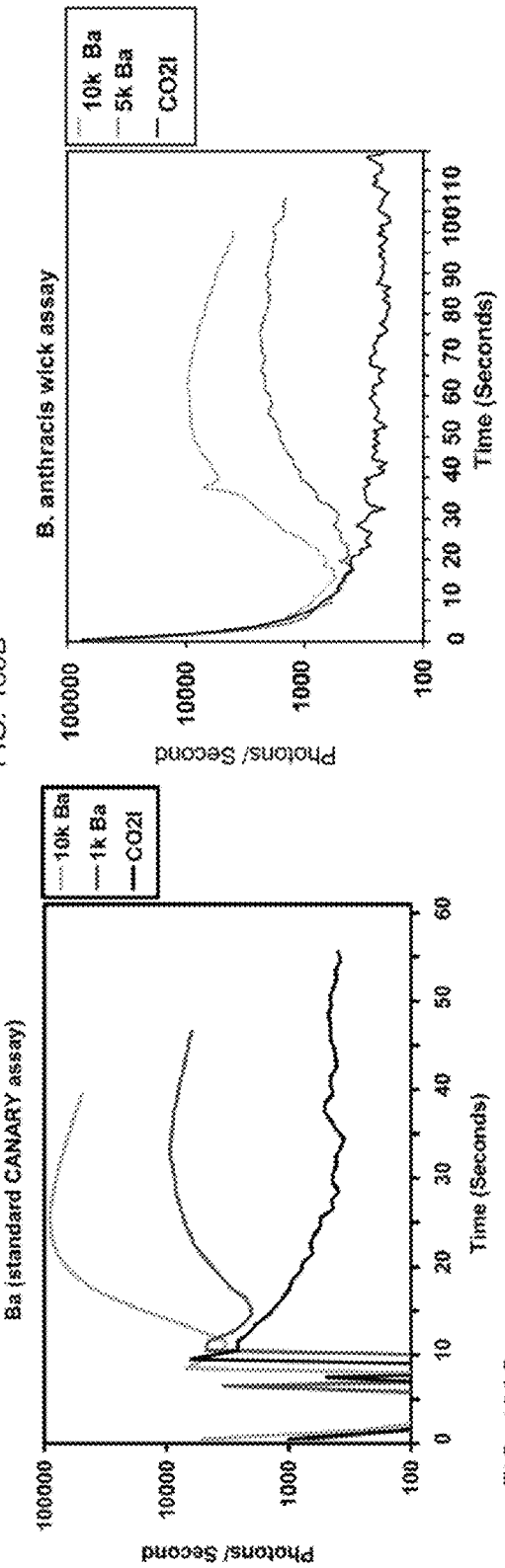
FIG. 186A
FIG. 186B
FIG. 186C
FIG. 186D

SEQUENCE LISTING

```
<160> NUMBER OF SEQ ID NOS: 22

<210> SEQ ID NO 1
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 1
gcaacgttgt tgccatt                                                  17

<210> SEQ ID NO 2
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 2
tacaggcatc gtggtgt                                                  17

<210> SEQ ID NO 3
```

```
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 3
gctcgtcgtt tggtatgg                                                   18

<210> SEQ ID NO 4
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 4
tcattcagct ccggttc                                                    17

<210> SEQ ID NO 5
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 5
acgatcaagg cgagttac                                                   18

<210> SEQ ID NO 6
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 6
gatcccccat gttgtgc                                                    17

<210> SEQ ID NO 7
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 7
aaagcggtta gctccttc                                                   18

<210> SEQ ID NO 8
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 8
tcctccgatc gttgtca                                                    17

<210> SEQ ID NO 9
<211> LENGTH: 17
<212> TYPE: DNA
<213> ORGANISM: Artificial Sequence
<220> FEATURE:
<223> OTHER INFORMATION: synthesized oligonucleotide

<400> SEQUENCE: 9
```

```
gtaagttggc cgcagtg                                                      17

<210> SEQ ID NO 10
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 10
tcactcatgg ttatggca                                                     18

<210> SEQ ID NO 11
<211> LENGTH: 18
<212> TYPE: DNA
<213> ORGANISM: Artificial Sequence
<220> FEATURE:
<223> OTHER INFORMATION: synthesized oligonucleotide

<400> SEQUENCE: 11
ccataccaaa cgacgagc                                                     18

<210> SEQ ID NO 12
<211> LENGTH: 21
<212> TYPE: DNA
<213> ORGANISM: Artificial Sequence
<220> FEATURE:
<223> OTHER INFORMATION: synthesized primer

<400> SEQUENCE: 12
gccaccatgg tgagcaaggg c                                                 21

<210> SEQ ID NO 13
<211> LENGTH: 12
<212> TYPE: PRT
<213> ORGANISM: Unknown
<220> FEATURE:
<223> OTHER INFORMATION: partial EGFP protein sequence
<220> FEATURE:
<221> NAME/KEY: NON_CONS
<222> LOCATION: (6)...(7)

<400> SEQUENCE: 13

Met Val Ser Lys Gly Glu Met Asp Glu Leu Tyr Lys
 1               5                  10

<210> SEQ ID NO 14
<211> LENGTH: 39
<212> TYPE: DNA
<213> ORGANISM: Unknown
<220> FEATURE:
<223> OTHER INFORMATION: partial EGFP nucleic acid sequence
<220> FEATURE:
<221> NAME/KEY: misc_feature
<222> LOCATION: (18)...(19)
<223> OTHER INFORMATION: non-consecutive nucleotides

<400> SEQUENCE: 14
atggtgagca agggcgagat ggacgagctg tacaagtaa                              39

<210> SEQ ID NO 15
<211> LENGTH: 33
<212> TYPE: DNA
<213> ORGANISM: Artificial Sequence
<220> FEATURE:
<223> OTHER INFORMATION: synthesized primer
```

-continued

<400> SEQUENCE: 15
cctgatccac cgccagactt gtacagctcg tcc                                33

<210> SEQ ID NO 16
<211> LENGTH: 33
<212> TYPE: DNA
<213> ORGANISM: Artificial Sequence
<220> FEATURE:
<223> OTHER INFORMATION: synthesized primer

<400> SEQUENCE: 16
tggcggtgga tcaggaatga ccagcgaaca ata                                33

<210> SEQ ID NO 17
<211> LENGTH: 12
<212> TYPE: PRT
<213> ORGANISM: Unknown
<220> FEATURE:
<223> OTHER INFORMATION: partial aequorin protein sequence
<220> FEATURE:
<221> NAME/KEY: NON_CONS
<222> LOCATION: (6)...(7)

<400> SEQUENCE: 17

Met Thr Ser Glu Gln Tyr Tyr Gly Gly Ala Val Pro
1               5                   10

<210> SEQ ID NO 18
<211> LENGTH: 39
<212> TYPE: DNA
<213> ORGANISM: Unknown
<220> FEATURE:
<223> OTHER INFORMATION: partial aequorin nucleic acid sequence
<220> FEATURE:
<221> NAME/KEY: misc_feature
<222> LOCATION: 18-19
<223> OTHER INFORMATION: non-consecutive nucleotides

<400> SEQUENCE: 18
atgaccagcg aacaatacta cggtggagct gtcccctaa                          39

<210> SEQ ID NO 19
<211> LENGTH: 16
<212> TYPE: DNA
<213> ORGANISM: Artificial Sequence
<220> FEATURE:
<223> OTHER INFORMATION: synthesized primer

<400> SEQUENCE: 19
ttaggggaca gctcca                                                   16

<210> SEQ ID NO 20
<211> LENGTH: 14
<212> TYPE: PRT
<213> ORGANISM: Artificial Sequence
<220> FEATURE:
<223> OTHER INFORMATION: partial protein sequence of EGFP-aequorin
<220> FEATURE:
<221> NAME/KEY: NON_CONS
<222> LOCATION: 2-3, 12-13

<400> SEQUENCE: 20

Met Val Tyr Lys Ser Gly Gly Gly Ser Gly Met Thr Val Pro
1               5                   10

<210> SEQ ID NO 21
<211> LENGTH: 51

-continued

```
<212> TYPE: DNA
<213> ORGANISM: Artificial Sequence
<220> FEATURE:
<223> OTHER INFORMATION: partial nucleic acid sequence of EGFP-aequorin
<220> FEATURE:
<221> NAME/KEY: misc_feature
<222> LOCATION: 12-13, 42-43
<223> OTHER INFORMATION: non-consecutive nucleotides

<400> SEQUENCE: 21
gccaccatgg tgtacaagtc tggcggtgga tcaggaatga ccgtccccta a            51

<210> SEQ ID NO 22
<211> LENGTH: 34
<212> TYPE: DNA
<213> ORGANISM: Artificial Sequence
<220> FEATURE:
<223> OTHER INFORMATION: synthesized primer

<400> SEQUENCE: 22
ctggcggtgg atcaggaatg accagcgaac aata                               34
```

PATHOGEN DETECTION BIOSENSOR

RELATED APPLICATIONS

This application is a continuation of U.S. application Ser. No. 12/085,495, now allowed, which has a 371(c) date of Mar. 27, 2009, now U.S. Pat. No. 8,216,797 which is the U.S. National Stage of International Application No. PCT/US2006/045691, filed Nov. 30, 2006, published in English, which is a continuation-in-part of U.S. application Ser. No. 11/001,583, filed Dec. 1, 2004, now U.S. Pat. No. 7,422,860, issued Sep. 9, 2008, which is a continuation-in-part of U.S. application Ser. No. 10/467,242, filed Jan. 16, 2004, now U.S. Pat. No. 7,214,346, issued May 8, 2007, which is the U.S. National Stage of International Application No. PCT/US02/03606, filed Feb. 6, 2002, published in English, which claims the benefit of U.S. Provisional Application No. 60/266,977, filed Feb. 7, 2001.

The International Application No. PCT/US2006/045691, filed Nov. 30, 2006, also claims the benefit of U.S. Provisional Application No. 60/741,271, filed on Nov. 30, 2005.

The entire teachings of the above applications are incorporated herein by reference.

GOVERNMENT SUPPORT

This invention was made with Government funds from U.S. Air Force contract no. F19628-00-C-0002. The Government has certain rights in the invention.

INCORPORATION BY REFERENCE OF MATERIAL IN ASCII TEXT FILE

This application incorporates by reference the Sequence Listing contained in the following ASCII text file being submitted concurrently herewith:

a) File name: 00502091015SEQ.txt; created Apr. 24, 2012, 5.28 KB in size.

BACKGROUND OF THE INVENTION

The need for small, fast, and sensitive detectors of biological agents which are able to monitor an environment for extended periods of time is underscored by the proliferation of biological and chemical weapons, the poor man's nuclear weapon. Under battlefield conditions, a useful detector would rapidly alert a soldier when a specific biological or chemical agent is detected so that countermeasures can quickly be implemented.

Such detectors would be useful in non-military applications as well. Rapid detection of antibiotic-resistant bacteria in a patient would help clinicians select a more effective therapeutic regimen. Continuous monitoring of a city's drinking water supply would provide early warning of potential pathogens, giving public works officials more time to manage the potential health risks to the public. In addition, the use of these detectors in meat and poultry inspections would be a significant improvement over the current "poke-and-smell" procedure. In general, such detectors are sorely needed analytical and diagnostic applications within the fields of medicine (e.g., veterinary medicine), agriculture, environmental protection (e.g., to diagnose sick building syndrome), and food processing or regulation.

All vertebrates acquire a specific immune response to a foreign agent (antigen) in part by generating an immense diversity of antibody molecules. Antibody molecules bind to antigen with high specificity, e.g., they can differentially bind to two closely related strains of bacteria, viruses, protein, nucleic acid, fungus, protozoa, multicellular parasite, or prion, as well as products produced or induced by those particles.

Antibodies are produced by B cells, a crucial component of the immune system. An antigen can activate a B cell by binding to antibodies on its surface, leading to a cascade of intracellular biochemical reactions which causes a calcium ion influx into the cytosol of the B cell.

For a review of antibody structure and function and B cell activation, see Paul, editor, Fundamental Immunology, 3rd ed., Raven Press, New York (1993).

Devices that exploit antibody diversity for detection of multiple and rare target particles or antigens have been described in U.S. Pat. No. 6,087,114 and U.S. Pat. No. 6,248,542.

These devices generally include a liquid medium containing sensor cells (e.g., a B cell, macrophage or fibroblast), also referred to herein as "CANARY" cells or "emitter" cells, an optical detector, and the liquid medium receiving target particles to be detected. Each of the cells has receptors (e.g., chimeric or single chain antibodies) which are expressed on its surface and are specific for the antigen to be detected. Binding of the antigen to the receptor results in a signaling pathway involving chemical or biochemical changes (e.g., an increase in calcium concentration). The cells also contain emitter molecules (e.g., aequorin or indo-1) in their cytosol which can emit photons in response to the signaling pathway (e.g., increased calcium concentration in the cytosol). The detector can be separated from the medium containing the cells by a covering (e.g., glass) that is transparent to the photons. Such a covering can serve to support the medium, protect a fragile surface of the detector, or be used as a lens. The optical detector, e.g., a charge-coupled device (CCD) is able to detect the photons emitted from the cells in response to the receptor-mediated signaling pathway and indicate to the user that the antigen to be detected is present. Other optical detectors which can be used in the device include photomultiplier tubes, photodiodes, complimentary metal oxide semiconductor (CMOS) imagers, avalanche photodiodes, and image-intensified charge-coupled devices (ICCD) (see for example, those available from Photek Ltd., East Sussex, UK). In some embodiments, the optical detector is able to distinguish individual cells.

SUMMARY OF THE INVENTION

Provided herein are methods for the detection of target particles. In particular, methods are provided for the detection of biological agents, pathogens, bacteria, viruses, soluble antigens, toxins, chemicals, explosives, nucleic acid sequences (for example, DNA or RNA), plant pathogens, blood borne pathogens, and the like.

Methods of detecting target particles include detection of target particles in liquid samples, aerosol samples, and dry samples.

Also provided herein is an emittor cell comprising a receptor, wherein the receptor can be an antibody specific for a target antigen, an antibody specific for a general target (for example a label such as biotin, or an immunoglobulin, and the like). In addition, the receptor can be an Fc receptor.

The emittor cell further comprises an emittor molecule for the detection of a target particle in a sample wherein binding of the receptor to the target particle stimulates a response from the emittor molecule. In one embodiment, the receptor stimulates an increase in intracellular calcium concentration, wherein the emittor molecule emits a photon in response to the increase in intracellular calcium. In one embodiment, the emittor molecule is aequorin. In another embodiment, the emittor molecule is an aequorin-GFP molecule.

Also provided is an optoelectronic sensor device for detecting a target particle in a plurality of samples using a photon detector. An optoelectronic sensor device can detect a target particle in a liquid sample. Alternatively, an optoelectronic sensor device can detect a target particle in an air or aerosol sample. In one embodiment, the sensor device comprises centrifugation means. In another embodiment, the sensor device does not comprise a centrifugation means. In one embodiment, the sensor device comprises and aerosol spray. In another embodiment, the sensor device comprises a wicking means. In a further embodiment, the sensor device comprises a moveable substrate. In one embodiment, the sensor device comprises a pinhead substrate for capture of target particles.

Detection of a target particle (such as a soluble antigen or a nucleic acid) is mediated in part by binding of the target particle to a receptor, either directly or indirectly, expressed on the cell surface of an emittor cell. Direct binding can be via a receptor, such as an antibody, which binds directly and specifically to the target particle. Indirect binding of the target particle can be through an Fc receptor that binds to an antibody that has been attached (bound) to the target particle.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 5 illustrates the B cell response to foot-and-mouth disease virus in the optoelectronic sensor.

FIG. 9 illustrates an automated cell-delivery module for the optoelectronic sensor.

FIG. 10 illustrates a dose response relationship for a sample of tularemia cells using the optoelectronic sensor.

FIG. 11 illustrate B cell resistance to chemical and biological contamination.

FIG. 14 is a schematic illustrating an optoelectronic sensor.

FIG. 16 is a schematic illustrating an air impactor/optoelectronic sensor.

FIG. 18 is a schematic illustrating a wet centrifuge/impactor concept in the optoelectronic sensor.

FIG. 19 is a schematic illustrating a wet centrifuge/impactor concept in the optoelectronic sensor.

FIG. 22 illustrates the effect of cell treatments on the response of *Yersenia pestis* specific B cells.

FIG. 26A. Plasmid DNA densely labeled with digoxigenin (approximately 4000 base pairs with 200 digoxigenin molecules attached) was detected with a limit of detection of approximately 1 ng/ml (50 pg absolute). FIG. 26B. DNA molecular weight standards of various sizes (81-8576 base pairs) sparsely labeled with digoxigenin (once per 200 base pairs) were detected at 1 µg/ml (50 ng absolute). FIG. 26C. DNA molecular weight standards of various sizes (8-587 base pairs) each labeled with 2 digoxigenins (one digoxigenin on each end of the DNA molecule) were detected at 100 ng/ml (5 ng absolute).

FIG. 27A. The tubes were centrifuged briefly to pellet the cells at the bottom of the tube, nearest the PMT, and photon emission as a function of time recorded. FIG. 27B. The cells and DNA were mixed manually and placed over the PMT without centrifugation.

FIGS. 32 A-B are bar charts. Effects of hybridization temperature on nucleic acid detection. Single-stranded phagemid DNA was hybridized to the indicated concentrations of probe at several temperatures, and maximum RLU plotted.

FIGS. 36A-C are graphs. FIG. 36A U937 cells exhibit an increase in Fcγ RI expression when treated with IFN(. The relative expression of Fc (RI on U937 cells treated with IFN ((200 ng/ml, open green peak) or untreated (solid purple peak) was measured by immunofluorescence. FIG. 36B U937 cells express functional aequorin protein. U937 cells transfected with the calcium-sensitive luminescent protein aequorin emit light when treated with ionomycin (50 M). FIG. 36C Light is detected following the crosslinking of the Fc receptors on U937 cells with stable aequorin expression. U937 cells were preincubated with 10 μg/ml human IgG, then washed and treated with goat anti-human IgG (Fab2').

FIGS. 37A-D are graphs. U937 cells can be engineered rapidly to respond to several different pathogens or simulants. U937 cells were treated for 24 h with IFN ((200 ng/ml) to increase expression of endogenous Fc (RI, and prepared for the CANARY assay. The cells were then incubated with the following antibodies: FIG. 37A mouse anti-*B. anthracis* spore, FIG. 37B rabbit polyclonal anti-*B. anthracis* spore, FIG. 37C mouse anti-*F. tularensis*, or FIG. 37D mouse anti-*B. subtilis* hybridoma supernatant. Cells were then used in the standard CANARY assay where they detected as few as 1000 cfu *B. anthracis* spores with the monoclonal antibody and 10,000 cfu spores with the rabbit polyclonal, as well as 10,000 cfu *F. tularensis* and 1,000 cfu *B. subtilis* spores.

FIGS. 38A-C are graphs. The rapidly engineered U937 cells are specific, and the specificity is determined by the antibody. FIG. 38A U937 cells incubated with mouse anti-*F. tularensis* antibodies did not respond to $10^5$ cfu of *B. anthracis* spores, but did to 106 cfu of *F. tularensis*. FIG. 38B Cells loaded with mouse anti-*B. anthracis* spore antibodies did not respond to *F. tularensis* but did to $10^6$ cfu of *B. anthracis* spores. FIG. 38C The cells did not show any response to the $10^6$ cfu of *F. tularensis* in the absence of anti-*F. tularensis* antibody [$10^6$ cfu F.t. (No ab)].

FIG. 39 is an illustration of a 16-channel sensor. A sensor was designed which allowed the simultaneous measurement of 16 samples using a single light-gathering channel. The sensor consists of a rotor holding sixteen 1.5-ml tubes horizontally, equally distributed about its circumference, and driven by a variable speed motor about a vertical axis. A single fixed photon-detecting element (e.g., a PMT) is positioned in the plane of the rotor just beyond the path of the tubes during rotation. In this way, each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

FIG. 40 is a graph. Data from the 16-channel sensor demonstrates an LOD identical to that obtained in a single-channel instrument, except that 16 samples are measured simultaneously. A single measurement consists of the following steps: preparing 16 samples (and/or controls) in individual 1.5-ml tubes, introducing an aliquot of emittor cells into each of the tubes, installing the tubes into the rotor situated in a dark box, localizing the emittor cells to the bottom of the tubes using a brief (5 sec) centrifugal spin at high RCF (~2000 g), reducing the rotor speed to 60 rpm for the duration of the measurement (each tube being sampled once every second), and generating a time-series of photon counts for each sample for display and/or input to a computer algorithm for evaluation.

FIG. 45 is an overview of a 16 channel sensor and results from using same.

FIG. 47 is an overview of a sensor cell that expresses aequorin and a generalized antibody receptor.

FIG. 57 is a schematic. Detection of soluble toxin simulant by CANARY. Monoclonal antibody against one epitope on the BoNT/A Hc protein (6E10-10) were produced from hybridomas, and conjugated to protein-G coated magnetic beads. Addition of these beads to solution containing BoNT/A will coat the beads with multiple copies of immobilized antigen, which can stimulate CANARY cells expressing antibody against a nonoverlapping epitope.

FIG. 58 is a graph. Protein A-coated beads were conjugated to 6E10-10 antibody, and these beads added to BoNT/A Hc diluted in CO2I medium. The tube was rotated for 2 minutes, CANARY cells expressing 6B2-2 antibody were added, and the mixture spun for 5 seconds. Light output was monitored using a PMT.

FIG. 59 is a bar chart. Effect of frozen storage on BoNT Hc solubility and antigenicity. 400 ng/ml BoNT Hc was used to challenge the bead-based CANARY assay. Fresh antigen gives a response 35 fold over background. Frozen and thawed agent gives slightly reduced response, and centrifuging that frozen-thawed material significantly decreases the response, indicating the generation of aggregates during the freeze-thaw process. A second lot of BoNT Hc from the same company shows less reactivity, indicating a significant lot-to-lot variation in the antigen.

FIG. 60 is a graph. Detection of BoNT/A Hc in Blood Products. CANARY is capable of detecting soluble BoNT/A Hc in blood products. BoNT/A Hc (400 ng/ml) spiked into CO2I and incubated with beads for 12 minutes, gives a strong signal. Whole blood spiked with BoNT/A Hc, prior to removal of cellular material, is also detected by CANARY. BoNT/A Hc spiked into plasma after removal of blood cells (prepared as described elsewhere) also produces a statistically significant response. Note that these assays tested frozen and thawed BoNT/A Hc, so the apparent sensitivity depicted is adversely affected by the loss of aggregated antigen during storage.

FIG. 61 is a graph. Detection of BoNT/A Hc in urine. No sample preparation was required for detection of BoNT/A in urine samples. Beads were added directly to the urine spiked with 400 ng/ml BoNT/A Hc, incubated for 12 minutes, and the beads removed magnetically. Media was added to the beads, followed by CANARY cells, and the sample spun for 5 seconds. Two of the three spiked urine samples show significant signal, while the signal from the third sample is low. Control urine, which was not spiked with BoNT/A Hc prior to bead addition, gives no signal, indicating that nonspecific stimulators are not present. Note that these assays used frozen and thawed BoNT/A Hc, so the apparent sensitivity depicted is adversely affected by the loss of aggregated antigen lost during storage.

FIG. 62 is a schematic. An alternate sample preparation procedure is used for samples derived from nasal swabs. Sample preparation requires the swab itself, a basket containing an integral 5 micron filter, and the assay tube. The swab is collected, the swab handle trimmed off, and the swab head is placed into the filter basket. CO2I medium is added to the swab, and the assembly capped and centrifuged. Beads are added to the filtrate and the assay carried out without further modification.

FIG. 63 is a graph. Nasal swabs were collected as described, placed into the filter basket, and CO2I media spiked with BoNT/A Hc at 400 ng/ml was added. The sample was filtered, beads added, and assayed. The response against these spiked samples was similar to responses against mock swabs, in which no nasal "material" was present, indicating that the nasal secretions prepared in this manner contain no inhibitors. Nasal swabs to which only CO2I was added show no response, indicating that nasal swabs do not contain any nonspecific stimulators of the assay. Note that these assays tested frozen and thawed BoNT/A Hc, so the apparent sensitivity depicted is adversely affected by the loss of aggregated antigen during storage.

FIG. 64 is a bar chart. Toxin detection in different liquids. BoNT/A Hc was spiked into each solution to the indicated concentrations. To 10 μl of that solution was added 1.4 μl of solution containing 560 mM NaCl, 1.4 M Hepes pH 7.9, and 6E10-10 conjugated paramagnetic beads. The sample was rotated for 12 minutes, 190 μl of assay medium added, and the beads magnetically captured (30 seconds). Unbound material was discarded, and the beads brought up in 50 μl of assay medium. 20 μl CANARY cells expressing antibody against the 6B2-2 epitope were added, the tube spun for 5 seconds, and place in a luminometer. Values are the peak light output (photons/second) divided by the light output of CANARY cells in medium without antigen (red bar, 0 ng/ml). The wash procedure removes nonspecific stimulators, as indicated by the similar responses of the cells to beads incubated in different matrices without antigen addition. The CANARY assay detects antigen spiked into both orange juice (green bar) and PBT/triton (light blue bar) about as well as control solution (assay medium) (red bar), with an LOD of 80 ng/ml. Sensitivity in milk (dark blue bar) is inhibited by greater than 5 fold.

FIG. 65 is a graph. The CANARY assay detects botulinum neurotoxin Type A. CO2I medium was spiked with the indicated concentrations of botulinum toxin. 6E10-10 beads were added and incubated for 2 minutes. CANARY cells expressing 6B2-2 antibody were added, the mixture spun for 5 seconds, and light output monitored. Samples containing 160 pg of toxin (16 ng/ml) stimulated the cells to more than 10 fold over background. Samples containing 32 pg of toxin (3.2 ng/ml) stimulate cells to more than 3 fold over background.

FIG. 66 is a graph. CO2I medium was spiked with the indicated concentrations of botulinum toxin. Protein G beads conjugated to S25 antibody were added and incubated for 2 minutes. CANARY cells expressing Raz antibody were added, the mixture spun for 5 seconds, and light output monitored.

FIG. 67 is a graph. Whole blood was spiked to the indicated concentration of BoNT/A. Blood cells were removed by centrifugation, and 6E10-10 antibody-coated magnetic beads added to 10 μl of the resulting plasma. The sample was rotated for 2 minutes, 190 ml of medium added, and the tube placed in a magnetic rack for 20 seconds. Media and plasma was aspirated, the tube removed from the magnet, and 50 μl of CO2I media added. CANARY cells were placed in the cap of the tube and the sample spun for 5 seconds to initiate bead-cell contact, the tube was placed in the luminometer and light output monitored.

FIG. 70 is a graph. Streptavidin coated magnetic beads were bound to a mixture of biotinylated 6C2-4 and 6E10-10 antibody. The beads were added to the indicated concentrations of BoNT/A and rotated for 15 minutes at room temperature. 6B2-2 CANARY cells were added, the tube spun for 5 seconds, and light output monitored on a PMT.

FIG. 71 is a graph. Beads were diluted 10 fold from the standard concentration. 100 microliters of 0.32 ng/ml BoNT/A in CO2I at the indicated concentration was added, and the tube rotated overnight at room temperature. 6B2-2 CANARY cells were added, the tube spun for 5 seconds, and light output monitored on a PMT.

FIG. 72 is a schematic.

FIG. 75 is a summary of the Fc receptor/universal cell line.

FIG. 76 is a summary of an experimental protocol for priming/loading U937 cells.

FIG. 77 is a summary of the protocol for an Fc receptor cell assay.

FIG. 78 is a summary of alternative embodiments.

FIG. 79 is a summary of alternative embodiments.

FIG. 80 is a series of graphs and a bar chart demonstrating a shift in light emission for aequorin with EGFP.

FIG. 86 is a schematic of multiplex signal detection.

FIG. 87 is a schematic of CANARY cells having different emission colors.

FIG. 88 is a schematic of a cloning strategy for EGFP-aequorin.

FIG. 91 is an outline of examples of embodiments of the invention.

FIG. 93 is a schematic for producing a universal macrophage cell line.

FIG. 97 is a summary schematic of universal CANARY cells.

FIG. 100 is a graph demonstrating detection of *Ralstonia solanacearum* in geranium extract as described herein.

FIG. 101 is a series of photographs illustrating geranium tissue processing for pathogen detection.

FIG. 102 is a graph demonstrating detection of polyvirus BYMV using the bead attachment method as described herein.

FIG. 103 is a series of photographs illustrating one embodiment of the apparatus for detection of blood borne pathogens in a blood sample and a graph demonstrating the results of pathogen detection.

FIG. 104 is a schematic illustrating components of the invention described herein.

FIG. 105 is a graph demonstrating pathogen detection in a blood sample.

FIG. 106 is a graph. Ba Standard with 20 ul cell delivery. 50 ul of Ba samples prepared in CO2(I) media and tested with 20 ul B cells. Results indicate low background and an LOD of 50 cfu Ba (n=2).

FIG. 107 is a graph. Ba B cell spray. 50 ul of Ba samples prepared in CO2 (I) media and tested with varying number of B cell sprays. Results indicate increased background with 2 sprays compared to 20 ul cell delivery. Number of sprays did not affect peak intensity with 50,000 cfu Ba (n=1).

FIG. 108 is a graph. Ba Standard with 1-spray cell delivery. 50 ul of Ba samples prepared in CO2 (I) media and tested with one spray of B cells. Results indicate similar backgrounds with 20 ul cell delivery and LOD of 5,000 cfu. 50 and 500 cfu Ba showed 50% chance of detection (n=2).

FIG. 109 is a graph. Ba Standard: 500 cfu Ba detection with 20 ul B cells. 50 ul of Ba samples with 500 cfu Ba was prepared in CO2 (I) media and tested with 20 ul B cells. Results 100% detection of 500 cfu even with higher background than normally seen (n=3).

FIG. 110 is a graph. Ba B cell Spray: 500 cfu Ba detection with 1-spray B cells. 50 ul of Ba samples with 500 cfu Ba was prepared in CO2 (I) media and tested with 1 spray of B cells. Results indicate 50% detection of 500 cfu and a 2-3× higher background (n=14).

FIG. 111 is a graph. Ba B cell Spray: 500 cfu Ba detection with 1-spray B cells and no spin. 50 ul of Ba samples with 500 cfu Ba was prepared in CO2 (I) media and tested with 1 spray of B cells. Samples were not spun for 5 seconds before reading. Results indicate no cell to agent interaction resulting in 0% detection of 500 cfu Ba (n=3).

FIG. 112 is a graph. Yp B cell Spray: 500 cfu Yp detection with 20 ul B cells. 50 ul of Yp samples with 500 cfu Yp was prepared in CO2 (I) media and tested with 20 ul B cells. Results indicate a typical background and 100% detection of 500 cfu Yp (n=4).

FIG. 113 is a graph. Yp B cell Spray: 500 cfu Yp detection with 1-spray B cells. 50 ul of Yp samples with 500 cfu Yp was prepared in CO2 (I) media and tested with 1 spray of B cells. Results indicate a slightly increased background with 100% detection of 500 cfu Yp (n=8).

FIG. 114 is a graph. Yp Standard: 500 cfu Ba detection with 20 ul B cells. 50 ul of Yp samples with 500 cfu Yp was prepared in CO2 (I) media and tested with 20 ul B cells. Results 100% detection of 500 cfu with a typical background (n=7).

FIG. 115 is a graph. Yp B cell Spray: 500 cfu dried Yp detection with 20 ul B cells. 5 ul of Yp samples with 500 cfu Yp was prepared in dH2O, dried overnight, and tested with 20 ul B cells. Results indicate 100% detection of 500 cfu Yp (n=10).

FIG. 116 is a graph. Yp B cell Spray: 500 cfu dried Yp detection with 1-spray B cells. 5 ul of Yp samples with 500 cfu Yp was prepared in dH2O, dried overnight, and tested with 1-spray B cells. Results indicate a higher background, but 100% detection of 500 cfu Yp (n=10).

FIG. 117 is a schematic representation of a B cell impaction experiment.

FIG. 118 is a schematic representation of an aspiration apparatus.

FIG. 119 is a schematic representation of aspiration based on Bernoulli's principle.

FIG. 120 is a schematic representation one embodiment of the invention.

FIG. 121 is a pair of photographs illustrating a portable 16 channel sensor of the present invention. The sensor consists of a rotor holding assay tubes horizontally, equally distributed about its circumference, and driven by a variable speed motor about a vertical axis. A single fixed photon-detecting element, in this case a PMT, is positioned in the plane of the rotor just beyond the path of the tubes during rotation. In this way each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

FIG. 122 is a schematic of possible methods of collecting suspected antigen onto the sample surface: (a) air impaction; (b) electrostatic collection; (c) electrophoretic collection from a liquid sample; (d) 2-part collection from a liquid sample: incubation with functionalized magnetic beads which capture antigen; capture of the beads by attraction in the non-uniform magnetic field of a magnetized 'pin' (in this case, using a sharp tip, rather than the 'head', may be desirable, as the force on the magnetic beads is related to non-uniformities in the magnetic field).

Figure 123:
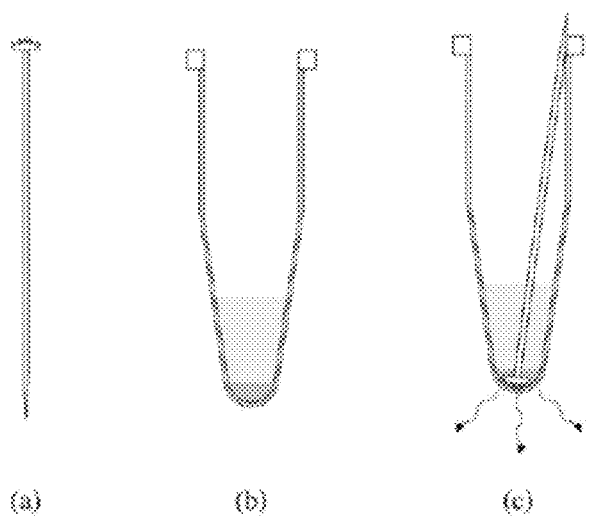

FIGS. 123(a)-(c) are schematics: FIG. 123(a) a 'straight pin' with particles collected on the 'head'; FIG. 123(b) cross-section of sample tube with media and settled CANARY B-cells; FIG. 123(c) pin inverted into B-cell tube, initiating luminous response.

Figure 124:
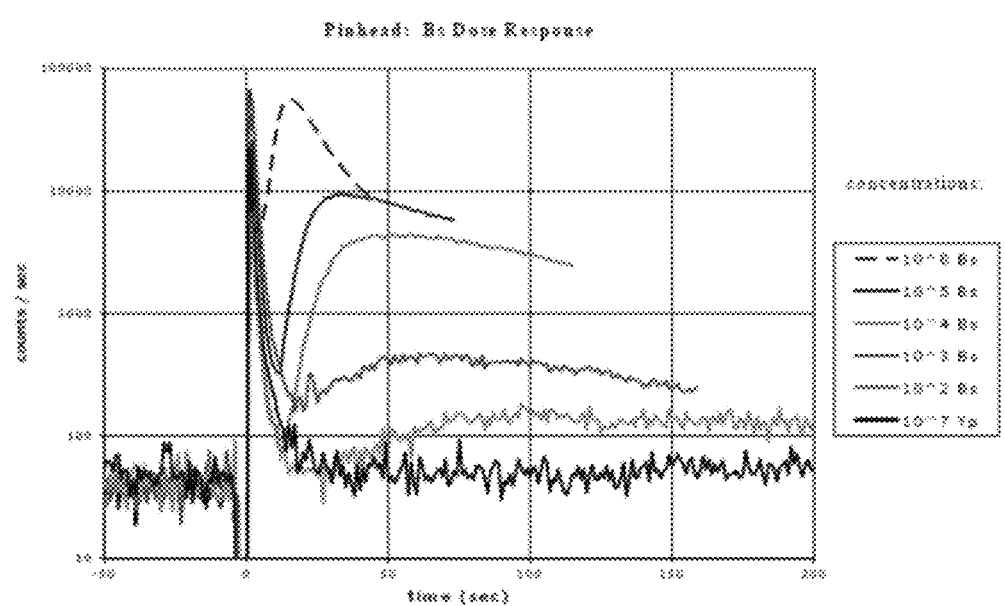

FIG. 124 is a graph of pinhead dose-response curves for Bs spores dried onto pinheads and introduced (at 0 seconds) into a 200-µl tube containing 50 µl of settled (by centrifugation) B cells sensitive to Bs. The concentrations of the Bs spore preparation are shown in the legend. Response to a pin prepared with 107/ml of Yp is shown as a negative control and an indication of a lack of cross reactivity.

Figure 125:
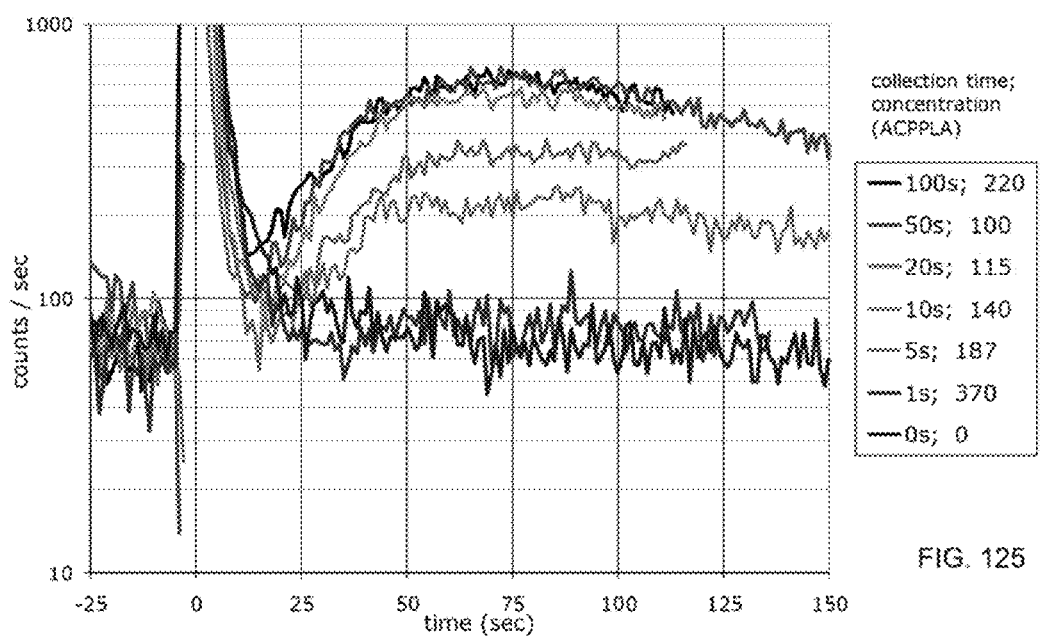

FIG. 125 is a graph of Bs B-cell response to electrostatically collected Bs spores. A potential of 5.5 KV was placed across opposed pin (as in FIG. 122(b)). Concentrations of Bs spores ranging from 100-370 ACPLA (agent containing particles per liter of air) were flowed past the pins at a rate of 2 l/min for varying lengths of time. An approximate correlation between collection time and B-cell response was observed.

Figure 126:
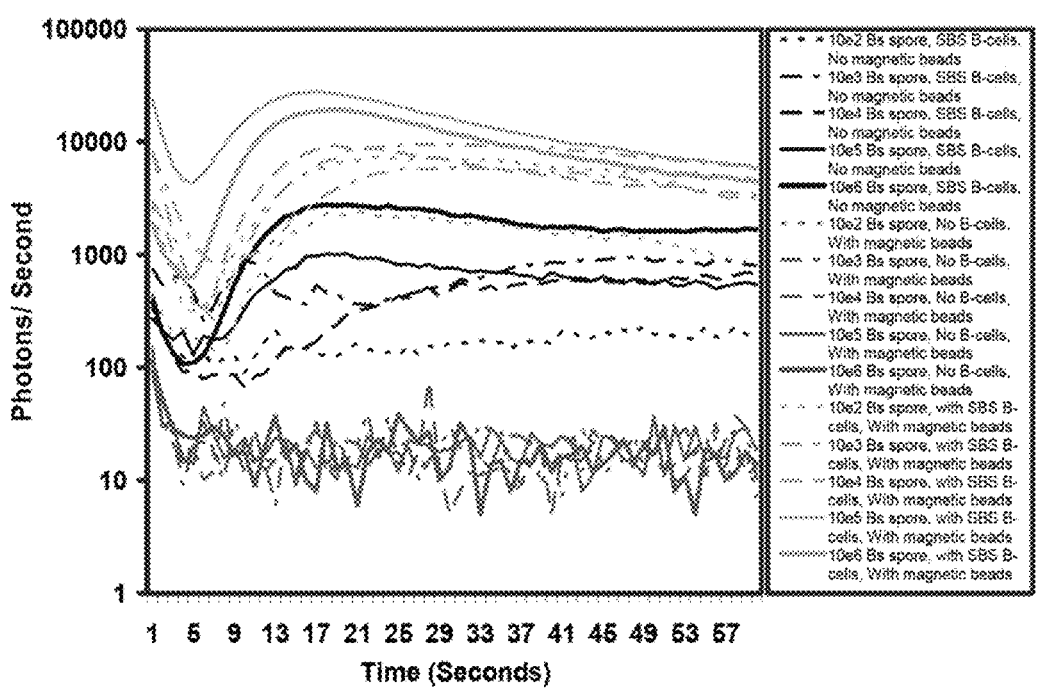

FIG. 126 is a graph. Magnetic "Pinhead" embodiment. *Bacillus subtilis* particles were dried onto the head of a pin (simulating air impaction or the product of any other suitable localized collection method) and then placed into a liquid containing magnetically labeled B cells. The pin was magnetized to attract B cells to the dried spores and placed into a luminometer.

FIGS. 127(a)-(b) are graphs of a Comparison between the standard, centrifugal CANARY assay and the dual-magnetic-bead assay. FIG. 127(a) *Y. pestis* in a standard CANARY assay and FIG. 127(b) *Y. pestis* in a dual-magnetic-bead assay. Magnetic beads specific for *Y. pestis* were mixed with a dilution series of *Y. pestis* agent for 5 min. After 5 min the magnetic beads were pulled to the bottom of the assay tube along with any bound *Y. pestis*, and the supernatant was removed. Magnetically labeled B cells were then added to the sample and pulled down to the bottom of the tube.

FIG. 128 is a schematic. Principle of sample capture in a lateral-flow format. Sample is added to the sample pad (~200 µl), which in turn saturates the pad and flows toward the capture membrane (0.2-µm membrane). The B cells (50 µl) are then added to the sample pad and slowly wick toward the capture membrane where they encounter captured antigen and emit photons.

FIG. 129 is a photograph of a handheld lateral-flow assay format. A sample of colored beads (1-µm diameter) were placed onto the sample pad and allowed to wick up to the capture membrane to demonstrate agent capture zone. Overall size is 1 in.×0.25 in.

Figure 130:
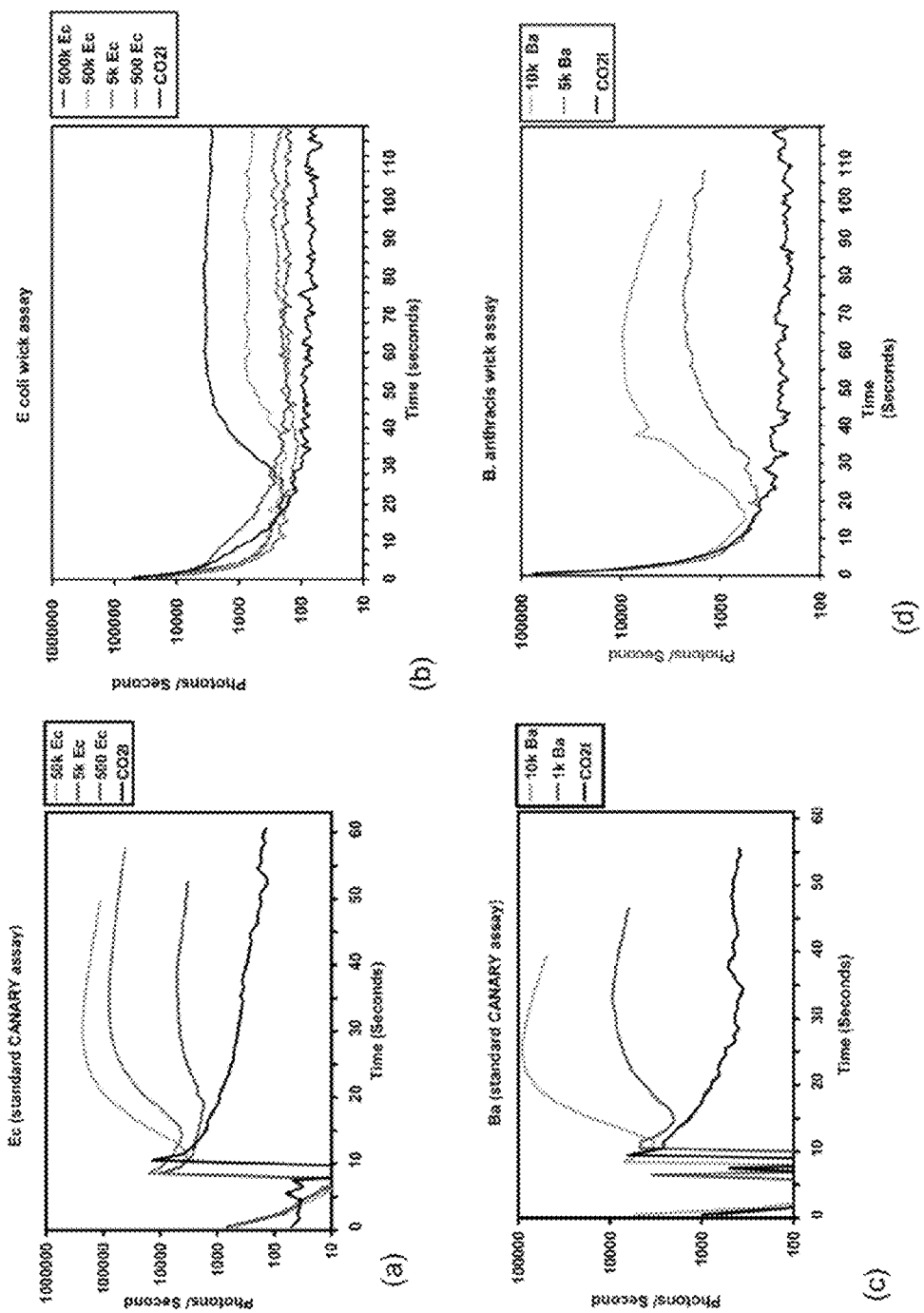

FIG. 130 is a series of graphs demonstrating lateral-flow assay results: (a) *E. coli* in a standard CANARY assay, (b) *E. coli* lateral-flow assay showing an LOD of 5000 particles per 200-ml sample, (c) *B. anthracis* in a standard CANARY assay, and (d) *B. anthracis* in a lateral-flow assay showing an LOD of 5000 particles per 200-ml sample.

Figure 131:
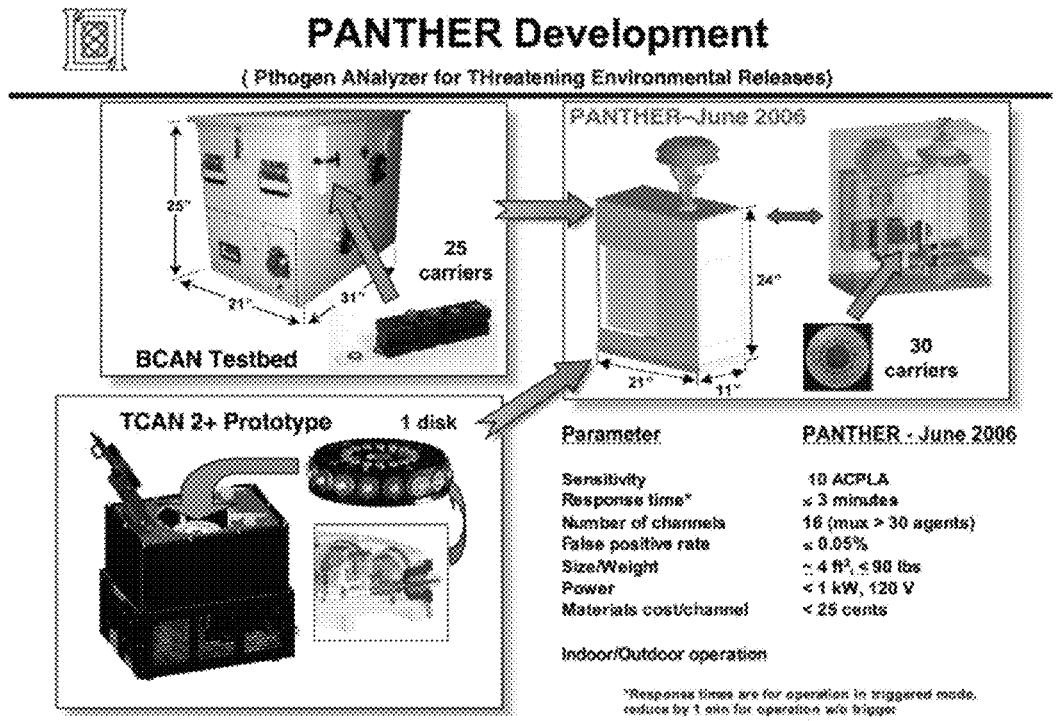

FIG. 131 is a schematic of embodiments of an automated CANARY bioaerosol sensor.

Figure 132:
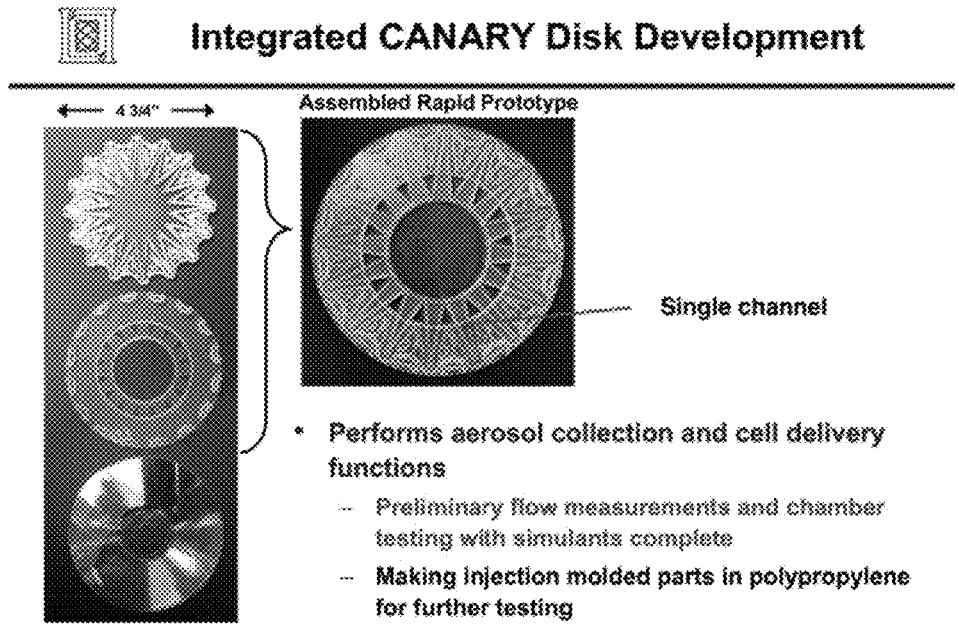

FIG. 132 is a pair of photographs illustrating an integrated CANARY disk of the present invention. The automated CANARY bioaerosol sensor disk performs aerosol collection and CANARY B-cell storage and delivery functions. For size comparison, a compact disk (CD) is shown.

FIG. 133 is a series of photographs illustrating collection details of the automated CANARY bioaerosol sensor disk.

FIG. 134 is a series of illustrations demonstrating the automated CANARY bioaerosol sensor disk aerosol collection optimization. A plurality of impactor geometries were designed and tested using CFD (Computational Fluid Dynamics) modeling and performance was experimentally verified by collection of aerosolized fluorescent 1 µm polystyrene spheres as model particles. All geometries tested demonstrated collection and the simplest functional geometries were identified and used in further development. Other geometries tested showed useful properties including particle focusing and re-direction that may be useful in developing novel impactor geometries capable of producing higher particle densities relative to standard geometries.

Figure 135:
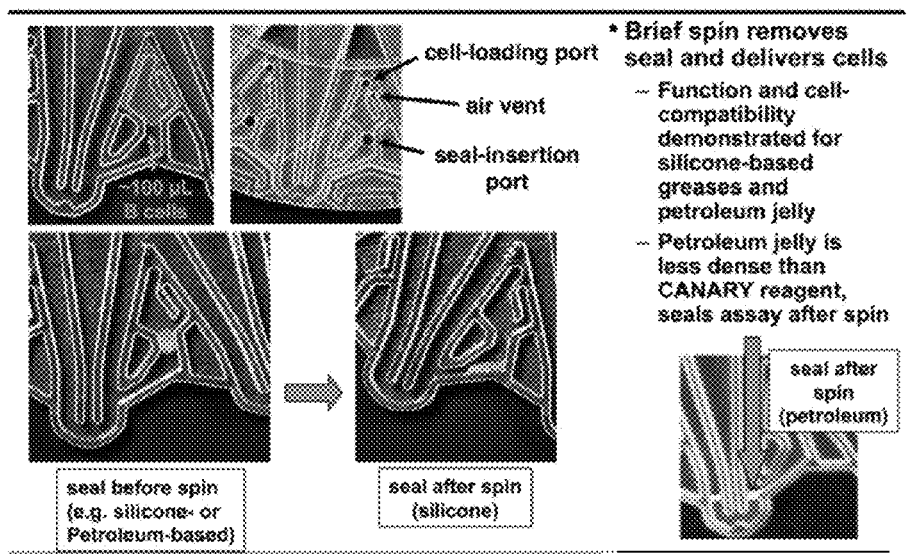

FIG. 135 is a series of photographs of the automated CANARY bioaerosol sensor disk cell delivery—Viscous Plug Embodiment. In this embodiment a chamber is formed with sufficient volume to contain CANARY B cells for a single assay in a configuration that can be sealed in the plane of the disk by a plug made of a high-viscosity, cell-compatible grease or gel (e.g. silicone grease, or petroleum jelly). The geometry of the walls where the viscous plugs are inserted into the disk is designed to constrain the plug and keep it stable during transport and handling, but to release the plug when sufficient centrifugal force is applied during a brief spin so that the cells are released to automatically move to the analysis site. The gel can be selected to be more or less dense than the aqueous medium that contains the CANARY B cells. If its density is greater than that of the B-cell medium (e.g. silicone grease) the viscous plug will settle to the bottom of the liquid in a defined region of the disk away from the CANARY analysis site. If the density of the gel is less than that of the B-cell medium (e.g. silicone grease) the viscous plug will settle on the top of the CANARY reagent and can be used to form a seal above the reaction site to stabilize it for storage and transport to a laboratory for further confirmatory testing.

Figure 136:
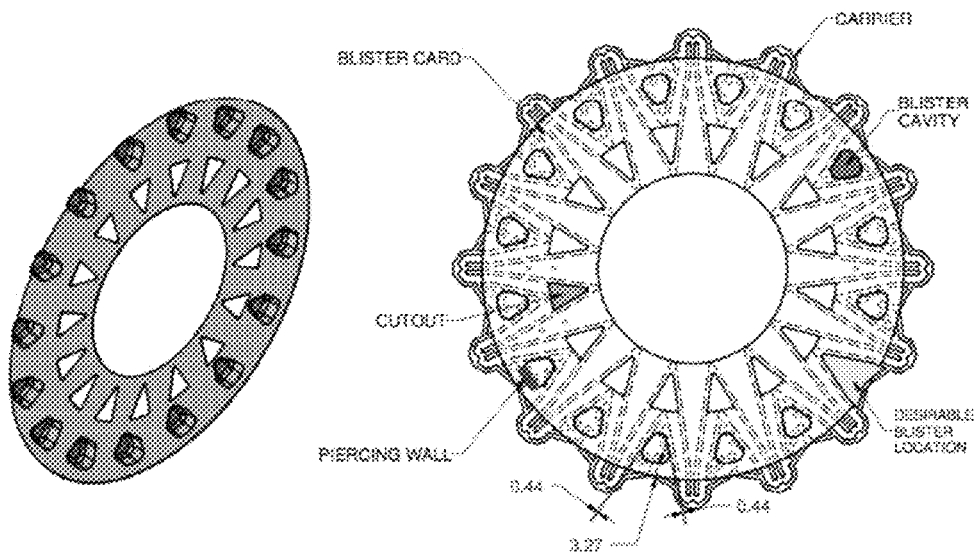

FIG. 136 is a schematic illustrating automated CANARY bioaerosol sensor cell delivery—Rupturable Blister Embodiment. In this embodiment CANARY B-cell storage compartments for each analysis site are built into the lid of the disk using traditional blister-packaging materials and methods. The shape and thickness of the blisters will be designed to enable localized pressure applied to the top of the disk to rupture the side of the blisters facing the assay sites to enable the CANARY B cells to be delivered to the assay site with a brief spin. The disk will contain features to support the blister evenly on the sides away from the reaction site and focus the applied force in a specified area to provide for reproducible liquid delivery. The blister card incorporating the blisters will have openings as shown to provide for proper interface with the manifold directing air flow through the disk for aerosol collection, and the whole card will be sealed to the disk to provide separation between each of the individual analysis channels.

Figure 137:
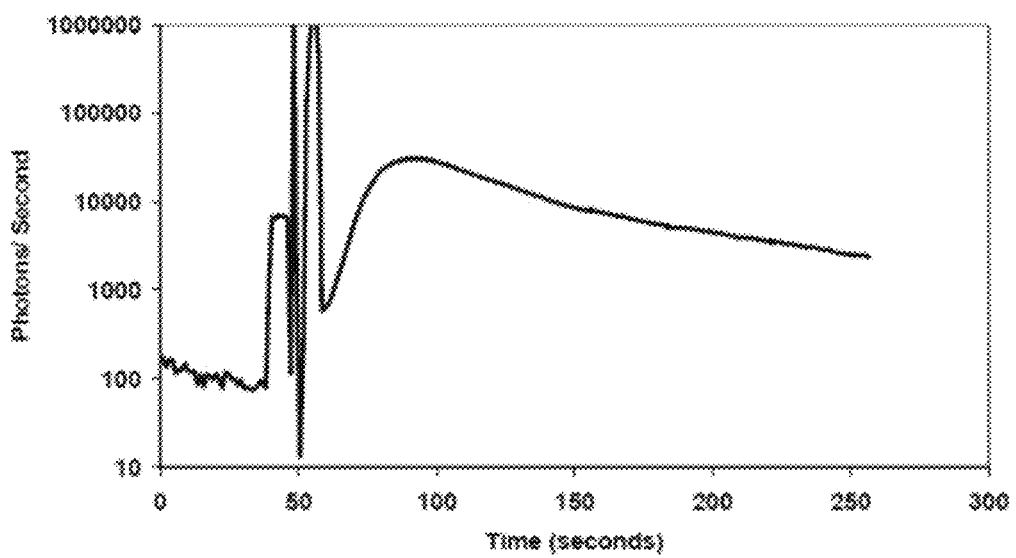

FIG. 137 is a graph. PANTHER Disk *Bacillus Subtilis* Spore Impaction Results. *Bacillus subtilis* particles (200 agent containing particles per liter of air, or ACPLA) were impacted into a test disk for one minute, using an aerosol chamber and Collison nebulizer. The subsequent test channels were subjected to B cells both specific (graph) and non-reactive (*Yersinia pestis* cell line) for *Bacillus subtilis*. No signal was seen for the non-reactive (*Yersinia pestis*) line.

Figure 138:
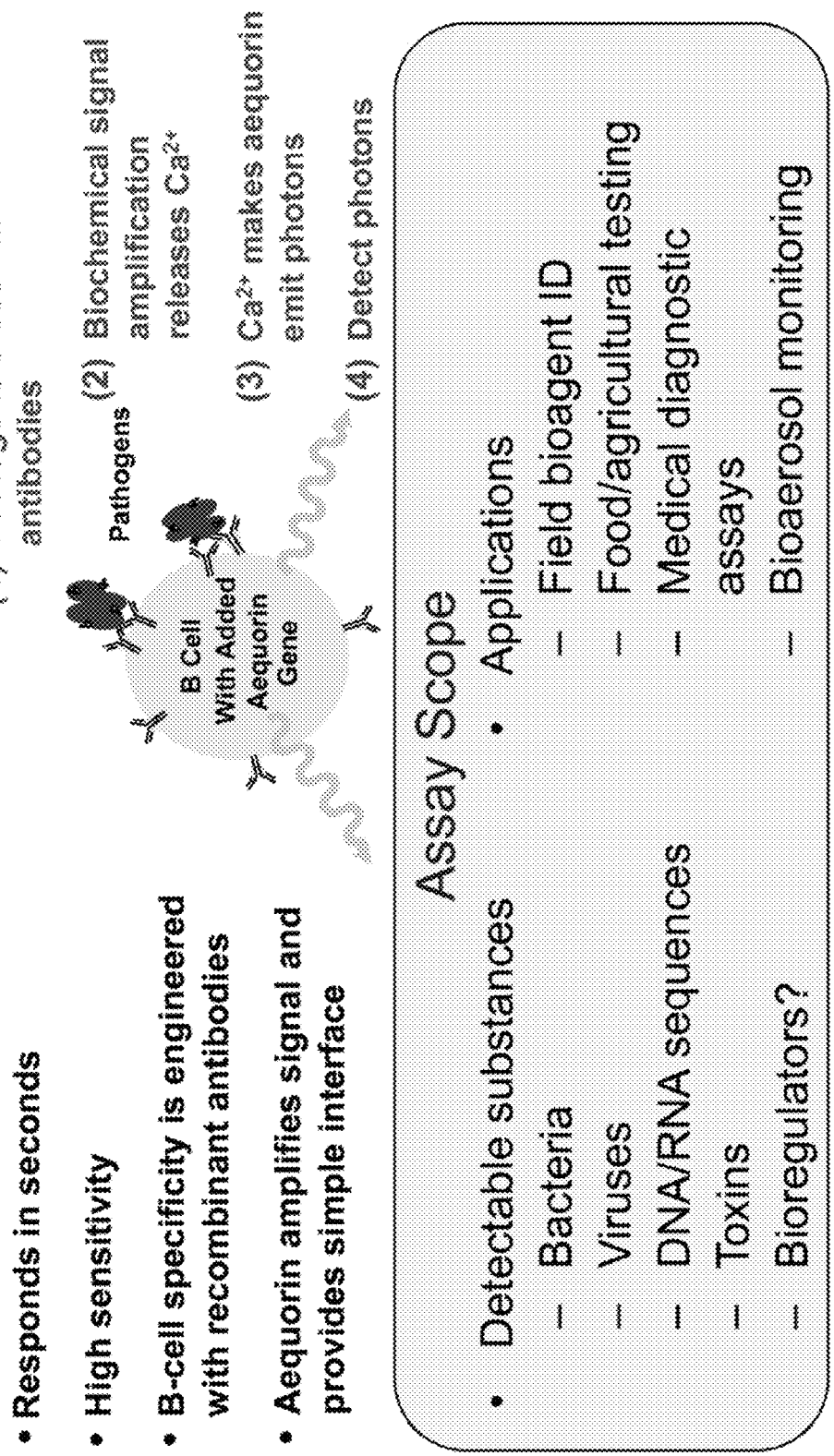

FIG. 138 is a summary of the CANARY technology.

FIG. 139 is a summary of pathogen-detecting cell lines.

FIG. 140 is a summary of universal CANARY cells for detecting emerging diseases.

FIG. 141 is a schematic of a CANARY assay for liquid and dry samples.

FIG. 142 is an example of a CANARY assay of a liquid sample.

Figure 143:
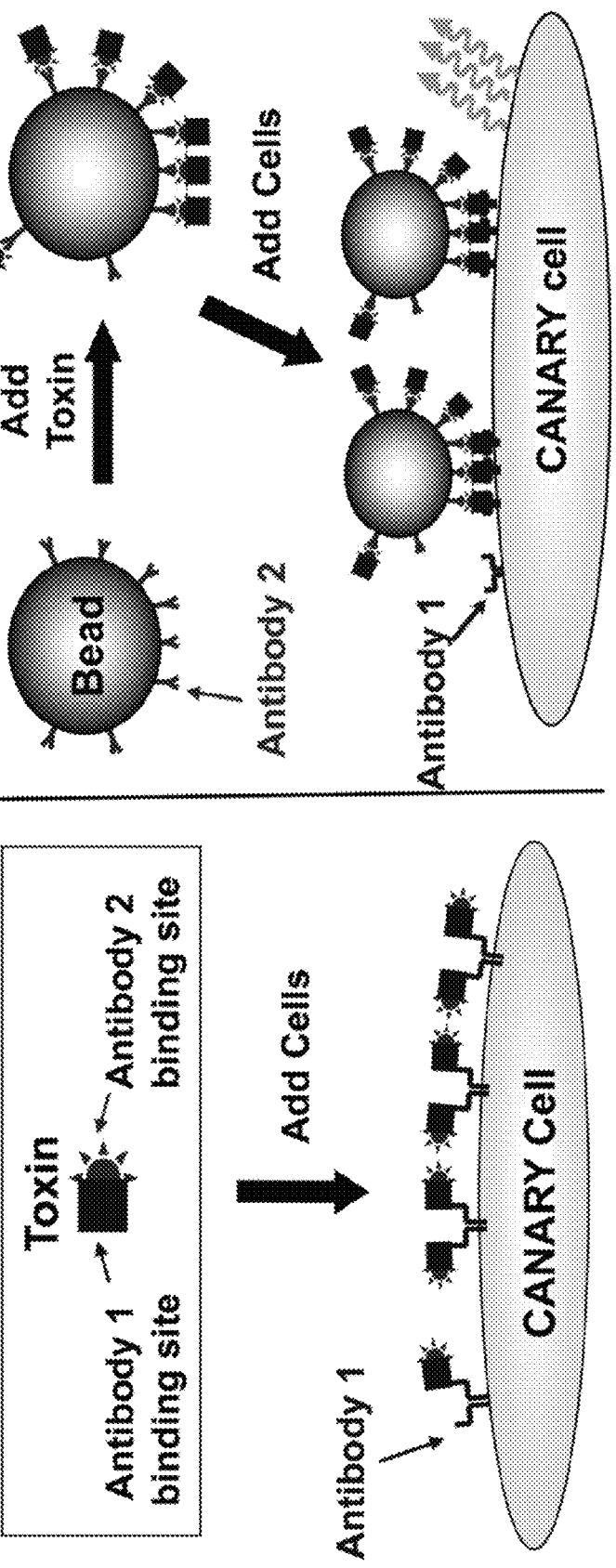

FIG. 143 is a schematic of toxin detection using the CANARY technology described herein.

FIG. 144 is an example of CANARY detection of Botulinum toxin using bead capture as described herein.

Figure 145:
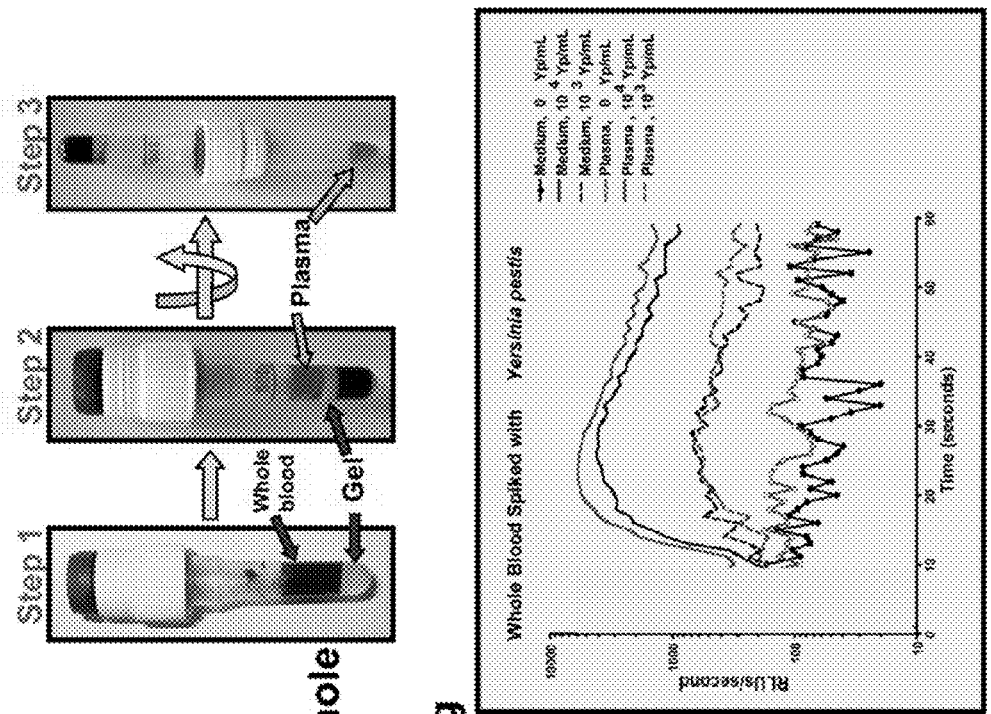

FIG. 145 is a summary of a CANARY assay for blood-borne pathogens.

Figure 146:
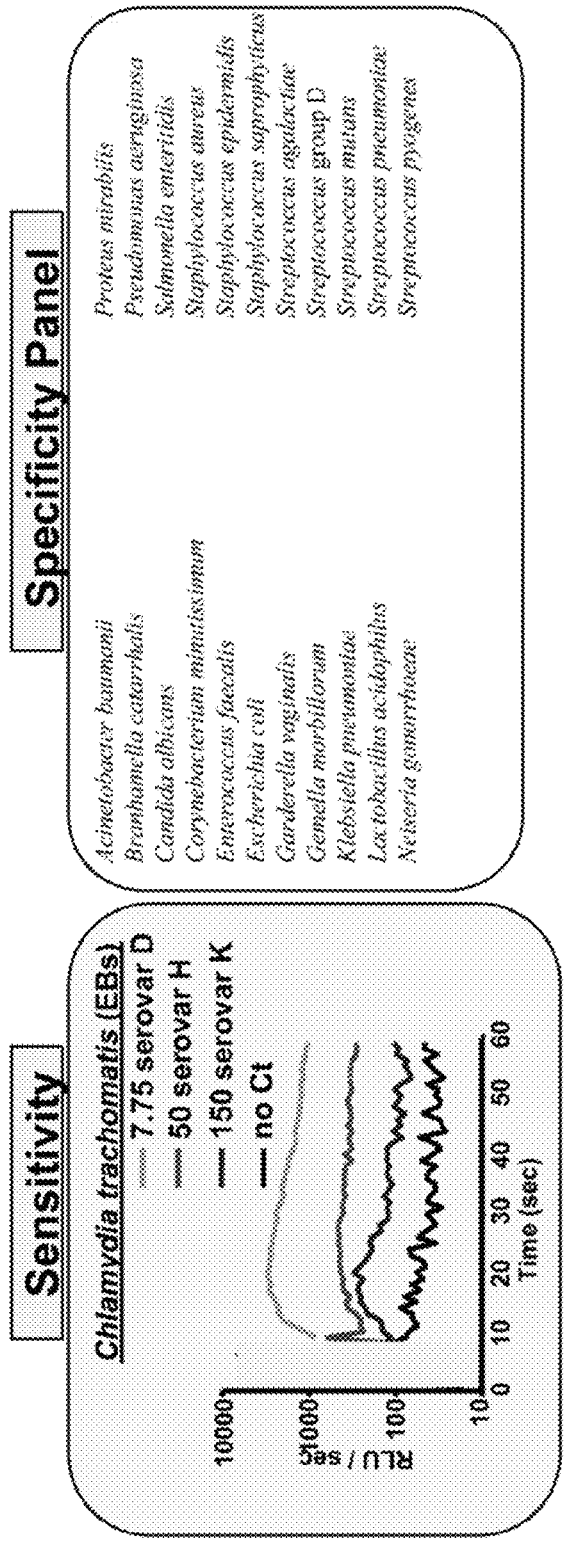

FIG. 146 is a summary of a *Chlamydia* study using CANARY technology.

Figure 147:
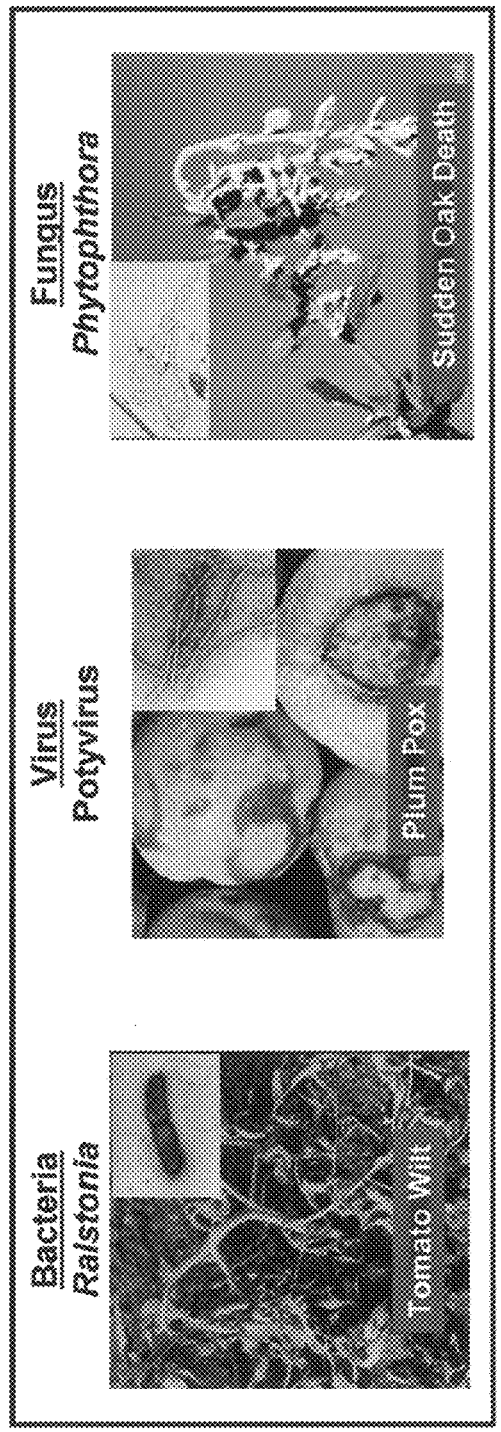

FIG. 147 is a summary of CANARY technology applied to agricultural pathogens.

Figure 148:
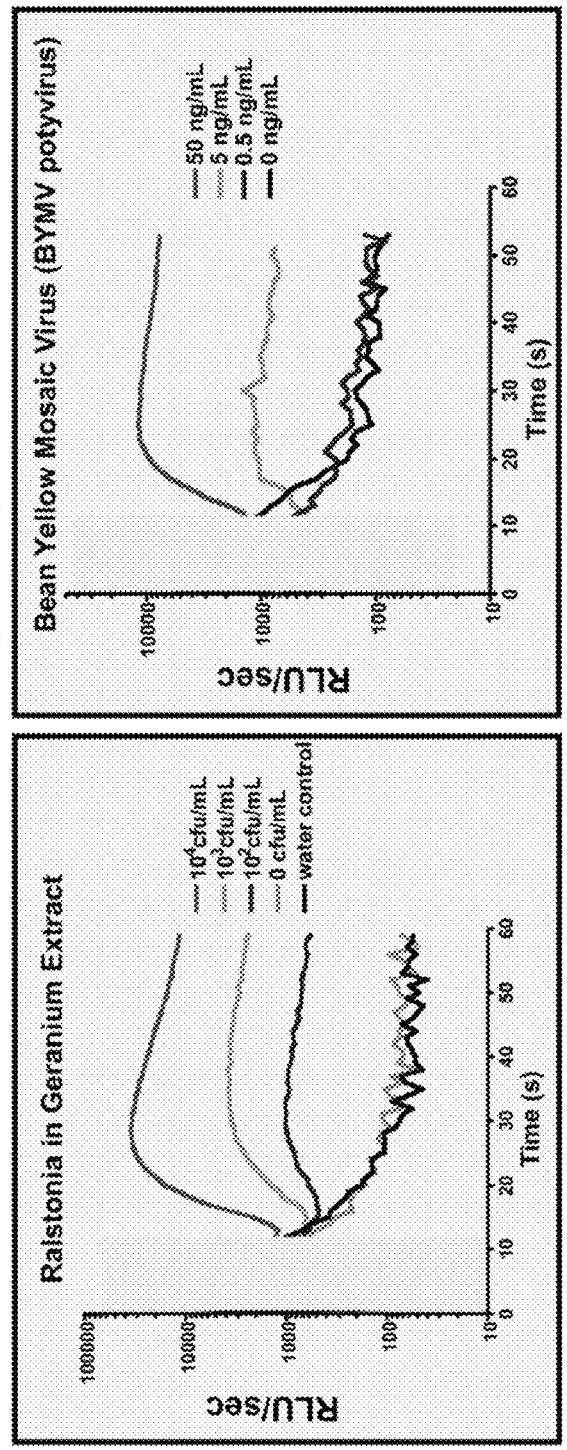

FIG. 148 is an example of CANARY detection of plant pathogens.

FIG. 149 is a pair of photographs of a portable 16-channel CANARY sensor.

Figure 150:
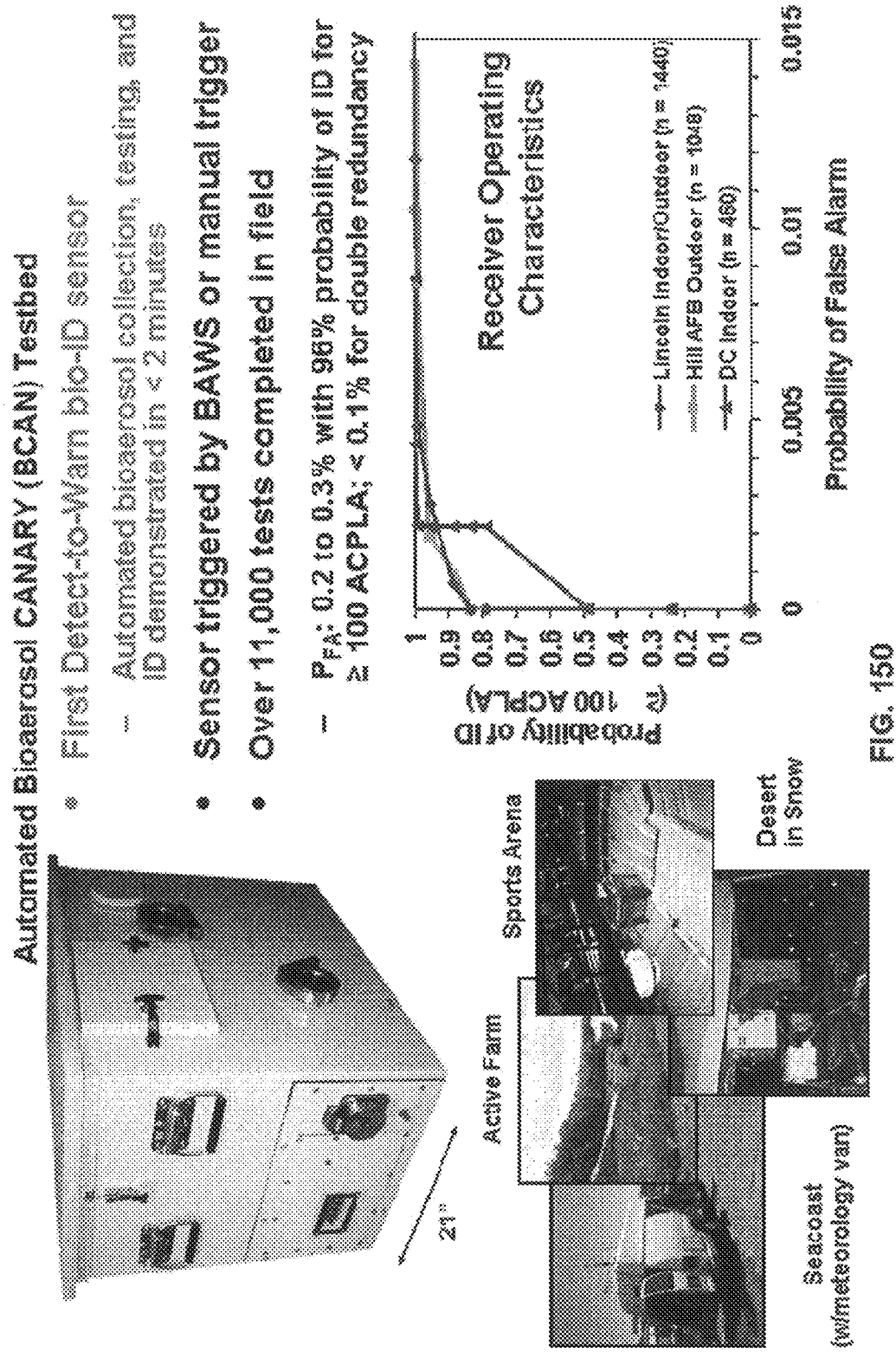

FIG. 150 is an illustration of an automated Bioaerosol CANARY (BCAN) testbed.

FIG. 151 is an illustration of pathogen analyzer for threatening environmental releases (PANTHER).

Figure 152:
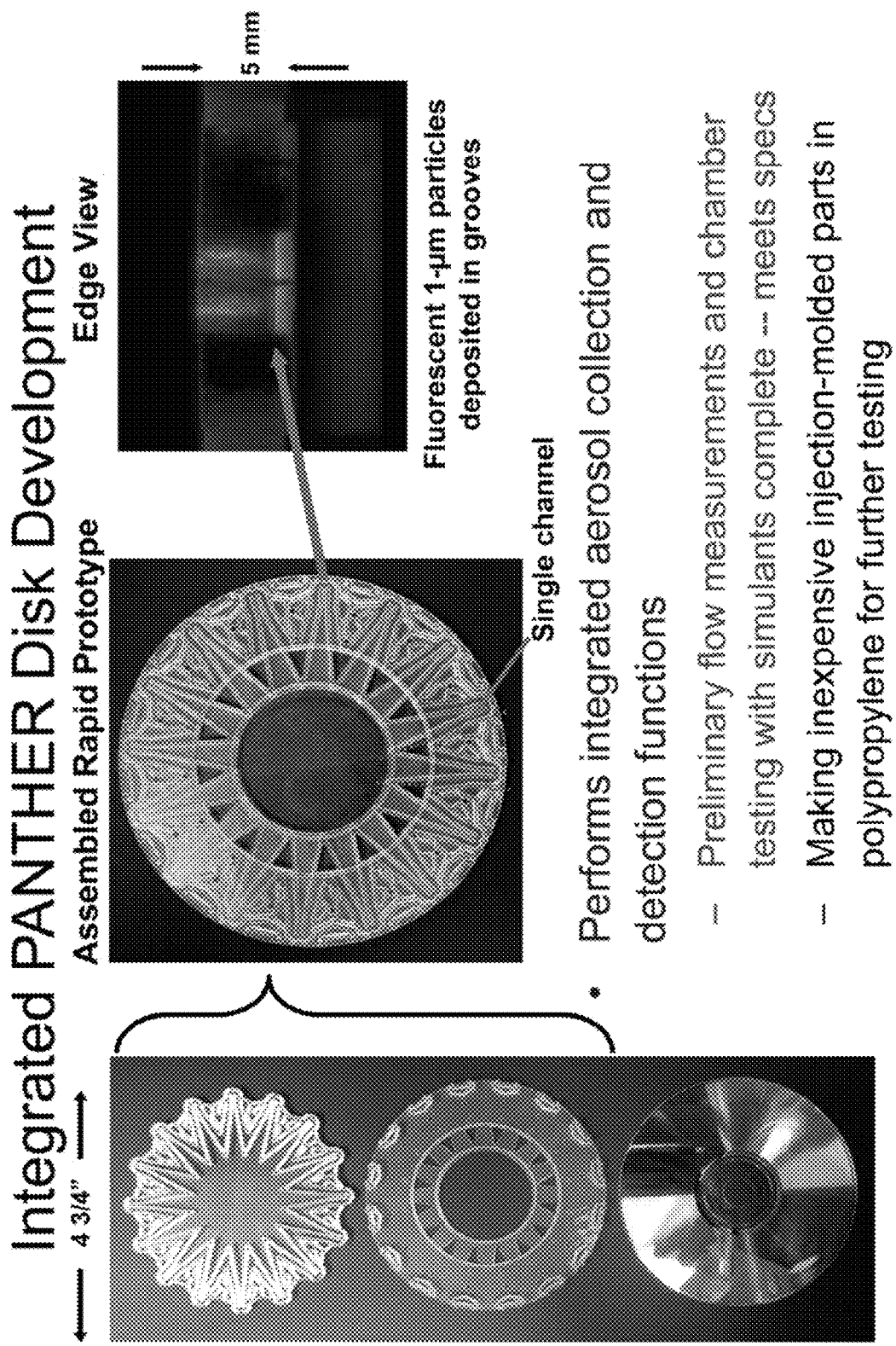

FIG. 152 is an illustration of an integrated PANTHER disk development.

FIG. 153 is a summary of CANARY technology.

Figure 154:
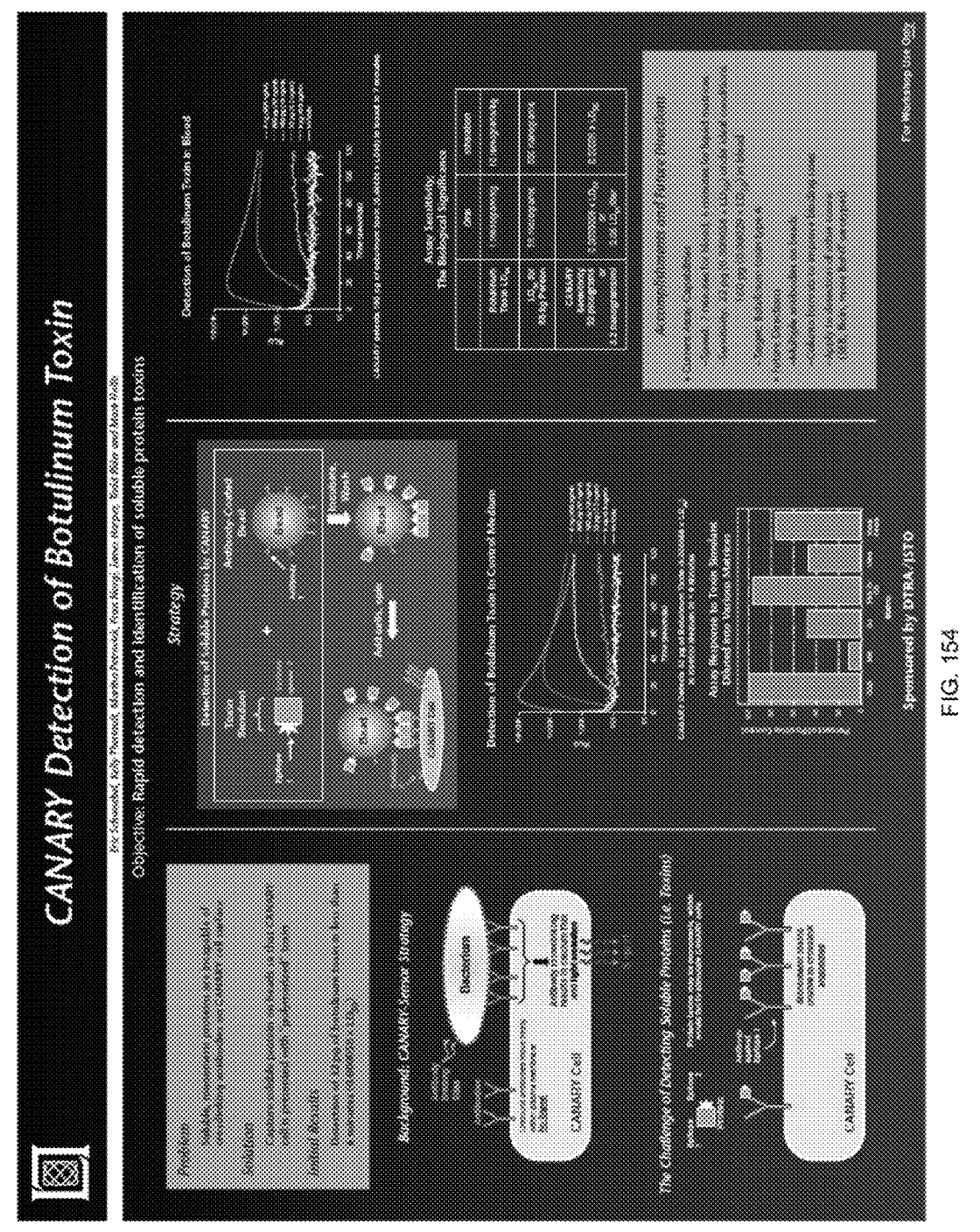

FIG. 154 is a summary of CANARY detection of Botulinum toxin.

Figure 155:
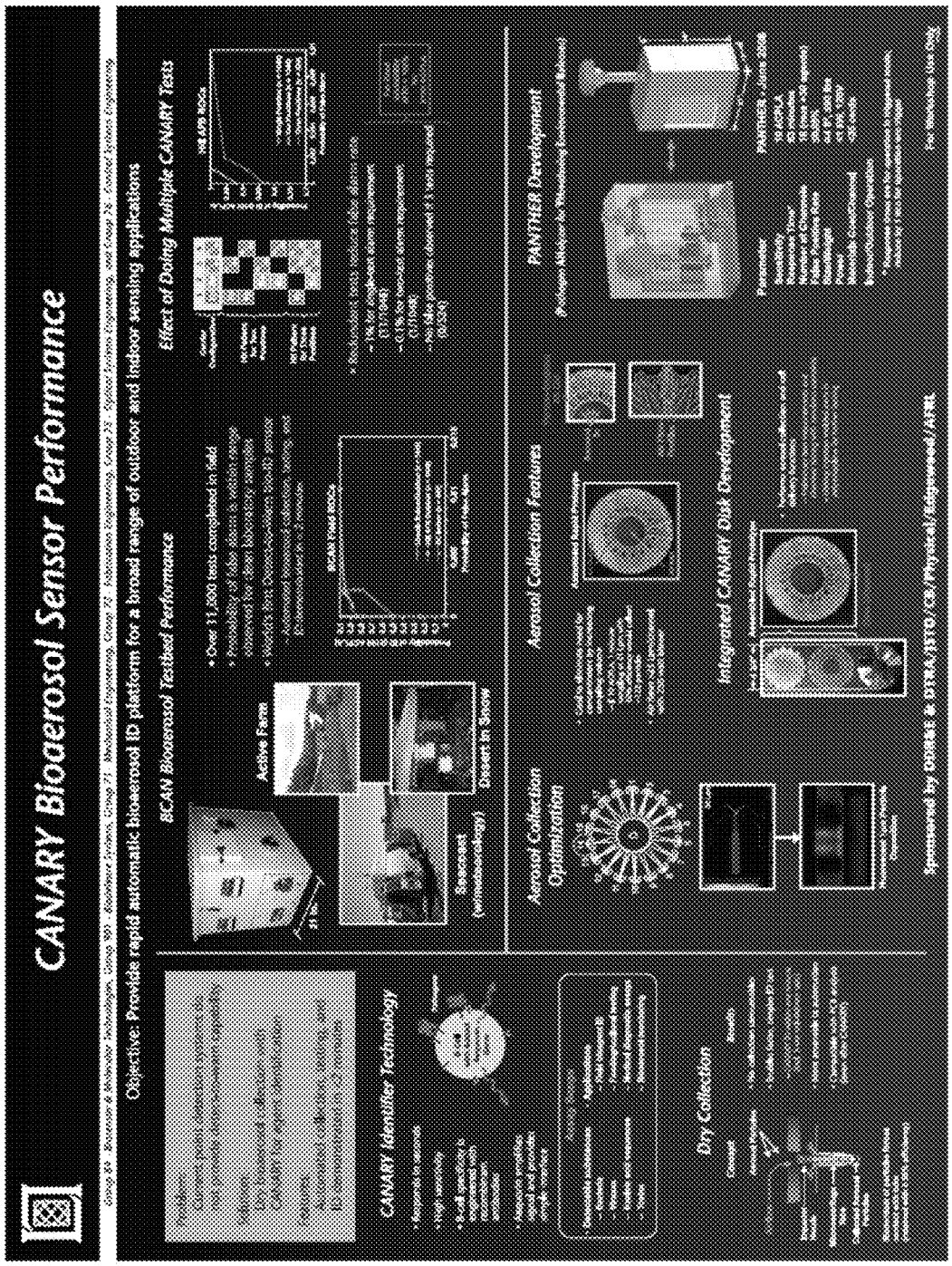

FIG. 155 is a summary of CANARY bioaerosol sensor performance.

FIG. 156 is a summary of virus extraction from plant tissue.

FIGS. 157A and B illustrate plant virus detection using CANARY. FIG. 157A illustrates the sample preparation. FIG. 157B graphs the results.

FIG. 158 are graphs of the results of detection of BoNT/A in urine. No sample preparation was required for detection of BoNT/A in urine samples. Beads conjugated to 6E10-10 antibody were added directly to urine spiked with active BoNT/A, incubated for 15 minutes, and the beads washed. Media was added to the beads, followed by CANARY cells, and the sample spun for 5 seconds. The limit of detection was 16 ng/ml, about 5 fold higher than BoNT/A diluted directly into assay medium. Control urine (0 ng/ml), which was not spiked with BoNT/A Hc prior to bead addition, gives no signal, indicating that any nonspecific stimulators have been removed.

FIG. 159 are graphs of the results of detection of BoNT/A Hc in blood. CANARY is capable of detecting soluble BoNT/A Hc in blood products. BoNT/A was spiked into whole blood and the plasma prepared as described elsewhere (see Fran's section on blood sample prep). 6E10-10 antibody coated Protein G beads were added to plasma, incubated 2 minutes, washed into media and assayed using 6B2-2 cells. The limit of detection for BoNT/A in this assay was 16 ng/ml.

Figure 160:
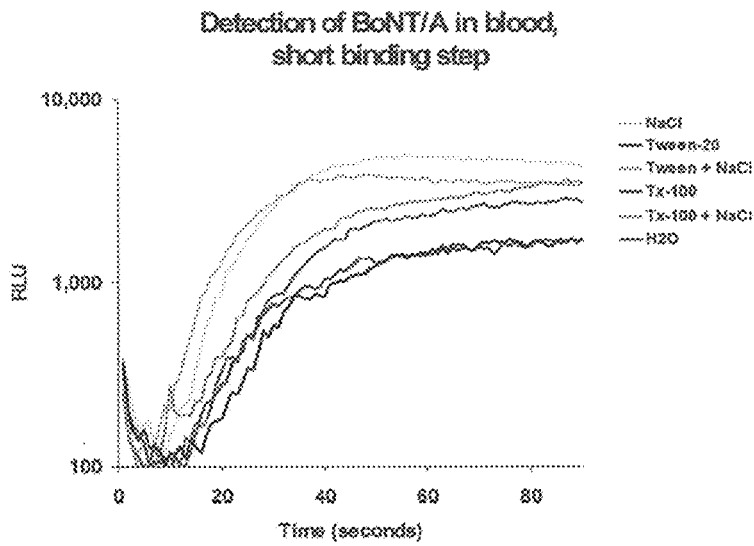

FIG. 160 are graphs of the results of the effects of adding NaCl, Tween-20, and Triton X-100 to plasma. Addition of NaCl (final concentration of 0.5M) produced the most dramatic improvement in signal amplitude, from 1700 RLU to 4800 RLU. Addition of Tween was ineffective, but addition of Triton improved the signal marginally to 2700 RLU. Combining salt with the detergent improved the signal compared to detergent alone, but not to levels above that achieved with salt alone.

Figure 161:
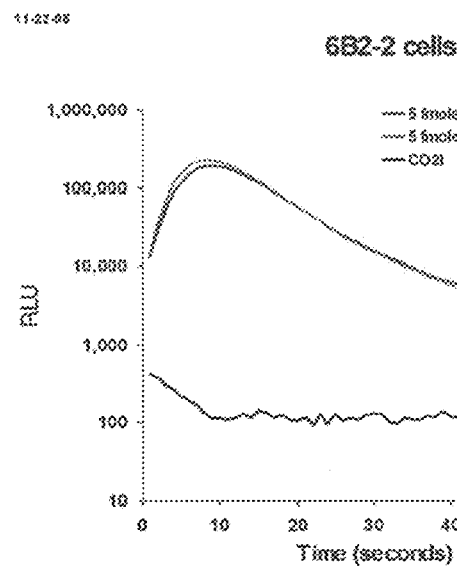

FIG. 161 are graphs of the results of BoNT/A (5 fmoles=800 pg) of and BoNT/A Complex (5 fmoles=5 ng) incubated for 20 minutes with 6E10-10 antibody bound to streptavidin beads. 6B2-2 cells were added and light output monitored. Similar responses by the CANARY assay to equimolar amounts of both preparations indicates that the complex proteins do not affect antibody binding to BoNT/A.

Figure 162:
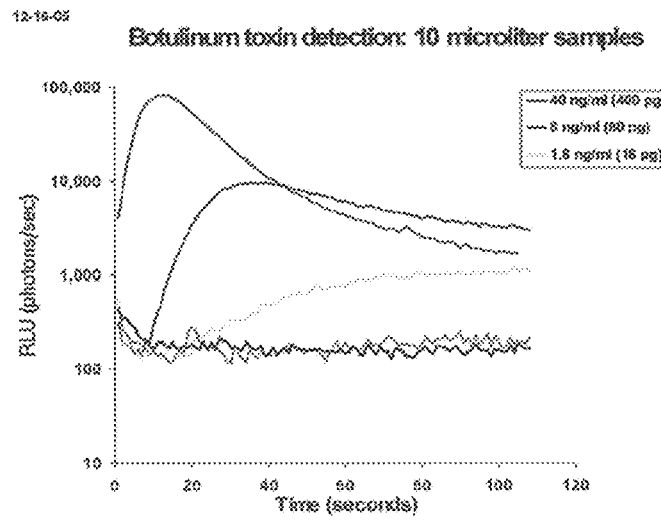

FIG. 162 are graphs of the results of the detection of BoNT/A in control medium. Magnetic beads coated with 6E10-10 antibody were added to media spiked with the indicated concentrations of BoNT/A. The sample was rotated for 2 minutes to allow toxin binding to the beads. 6B2-2 CANARY cells were added, the mixture spun for 5 seconds and light emission monitored. Samples containing 160 pg of BoNT/A Hc (16 ng/ml) produced signals 6 fold over background.

Figures 163, 164, 165:
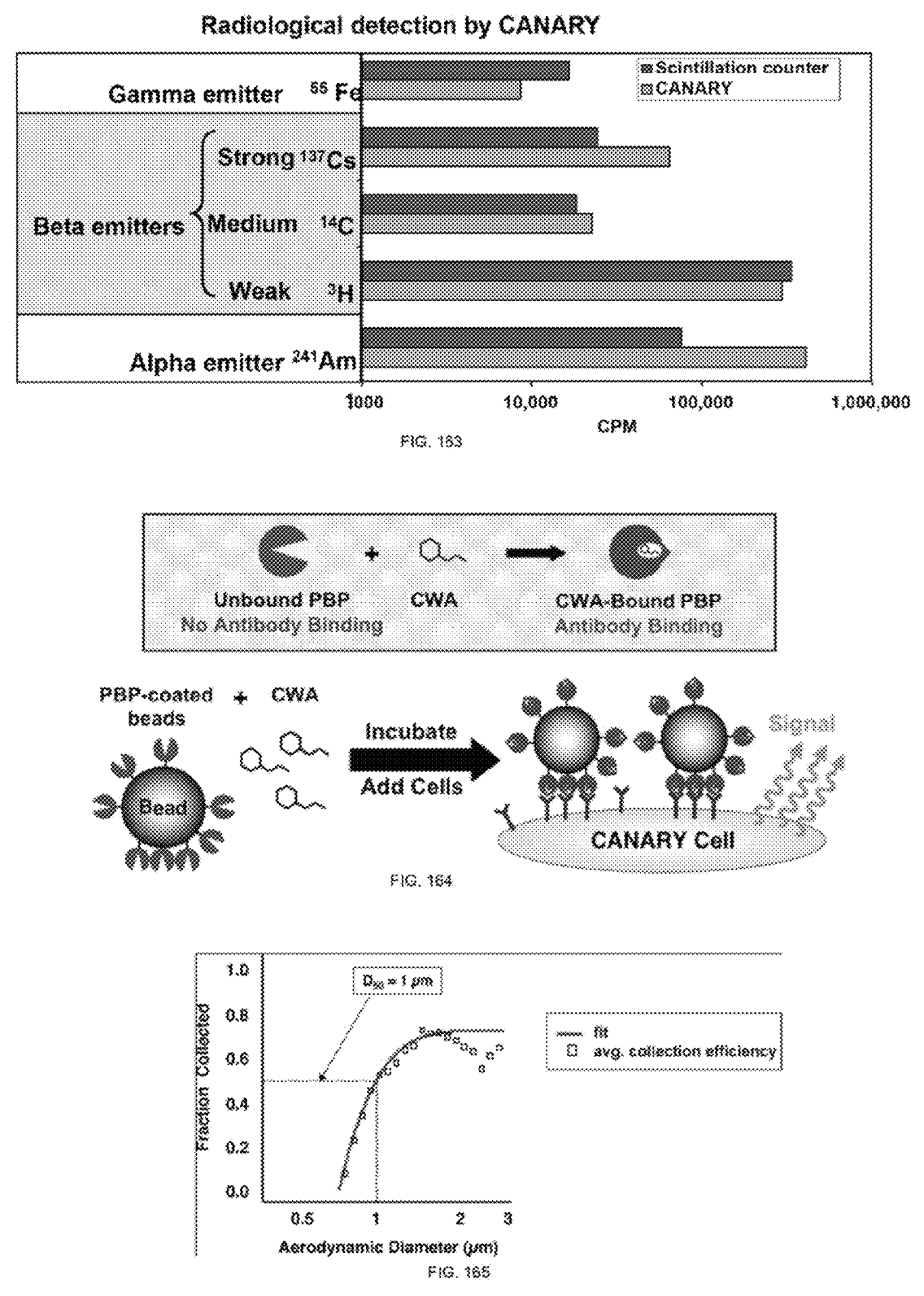

FIG. 163 is a bar chart. Equal amounts of various radiological materials covering all three emitter types (alpha, beta, and gamma) were analyzed. The response of CANARY compares favorably to a commercial, laboratory-based instrument.

FIG. 164 is a schematic of chemical detection by CANARY cells. Conceptually, detection of chemicals, such as biowarfare agents, by CANARY is very similar to detection of protein toxins. Periplasmic binding proteins (PBPs) are attached to the surface of a bead. The presence of the target chemical converts the PBP into a form that is recognized by antibodies on the surface of the CANARY cell, thereby stimulating light emission.

FIG. 165 is a graph. The data points represent the average efficiency measured from 6 impaction runs with polydisperse polystyrene-latex spheres aerosolized with the Pitt generator. A single APS particle sizer was switched between the inlet and the outlet of the impactor. The solid red line is an exponential fit to the averaged data between 0.7 and 1.5 µm. Above 2 µm, the calculated efficiency numbers become less reliable due to the lower aerosolization efficiency (and therefore low particle counts) for these larger particles in the Pitt generator.

Figures 166A, 166B, 167:
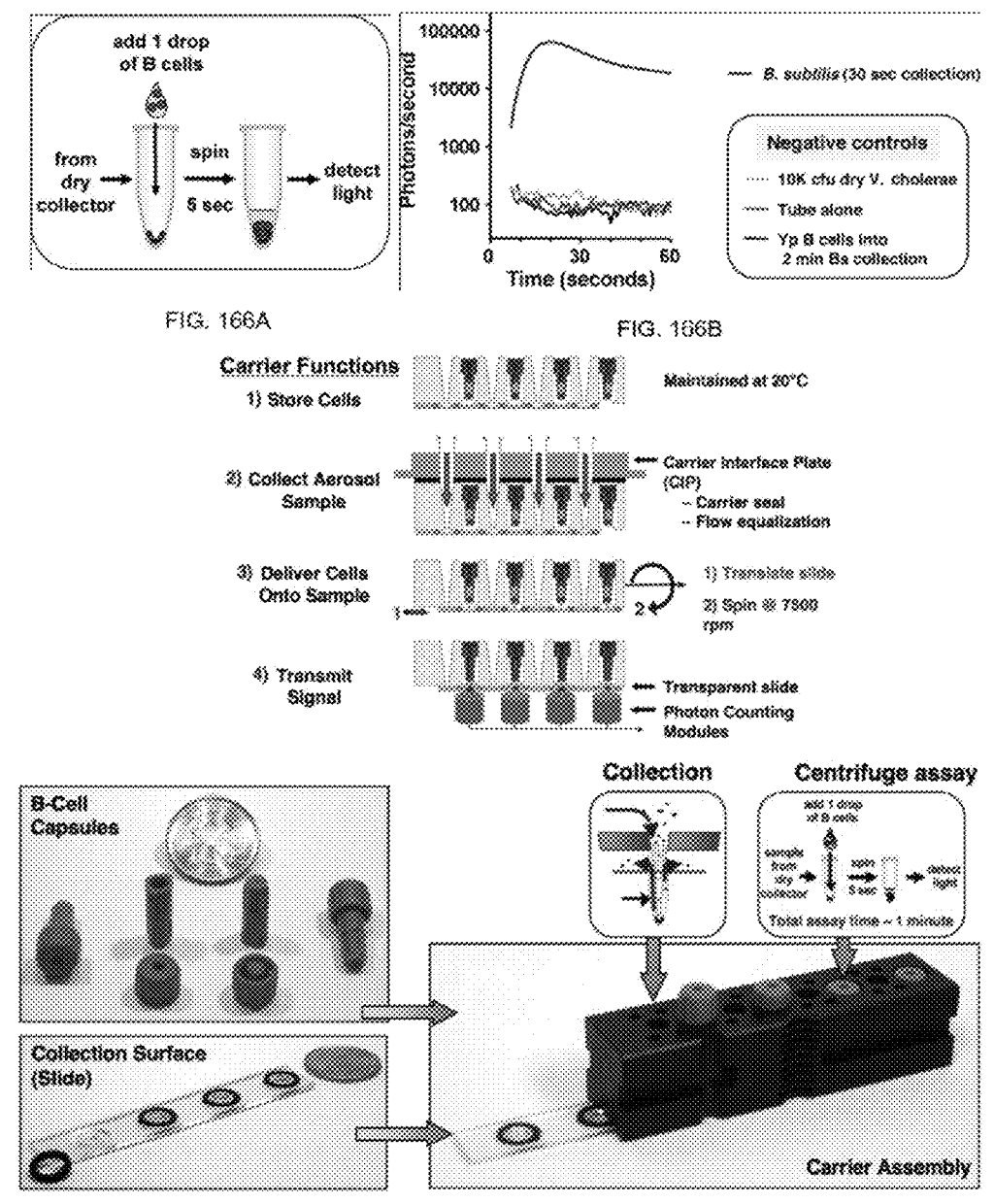

FIGS. 166A and B illustrate the method and results of dry identification of Bacillus subtilis spores. As shown in the schematic of the dry assay protocol (FIG. 166A), B Cells specific for B. subtilis are added and a brief centrifugal spin drives the cells to the collection site at the bottom of the sample tube. Specificity demonstrations in the dry assay format (FIG. 166B): Blue curve: B. subtilis impacted onto sample tubes and detected with cells against B. subtilis demonstrate the ability of CANARY to detect impacted samples. Negative Controls: baseline responses were observed for exposure of B. subtilis cells to dried V. cholerae (Gray curve), air contaminants impacted in an empty tube in the absence of pathogen (Red curve), and when cells against Yersinia pestis were exposed to dry-impacted B. subtilis spores (Black curve).

FIG. 167 illustrates BCAN carrier for automated bioaerosol collection and CANARY analysis.

FIG. 168 illustrates a CANARY Disc (CD) designed to integrate aerosol collection and B-cell delivery.

FIG. 169 illustrates the aerosol collection module cutaway with impaction nozzle and transparent tube.

FIG. 170 illustrates a CANARY B-cell delivery module with valve delivery system.

FIG. 171 illustrates a TCAN-2 automated biosensor with light-tight cover removed.

FIG. 172 illustrates one embodiment of the invention. The PANTHER disk (left) is a self-contained bioaerosol sampling and CANARY analysis tool that can be loaded like a CD into the portable PANTHER CUB sensor (center) or ultimately into a high-throughput automated point detection and identification sensor (right).

Figure 173A:
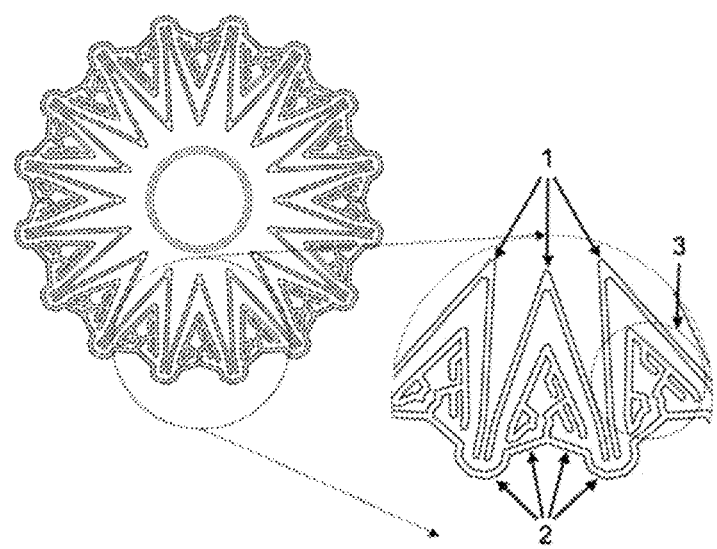

FIGS. 173A and B are schematic diagrams of an embodiment of the invention as described herein.

Figure 174:
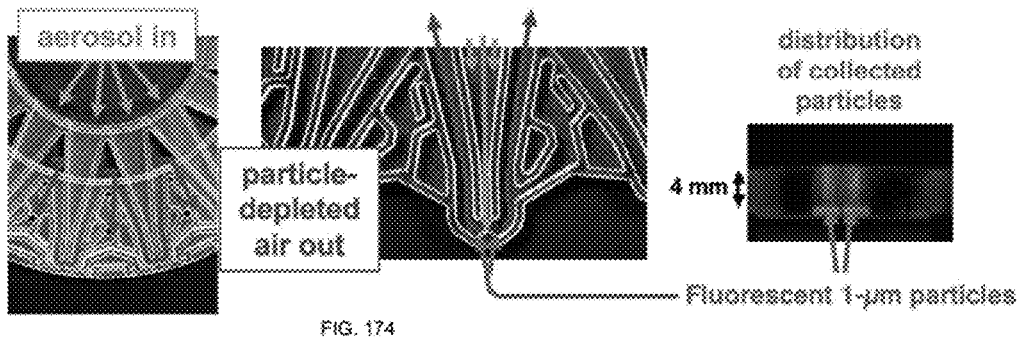

FIG. 174 is a further schematic of an embodiment of the invention.

Figure 175:
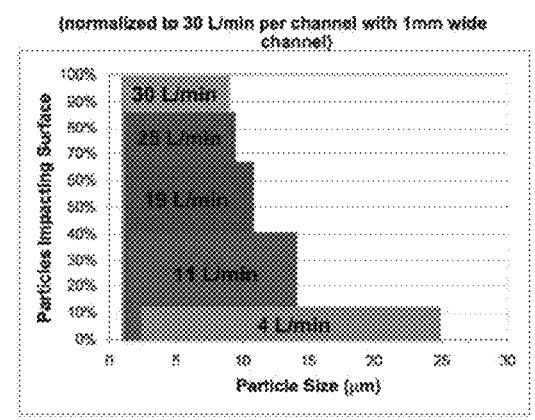

FIG. 175 is a bar chart illustrating the relationship between the flow rate and the size of particles that are effectively transported through the disk and directed to impact onto the collection surface of the device described herein.

Figure 176:
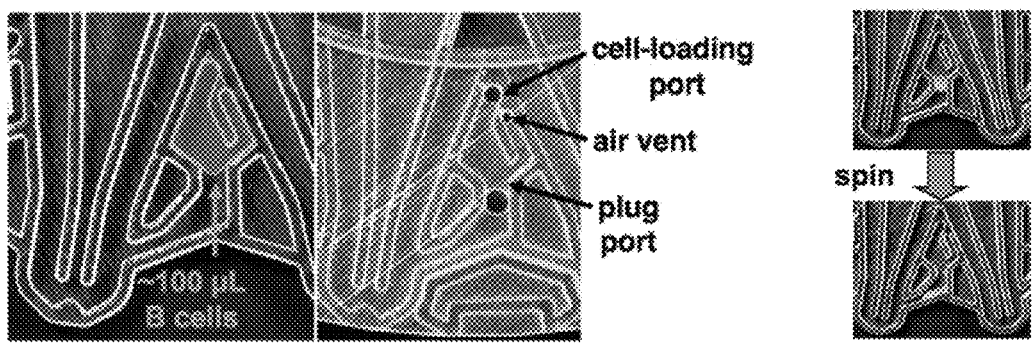

FIG. 176 illustrates an embodiment of the invention.

Figure 177:
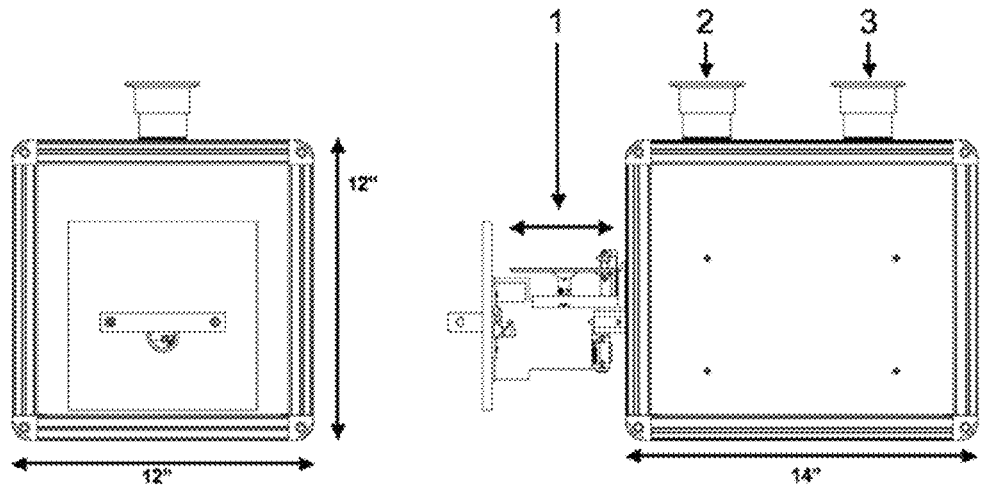

FIG. 177 illustrates a compact sensor equipment that automatically process the illustrated CANARY disks.

Figure 178:
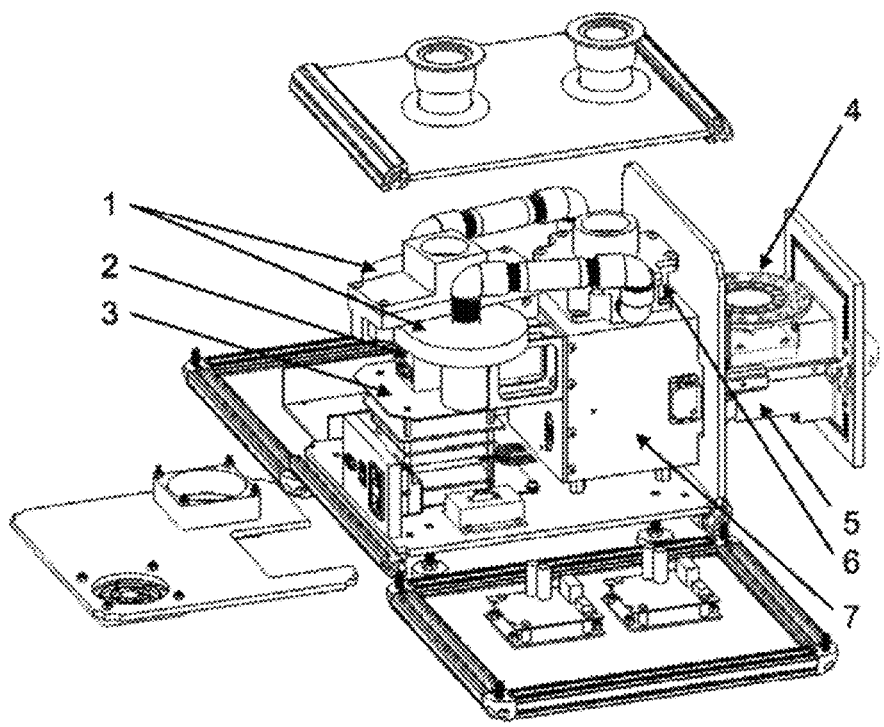

FIG. 178 illustrates the core components of a CANARY device described herein.

Figures 179, 180:
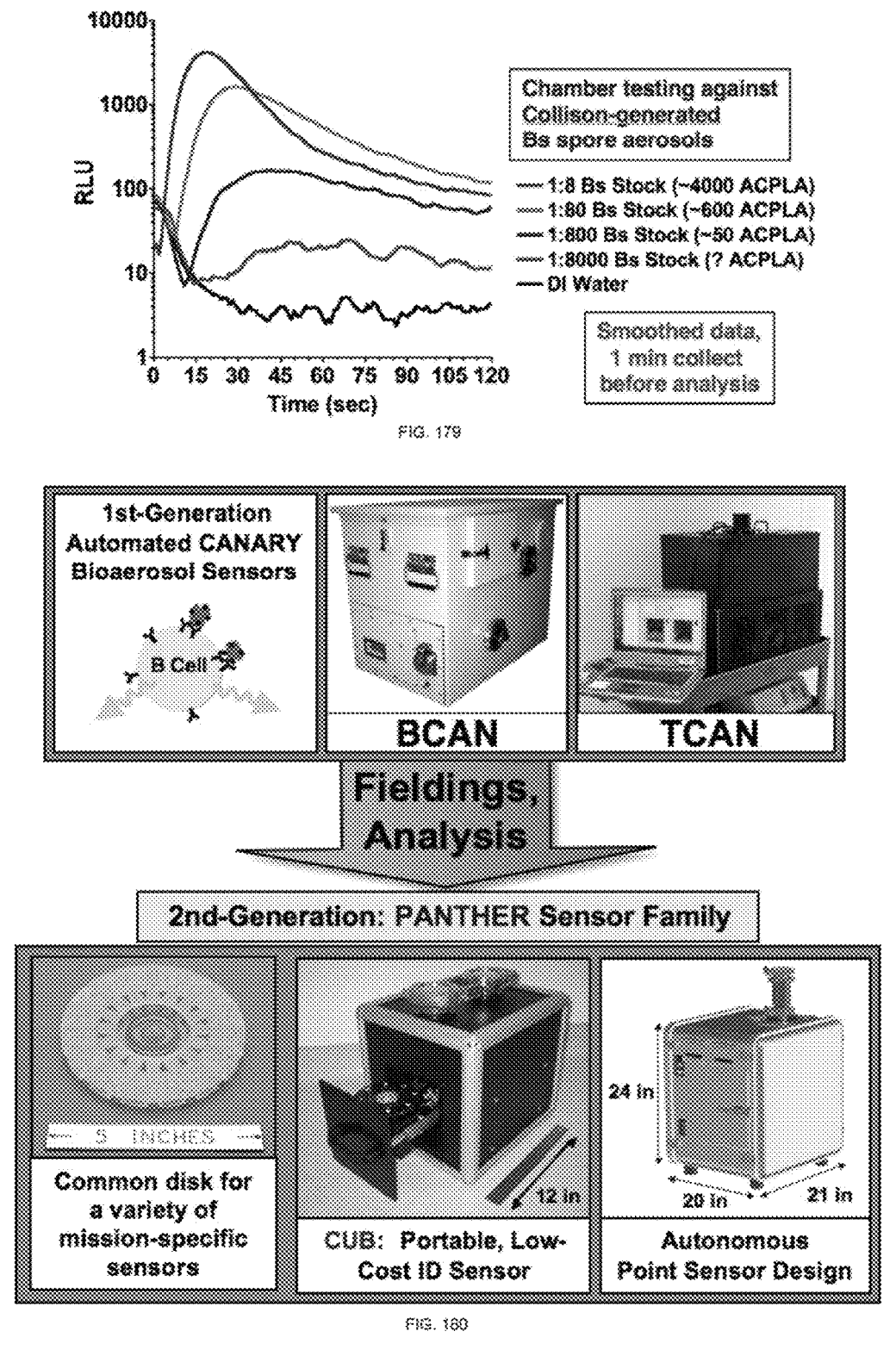

FIG. 179 is a graph of the performance characteristics of the CUB sensor. Typical signals from CUB analysis of Bacillus subtilis spore aerosols.

FIG. 180 illustrate different embodiments of the invention.

FIG. 181 is a schematic illustration of positive and negative dielectrophoresis concepts.

FIG. 182 Fabrication process for DEP test chips.

FIGS. 183A and B illustrate (a) the basic design of DEP chip, consisting of interdigitated tungsten thin film electrodes on a quartz substrate. (b) a table of combinations of linewidths and spacings.

Figure 184:
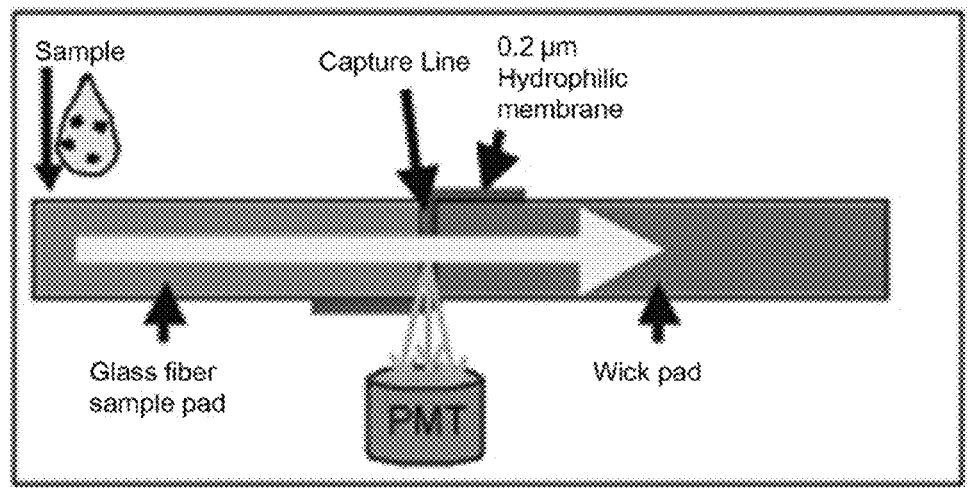

FIG. 184 is a schematic of the principle of sample capture in a lateral-flow format. Sample is added to the sample pad (~200 µl), which in turn saturates the pad and flows toward the capture membrane (0.2-µm membrane). The B cells (50 µl) are then added to the sample pad and slowly wick toward the capture membrane where they encounter captured antigen and emit photons.

Figure 185:
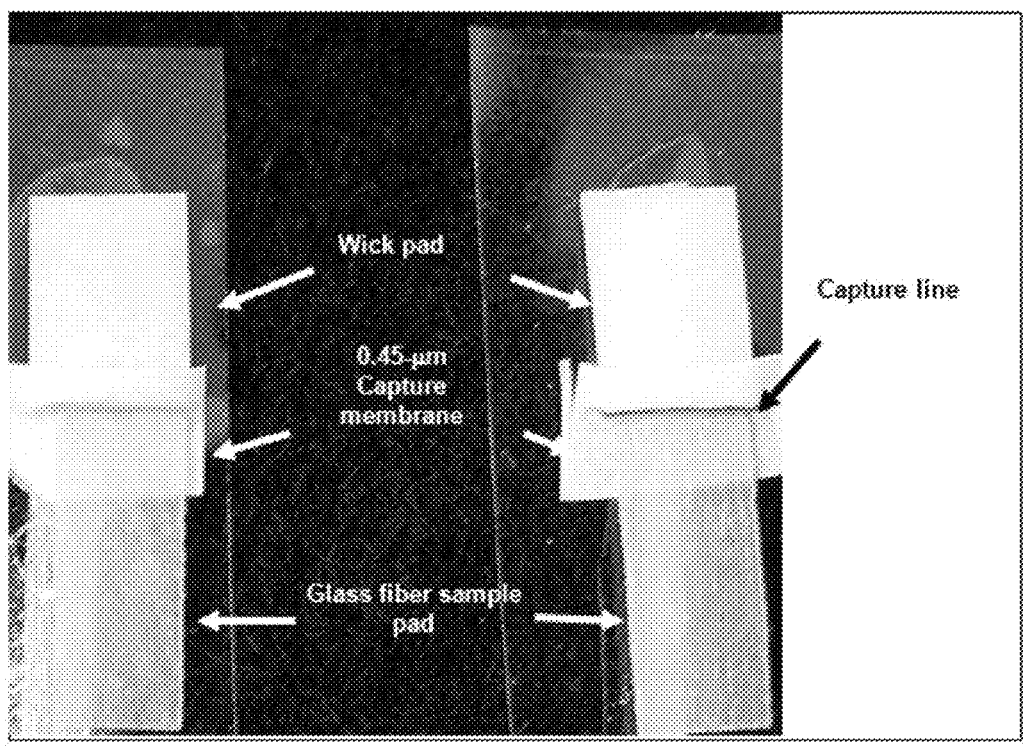

FIG. 185 is a photograph of a handheld lateral-flow assay format. A sample of colored beads (1-µm diameter) were placed onto the sample pad and allowed to wick up to the capture membrane to demonstrate agent capture zone. Overall size is 1 inch×0.25 inches.

FIGS. 186A-D are graphs of lateral-flow assay results: FIG. 186A: *E. coli* in a standard CANARY assay, FIG. 186B: *E. coli* lateral-flow assay showing an LOD of 5000 particles per 200-ml sample, FIG. 186C: *B. anthracis* in a standard CANARY assay, and FIG. 186D: *B. anthracis* in a lateral-flow assay showing an LOD of 5000 particles per 200-ml sample.

Figure 187A:
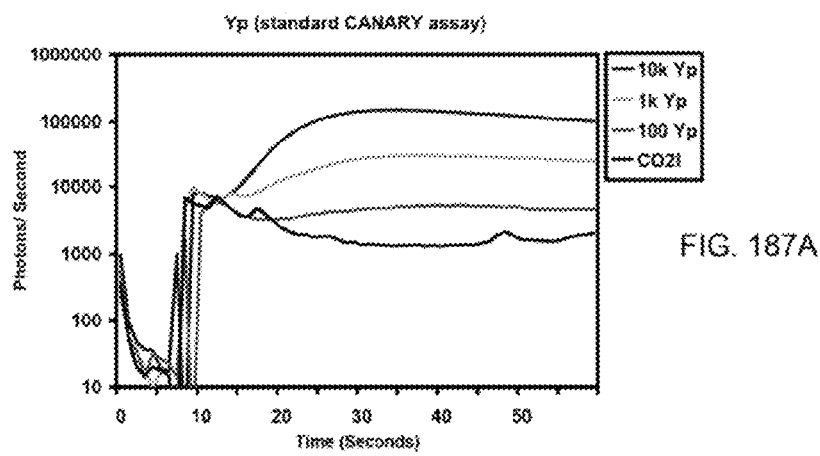

FIGS. 187A and B are graphs of a cComparison between the standard, centrifugal CANARY assay and the dual-magnetic-bead assay. (a) *Y. pestis* in a standard CANARY assay and (b) *Y. pestis* in a dual-magnetic-bead assay. Magnetic beads specific for *Y. pestis* were mixed with a dilution series of *Y. pestis* agent for 5 min. After 5 min the magnetic beads were pulled to the bottom of the assay tube along with any bound *Y. pestis*, and the supernatant was removed. Magnetically labeled B cells were then added to the sample and pulled down to the bottom of the tube.

Figure 188:
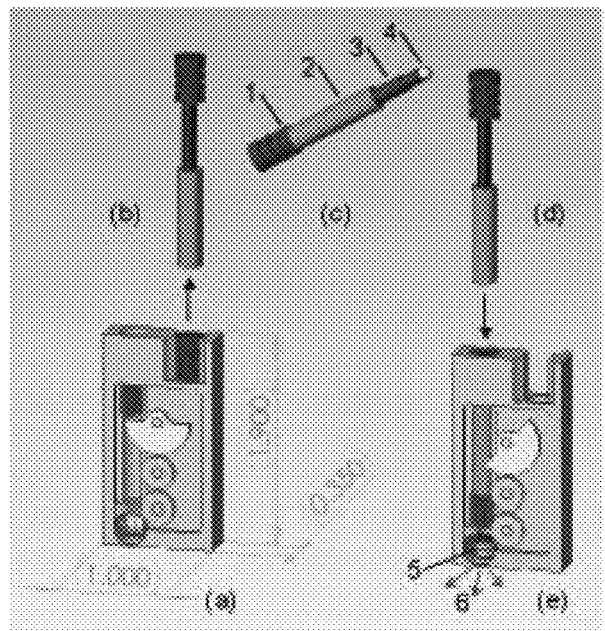

FIG. 188 is a schematic of a handheld sensor cartridge. (a) Cartridge with magnetic swab in stored position. (b) Swab withdrawn from cartridge. (c) Swab ready for use, with: 1—grip, 2—protective sleeve (withdrawn), 3—shaft, 4—magnetic tip. (d) Swab ready for insertion to read position. (e) Cartridge with swab in read position: 5—B-cell capsule rotated into place to receive the magnetic tip, 6—photon emission through hole in bottom of cartridge.

Figure 189:
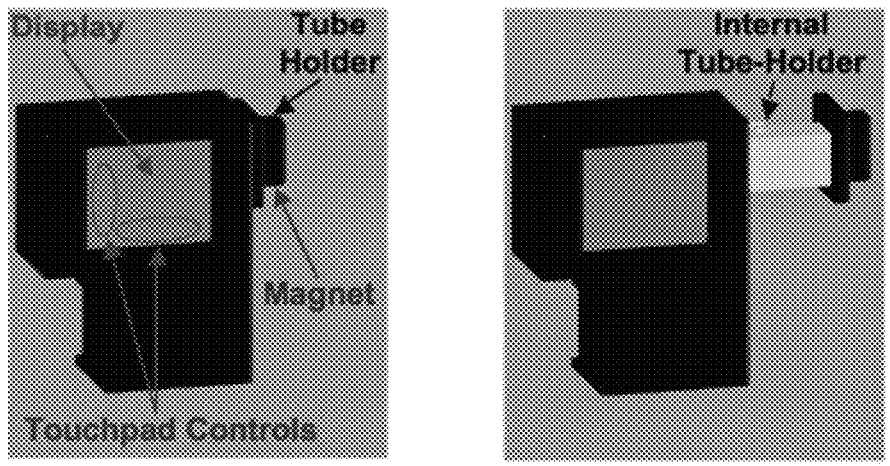

FIG. 189 is a pair of schematics of a handheld CANARY sensor design. This design reorients the PMT so that it is directed directly at the bottom of the assay tube where the CANARY cells collect for maximum signal collection. The sample-insertion mechanism was designed to operate via a sliding mechanism that allowed easy operation, minimum distance between the sample and the PMT, and shielding of the PMT from ambient light during the sample load step to minimize instrument noise during readout. The handle of the door was designed to incorporate a strong rare earth magnet for sample manipulation, and a tube receiver to hold the tube in position near the magnet while these manipulations are performed.

Figure 190:
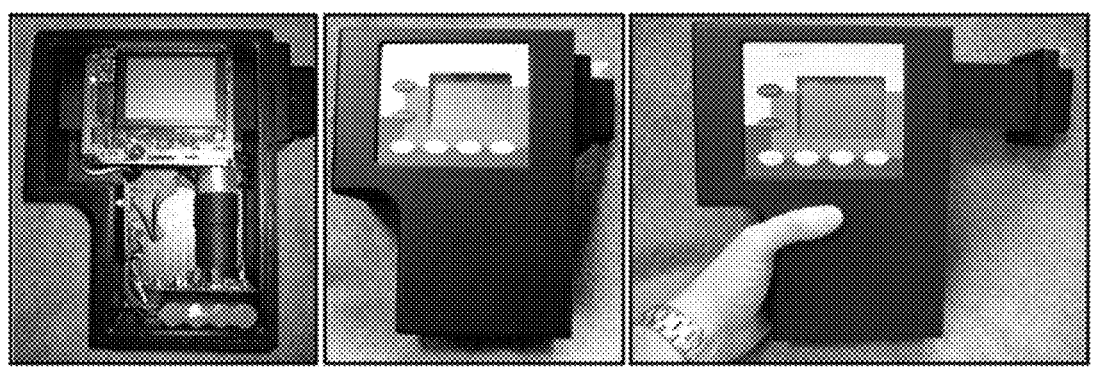

FIG. 190 is a series of photographs of a handheld CANARY sensor prototype. The PMT has a bialkali cathode with an effective spectral sensitivity range of 300-650 nm. It is operated in photon-counting mode and the signals are recorded and can be transferred to a laptop via a RS-232, 9-pin plug for further analysis. The handheld unit has the option of running for up to 8 h using rechargeable NiCd batteries built into the sensor or running indefinitely when attached to a 12-V power supply (also used for recharging the internal battery pack

DETAILED DESCRIPTION OF THE INVENTION

The invention described herein provides methods for detecting soluble antigens. For example, the soluble antigen can be a soluble protein or a chemical. In one embodiment, the soluble antigens comprise only one or two antigenic epitopes. Detection of soluble antigens using an antibody expressed on the surface of a cell, whereby binding of the antibody to the antigen triggers an increase in calcium concentration which in turn stimulates an emittor molecule to emit a photon in response to the increase in intracellular calcium depends on the ability of the antigen to crosslink (or aggregate, thereby immobilizing the antibody on the cell surface) the antibodies on the cell surface, thereby stimulating an increase in intracellular calcium. A soluble antigen can be inefficient at crosslinking antibodies expressed on the surface of a cell, and therefore is inefficient at stimulating an increase in intracellular calcium. Described herein are methods for detecting a soluble antigen wherein crosslinking of antibodies is achieved by the methods described, which stimulate an increase in intracellular calcium and cause emission of a photon from an emittor molecule that responds to the increase in calcium concentration.

The soluble antigens and chemicals of interest to be detected include a wide variety of agents. For example, and without limitation, the methods of the invention described herein can be used to detect protein toxins such as Botulinum toxins, serotypes A, B, C, D, E, F, G, Staphylococcal enterotoxin-B (SEB) and other superantigens, ricin, pertussis toxin, Shiga toxin, conotoxins, *Clostridium perfringens* epsilon toxins, Shiga-like ribosome inactivating proteins, other soluble bacterial products, such as F1 antigen from *Y. pestis*, protective antigen, Lethal factor, edema factor from *B. anthracis*. Other molecules of interest in detecting include bacterial quorum sensing molecules, e.g., homoserine lactones. Examples of chemical warfare agents, or their breakdown products after hydrolysis that can be detected using the methods described herein include, without limitation, cyanide (Hydrocyanic acid), Phosgene (Carbonic dichloride), CK (Cyanogen chloride), CL (Chlorine), CX (Carbonimidic dichloride, hydroxy), DP (Carbonochloridic acid, trichloromethyl ester), GA, Tabun (Dimethylphosphoramidocyanidic acid, ethyl ester), GB, sarin 9Methylphosphonofluoridic acid, (1-methylethyl)ester), GD, Soman (Methylphosphonofluoridic acid, 1,2,2-trimethylpropyl ester), GF (Methylphosphonofluoridic acid, cyclohexyl ester), Mustard (1,1'-Thiobis[2-chloroethane]), HN-1, Nitrogen Mustard (2-Chloro-N-(2-chloroethyl)-N-ethylethanamine), HN-2, Nitrogen mustard (2-Chloro-N-(2-chloroethyl)-N-methylethanamine), Lewsite ((2-Chloroethenyl) arsonous dichloride), PFIB (1,1,3,3,3-pentafluoro-2-trifluoromethyl-1-propene), Triphosgene (Carbonic acid, trichloromethyl ester), V-gas (Methylphosphonothioic acid, S[2-(diethylamino)ethyl]O-2-methylpropyl ester), VX (Methylphosphonothioic acid, S-[2-[bis(1-methylethyl)amino] ethyl]O-ethyl ester), binary components of VX (O-Ethyl O-2diisopropylaminoethyl methylphosphonite and Sulfur), binary components of GD (Methylphosphonyl difluoride (DF) and a mixture of pinacolyl alcohol and an amine, binary components of GB (Methylphosphonyl difluoride (DF) and a mixture (OPA) of isopropyl alcohol and isopropyl amine. Additionally, other biologically-derived chemicals can also be detected by the methods of the present invention, including Mycotoxins, particularly trichothecene (T2) mycotoxins, Diacetoxyscirpenol Diverse group, Saxitoxin, or other dinoflagellage products, Microcystins (various types), Palytoxin, Satratoxin H, Aflatoxins, and Tetrodotoxin.

Additional proteins of interest to detect include, APP (Amyloid Precursor Protein), prion proteins associated with CJD, BSE, Scrapie, Kuru, and PSA (prostate specific antigen). Furthermore, the detection of appropriate soluble antigens or chemicals is useful in a variety of applications, such as clinical applications, for example, thyroid function, adrenal function, bone metabolism, fertility, infertility, IVF, pregnancy, growth and growth hormone deficiency, diabetes, hematology, cardiac function, cancer, allergy, autoimmune diseases, therapeutic drug monitoring, drugs of abuse, research immunoassay applications, genetically engineered proteins, milk drug residue, liver function, antibiotics and antibiotic synthesis pathways. Suitable soluble antigens for analysis in these applications are known by those of skill in the art (see, for example, The Immunoassay Handbook" (second edition), David Wild, ed. Nature Publishing Group 2001. NY N.Y.).

The present invention also provides for the detection and identification of specific nucleic acid (NA) sequences. In one embodiment, antigens are attached to the target NA using oligonucleotide probes. These probes decorate specific NA sequences with antigen(s). This antigen-decorated (also referred to herein as antigen-conjugated) oligonucleotide is capable of stimulating emittor cells expressing antibody against that antigen. Free probe, if present, is monomeric, and therefore does not stimulate emittor cells. Likewise, background binding of labeled oligonucleotide to nonspecific sites on NA will not significantly stimulate the emittor cells, because the antigens resulting from these rare background binding events will be too disperse to effectively crosslink antibodies.

The choice of antigen depends on many factors, including the availability and characteristics of corresponding antibodies, the absence of crossreactive antigens in the samples to be tested, and the solubility, stability, and cost of the antigen-oligonucleotide conjugate, as will be understood by one of skill in the art. As used herein, an oligonucleotide can be DNA, RNA, peptide nucleic acid (PNA), locked nucleic acids, or any variety of modified nucleic acid surrogates that have specialized and unique characteristics as is known in the art. Additionally, the addition of cationic amino acids (in peptide or protein form) to such probes can increase hybridization rates. If desired, those cationic peptides/proteins could serve double-duty as the antigen detected by the emittor cell. Therefore, in one embodiment of the invention, a detection system based on emittor cells having one or more antibodies on their surface and comprising a compound (an emittor molecule) that emits a photon upon stimulation by antigens that are multimeric due to the presence of target NA, in particular, photon emission is stimulated by an increase in intracellular calcium concentration.

Also provided in the invention described herein is a sensor cell that detects a target particle that is bound by one or more antibodies. Specifically, the sensor cells comprise an emittor molecule and an Fc receptor that binds to an antibody which is bound to the target agent or particle. In one embodiment, the sensor cell comprising an Fc receptor is a macrophage cell, such as the human macrophage cell line U937. Other suitable cells or cell lines will be known to those of skill in the art. The Fc receptors are a family of membrane-expressed proteins that bind to antibodies or immune complexes. They are expressed on several hematopoietic cells including monocytes and macrophages. Several subclasses of Fc receptors exist including Fc gamma Receptor I (FcγRI), a high-affinity binder of soluble antibody. FcγRI binds to the constant region (Fc portion) of Immunoglobulin G (IgG) leaving the antigen-binding region of the antibody free. Crosslinking of the antibody-bound Fc receptor by specific antigen initiates a signaling pathway that stimulates calcium release. Therefore, crosslinking of the Fc receptor on the sensor cell results in an increase in intracellular calcium concentration and the emittor molecule thereby emits a photon in response to the increase in calcium concentration.

Also provided in the invention described herein is a 16-Channel Sensor. In its simplest form, an emittor cell assay consists of preparing a sample in a transparent tube, introducing an aliquot of specially prepared emittor cells into the tube, driving the emittor cells to the bottom of the tube using a quick centrifugal spin, and measuring the light output from the tube with a photon-counting sensor. In the laboratory, most emittor cell assays are made sequentially, one sample at a time; in the automated BAWS/CANARY instrument, four samples are measured simultaneously, each sample having its own light-gathering channel. The former system requires more time, while the latter requires more complex (and expensive) hardware.

A different approach that reduces the time to measure multiple samples (while keeping the hardware requirements minimal) is described herein. A sensor has been designed that allows the simultaneous measurement of a plurality of samples using a single light-gathering channel. The sensor consists of a rotor holding sixteen 1.5-ml tubes horizontally, equally distributed about its circumference, and driven by a variable speed motor about a vertical axis (FIG. 39). A single fixed photon-detecting element (for example, a PMT) is positioned in the plane of the rotor just beyond the path of the tubes during rotation. In this design, each of the tubes is sequentially and repetitively brought into close proximity to the photon-detecting element, allowing its light output to be sampled on each pass. Finally, an optical switch consisting of an optical source (an infrared LED) and a detector (a phototransistor) is used to control the counting of detected photons and the reorganization of the data into the 16 fields, each associated with a specific sample.

Figure 42:
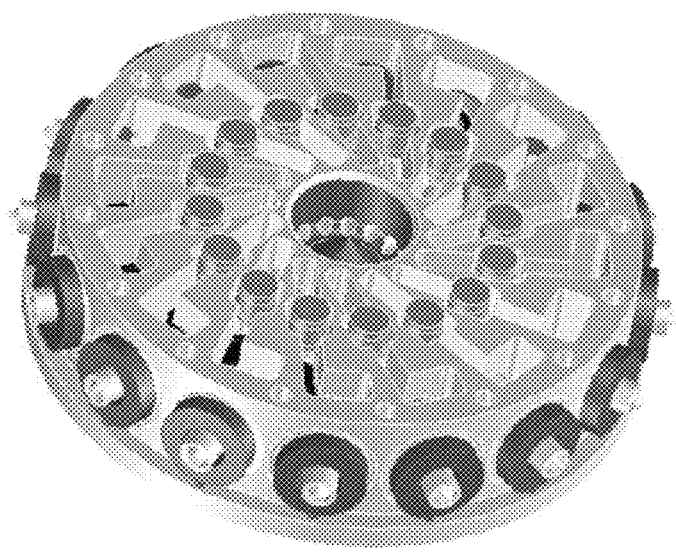
FIG. 42 is an illustration of a CANARY Disc (CD) integrated aerosol collection and emittor cell delivery.
Figure 43:
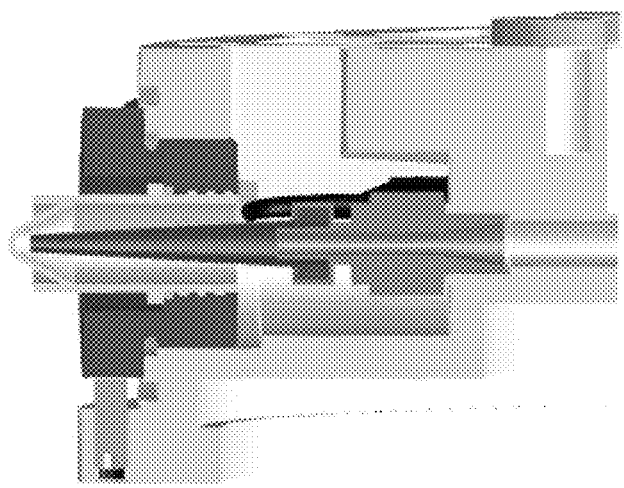
FIG. 43 is an illustration of an aerosol collection module cutaway with impaction nozzle and transparent tube.

A further implementation of this 16-channel design is referred to as a TCAN sensor. The TCAN (Triggered-CANARY) biosensor is an automated biosensor which combines both aerosol collection and emittor cell liquid delivery into an integrated radial disc format. The TCAN CANARY disc (CD) (FIG. 42) interfaces with a manifold assembly which splits an air flow into separate channels. The aerosol collection assembly (FIG. 43) uses dry impaction techniques to then localize particles from the air flow into the bottom of clear plastic tubes.

Figure 44:
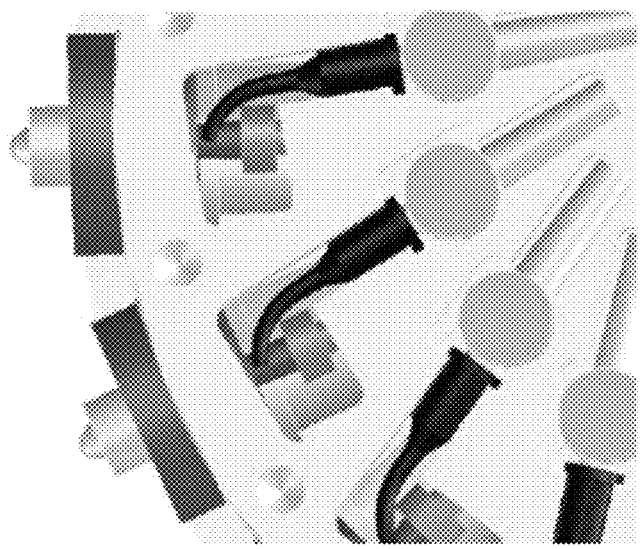
FIG. 44 is an illustration of an emittor cell delivery module with valve delivery system.
Figure 46:
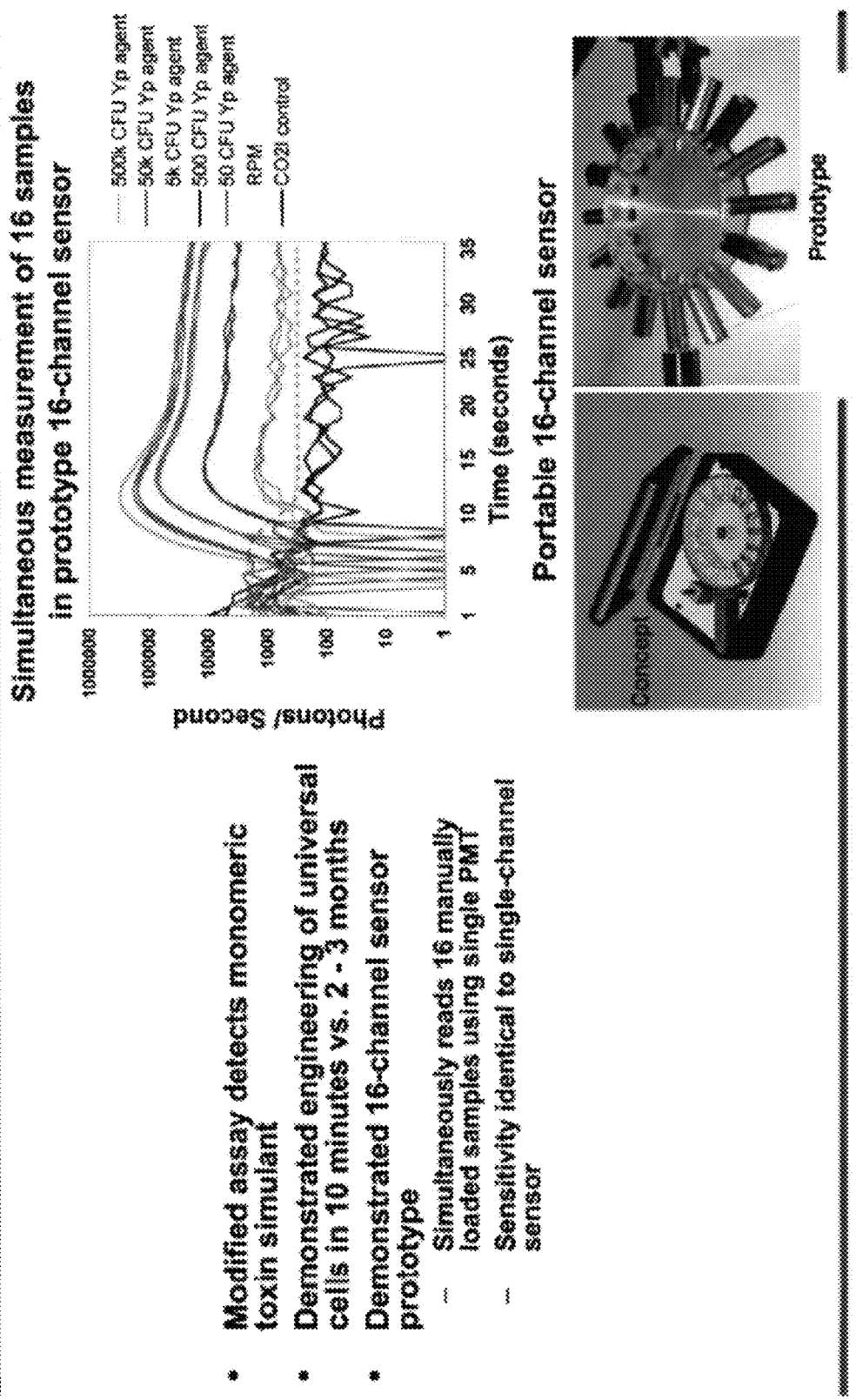
FIG. 46 is an overview of the detection of toxins.

After impaction of aerosol particles, the CD interfaces with the manifold assembly to actuate valves located in the disc. The disc is rapidly spun, which in turn causes the emittor cell liquid to deliver to individual tubes using centrifugal force (FIG. 44). An optical detector is then used to identify potential bioagents based on the photon output of emittor cells interacting with the aerosol particles. This process of aerosol collection and emittor cell delivery can be repeated several times in one disc. This feature allows multiple emittor cell assays to be performed after several trigger events without changing the CD.

The materials and procedures suitable for use in the invention are described in further detail below.

Emittor Cells

The emittor cell (also referred to herein as a sensor cell or a CANARY cell) can be any prokaryotic or eukaryotic cell that has a suitable receptor, signaling pathway, and signal output method, either naturally, through genetic engineering, or through chemical addition. The cell can be an artificial or nonliving unit provided that it has a functional receptor, signaling pathway, and signal output method. Upon binding of antigen receptor, such as to the antibodies, the cell mobilizes calcium ions into the cytosol. An example of a cell useful in the device and methods of the invention is a B cell (i.e., a B cell from a cold or warm-blooded vertebrate having a bony jaw) which can be genetically engineered to express one or more surface-bound monoclonal antibodies. Another example of a cell useful in the device is a macrophage cell, such as the human cell line U937, which expresses an Fc receptor on the cell surface. An antigen can be bound to an antibody by addition of the antibody to the target and this antigen-antibody complex will bind to the Fc receptor on the cell and stimulate signaling which results in an increase in intracellular calcium.

A monoclonal antibody can be produced by, for example, immunizing an animal with the antigen to be detected and harvesting the B cell from the immunized animal. DNA encoding the monoclonal antibody can then be isolated and transferred into an immortalized cell line and the cells screened for production of a surface monoclonal antibody specific for the antigen to be detected. B cells are useful for both qualitative and quantitative analyses, particularly because the emission signal from them typically does not significantly diminish as additional target specimen is exposed to it and also because such emission signal is linear.

Alternatively, the cell can be a fibroblast. However, fibroblasts do not contain the signal transduction machinery necessary to transfer a signal from the cytoplasmic portion of a surface antibody to calcium stores in the cell. To overcome this problem, a chimeric surface antibody can be expressed in the fibroblast. This chimeric antibody contains a cytoplasmic amino acid sequence derived from a polypeptide (e.g., a fibroblast growth factor receptor) that can transduce a signal from the inner surface of the plasma membrane of the fibroblast to intracellular calcium stores. Thus, when an antigen binds to the extracellular portion of the chimeric antibody to cause antibody aggregation on the surface, calcium mobilization is induced. A similar strategy using chimeric antibodies can be employed for any other cell type which is not a B cell, so that the cell is suitable for use in the devices and methods of the invention.

Cells useful in the devices and methods herein are those designed to recognize a specific substance, including those having receptors on their surface that specifically bind to that substance. A preferred receptor is an antibody or single-chain antibody, although other suitable receptors include a mitogen receptor (such as a lipopolysaccharide (LPS) receptor), a macrophage scavenger receptor, a T cell receptor, a cell adhesion molecule, a DNA binding protein such as part of a sequence-specific restriction enzyme or transcription factor, single-stranded-RNA- or double-stranded-RNA-binding protein, an oligonucleotide complementary to a DNA or RNA sequence to be recognized, or other ligand-binding receptor (e.g., Fas; cytokine, interleukin, or hormone receptors; neurotransmitter receptors; odorant receptors; chemoattractant receptors, etc.) that will specifically bind the substance to be recognized. The receptor can be attached to the cell surface via a transmembrane domain, a membrane-bound molecule that specifically binds to the receptor (such as Fc receptors bind to antibodies), or a covalent or noncovalent attachment (e.g., biotin-streptavidin, disulfide bonds, etc.) to a membrane-bound molecule. The receptor can also be a chimeric molecule; for instance, it can have an extracellular domain such as an antibody, single-chain antibody, lectin or other substance-specific binding domain or peptide, and an intracellular domain such as that from the insulin receptor, fibroblast growth factor, other protein that triggers a second messenger cascade, etc. Instead of directly binding to the substance to be recognized, the receptor might specifically bind to another molecule or object that in turn specifically binds to the substance to be recognized, such as a secondary antibody, labelled bead, antigen-conjugated oligonucleotide, etc.

Alternatively, only one of these binding steps may need to be specific. For instance, DNA or RNA containing specific sequences may be pulled out of solution using oligonucleotide probes conjugated to one antigen (or directly to a bead, or on a matrix), and a second set of nonspecific antigen-conjugated oligonucleotide probes annealed to the target DNA/RNA would be used to stimulate cells specific for that second antigen. Also, non-specific nucleic acid binding proteins (histones, protamines, RNA-binding proteins) expressed as chimeras on the cell surface, or antibodies against those binding proteins, could also be used to detect the presence of nucleic acids after a sequence specific selection step.

Antibodies

Whatever original cell type, the antigen-binding variable regions of monoclonal antibodies can obtained either as DNA sequence from a public source, or cloned by RT-PCR from a hybridoma cell line. RT-PCR is accomplished using sets of primers designed to anneal, at the 5-prime end, to either the leader or framework regions of the variable region, and at the 3-prime end to the constant region.

The antibody variable regions are then cloned into expression vectors that already contain the constant regions for light and heavy chain. The light chain expression vector described in Persic et al., Gene 187:9-18, 1997 is especially suitable for this purpose. VKExpress, described in Persic et al., contains the EF-1α promoter, a leader sequence, multiple cloning sites, and the human Ig kappa constant region and polyadenylation signal. The heavy chain expression vector is derived from Invitrogen's pDisplay. This vector contains a CMV promoter, a leader sequence, an HA tag, multiple cloning site, and myc tag, followed by the PDGFR transmembrane domain and bovine growth hormone polyadenylation signal.

pDisplay can be modified for heavy chain expression as follows. The PDGFR transmembrane domain of pDisplay is replaced with the murine IgM constant region without the exon that allows for secretion. This ensures that the protein will remain membrane-bound. The neomycin-resistance gene can be replaced by any of a number of antibiotic-resistance genes including, but not limited to, hygromycin, bleomycin, puromycin, kanamycin, and blasticidin genes. The heavy chain (or alternatively light chain) variable region can be inserted in a two-step process, using overlap-extension PCR, to remove the HA and myc tags present on either side of the multiple cloning site of pDisplay. A vector can also be developed to allow insertion of an overlap extension product containing the variable region fused to approximately 300 base pairs of the IgM constant region, so that cloning can be done in a single step.

The examples below were implemented using the antibody vector construction procedure described immediately above.

An antibody which specifically binds to the antigen to be detected is a molecule which binds to the antigen or an epitope of the antigen, but does not substantially bind other antigens or epitopes in the sample. Such antibodies can be chimeric (i.e., contain non-antibody amino acid sequences) or single chain (i.e., the complementarity determining region of the antibody is formed by one continuous polypeptide sequence).

Alternatively, surface antibody-producing cells can be obtained from the animal and used to prepare a monoclonal population of cells producing surface antibodies by standard techniques, such as the hybridoma technique originally described by Kohler et al., Nature 256:495-497 (1975); Kozbor et al., Immunol Today 4:72 (1983); or Cole et al., Monoclonal Antibodies and Cancer Therapy, Alan R. Liss Inc., pp. 77-96 (1985). The technology for producing cells expressing monoclonal antibodies is well known (see, e.g., Current Protocols in Immunology (1994) Coligan et al. (eds.) John Wiley & Sons, Inc., New York, N.Y.), with modifications necessary to select for surface antibodies rather than secreted antibodies.

Any of the many well known protocols used for fusing lymphocytes and immortalized cell lines can be applied for the purpose of generating a cell producing a surface monoclonal antibody (see, e.g., Current Protocols in Immunology, supra; Galfre et al., Nature 266:55052, 1977; Kenneth, In Monoclonal Antibodies: A New Dimension In Biological Analyses, Plenum Publishing Corp., New York, N.Y., 1980; and Lerner, Yale J Biol Med 54:387-402 (1981). Moreover, the ordinarily skilled worker will appreciate that there are many variations of such methods which also would be useful.

Polyclonal cells expressing antibodies can be prepared by immunizing a suitable animal with the antigen to be detected. The cells producing antibody molecules directed against the antigen can be isolated from the animal (e.g., from the blood) and further purified by well-known techniques, such as panning against an antigen-coated petri dish. As an alternative to preparing monoclonal cells, a nucleic acid encoding a monoclonal antibody can be identified and isolated by screening a recombinant combinatorial immunoglobulin library (e.g., an antibody phage display library) with the antigen to thereby isolate immunoglobulin library members that bind the antigen. Kits for generating and screening phage display libraries are commercially available (e.g., the Pharmacia Recombinant Phage Antibody System, Catalog No. 27-9400-01; and the Stratagene SurfZAP® Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication WO 92/20791; PCT Publication No. WO 92/15679; PCT Publication WO 93/01288; PCT Publication No. WO 92/01047; PCT Publication No. WO 92/09690; PCT Publication No. WO 90/02809; Fuchs et al., Bio/Technology 9:1370-1372 (1991); Hay et al., Human Antibod Hybridomas 3:81-85 (1992); Huse et al., Science 246:1275-1281 (1989); Griffiths et al., EMBO J. 12:725-734 (1993).

After the desired member of the library is identified, the specific sequence can be cloned into any suitable nucleic acid expressor (e.g., a vector) and transfected into a cell such as a fibroblast. The expressor can also encode amino acids operably linked to the antibody sequence as appropriate for the cell which is to express the antibody. As discussed above, the cytoplasmic transmembrane sequence of a fibroblast growth factor receptor can be linked to a single-chain antibody specific for the antigen to be detected, so that the cell immobilizes calcium when contacted with the antigen. Although separate recombinant heavy chains and light chains can be expressed in the fibroblasts to form the chimeric antibody, single chain antibodies also are suitable (see, e.g., Bird et al., Trends Biotechnol 9:132-137, 1991; and Huston et al., Int Rev Immunol 10:195-217, 1993).

Photon Emitter Molecules

Binding of the desired substance to the cell-surface receptor should trigger a signaling pathway inside the cell. A preferred signaling pathway is the second-messenger cascade found in B cells, T cells, mast cells, macrophages, and other immune cells, wherein crosslinking of the cell surface receptors activates a tyrosine kinase, which then phosphorylates phospholipase C, which then cleaves phosphatidylinositol 4,5-bisphosphate (PIP2) into inositol 1,4,5-trisphosphate (IP3) and diacylglycerol; IP3 then opens calcium channels to release calcium from intracellular stores such as the endoplasmic reticulum or to let in extracellular calcium, thereby elevating the calcium concentration in the cell's cytosol. Depending on the receptor type, cell type, and desired signaling method, alternative second-messenger cascades could be employed, such as a G-protein-adenylyl cyclic-cAMP-protein kinase A cascade.

A method should be provided for monitoring the internal signaling of the cell in response to substances to be identified. If the internal signaling involves an increase in cytoplasmic calcium, a preferred detection method is a calcium-sensitive luminescent or fluorescent molecule, such as aequorin, obelin, thalassicolin, mitrocomin (halistaurin), clytin (phialidin), mnemopsin, berovin, Indo-1, Fura-2, Quin-2, Fluo-3, Rhod-2, calcium green, BAPTA, chameleons (A. Miyawaki et al., (1999) Proc. Natl. Acad. Sci. 96, 213540), or similar molecules. It is anticipated that the relative intensities of light and the sensor cell storage characteristics enabled by using calcium-sensitive molecules may vary depending on the efficiency of light production for the specific emitter molecule and the half-life of the activated emitter molecule—in some cases providing significant benefits (e.g., improved sensitivity, quantitative or qualitative detection). Additional performance enhancements may arise from the use of structural analogs of the natural cofactors of photoprotein emitter molecules. Various calcium-sensitive fluorescent dyes which can be taken up by live cells are available from commercial sources, including Molecular Probes, Inc., Eugene, Oreg. Proteins such as aequorin, obelin, thalassicolin, mitrocomin (halistaurin), clytin (phialidin), mnemopsin, berovin or chameleons could be added genetically, injected into the cells, or delivered by a protein uptake tag from HIV TAT (approximately amino acids 47-57; A. Ho et al. (2001) Cancer Research 61, 474-477) or by other means. If desired, such reporter molecules can include targeting signals to target them to the cytoplasmic face of the endoplasmic reticulum or the plasma membrane, the interior of the mitochondria, or other locations where the change in local calcium concentration might be particularly large. Optical methods of detecting activity from other points in the signaling pathway could also be used, such as fluorescence resonance energy transfer (FRET) of fluorescent groups attached to components of the signaling pathway (S. R. Adams et al. (1991) Nature 349, 694-697). Where the internal signaling involves an increase in reactive oxygen species (e.g. superoxide anion radicals, hydroxyl radicals, compound I or II of horseradish peroxidase, etc.), a preferred detection method is a reactive-oxygen-sensitive luminescent or fluorescent molecule, such as the photoprotein pholasin (a 34-kDa glycoprotein from the bioluminescent mollusc, Pholas dactylus) or similar molecules. Alternatively, a reporter gene for any luciferase could be linked to a promoter induced by the signaling pathway. In some cells such as T cells and mast cells, the signaling pathway triggers exocytosis of granules containing proteases such as granzymes, tryptases, or chymases. Exocytosis of these proteases could be detected by calorimetric or fluorometric methods (e.g., p-nitroanaline or 7-amino-4-trifluoromethyl coumarin (AFC) linked to peptides cleaved by the proteases [S. E. Lavens et al. (1993) J. Immunol. Methods 166, 93; D. Masson et al. (1986) FEBS Letters 208, 84; R&D Systems]). Also, microelectrodes or other methods to detect the electrical activity associated with the calcium flux or other signaling ion fluxes are suitable to monitor signaling response in the cell.

A suitable emitter molecule is any molecule that will emit a photon in response to elevated cytosolic calcium concentrations, including bioluminescent and fluorescent molecules. One emitter molecule, the bioluminescent aequorin protein, is described in Button et al., Cell Calcium 14:663-671 (1993); Shimomura et al., Cell Calcium 14:373-378 (1993); and Shimomura, Nature 227:1356-1357 (1970). Aequorin generates photons by oxidizing coelenterazine, a small chemical molecule. Coelenterazine diffuses through cellular membranes, so coelenterazine or an analog thereof can be added to the culture medium surrounding the cells. Alternatively, genes encoding enzymes that make coelenterazine can be introduced into the cells. In another embodiment, bioluminescent green fluorescent protein (GFP) (see Chalfie, Photochem Photobiol 62:651-656 [1995]) or yellow fluorescent protein (YFP) can be used. In this embodiment, the cell cytosol contains both GFP and aequorin. In response to elevated calcium in the cytosol, aequorin donates energy to GFP in an emissionless energy transfer process. GFP then emits the photon. Alternatively, the emitter molecule can be a calcium-sensitive fluorescent molecule (e.g., indo-1) which is illuminated by a wavelength of light suitable to induce fluorescence.

Aequorin, or any other emitter molecule, can be introduced into the cell by methods well known in the art. If the emitter molecule is a protein (as is the case with aequorin), the cell can contain an expression vector encoding the protein (i.e., a nucleic acid or virus which will produce the emitter molecule when introduced into a cell). An expression vector can exist extrachromosomally or be integrated into the cell genome.

Conjugated Antigens/Tags

One or more antigens or tags can be added (also referred to herein as conjugated) to molecules to provide a known antigenic epitope. For example, one or more antigens can be conjugated to an oligonucleotide to produce an antigen-conjugated oligonucleotide with a known antigenic epitope. An antigen-conjugated molecule can comprise one antigen or multiple antigens that are either the same of different. For example and without limitation, an antigen or tag to be conjugated to a molecule for detection includes small antigens such as digoxigenin, digoxin, phosphocholine, fluorescein or other fluorophores, and biotin, and peptides such as HIS, VSV-G, FLAG, and C(AAKK) multimer (as described in Corey, J. Am. Chem. Soc., (1995) 117: 9373-4).

Oligonucleotides

In addition to conventional DNA and RNA probes, a variety of modified nucleic acids have been shown to hybridize in a sequence-specific manner to target nucleic acid sequences. These include peptide nucleic acids (PNA) (Nielsen et al., (1991) Science 254: 1497-1500), Bis-PNAs (Griffith et al., (1995) J. Am. Chem. Soc 117: 831-832), Tail-clamp PNA (Bentin (2003) Biochemistry 42: 13987-13995), PD loops (Bukanov et al., (1998) PNAS 95: 5516-5520), PNAs incorporating pseudocomplementary bases (Lohse et al., (1999) PNAS 96 (21) 11804-11808), or locked nucleic acids (Braasch and Corey (2001) Chem. Biol. 8: 1-7). A variety of these modified nucleic acids have been shown to have differ in hybridization characteristics, stability, affinity, and specificity, and could be used in place of conventional DNA oligonucleotides (reviewed by Beck and Nielsen, pp. 91-114, in Artificial DNA: Methods and Applications. CRC Press, Y. E. Khudyakov and H. A. Fields eds.). Attachment of cationic proteins, peptides, or DNA binding proteins has been shown to improve hybridization kinetics (Corey (1995) J. Am. Chem. Soc 117: 9373-9374; Zhang et al., (2000) Nuc. Ac. Res. 27 (17) 3332-3338).

The binding of oligonucleotides has been shown to improve with the addition of helper oligonucleotides (O'Meara et al., (1998) Anal. Biochem. 225: 195-203; Barken et al, Biotechniques (2004) 36: 124-132). Specificity can be improved by addition of unlabeled hairpin competitor probes (Huang et al., (2002) Nucleic Ac. Res. 30: (12) e55).

Removal of unbound oligonucleotides after hybridization to target is not necessary for nucleic acid sequence detection, but may be desirable. The unbound labeled oligonucleotide could be removed using a variety of conventional chromatography techniques, including size exclusion, hydrophobic interaction, or ion exchange, depending on the chemistry of the particular probe used.

Other Nucleic Acid-Binding Molecules

Oligonucleotides are not the only molecules that are able to identify specific nucleic acid sequences. Proteins are also capable of such discrimination, and can be expressed on the surface of the emitter cell, recombinantly attached to a cytoplasmic domain that would, upon binding, initiate a calcium response. This would include nucleic acid binding proteins attached to the Fc portion of antibodies, for example. Expression of nucleic acid binding proteins on the surface of the emittor cell would eliminate having to denature double-stranded nucleic acid prior oligonucleotide hybridization, and additionally, the system produces all the necessary components: no exogenously synthesized oligonucleotides would be required. Possible sequence specific DNA binding proteins include: (1) DNA restriction enzymes (preferably with the DNA-cutting catalytic site removed or inactivated, e.g. L. F. Dorner & I. Schildkraut (1994) Nucl. Acids Res. 22, 1068-1074); (2) Transcription factors or other specific DNA- or RNA-binding proteins, especially those that recognize unique DNA or RNA sequences in pathogens or organisms of interest (e.g., HIV TAT transcription factor: C. Brigati et al. (2003) FEMS Microbiology Letters 220, 57-65; poxvirus transcription factors: S. S. Broyles (2003) Journal of General Virology 84, 2293-2303). Emittor cells with such receptors could be designed to crosslink on target DNA/RNA with either a specific repeated sequence or alternatively two or more unique sequences.

Capture Oligonucleotides

Although not necessary for detection, capture of the target nucleic acid sequence on sedimentable or solid support can improve assay sensitivity. Single-stranded DNA target can be captured using, for example, biotin-labeled capture oligonucleotides bound to streptavidin-coated polystyrene or paramagnetic beads. The captured material can be separated from unbound material by centrifugation or exposure to a magnetic field, as appropriate. The use of an intermediate binding reaction (avidin-biotin) in attaching the oligonucleotide to the bead may not be necessary as any interaction that would attach the oligonucleotide to a solid support can be used, including direct conjugation. In addition, any solid support to which the capture oligonucleotide can be attached would suffice. This can be in the form of a two-dimensional array, in which specific capture oligonucleotides are placed in specific positions on the array. Alternatively, target nucleic acid sequences can be captured in a non-specific manner (e.g. ion exchange resin, precipitation, histone or protamine binding). Target capture will also concentrate the target nucleic acid sequence and/or remove assay interferents.

Polyvalence

Emittor cell stimulation is dependent on the antigen appearing multivalent to the emitter cell. In general, this can be accomplished in at least two ways. First, multiple copies of antigen can be attached to a target molecule, for example, hybridizing multiple antigen-conjugated oligonucleotides to the target nucleic acid sequence. Second, several copies of the target nucleic acid sequence, each with a single antigen attached, can be bound to each other or bound in close proximity to each other (e.g., attached to a bead). In this example, the individual target nucleic acid sequence would not be polyvalent, but the bead with multiple copies of the target nucleic acid sequence attached would present a polyvalent antigen.

Reaction Chambers

The reaction chambers suitable for use in the invention can be any substrate or vessel to which emitter cells and candidate particles can be mixed and contacted to each other. In one embodiment, the reaction vessel is a centrifuge tube (e.g., a microcentrifuge or Eppendorf tube). As described herein, centrifugation is a particularly well-suited means to pellet candidate particles or emitter cells first, before the other is driven into the first pellet. To further increase the pelleting of both particles and cells, the side walls of the tube can be coated with a non-sticky carrier protein such as bovine serum albumin to prevent the sticking of emitter cells to the side walls, and the bottom of the tube can be coated with poly-L-lysine to help ensure that the target particles stay adhered to the bottom of the tube. Other proteins or molecules that either prevent or promote cell adhesion are known in the art of cell biology and are suitable for use in the invention.

Centrifuge tubes with customized sample well geometries can provide an additional embodiment that uses centrifugation to increase emitter cell interactions with difficult-to-sediment particles and reduces the need to customize spin sequence. In this embodiment the particle-containing sample to be analyzed is placed in a tube where the maximum width of the sample chamber is approximately equal to the diameter of an emitter cell. Layering a concentrated emitter cell suspension over the sample followed by centrifuging drives a large number of closely packed emitter cells through the smaller particles while the constrained geometry increases the probability of emitter cell antibody interaction with particles. Binding of the cell-associated antibody to the particle captures the poorly sedimenting particle and will rapidly draw it to the bottom of the tube with the emitter cell where the resulting light can be observed by a photo multiplier device.

In another embodiment, the reaction chambers are wells in a two-dimensional array, e.g., a microtiter plate, or spots or wells along a tape, as shown in the figures. These arrangements allow multiplex detection of either multiple samples and/or multiple target particles. For automated delivery of candidate particles and/or emitter cells, either the reaction chambers or the specimen collector and emitter cell reservoir is addressable in at least two dimensions. The wells of arrays can also be treated with sticky and non-sticky coatings as described above for centrifuge tubes to facilitate contact between emitter cells and candidate particles.

Specimen Collectors

Different devices can be used to collect samples from, e.g., air. In general, an air sampling device has a collection chamber containing liquid through or beside which air or gas is passed through, or containing a porous filter that traps particulates (e.g., target particles) as air or gas passes through the filter. For collection chambers containing liquid, the collection liquid can be centrifuged or otherwise treated to separate particles from the liquid. The separated particles are then deposited in a reaction chamber. For collection chambers containing a filter (e.g., nitrocellulose), the filter or portions of the filter can act as the reaction chamber. Alternatively, particles can be washed from the filter, or the filter can be dissolved or otherwise removed from the particles. A filter collection chamber can also be adapted to collect particles from a liquid (e.g., water supply sample or cerebral spinal fluid) flowing through the filter. In addition, as discussed above, a liquid sample can be centrifuged to remove any particulate material present in the liquid. A variety of samplers are known and available for use with the present invention. See SKC, Inc., which sells the SKC BioSampler®. and other sampling devices.

Other air samplers can be used. For example, an alternative device is the Air-O-Cell sampling cassette (SKC, Inc.). In this device, the airborne particles are accelerated and made to collide with a tacky slide which is directly suitable for various staining procedures and microscopic examination.

Aerosol particulates may be collected using inertial separation in a device known as an impactor. An airflow containing particles to be collected is drawn from the environment of interest into the impactor where it is directed towards a surface for impaction. With appropriate geometrical parameters and flow rates in the impactor, particles with sufficient inertia will not follow the flow streamlines, but will impact onto the surface. A significant proportion of the particles impacting the surface adhere through electrostatic and/or van der Waals interactions and are thereby collected and concentrated. In this way, aerosol particles containing proteins (including toxins), viruses, bacteria (vegetative and spore forms), parasites, pollen and other detectable substances can be collected for detection using a variety of available assay technologies including the devices and methods herein.

Dry sample collection for bioassays using an air impactor provides general advantages over traditional air-to-liquid sample collection by reducing or eliminating fluid consumables and transfer mechanisms which reduces assay cost and simplifies automation. Of particular benefit to the devices and methods herein, collection using dry impaction ensures that all of the collected sample is located on the surface prior to the addition of sensor cells of the devices and methods herein, regardless of the size of the individual analyte particles. This achieves localization of all analytes regardless of their sedimentation coefficient in fluid, thereby maximizing the sensitivity of the devices and methods herein and accelerating many implementations of the assay by eliminating a time-consuming step.

Any surface that retains a proportion of particles that impact onto it and that is compatible with subsequent bioassays is suitable as a collection surface. Suitable materials include biocompatible metals, plastics, glasses, crystals, aerogels, hydrogels, papers, etc. Particularly useful configurations of these materials include microcentrifuge tubes, multi-well plates used in high-throughput screening, continuous tapes, filters, conjugate release pads of lateral flow immunoassays, etc. The collection efficiency can be increased by modifications to the collection surface including: the addition of coatings promoting adhesion of biological particles (these coatings can be chemical or biochemical in nature, e.g. polylysine), increased surface roughness to increase the surface area available for collection, and customized surface geometries that promote deposition of particles in defined regions on the surface. Furthermore, additional improvements in collection efficiency can be achieved by manipulating the electrostatic charges on the collection surface and the incoming particles such that additional attractive forces are generated.

Additional improvements can be made to the dry impaction collector by using an air-to-air concentrator upstream of the collector to increase the number of particles in each unit of air sample impacted onto the collection surface. This can significantly reduce the amount of time needed to collect a sufficient number of aerosol particles to provide reliable results for the detector.

Figure 23:
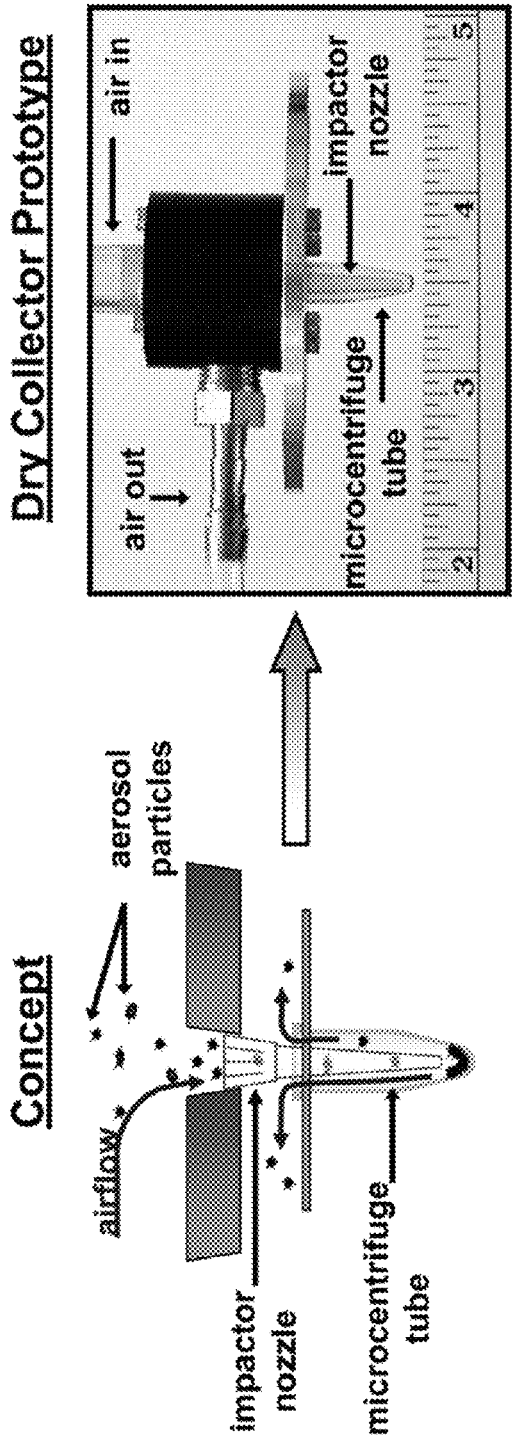
FIG. 23 illustrates an impactor configured to collect aerosol samples.
Figure 24:
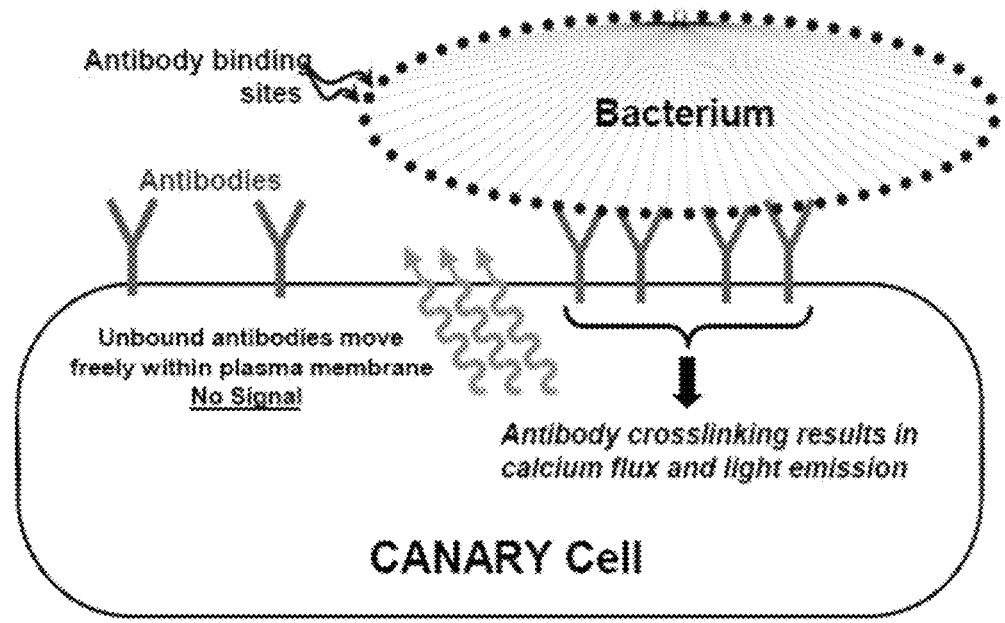
FIG. 24 is a schematic overview of the concept underlying the "CANARY" sensor. B cells have been modified such that they express aequorin within the cell interior and antibodies to pathogen on the cell surface. In the presence of pathogen, the antibodies are "crosslinked" (immobilized, aggregated) on the surface of the cell, stimulating a signaling cascade that results in increased intracellular calcium. Aequorin responds to this increase in intracellular calcium by oxidizing aequorin, and emitting light. Photon output can be monitored using a PMT.
Figure 25:
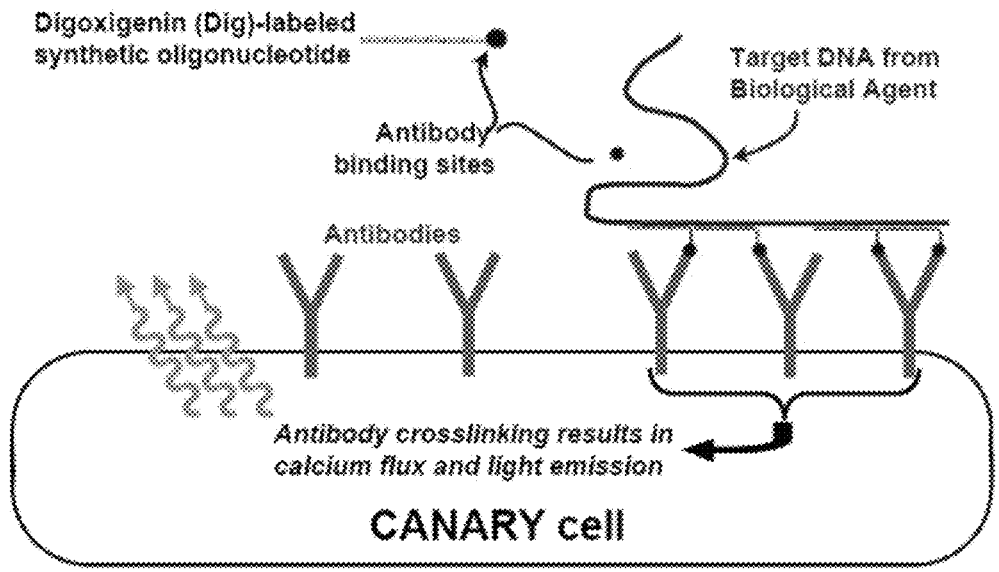
FIG. 25 is a schematic of DNA detection. Oligonucleotides complementary to target DNA sequences and containing a terminal digoxigenin label are hybridized to the target DNA. Multiple digoxigenin-labeled oligonucleotides bound along the target DNA bind to digoxigenin antibodies on the surface of the CANARY cell (emittor cell), stimulating light emission.

In one example of this collection concept, the impactor described in FIG. 23 has been configured to collect aerosol samples on the bottom of a commercially available plastic tube. A nozzle projects down into the tube and the exit is positioned at the radius of curvature of the tube's inner surface. This positioning increases the likelihood of particle impaction upon the tube bottom where the device sensor cells are most likely to contact them. Once collection is completed, a single droplet containing device sensor cells is added directly to the tube containing collected aerosol particles, spun for 5 seconds to accelerate cell delivery to the tube surface, and emitted light is measured using a photon detector (e.g., PMT, CCD, photodiode, etc.). Using this apparatus, dry bacterial spores can be collected from an aerosol and identified directly with optoelectronic device in less than one minute. This method can be implemented with a plurality of tubes used to collect samples and an automated system to conduct subsequent assays. An example of how a system capable of conducting at least 10 independent assays is shown in FIGS. 4, 6, 9, 12, and 15. By implementing an approach where assays are made capable of looking for multiple analytes in a single tube (multiplexed) the number of detectable substances for a single assay cycle can be made greater than the number of available tubes. This can be done by creating individual optoelectronic detection device cell lines expressing a plurality of receptors with affinity for different analytes or by combining multiple cell lines with different specificities in a single tube.

Figure 4:
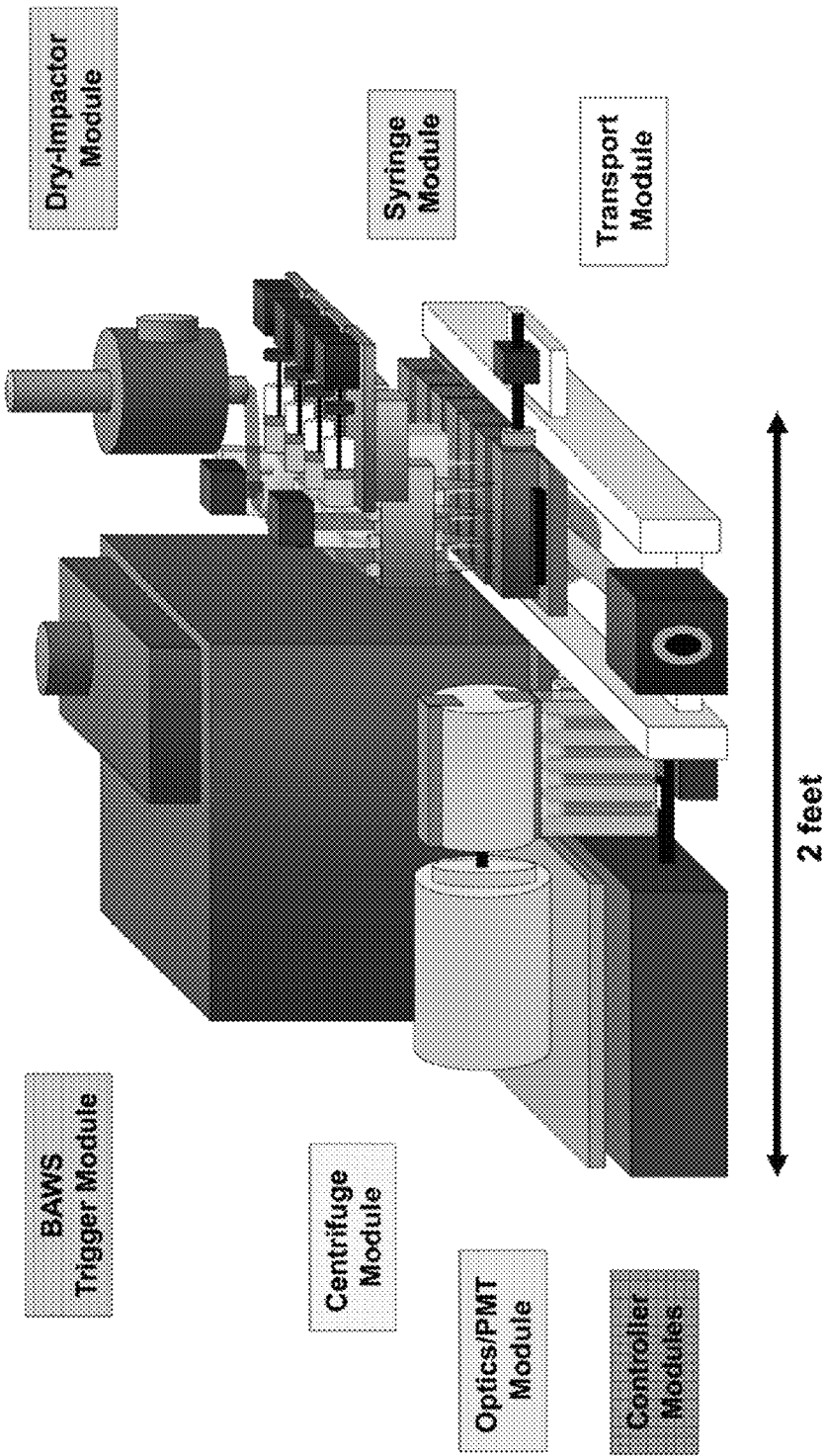
FIG. 4 is a schematic of an integrated biological aerosol warning sensor (BAWS)/optoelectronic sensor system.

FIG. 4 is a schematic of an integrated biological aerosol warning sensor (BAWS)/optoelectronic sensor system. The BAWS trigger module is used to preliminarily detect the presence of particles, e.g., those of a pre-determined size range. If particles meeting specifications are detected, BAWS triggers an air-to-air concentrator that allows particles of a particular size range to be collected and deposited in a well (e.g., reaction chamber, tube) via a dry-impactor module. The dry-impactor module allows for dry sample collection and is in communication with a syringe module for cell (e.g., emitting cells) delivery into a reaction chamber (e.g., tube). A transport module is used to transfer the reaction chamber assembly (having one or more chambers or tubes) to a centrifuge module for sedimentation or mixing of the particle sample and cells. The centrifuge module can be, but need not necessarily be, in communication with an optics/PMT module for detection of photon emission. A controller module is useful for control of operation of the system.

Figure 6:
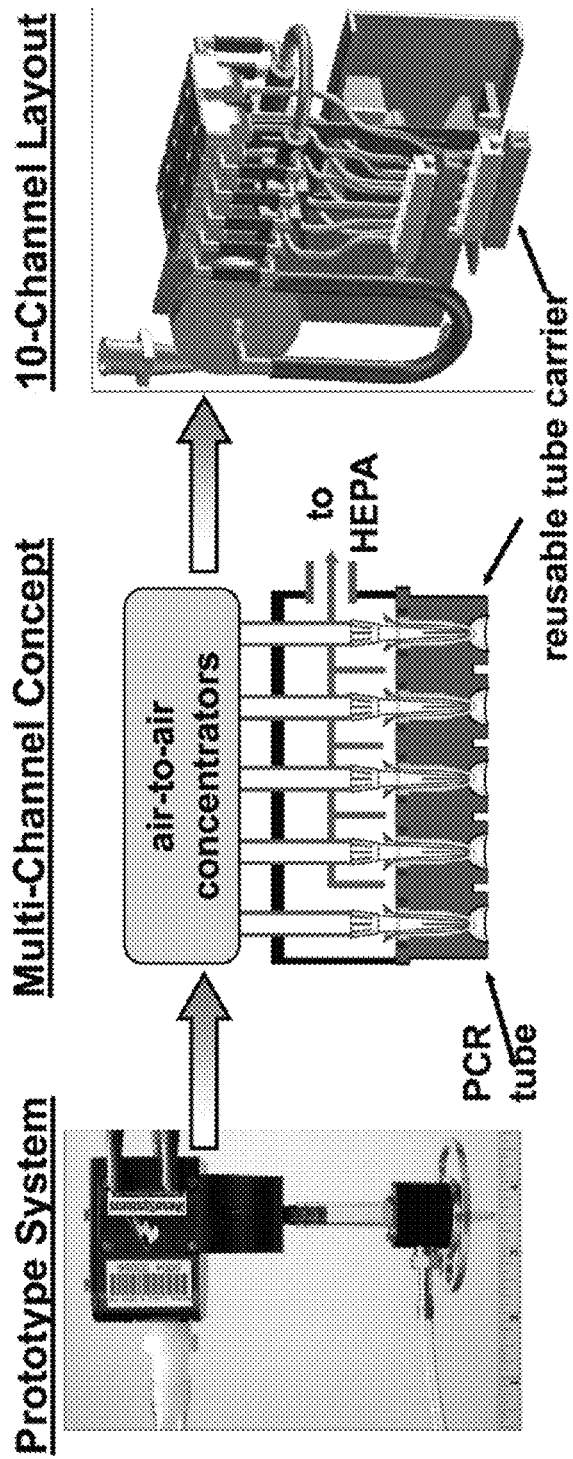
FIG. 6 illustrates a dry-impactor module for the optoelectronic sensor.

FIG. 6 shows an example of a dry-impactor module concept. In this example a single (e.g., prototype system) as well as a multi-channel device is illustrated, including individual sample tubes (e.g., PCR tubes) and tube carriers, in communication with air-to air concentrators from which the particle test sample is collected.

FIG. 9 shows an example of a cell-delivery that can be automated. The sensor cells (e.g., emitting cells) are introduced to the system by means of a syringe and syringe pump arrangement, which can include pipettors or other delivery equipment. This type of assembly allows for multiple and simultaneous introduction of sensor cells to the particle samples (e.g., samples in reaction chambers (e.g., tubes).

Figure 12:
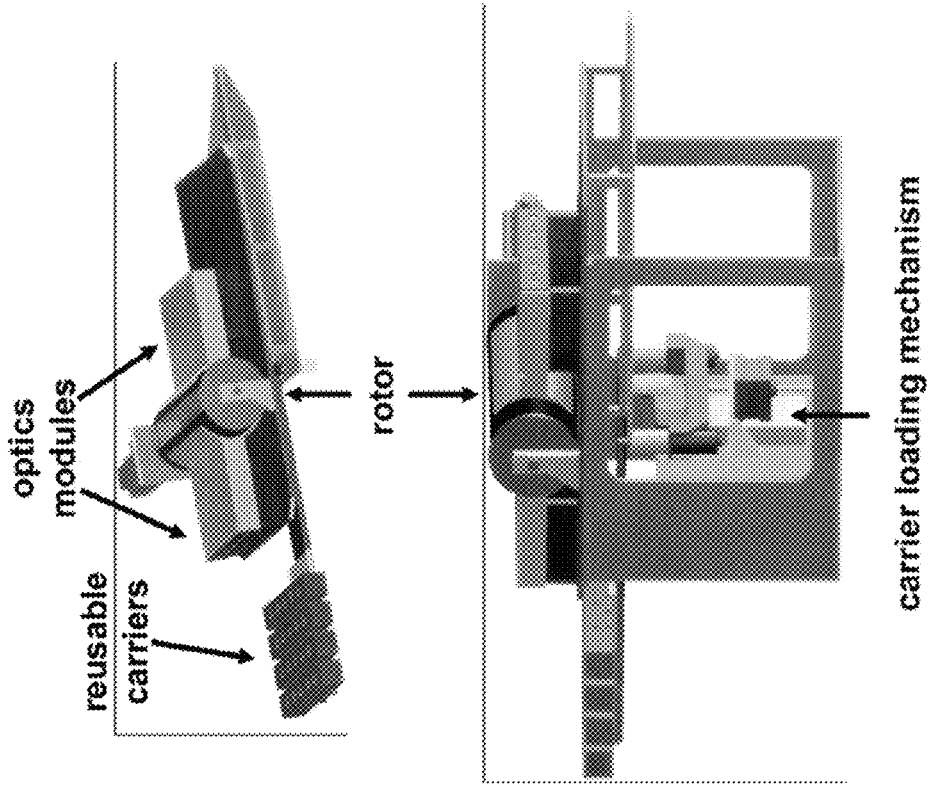
FIG. 12 illustrates an automated centrifuge module for the optoelectronic sensor.

FIG. 12 shows an example of a centrifuge module concept used to spin the particle samples or cell samples. Carriers having the sample tubes are introduced via a loading mechanism into a rotor assembly that is suitable for receiving the carriers. The rotor spins the samples. The rotor assembly is in communication with optics modules for signal collection (e.g., photon emission), and an indexed motor can be used to allow for alignment of the samples chambers with the detector (e.g., optics modules).

Figure 15:
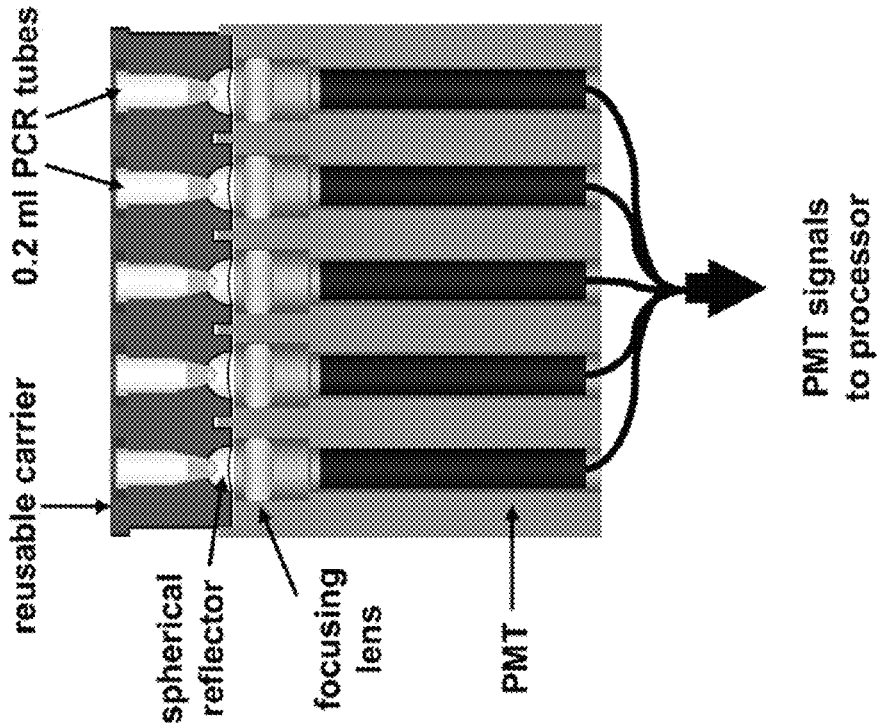
FIG. 15 illustrates an optics-photomultiplier (PMT) module for the optoelectronic sensor.

FIG. 15 shows an example of an optics module. Depending on the precise configuration, the module allows for a plurality of simultaneous testing of samples (e.g., in the reaction chambers, tubes). The carrier and tubes therein are introduced to the unit such that they are in communication with lens assemblies (e.g., integrated reflectors, lenses) if necessary, and ultimately a photodetector (e.g., a PMT). The PMT produces signals that are then sent to a processor for processing and display.

Figure 21:
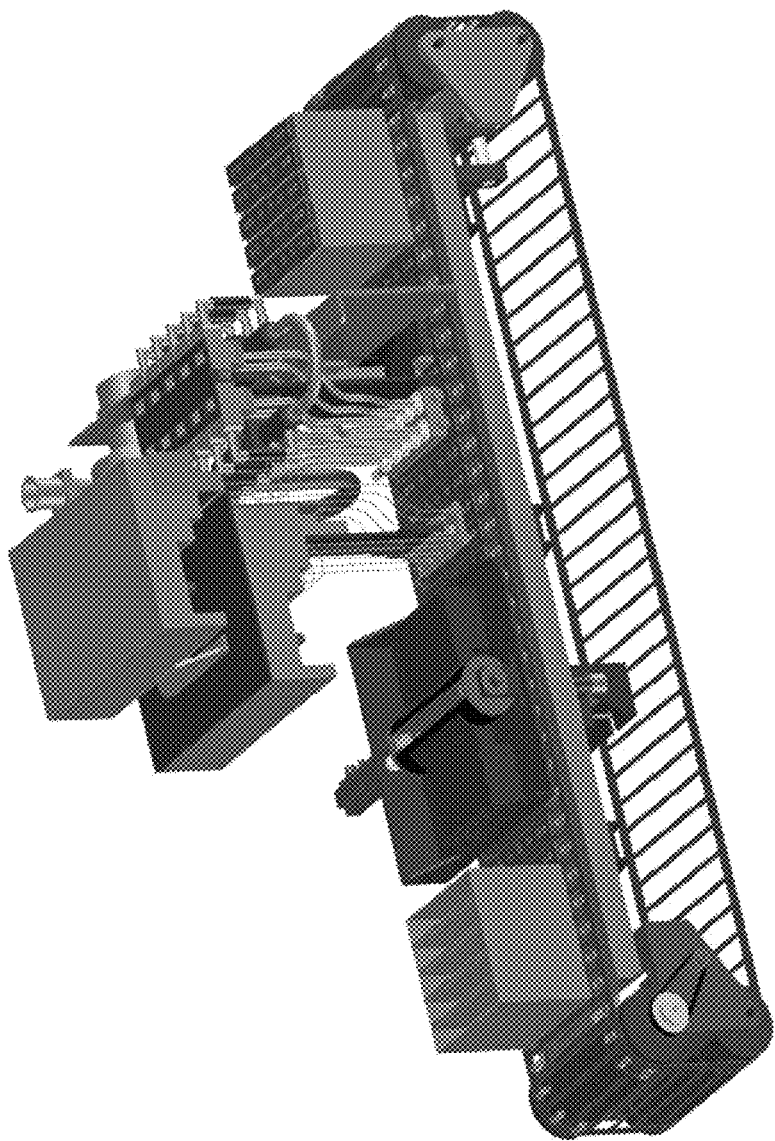
FIG. 21 illustrates an integrated dry-impactor/optoelectronic sensor.

FIG. 21 illustrates an integrated dry-impactor/optoelectronic sensor. In this sensor the modules described above are assembled in a linear arrangement with a cassette holding 30 carriers deliverable to a belt-driven carrier transport module. This transport module moves the assay tubes sequentially from the collector to the cell delivery module to the centrifuge module, and finally to the confirmatory sample storage module following completion of photon detection. The overall size of this integrated sensor is approximately 54 inches wide by 33 inches high by 22 inches deep.

Real-world samples may contain substances that either inhibit the assay (false negative) or cause a response in the absence of specific antigen (false positive). In many instances, these samples can be treated prior to the assay to remove these substances. For example, soluble substances such as detergents or serum factors can be removed by pre-centrifugation step, where the agent is concentrated in the bottom of the tube and the liquid is replaced with assay medium (Portal Shield samples). Insoluble, large particulate substances can be removed from the sample by filtration, using commercial filters of a pore size (3-5 µm) that allows the passage of the agent, but retains the contaminant (diesel or soot samples). Samples can be processed rapidly through syringe filters, adding only a few minutes to the total assay time.

Specimen Localization

As part of the specimen collector or reaction chamber, different mechanisms (other than centrifugation) can be implemented to facilitate contact between emitter cells and candidate particles. For example, the use of electrophoresis, isoelectric focusing, dielectrophoresis, magnetically tagged particles, and the like in bioelectronic devices can be integrated into a system of the invention. See, e.g., U.S. Pat. No. 6,017,696 and other patents assigned to Nanogen, Inc.; Goater et al., Parasitology 117:S177-189, 1998; and U.S. Pat. Nos. 5,512,439 and 4,910,148 and other patents assigned to Dynal AS.

Mixing a aqueous sample containing target particles (particles here can be anything recognized by the emitter cells-proteins/toxins, viruses, bacteria, parasites, nucleic acids, etc.) with an aliquot of media containing emitter cells results in particle-cell contact leading to transient increase in the rate of photon emission. The time between the start of the mixing process and the maximum emission rate depends on the characteristic response of the particular cells to stimulation as well as the time over which the mixing occurs (the mixing time) and the typical time for the particles and cells to come into contact after mixing (the diffusion time).

Because a background rate of detected photons will exist even in the absence of target particles (background cell emission and thermal noise in the photon detector and its electronics, for example), photons emitted from single target-cell interactions can be difficult to distinguish from this background. To be useful as a signal, there must be a significant increase in the rate of photons detected over that of the background. For a given sample, this rate is maximized when the mixing time and diffusion time are minimized. Other possible signals that target particle are present in a sample include: an increase in the total number of photons detected in a period of time above that of the background alone, a change in the statistics of detected photons, or a change in the spectral qualities of the detected photons.

The diffusion time can be minimized by reducing the average distance between particle and cell after mixing. This can be accomplished by localizing the particles and/or cells to within a small volume, often a layer, within the larger mixed volume. However, the time to localize the particles and/or cells may be longer than the characteristic response time of the cells. Mixing between particles and cells over this prolonged localization could produce a lower rate of photon emission, and therefore a lower signal, by increasing the average time between emissions. To avoid this, one or both should be localized separately, while minimizing contact between them. This localization can also lead to a reduced mixing time.

Generally, the means to move particles or cells include the following: sedimentation (by gravity or centrifuge); fluid flow (forced or convective); electric forces (electrophoresis and dielectrophoresis); magnetic forces (using magnetic beads); and acoustics/ultrasonics (standing or traveling waves).

Localization requires a means of moving particles and/or cells combined with a barrier where particles and/or cells can collect, such as the solid surface of a channel or container, the surface of a filter, or the potential energy barrier surrounding an electric-field minimum. Examples include: sedimentation (localizing cells on the lower surface of a chamber); air impaction (impacted particles stick to or settle onto a collection surface); filtering (particles or cells collect on to the surface or into the body of a filter); affinity capture particles or cells can be localized through specific or non-specific binding interactions); magnetic capture (magnetic beads held against a solid surface, a filter surface, or in the body of a filter by localized magnetic forces; beads may or may not have surface chemistry to promote attachment of particles or cells); electrophoresis (charged particles only; collection on to an electrode surface); and dielectrophoresis (positive: collection of particles or cells on to an electrode surface; negative: collection into a region of minimum field).

Localization and mixing of particles and cells can be achieved by combining the above methods, as well as others. In the table below, examples of various localization/detector combinations are provided. Certain of the representative examples illustrate methods to localize particles or cells 2-dimensionally, allowing improvement in sensitivity or discrimination between different particles if an array of photon detectors (including a CCD) is used as opposed to a single photon detector (such as a PMT).

| Example | Method of localizing cells | Method of localizing particles | Mixing: particles or cells/means | Detector |
| --- | --- | --- | --- | --- |
| centrifuge | centrifuge (short) | centrifuge (long) | cells/sediment (cent.) | single |
| flow cell | sediment and attach to surface | shallow channel above cells | particles/sediment (grav.) | single |
| flow cell (multiple cell lines) | sediment and attach to surface | shallow channel above cells | particles/sediment (grav.) | imaging |
| flow cell/magnetic bead | sediment and attach to surface | localized magnetic bead capture | particles (on beads)/sediment (grav.) | imaging |
| flow cell/electric field | sediment and attach to surface | shallow channel above cells | particles/ electrophoresis | single |
| tape/wick | flow (into wick) | air impact (tape) | cells/sediment (grav.) | single |
| air impact | centrifuge (short) | air impact (tape) | cells/sediment (cent.) | single |
| uniprep/magnetic bead | sediment to surface | magnetic beads on filter surface | particles (on beads)/sediment (grav.) | single |
| flow past cells | cells on filter surface | | flow past cells | single |
| counter flow | cells held on filter surface by centrifugation | retained on filter surface | particles/flow past cells counter to cent. Force | single |
| centrifuge tube dielectrophoretic trap | centrifuge onto filter surface | retained in flow by dielectrophorectic force | cells/sediment (cent.) | single |
| traveling-wave dielectrophoresis | sediment and attach to traveling-wave dielectrophoresis | traveling-wave dielectrophoresis | particles/sediment (grav.) | single |
| dissolvable-membrane tube | separate compartment | centrifuge (long) onto dissolvable membrane | cells or particles/traveling-wave dielectrophoresis dissolve membrane and sediment (cent.) | single |
| acoustic/ultrasonic | | | | |

Localization Examples

In each of the following examples, it is assumed, unless stated otherwise that the sample is an aliquot of aqueous solution compatible with short-term cell life and function, possibly containing target particles (though the descriptions below will assume the presence of particles). An aqueous sample can be obtained from environmental, clinical, air-toliquid, washed-swab, or other samples. An air sample can be obtained from a driven air stream (air sampler or surface pickup), electrostatic capture, or settled airborne particles. References to cells should be understood to mean emitter cells in an aqueous media that is compatible with their life and function. A particle and cell brought into contact is assumed to result in emission of one or more photons. A single or array photon detector exists external to the chamber in which the sample and cells are mixed, and there may be additional optical elements to enhance capture and detection of emitted photons (such as mirrors, lenses, lightpipes, etc.) either external or internal to the chamber. The chambers are either assumed to be transparent in part or in whole or to have another means to allow emitted photons to reach the detector. Additional descriptions of specific embodiments of the invention are provided in the Examples.

Centrifuge

A sample can be centrifuged in a chamber for a time sufficient to sediment the particles. Cells can be introduced to the chamber without disturbing the particles and briefly centrifuged to sediment them onto the particles. Photon detection can occur during or, more typically, after the spin.

Affinity Capture (Surface Capture)

A sample can be introduced into a microcentrifuge tube, multi-well plate, filter unit, or other suitable device where some portion of the surface in contact with the sample has been modified to be able to bind and retain particles that may be present in the sample through specific or non-specific binding interactions. Non-specific binding may be facilitated via electrostatic/ion-exchange interactions, hydrophobic interactions, hydrophilic interactions, etc. Specific binding may be facilitated by immobilizing components to the surface that bind to substrates on the particles (e.g. antibodies, receptors, glycoproteins, proteins, peptides, carbohydrates, oligonucleotides, etc.), or by immobilizing components that are bound by receptors on the surface of particles (small molecules, peptides, proteins, carbohydrates, etc.).

Affinity Capture (onto Mobile Substrate)

Similar to affinity capture on a surface, but particles are bound to mobile substrates (polymer beads, cells, charged molecules, magnetic beads, bacteria, etc.) that provide additional means of moving and/or localizing the particles or cells by various methods including those described herein.

Flow Cell

Emitter cells can be introduced to a shallow flow cell and allowed to attach to the bottom surface; non-adherent cells can be removed by additional flow. A sample is introduced, displacing much of the cell media, and particles can sediment out onto the attached cells. Photons are emitted as particles contact cells.

Flow Cell (Multiple Cell Lines)

Similar to the Flow Cell, with distinct regions of emitter cell sensitive to different target particles. Photon detection by imaging detector to allow identification of which cells are stimulated, and, therefore, which target particles are present in the sample.

Flow Cell (Magnetic Bead)

This is similar to the Flow Cell. Appropriate magnetic beads are mixed with the sample, allowing target particles to attach to the beads. These decorated beads can be introduced to the flow cell where a strong localized magnetic field (due to a permanent magnet or electromagnet) captures them on the surface above the attached cells. Mixing can be initiated by either removing the magnetic force and allow the beads to sediment onto the cells, or moving the magnetic force to attract the beads to the surface to which the cells are attached.

Flow Cell (Electric Field)

Similar to Flow Cell, with the surface to which the cells attach and the one parallel to it being separate electrodes (at least one of which might be transparent). A sample can be introduced, displacing much of the cell media. An appropriate DC voltage is applied between the electrodes and the particles are moved to the attached cells by electrophoresis.

Tape/Wick

An air sample, possibly containing target particles, can be impacted on a transparent surface, which can be rigid or flexible (e.g., a tape), porous or nonporous. An absorbing material, or wick, can be attached, surrounding the impact area or, in the case of a porous surface, on the opposite side of that surface. Cells can be placed on the impact area, and, due to the wick, excess media will be absorbed, reducing the volume and depth of the media bearing the cells and bringing them closer to the particles. Cells sediment out onto the impacted particles or are, additionally, drawn toward them by flow if the surface is porous with the wick material behind.

Air Impact

An air sample, possibly containing target particles, can be impacted into a (fixed and initially empty) chamber which is suitable for centrifugation. Cells can be introduced to the chamber without disturbing the particles and briefly centrifuged to sediment them onto the particles. Photon detection can occur without, during, or, more typically, after the spin.

Filter Device/Magnetic Bead

A modified syringeless filter device, consisting of a chamber and a plunger with a suitable filter (Whatman™, Mini-Uniprep™, or similar), can be loaded with cells which are allowed to attach to the bottom surface of the chamber; unattached cells can be washed away. A sample can be introduced to the chamber along with magnetic beads with a suitable surface affinity. A modified plunger with a suitable magnet inserted inside and fixed near the back-side of the filter can be inserted into the chamber until the entrapped air escapes through the filter. This assembly can be inverted and (possible after a time to allow the beads to sediment onto the filter's surface) the chamber pushed down onto the plunger. Magnetic beads and particles can accumulate on the filter surface by filtration, sedimentation, and magnetic attraction. Particles can attach to the magnetic beads or be caught among them. Upon re-inverting the assembly, the particles, are held off the cells by the magnetic beads which, in turn, are held by the magnet inside the plunger. Removing that magnet releases the beads, and the particles, which sediment across the short distance onto the cells.

Flow Past Cells

One or more layers of cells can be allowed to sediment onto the surface of a suitable filter or membrane at the bottom of a chamber. A sample can be introduced to the chamber above the cells and pressure applied (by plunger or external pump, for example). As the sample flows past the cells, which are in intimate contact, particles are brought within close range of the cells, allowing contact.

Counter Flow

One or more layers of cells can be allowed to sediment onto the surface of a suitable filter or membrane at the bottom of a 'cell' chamber. A sample can be placed in a separate 'sample' chamber which is connected by some flow channel to the cell chamber at a point below the filter. The chambers can be arranged relative to one another such that, in a centrifuge, the sample chamber is closer to the axis of rotation; the level of the fluid in the sample chamber being closer to the axis of rotation than the fluid in the cell chamber. By this means, during the rotation of the centrifuge, fluid will flow between the chambers seeking a common distance from the axis of rotation. This can force some of the sample up through the filter supporting the cells and past the cells which are being held against that flow by the outward centrifugal force. As the sample flows past the cells, which are in intimate contact, particles are brought within close range of the cells, allowing contact.

Centrifuge Tube Filter

A sample can be introduced to the filter basket of a centrifuge tube filter with a suitable size cutoff. Under appropriate centrifuge conditions, the sample will be forced through the filter, accumulating particles larger than the filter's cutoff size on the surface of the filter. Cells can be added to the filter basket and be given a brief centrifugation to bring them onto the filter surface and the particles.

Dielectrophoretic Trap

Similar to the Flow Cell, but with suitable electrodes on any of the surfaces or projecting into the flow cell. A sample can be introduced by continuous flow past the electrodes, which can be connected to and electrically driven by and external source. For a suitable combination of flow rate, frequency, waveform, and amplitude, particles can be guided to and captured in a region of minimum electric field intensity above the cells by negative dielectrophoresis. After stopping the flow and changing the electrical drive to the electrodes (possibly including a DC voltage on between some electrodes to create an electrophoretic force), the particle can sediment or be driven (by electrophoresis or positive dielectrophoresis) onto the attached cells.

Traveling-Wave Dielectrophoresis

In a shallow cylindrical chamber, suitable electrodes (perhaps transparent) can be fabricated on one or both of the parallel faces, including a central planar electrode to collect particles, an electrode around the periphery, and a set of spiral electrodes (either on the same surface as the central one or the opposite surface). A sample can be introduced to the chamber, and a DC potential applied between the peripheral and central electrodes to attract the particles to the central electrode by electrophoresis. By an exchange of fluids, cells can be introduced to the chamber. Energizing the spiral electrodes with the appropriate phase-shifted AC voltages can sweep the cells to the center by traveling-wave dielectrophoresis, where they can sediment onto the particles.

Dissolvable-Membrane Tube

Figure 20:
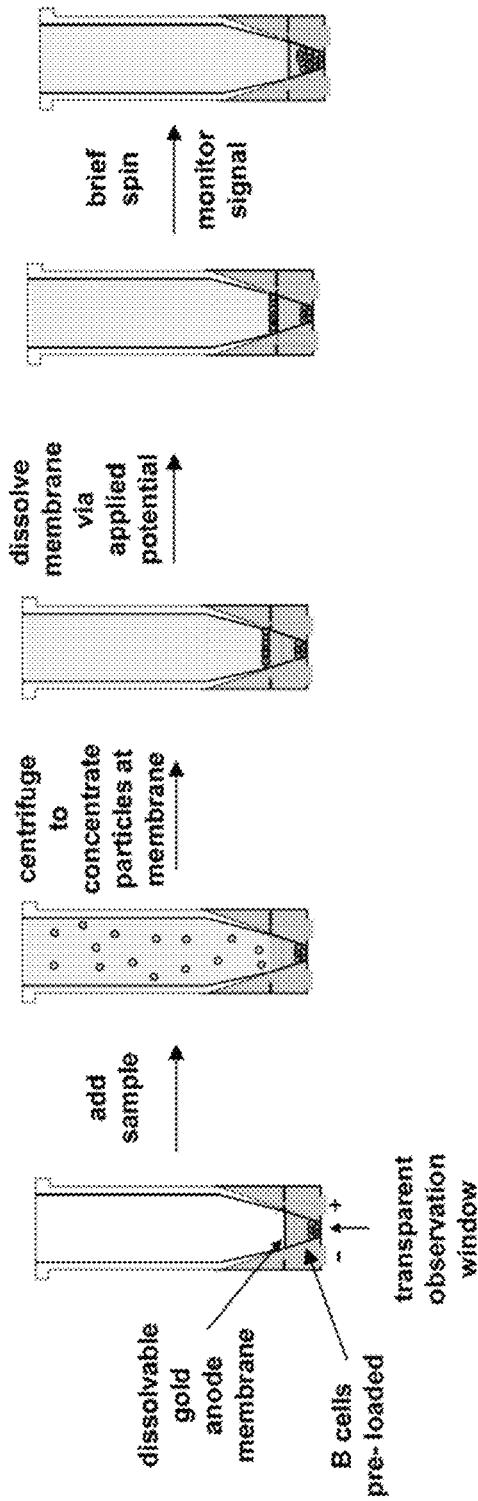
FIG. 20 is a schematic of a custom tube for the optoelectronic sensor.

Use can be made of a electrically-actuated dissolvable gold membrane to maintain isolation between target particles and emitter cells during the localization of the particles by centrifugal sedimentation. Either the particles can be sedimented onto a membrane over the cells (as shown in FIG. 20), or the cells can be held off from the bottom of the chamber by a membrane spanning the bottom of a separate chamber (perhaps an insert). In either case, after the membrane has be dissolved by electrical activation, the particles and cells are mixed by sedimentation, possibly centrifugal.

Acoustics/Ultrasonics

Concentration of particles may be accomplished using acoustic or ultrasonic signals. Particles can accumulate at nodes in a sanding wave pattern, or be move by a traveling-wave pattern. Cells can also be moved this way, or delivered by any of several means discussed above.

Toxin Detection

In order to detect monovalent antigens, it is necessary to induce crosslinking of surface antibodies using one of two general strategies. First, one can express two independent binding sites on the cell surface, such that two receptor molecules can bind to a single ligand. Alternatively, one binding site can be expressed on the cell surface if the ligand is presented to the cell in a manner in which it appears to be polyvalent. The following are specific examples using the model of antibody-antigen recognition.

First, two antibodies can be expressed on the surface of a single cell line, each specific for different epitopes of a individual molecule (epitopes 1 and 2). The binding of a single molecule to two antibodies (one antibody against epitope 1 and another antibody against epitope 2) would initiate crosslinking and light emission. More specifically, a single B cell line is engineered to express two independent antibodies, each recognizing a different epitope on a single molecule. The presence of monomeric antigen is now capable of crosslinking the surface antibodies, resulting in increased intracellular $Ca^{2+}$ and emission of light by aequorin. A cell line that expresses functional antibodies against both *Y. pestis* and *F. tularensis* (in addition to the endogenously expressed PC antibody) has been tested (see Examples). Each of these agents is recognized independently by this cell line, indicating that both antibodies are functional and demonstrating that emitter cells are capable of expressing two functional antibodies simultaneously.

Another potential issue is the sensitivity of the optoelectronic device and methods with an antigen that cannot be pelleted using centrifugal force. The *Yersinia pestis* F1 antigen exists as a low molecular weight polymer in solution, and is therefore not sedimentable in our assay. However, B cells expressing antibody against F1 are capable of detecting soluble F1 antigen at 5 ng/ml. This compares favorably with current immunoassay techniques and demonstrates that the optoelectronic device can be quite sensitive to soluble agents. A complementary experiment was carried out using phosphorylcholine antigen conjugated to ovalbumin. The ability of this small antigen to stimulate antibody crosslinking on the cell surface indicates that this low molecular weight antigen, containing multiple copies of PC epitopes, is able to effectively crosslink surface antibodies and generate calcium influx and photon emission.

A second strategy can improve the limit of detection for monovalent antigens shown above by taking advantage of the centrifugal format. This approach utilizes a scheme where one of the toxin antibodies is expressed on the surface of benign bacteria and the second antibody on the surface of B cells. The toxin can now be sedimented by centrifugation, and B cells expressing the second antibody added. Because multiple antigens are immobilized on the surface of the bacteria, the toxin will in essence appear polyvalent to the B cell, and will initiate a crosslinking event and photon emission. More specifically, Antibody against epitope 1 of a monomeric antigen (e.g. toxin) is expressed on the surface of bacteria. Soluble toxin binds to these antibodies, coating the bacteria with toxin antigen. These toxin-coated bacteria are sedimented by centrifugation prior to addition of B cells expressing antibody against epitope 2. Crosslinking of the B cell antibodies results in light emission by aequorin. Experimental results on this strategy demonstrate the feasibility of detection of bacterial surface antigens, and the increased sensitivity resulting from sedimenting those bacteria prior to the addition of B cells. Similar approaches can also be used for any poorly sedimenting agent to improve its presentation to B cells.

Crosslinking

Crosslinking of target particles can be achieved by any known means. For example, crosslinking can be achieved using one or more intermediate agents or molecules such as a peptide, an antibody, a chemical compound, an antibody, biotin, streptavidin, in addition, crosslinking can be via covalent or non-covalent bonding. Methods for crosslinking also include precipitation or attachment to a solid phase via ligands, antibodies or chemical functional groups, as are known in the art.

Multiplexing Assays

The following is a description of how B cell mixtures can be used to increase the number of detectable antigens without increasing the number of detection channels (tubes, etc). The simplest way to detect multiple analytes is to use a single emittor cell type per detection channel and to increase the number of cell assays by increasing the number of detection channels. This is acceptable for small numbers of assays but, as increasing numbers of analytes are added, the process becomes more complex and resource intensive. It is possible, however, to conduct up to 31 tests with concurrent negative controls in only a 5-channel system if different B cell lines are mixed together.

As an example, if one has a single channel, one can at most detect a single B cell assay. If, however, one has two channels, then one can detect 3 separate assays, where each channel contains an equal mixture of 2 of the 3 separate B cell lines:

For example, if one has 3 B cell lines: A, B, C
And one mixes them into two channels thusly—
2 Channel 1: A, B Channel 2: B, C
Then there are three positive readout possibilities:

| Channel 1 | Channel 2 | |
|---|---|---|
| Yes | No | implies only A is present |
| No | Yes | implies only C is present |
| Yes | Yes | implies only B is present (or that more than one agent is present, which we will consider unlikely for now) |

Similarly, if one has 3 channels, one can detect 7 independent assays, by mixing groups of four cell lines together—

(A convenient shorthand will hereafter be utilized where the cell lines for individual agents are labeled A through a letter corresponding to the number of cell lines, and the channel numbers will be written to indicate what channels are required to detect positively for each individual agent as follows—123: F—means channels 1, 2, and 3 must all register positive to ID agent F).

| Channel 1 | Channel 2 | Channel 3 |
|---|---|---|
| A, B, G, F | B, C, E, F | C, D, G, F |
| 1: A | 12: B | 123: F |
| 2: E | 13: G | |
| 3: D | 23: C | |

A formula embodying the relationship that simply describes the number of independent assays that can be accessed by a given number of channels, assuming all assays are mixed in equal proportion is:

Cell assays=$2^n-1$ where n is the number of channels and the number of cell assays that need to be mixed in each channel is given by $2^{(n-1)}$.

Thus, to mix 16 different B cell lines together, 5 channels are needed to interrogate 31 different assays. The design for a 10-channel system could, in fact, be used to provide ID for 31 separate agents with concurrent negative controls (5-channel positive ID, 5-channel negative control).

The channel mixtures and positive detection correlation for a 4-channel system (15 different assays) is shown below:

| Channel 1 | Channel 2 | Channel 3 | Channel 4 |
|---|---|---|---|
| A, B, G, F, I, K, L, M | B, C, H, I J, L, M, N | F, C, D, I J, K, M, O | D, E, G, H J, K, L, M |
| 1: A | 23: C | 123: I | 1234: M |
| 2: N | 24: H | 234: J | |
| 3: O | 34: D | 134: K | |
| 4: E | 12: B | 124: L | |
| | 13: F | | |
| | 14: G | | |

Without further elaboration, it is believed that one skilled in the art can, based on the above disclosure and the examples below, utilize the present invention to its fullest extent. The following examples are to be construed as merely illustrative of how one skilled in the art can practice the invention, and are not limitative of the remainder of the disclosure in any way.

EXAMPLES

Figure 1:
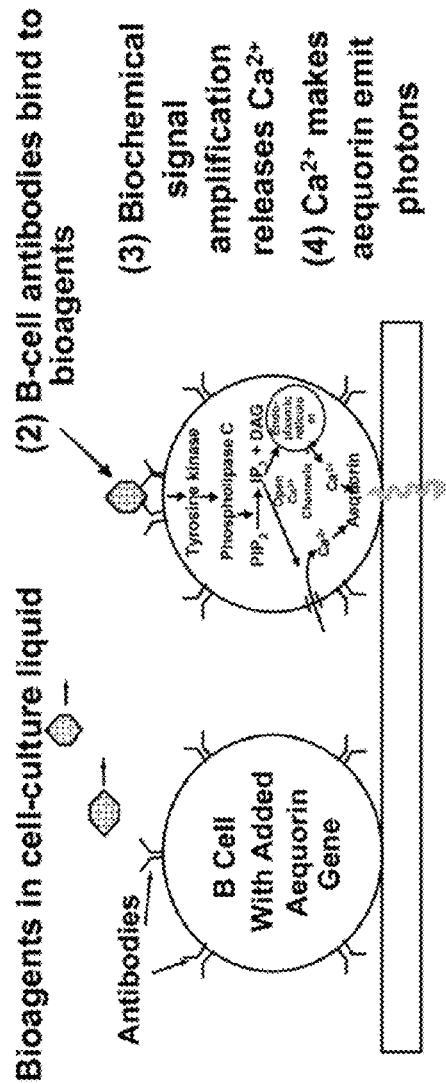
FIG. 1 is a schematic of the optoelectronic sensor cellular concept.

FIG. 1 is a schematic diagram showing the general cellular components of the invention. A cell (here a B cell) that contains an emitter molecule (here aequorin) has antibodies present on its surface. These antibodies are specific for an antigen on a target particle, such as a biological warfare agent. Binding of the target particle to antibodies on the B cell brings two or more antibodies close together on the cell surface, causing a signal transduction cascade that leads to release of calcium from intracellular stores into the cytoplasm. This increase in cytoplasmic calcium concentration causes aequorin to emit a photon. The photon is then captured and registered by a photo multiplier device, such as a CCD. Thus, a cellular biosensor can be implemented using cells having functional surface antibodies and containing a cytoplasmic emitter molecule that responds to increased calcium concentration.

Such a cell-based detection system provides rapid, sensitive, specific, accurate, and flexible detection of any antigen on any target particle. In regard to flexibility, the system can be modified to target any particle or groups of particles. In one example, a single emitter cell can contain a plurality of antibody types, each type being specific for non-overlapping groups of target particles. This single emitter cell can then be used to identify a genus of target particle species at once.

In a second example, a reaction chamber can contain two types of emitter cells. One type of emitter cell contains antibodies that are specific for a genus of target particles (e.g., bacteria) and emits a photon of a first wavelength in response to contact with any member of the genus. The second type of emitter cell contains antibodies that are specific for a particular species within the genus (e.g., *Yersinia pestis*) and emits a photon of a second wavelength different from the first wavelength in response to contact with the species. This arrangement offers extremely high accuracy by reducing or eliminating false positive signals. Only when photons of the first and second wavelength are detected, would a positive event be registered. This nesting of emitter cell specificities can be extended to more than two levels as necessary to reduce or eliminate false positive signals.

Figure 2:
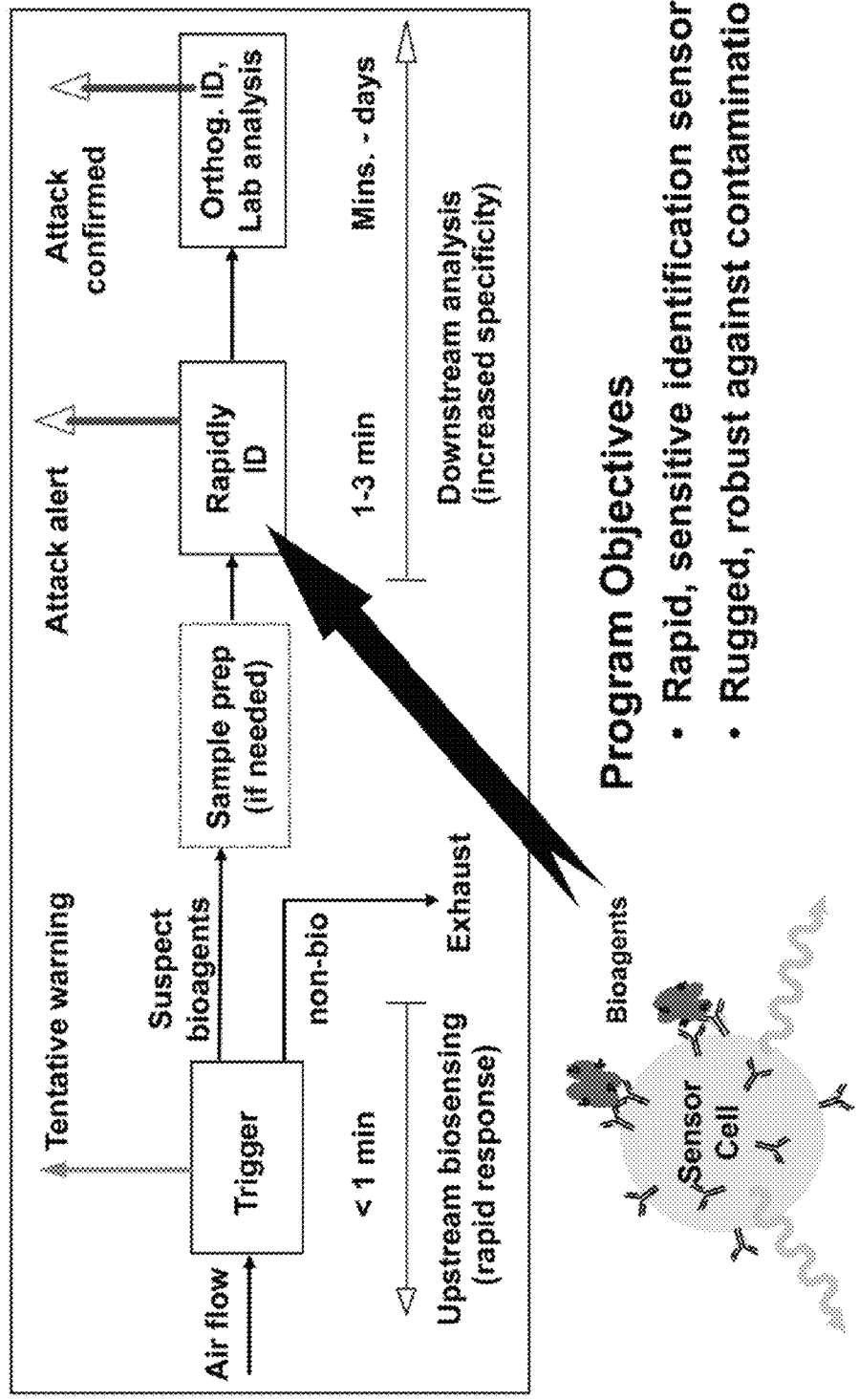
FIG. 2 is a schematic showing the general architecture of an optoelectronic sensor having a sampler (trigger) for preliminary sensing of suspect agents.

FIG. 2 is a schematic diagram of a general architecture and use environment for the invention.

Figure 3:
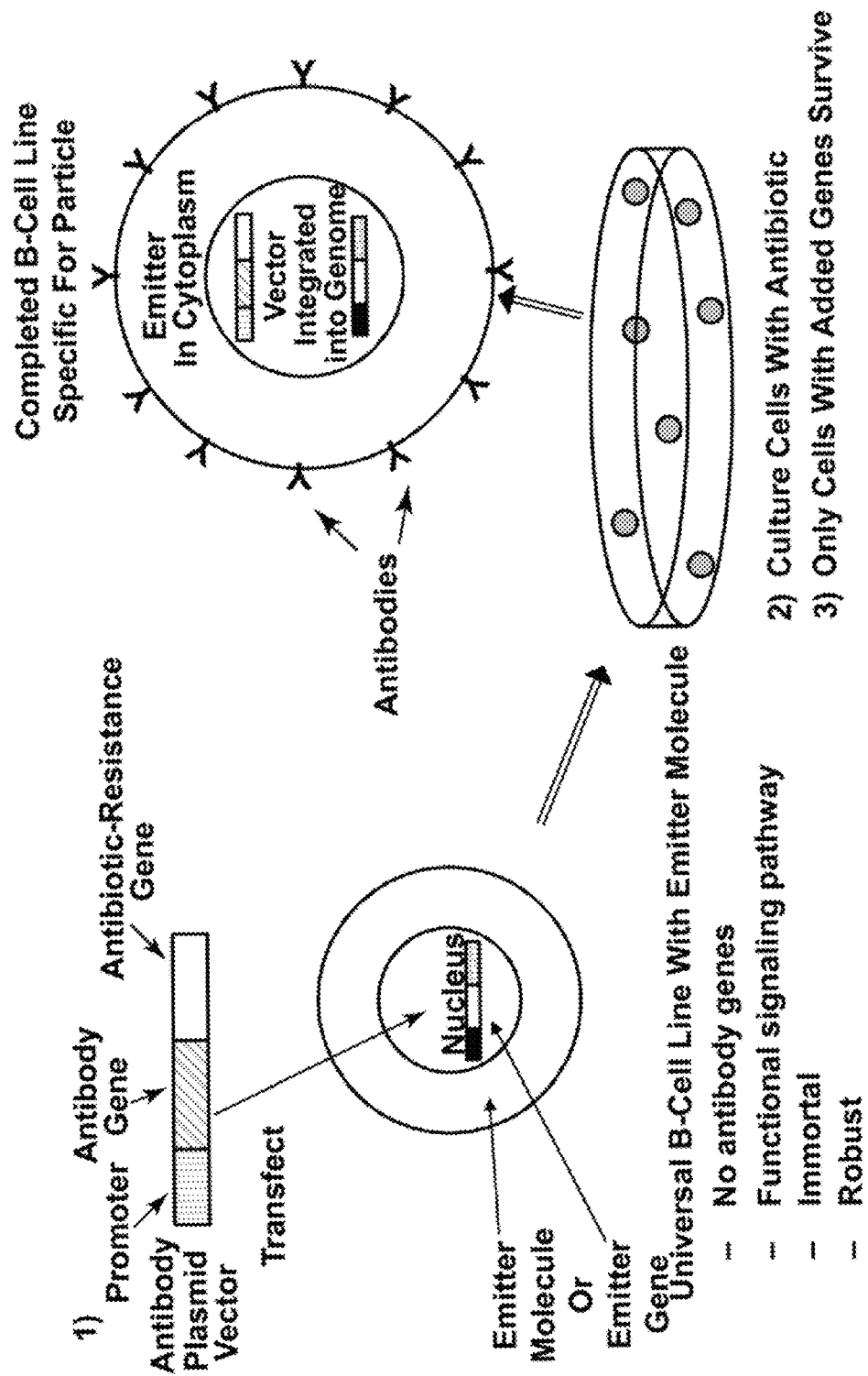
FIG. 3 is a schematic illustrating the creation of cell lines for use in the optoelectronic sensor.

FIG. 3 is a schematic diagram of the molecular biology employed in one embodiment of the invention. In this example, a universal B cell line that expresses an emitter molecule (e.g., aequorin) but does not express antibodies becomes the basis for generating B cells that can express any antibody specific for any antigen. An antibody expression vector is introduced into the universal B cell, selected for the presence of the expression vector, and expanded for use in a detection system of the invention. Using this strategy, in conjunction with pDisplay and VKExpress (described in "Antibodies" section above), target-specific emitter cells were generated for a variety of targets. Emitter cells specific for Foot and Mouth Disease virus (FMDV), Venezuelan Equine Encephalitis (VEE) virus, *Yersinia pestis, Francisella tularensis, Brucella* spp., the O1 and O139 strains of *Vibrio cholera*, and *orthopox* viruses have been produced. The cDNA and sequence for the FMDV antibody variable regions were obtained from the USDA. The cDNAs and sequences for the *Yersinia pestis, Francisella tularensis, Brucella* spp., the 01 and 0139 strains of *Vibrio cholera* antibody variable regions were obtained from investigators at NMRC. The variable regions of the VEE and *orthopox* antibodies were cloned from hybridomas obtained from the CDC and USAMRIID, respectively. Foot and Mouth Disease Virus (FMDV), *Yersinia pestis, Francisella tularensis*, and Venezuelan Equine Encephalitis Virus (VEEV) are responsible for Foot and Mouth Disease, the Plague, tularemia, and encephalitis, respectively. Cloning from the hybridomas was done with a combination of primers described in several published articles. Emitter cells specific for *Bacillus globigii* are being produced because this non-pathogenic bacterium is used by some military agencies as a test organism in field trials of biological warfare agent detection systems. FIG. 5 includes a line graph showing the photon emission response when several clones of FMDV-specific emitter cells were contacted with live FMDV targets. In each case, the emitter cells fired photons within about 20-30 seconds after contact between the target and the cells. Included in the graph is data showing a lack of emission when a mutant FMDV (having single amino acid mutation in the viral coat protein) that would not be expected to bind to the emitter cell was contacted with an emitter cell clone. The negative control supports the high specificity that is built into the detection system.

Various configurations of a centrifuge and photomultiplier tube (PMT) arrangement can be incorporated into a system of the invention. The arrangement includes a rotor (motor) that spins a sample microfuge tube from a swinging harness and includes a balance tube in a fixed position. The PMT is shown at the bottom, facing upwards toward the bottom end of sample tube at rest. In a typical experiment for a target particle that is smaller than the emitter cell, the particle-containing liquid sample is placed in the sample tube and centrifuged under conditions sufficient to sediment the majority of the particles to the bottom of the tube (e.g., 60 seconds at 5600×g for *Francisella tularensis*). A suspension of emitter cells is then layered onto the sample in the tube (so as not to disturb the sedimented particles) and spun briefly to pellet the cells into contact with the target particles. If target particles are present in the candidate particles, photons of a specific wavelength should be emitted from the cells and captured and registered by the PMT.

In specific embodiments, the PMT can be a Hamamatsu HC 125-08 PMT interfaced with a Stanford Research systems SR400 Two Channel Gated Photon Counter. The centrifuge can be a Sapphire 17 turn, 18.5 AWG, 5 amp motor having a swinging bucket configuration.

The centrifuge tube (reaction chamber) can be altered and upgraded as needed to aid contact between candidate particles and the emitter cells. In one embodiment shown in FIG. 20, the tube contains an enclosed compartment that holds pre-loaded emitter cells at the bottom of the tube. This compartment is separated from the rest of the tube by a dissolvable gold anode membrane. In operation, a same containing candidate particles is deposited into the tube and spun to concentrate candidate particles at the membrane. The membrane is then dissolved, and the tube briefly spun to contact the particles with the emitter cells. This dissolvable membrane system is described by Langer and colleagues in Angewantde Chimie International Edition 39:2396-2407, 2000; and Nature 397:335-338, 1999.

The steps in the centrifuge process can be automated or alternatively designed so that the user need not stop the centrifuge at all. For example, the introduction and removal of liquids and samples can be accomplished without the need to stop the rotor by adapting the mechanical features of preparative centrifuges (e.g., ultracentrifuges) available from Beckman Instruments. In addition, it may be desirable to detect photon emission while centripetal forces are still being applied (e.g., when the contact between emitter cells and target particles are unstable without centrifugation). To detect photons emitted from the sample tube while it is spinning, the PMT can be arranged in a radial position relative to the rotor axis. In most cases, the PMT in this arrangement need not be spinning along with the sample tube, but instead can be stationary and simply register emission of photons when the sample tube passes in front of the PMT. If the emission signal is very weak, then the detector (e.g., PMT, a CCD chip) can be coupled to the rotor and spun along with the sample tube. Alternatively, multiple PMrs can be arrayed around a circumference of a rotor for detecting emissions.

Figure 17:
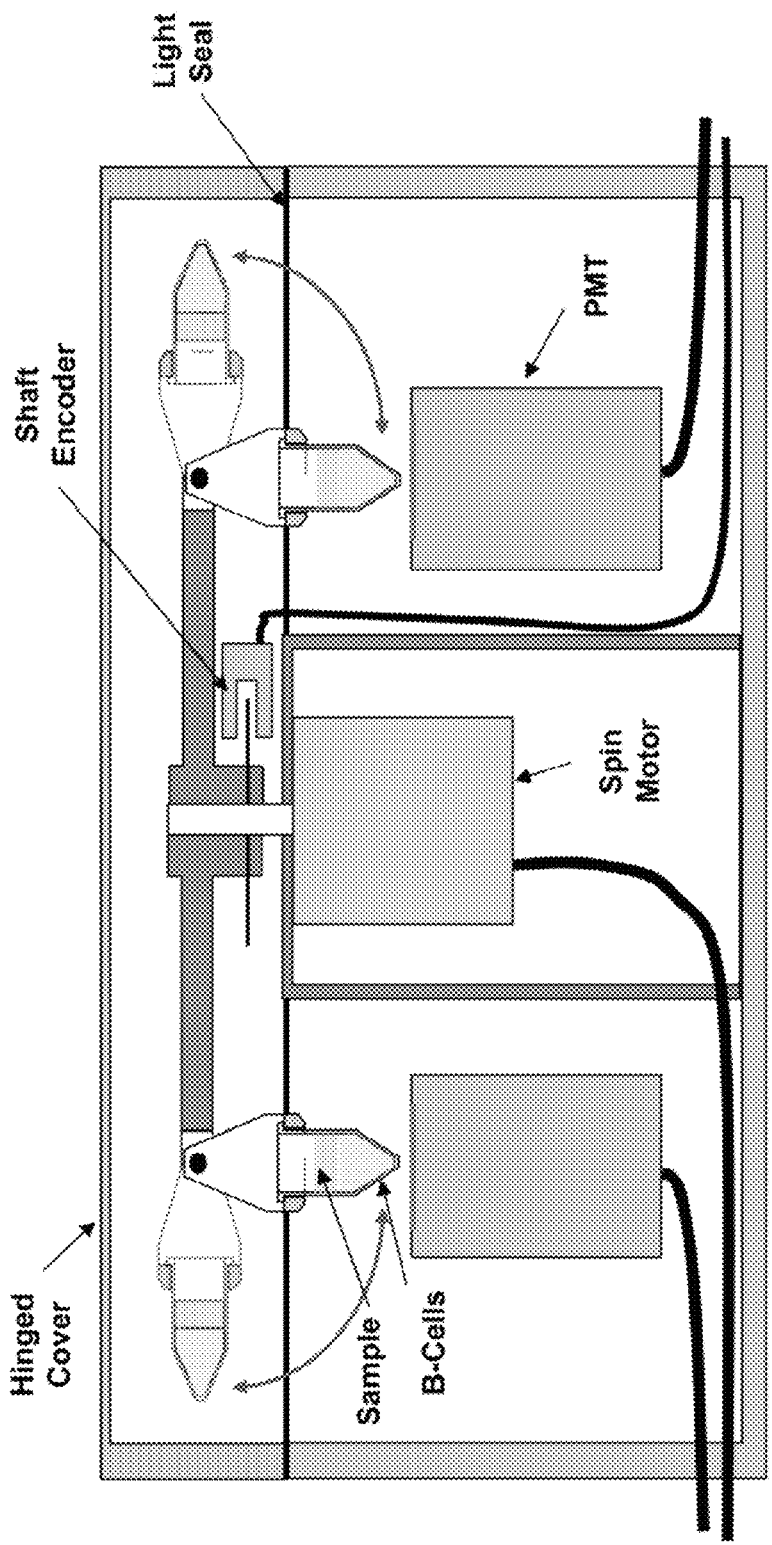
FIG. 17 is a schematic illustrating a multi-channel centrifuge in the optoelectronic sensor.
Figure 18:
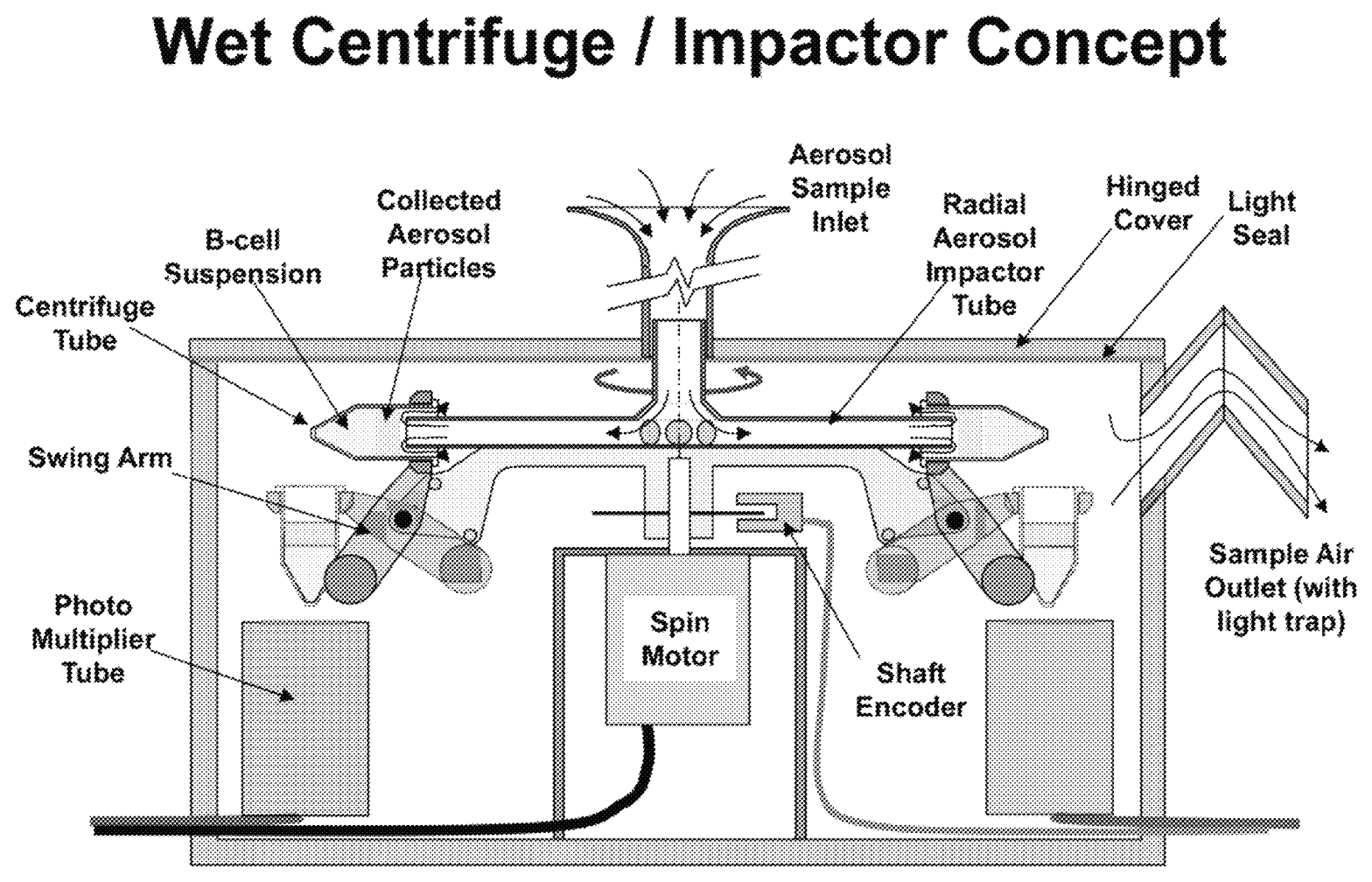
Figure 19:
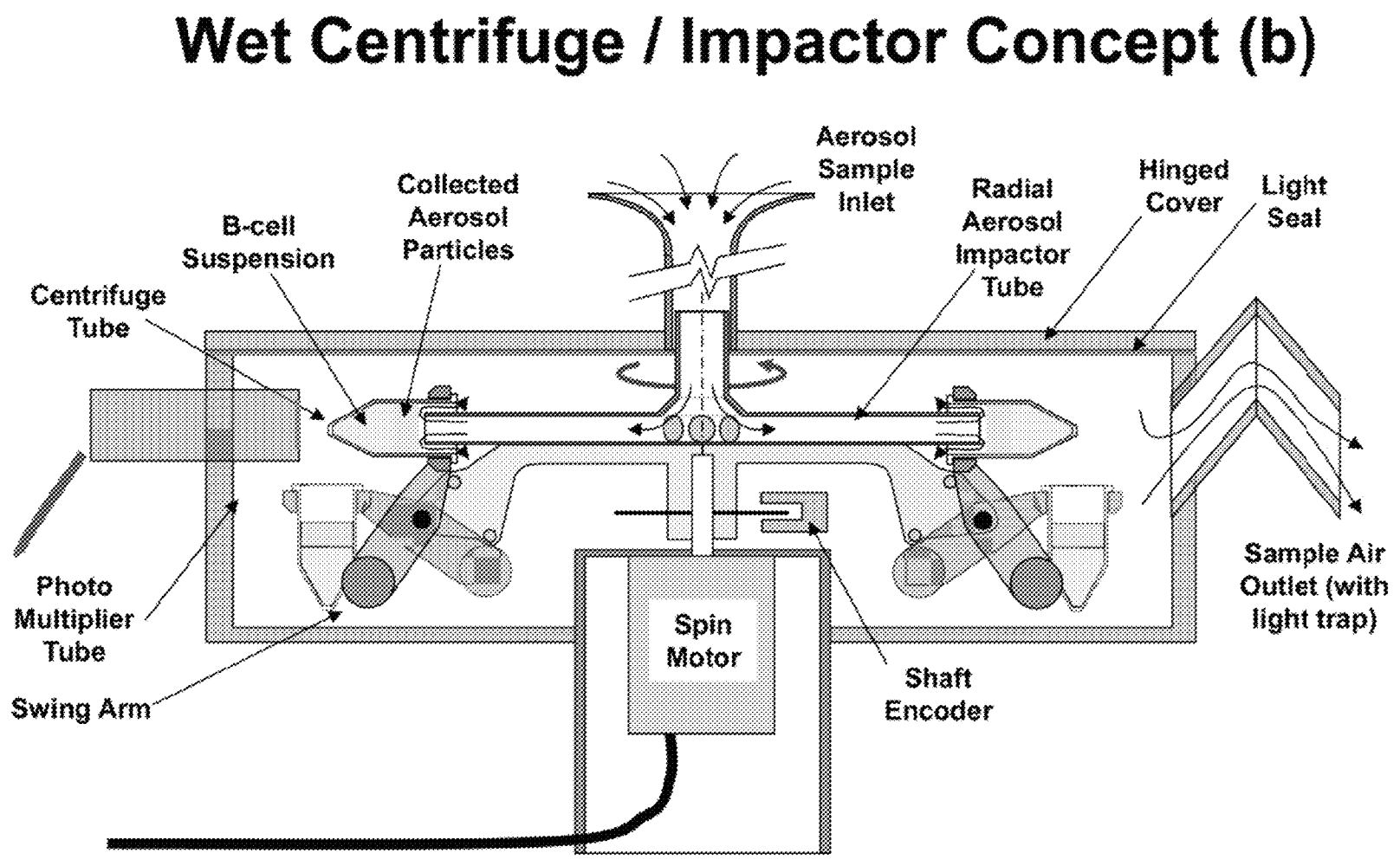

If multiple samples are spun on the same rotor, the positioning or signal processing of the PMT can be altered if necessary. In one embodiment, the rotor accommodates 4 sample tubes, each containing cells that emit at the same wavelength. To differentiate emissions originating from one sample over the emissions from another, a single radially aligned PMT can detect emissions continuously. The continuous emission data is then resolved using a timing trace from the rotor, which monitors the position of each sample over time, to allocate the emissions to each sample. Other variations are understood to be within the invention. For example, FIG. 17 is a schematic drawing of two reaction tubes coupled to a rotor, with two PMTs aligned below the tubes. At a resting position, the rotor positions each of the tubes below the corresponding PMT, using the rotor position encoder. In another example, the centrifuge system shown in FIG. 17 can be integrated with an air sample collector to achieve the system shown in FIG. 18. The radial aerosol impactor tube can include any type of particle monitor, such as described in U.S. Pat. No. 5,932,795 and references cited therein. In still another example, the system described in FIG. 18 can be altered so that only one PMT aligned radially in relation to the rotor axis is required, as shown in FIG. 19. As discussed above, emissions registered by the PMT are resolved for each sample tube using the shaft encoder.

Referring back to FIG. 17, fluid components including, but not limited to, suspensions of B cells engineered to recognize specific bioagents, buffer solutions, preservatives, cell culture medium, can be placed in each of several centrifuge tubes, mixed with a liquid suspension of the sample particles that has previously been collected from aerosol samples in a separate process particles may include but are not limited to, proteins, peptides, chemicals, viruses, bacteria in vegetative and spore forms, fungal spores, pollen grains, protozoa, blood or tissue derived cells, and fragments thereof either alone or in conjunction with carrier particles such as dust). When the spin motor is started, the centrifuge tubes swing out into a radial position, and the B cells and/or sample particles are driven to the bottom of the centrifuge tubes at rates depending upon the size and density of the particles. The exact sequence whereby cell and sample-containing fluids are added and centrifuged can be customized based on their relative sedimentation velocities to maximize signal. In general, it is expected that maximum photon output can be obtained from particles that sediment more slowly than B cells by spinning these samples (a pre-spin) for appropriate times before the addition of B cells and spinning to bring them into contact. For particles sedimenting at similar or faster rates than B cells, a single spin of the mixed sample and B cell components will initiate maximal photon output from the system. Data from particle size analyzers (including but not limited to BAWS units, and fluid particle analyzers) incorporated upstream of the centrifugation device can be used to automatically determine the optimal operation sequence and initiate appropriate computer-controlled automated sample handling.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photomultiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Referring back to FIG. 18, the process of collection of the aerosol particles is integrated with the process of bringing the aerosol particles into contact with the B cells. Here, the centrifuge tubes are attached to swing arms that allow them to cover the ends of radial impactor tubes while spinning, and the aerosol sample is induced to flow into the sample inlet by the centrifugal forces acting on the air in the rotating radial impactor tubes (can be assisted as necessary by additional blower units). The high velocity of the flow causes aerosol particles to impact on the inner surface of the centrifuge tube or the surface of a liquid contained in the tubes and results in the capture of the particles on the surface of the tube or in the liquid, respectively. When a liquid is present, centrifugal pressures acting on the liquid will balance the force imparted by the high velocity air flow required for particle capture in the liquid and prevent it from being blown out by the impacting air. The aerosol particles are retained following impact with the tube surface or liquid and in the case of liquid collection, forced to flow radially outward thereby providing increased local particle concentrations at the maximum radius (the bottom of the centrifuge tube). Addition of B cells and spinning them into the locally concentrated particle zone following the collection phase will initiate photon output. Alternatively, the B cells can be present in the fluid during collection and light output monitored in real time while spinning with a single photomultiplier tube (FIG. 19). In a modified version of this implementation, the fluid components (including but not limited to particle samples collected via an alternative bioaerosol collector, and suspensions of engineered B cells) could be added to the inlet(s), and the centrifugal forces can be used to distribute them to the tubes.

When the "spin cycle" is terminated and the rotor comes to a controlled stop in a pre-determined position controlled by the spin motor and shaft encoder, the swing arms rotate under gravity forces so that the bottoms of the centrifuge tubes are presented to the sensitive surface of the photo multiplier tubes, and any light signals are then recorded. In a modified version of this implementation, a single photomultiplier tube can be positioned at the maximum radius of the rotor/tube configuration and used to collect photons from each tube as they pass by the sensitive surface of the photomultiplier tube in succession. The photon output measured from individual tubes can be assigned and combined based on the monitoring of the shaft encoding system.

Figure 7:
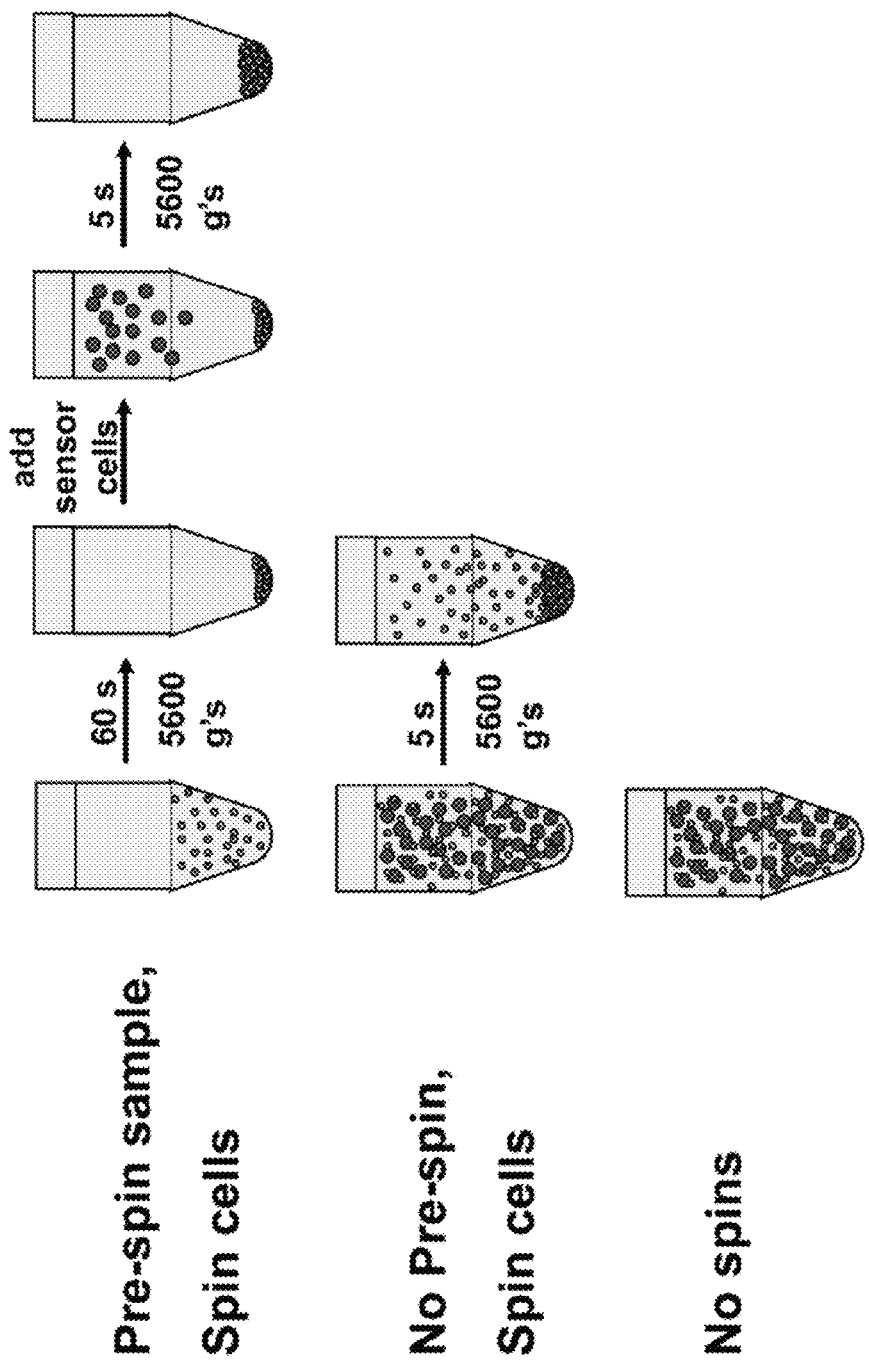
FIG. 7 is a schematic illustrating the effect of localization and mixing.

FIG. 7 is a schematic representation of the results of sequential centrifugations. For target particles smaller than emitter cells but having the same density of emitter cells, it is beneficial to first spin the candidate particles (e.g., at high speed) to pellet them. Thereafter the emitter cells can be added and spun under conditions which can be milder to prevent reduction of their responsiveness as needed (top series). In addition, this sequence of centrifugation forces almost all candidate particles and emitter cells into a relatively small volume at the bottom of a centrifuge tube. In contrast, mixing the candidate particles and the emitter cells together and spinning them at one time will lead to separation rather than contact between the particles and emitter cells (middle series). Of course, no spin at all dramatically reduces the effective concentration of particles and emitter cells in the reaction (bottom series).

Figure 8:
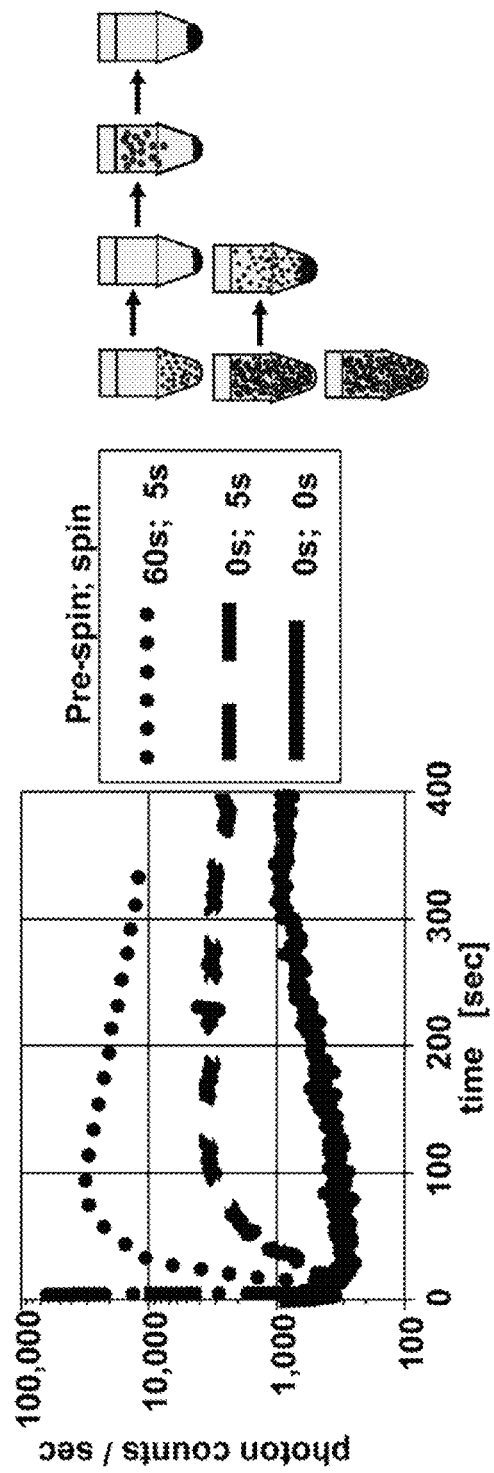
FIG. 8 illustrates the effect of localization using tularemia cells.

FIG. 8 includes a line graph showing in an actual experiment confirming the consequences proposed in FIG. 7. Emitter cells specific for *Francisella tularensis* were mixed with killed *Francisella tularensis* cells in the three methods shown in FIG. 7. As seen in the line graph, the sequential spin method resulted in fast and efficient emission after contact. In contrast, the emission profile of the single spin method was far less pronounced in both timing and magnitude. The no-spin method barely exhibited a reaction.

A similar emission profile was generated in a separate experiment, as summarized in the line graph shown in FIG. 8. Inspection of the emission traces suggested that the single spin method resulted in target-specific emissions a little quicker than the two-spin method. However, this result was found to be primarily an artifact of the longer spin required for the two-spin method and does not reflect an actual improvement in the response time of the B cells. In fact, the initial slope of the two-spin method was significantly greater than that for the single spin method, indicating that the two-spin method led to a robust emitter response.

Figure 10:
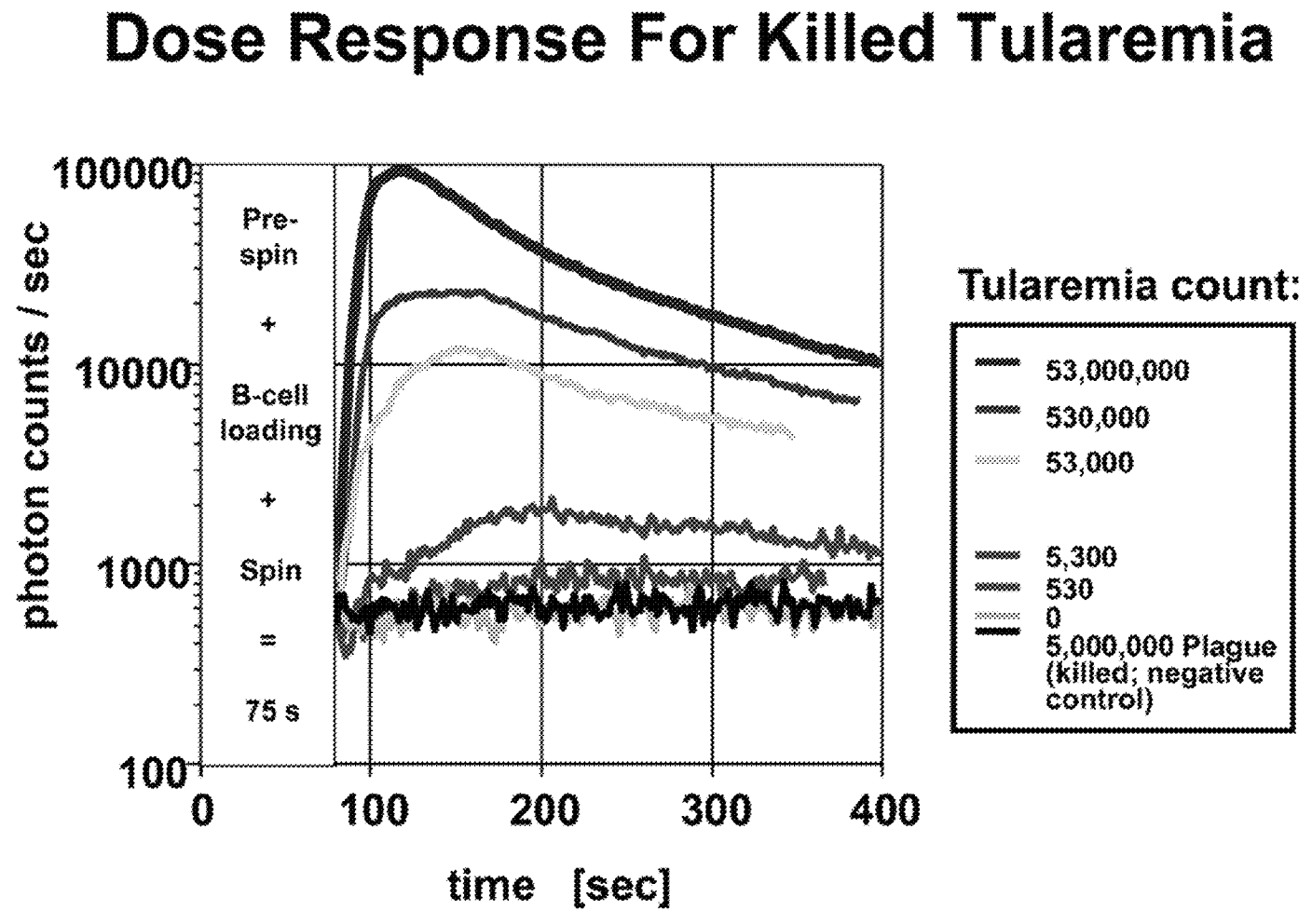

The sensitivity of the detection system shown in FIG. 8 was evaluated by titrating the number of tularemia cells deposited into the centrifuge tube. The results are summarized in the line graph shown in FIG. 10. It appears that 25,000 emitter cells were capable of emitting photons detectable above background in response to about 5,300 tularemia target particles. It is expected that further optimization of reaction conditions will increase sensitivity.

Cell responses are improved after a single freeze-thaw cycle (see FIG. 22). In this experiment, cells specific for *Yersenia pestis* (YP) were centrifuged, resuspended in freezing medium (RPMI with 10% DMSO and an additional 10% FBS), frozen at −80° C., and transferred to liquid nitrogen. Cells were thawed at 37° C. and 1 ml ($2\times10^6$) cells were diluted into to 4 mls of RPMI and incubated overnight at 37° C. The following day the cells were loaded with coelenterazine for 2 hours, washed into $CO_2$—Independent medium ($CO_2$—I) and recovered for 24 hours. 10,000 cells were challenged with $5\times10^5$ YP (50 ul of YP at $10^7$/ml). Untreated cells displayed a response of 9500 photons per second, while frozen thawed cells emitted approximately 6 fold more photons in response to YP. This stimulatory effect could be largely replicated by exposing the cells to freezing medium, without the actual freezing (5 fold stimulation). It appears that the stimulatory factor in the freezing medium is the DMSO.

When cells were treated with 2% DMSO (the final concentration of DMSO when 1 ml of cells in freezing medium containing 10% DMSO is diluted into 4 mls of normal medium) a similar level of stimulation was detected. The DMSO effect may be due to a number of factors. DMSO is known to effect hematopoetic cell differentiation, and may be stimulating the cells through this pathway. Additionally, cells frozen in medium containing glycerol also show similar levels of stimulation. Thus, it appears that the effect can also in part be due to a stress response induced by the DMSO and it can be possible to replicate this stimulation using any of a number of conditions that stimulate a "heat shock" response.

The cells can be stored frozen in the coelenterazine-charged state. Cells were loaded with coelenterazine, allowed to recover for 24 hours, and then frozen. Upon thawing the cells were washed through 10 ml of $CO_2$—I medium and the cells were resuspended in $CO_2I$ medium to a concentration of $5 \times 10^5$ cells/ml. These cells were capable of detecting YP (in this case about 1 hour after thawing, but shorter times are possible). These cells remained capable of detecting agent for several days when stored at RT. Pretreatment of these cells with DMSO, prior to loading with coelenterazine and freezing, can increase the sensitivity of the cells to agent after thawing.

In FIG. 22, cells were challenged with 50 ul of 10,000,000 YP/ml diluted in $CO_2$—I after various cell treatments. Untreated: Cells were grown in RPMI, loaded with coelenterazine, washed, recovered for 24 hours, and challenged with YP. Freeze/Thaw: Cells were grown in RPMI, transferred to freezing medium, and frozen. Thawed cells (1 ml) were placed into 4 mls of RPMI and incubated at 37° C. for 24 hours, loaded with coelenterazine, washed, recovered for 24 hours, and challenged. Freezing Medium: Cells were grown in RPMI, transferred to freezing medium and incubated at RT for 10 minutes. Cells (1 ml) were placed into 4 mls of RPMI and incubated at 37° C. for 24 hours, loaded with coelenterazine, washed, recovered for 24 hours, and challenged. 2% DMSO: Cells were grown in RPMI, transferred to RPMI containing 2% DMSO and incubated at 37E C for 24 hours, loaded with coelenterazine, washed, recovered for 24 hours, and challenged.

A successful biological warfare detection system should be resistant to contamination by common environmental substances present on a battlefield. To evaluate whether emitter cells can operate under environmental stress or contamination, emitter cells were mixed with a target particle after exposure of the emitter cells to one hour of full strength diesel exhaust (left line graph in FIG. 11), or when the emitter cells were contaminated by $10^7$ *E. coli* (right line graph in FIG. 11), which was used as a surrogate contaminant for any field bacterium. As shown in FIG. 11, the particular chemical and biological contaminants tested did not affect the ability of emitter cells to fire photons in response to a target particle.

Figure 13:
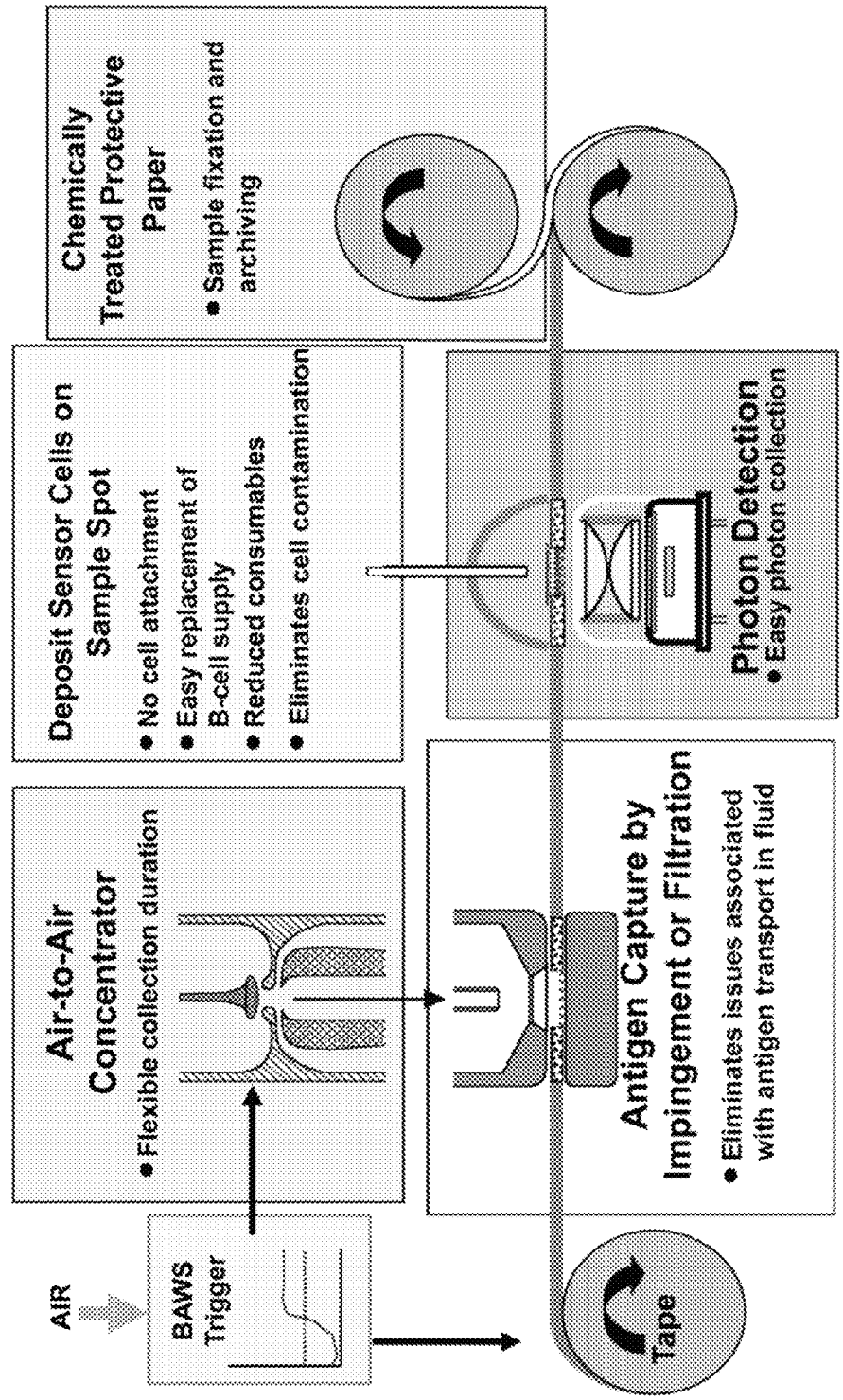
FIG. 13 is a schematic illustrating an air impactor/optoelectronic sensor.
Figure 14:
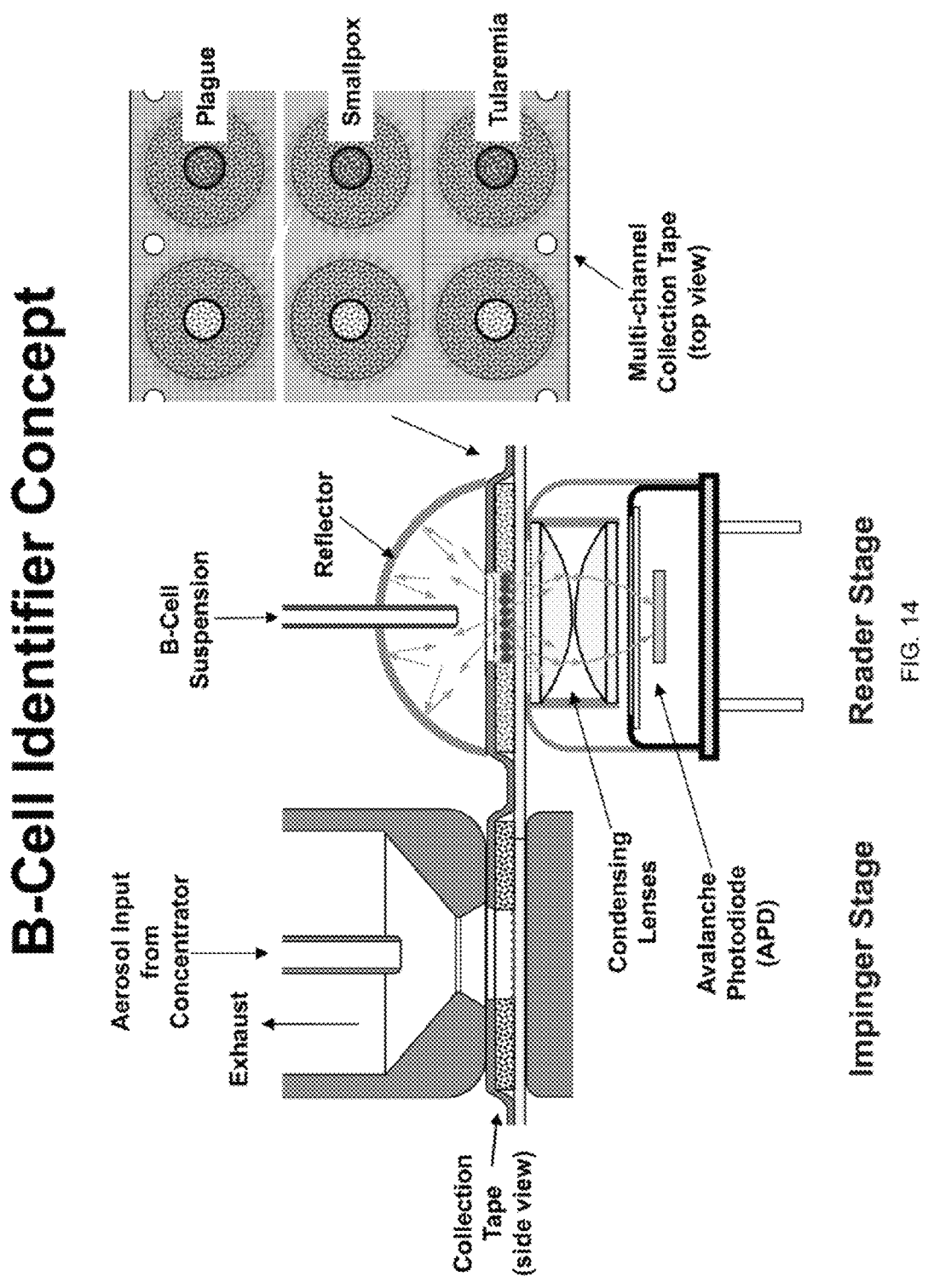

FIGS. 13-14 describe a different embodiment of the invention that does not require centrifugation. The schematic diagram of FIG. 13 shows the various components of this embodiment. A biological aerosol warning sensor (BAWS) detects the present of particles, e.g., within a pre-determined size range. An example of a BAWS is described in Primmerman, Lincoln Laboratory Journal 12:3-32, 2000. If particles meeting specifications are detected, BAWS triggers an air-to-air concentrator (specimen collector; as described in U.S. Pat. No. 5,932,795) that allows particles of a particular size range to be collected and deposited in a well (reaction chamber) on a portion of a specimen tape at a first station, which is shown in different views in FIG. 14. After candidate particles are deposited in the well, the tape advances to a second station under a reservoir of emitter cells and over a PMT. Emitter cells specific for a particular antigen on a target particles are deposited in the well, and the photon emission from the well monitored.

During the time that candidate particles are detected by BAWS, the candidate particles can be deposited on consecutive wells as the tape is advanced through the first station (FIG. 14). In the second station, a plurality of emitter cell reservoirs, each containing emitter cells having different target specificities, are mounted on a turret that rotates a particular reservoir into position to deposit different emitter cells into the well. In this manner, different targets within the candidate particles can be detected, as shown in the schematic top view of the wells in FIG. 14. Of course, if the different emitter cells emit at different wavelengths, it is possible to deposit the different emitter cells into a single well containing candidate particles, provided that the PMT below the second station can distinguish photons of different wavelengths.

FIG. 16 shows schematically yet another embodiment of a system of the invention. In this embodiment, air particles are deposited in each of six wells within a row of a two-dimensional array (e.g., a tape having 6 rows and hundreds of columns) at a first station. As the array is advanced by one row, positioning the row in a second station, different emitter cells are deposited into each well within the row, and emission from all six reactions is detected simultaneously by a row PMTs under the second station. To aid adhesion of particles to the wells on the tape, the wells can be coated with an adhesive or a liquid.

Particular Exemplifications
Methods and Materials
Cell Culture and Transfection

M12g3R cells were maintained at 37° C. in a humidified atmosphere of 5% $CO_2$ in RPMI 1640 supplemented with 10% fetal bovine serum, 1-mM sodium pyruvate, 2-mM L-glutamine, 100-µM nonessential amino acids, 50-µM 2-mercaptoethanol, 50-µg/ml streptomycin, and 50-U/mL penicillin (Life Technologies). Cells were transfected with linearized pCMV.AEQ.IRES.NEO [11] (20 µg of DNA per $10^7$ cells) via electroporation (270 V, 950 µF) and selected in 1-mg/mL G418 for 2 weeks. Antibiotic-resistant cells were incubated in growth medium with 10 µM coelenterazine (Molecular Probes) for 2 h at room temperature, covered in foil, washed twice and resuspended in growth medium. The cells were screened for photon emission in response to anti-murine IgM F(ab')$_2$ in a luminometer.

U937 cells were maintained in RPMI 1640 supplemented with 10% fetal bovine serum. The day before transfection cells were diluted to $5 \times 10^6$/mL. On the next day $2 \times 10^7$ U937 cells were washed once in HBSS and resuspended in 900 µl of HBSS. Twenty micrograms of linearized pCMV.AEQ.IRES.NEO was added to the cells and allowed to incubate for 10 min at room temperature. The mixture was then transferred to an electroporation cuvette (0.4 cm) and electroporated at 250 V and 975 µF. The cells were incubated in growth medium at 37° C. for 48 h, then cloned in medium containing 5-µg/ml Blasticidin by limiting dilution in 96 well plates. After 10-14 days colonies were selected and grown up for screening. Clones were loaded with coelenterazine and screened for response to 5-mM ionomycin. Positive clones were further expanded and characterized.

Antibody Expression Vectors

The light chain expression vector, VKExpress, contains the constant region for the human kappa gene downstream of a multiple cloning site (MCS), under control of the human elongation factor-1α (EF-1α) promoter.

The heavy chain vector was generated by modifying pDisplay (Invitrogen), retaining the cytomegalovirus (CMV) promoter and leader sequence, but replacing the platelet-derived growth factor receptor transmembrane domain with the gene for the membrane-bound constant region of murine IgM and removing both tags on either side of the MCS. The genomic sequence of the membrane-bound constant region of the murine IgM, CμM, was amplified by PCR using primers that contained EcoR I and Not I sites (5' and 3', respectively). The insert, prepared with a blunted EcoR I site and digested with Not I, was cloned into pDisplay-hygro with blunted Bsm I and digested with Not I. The neomycin-resistance gene was replaced with one that confers resistance to hygromycin (Hygro®, obtained from pcDNA3.1 Hygro, Invitrogen) by adding Cla I and BstB I restriction sites to the 5' and 3' ends of the Hygro® gene, respectively, by PCR, and cloning the new antibiotic-resistance gene into those sites in pDisplay. The appropriate restriction sites are added to the antibody variable regions using PCR, and the sequence of all PCR products is confirmed before cloning into the expression construct.

Cloning Antibody Genes

RNA was extracted with Trizol reagent (Life Technologies), according to the manufacturer's recommendations, and first strand synthesis was performed using the Retroscript kit (Ambion). PCR was accomplished using sets of primers designed to anneal to the leader sequences or the framework regions at the 5' end, and the constant or framework regions at the 3' end. Cloning of the variable regions into the expression vectors proceeded as follows. ApaL I and BamH I restriction sites were added to the 5' and 3' ends of the light chain variable regions by PCR with primers containing those sequences, and cloned into VKExpress. The heavy chain variable regions ($V_H$) were cloned into pDisplay-CμM in a two-step process to eliminate the HA and myc tags. First, overlap extension PCR was used to fuse the $V_H$ to the first 300 base pairs (bp) of CμM while, at the same time, adding a Bgl II restriction site to the 5' end. The insert was digested with Bgl II, which also cuts at by 293 of the constant region, and cloned into pDis-CμM digested with the same enzyme. A second overlap extension product fused the $V_H$ to the IgK leader sequence, which was cloned in using the Kpn I and Bgl II sites. We have subsequently modified this cloning process by producing a pDisplay-CμM vector with a Bgl II site immediately following the leader to allow for a single cloning step that eliminates both tags.

CANARY Assay

B cells were prepared for the luminescence assay by incubation in growth medium with the addition of 2% DMSO at a concentration of $5\times10^5$ cells/mL. After 20-24 h, cells were incubated in the dark at room temperature for 2 h in assay medium [CO$_2$-Independent medium, 10% fetal bovine serum, 50-μg/ml streptomycin, 50-U/ml penicillin, and 250-ng/mL amphotericin B (Life Technologies)] with 50-μM coelenterazine (Molecular Probes, Eugene, Oreg.). The cells were then washed twice, resuspended in assay medium at a final concentration of $5\times10^5$ cells/mL in 1.5-mL microcentrifuge tubes, and left to rotate overnight at room temperature.

Test samples were diluted in assay medium and centrifuged in 0.2-mL or 1.5-mL tubes for 2 min in swing-bucket or horizontal centrifuge at maximum speed. The B cells were gently mixed by inversion and 20 μl of cells were deposited on the side of the sample tube. The sample tube was centrifuged for 4 sec in a small, benchtop microfuge (Daigger) fitted with a custom-made horizontal rotor, then inserted in the luminometer (Zylux, FB12). Responses were recorded using the Single Kinetic profile set for 1-sec intervals for a total of 60 sec. Positives were defined as having a signal-to-background ratio≥3 and a peak photon output within the range of 15-30 sec from the start of the 4-sec centrifugation.

U937 cells ($5\times10^5$ cells/ml) were incubated overnight with IFN gamma (200 ng/mL, Sigma) at 37° C. The next day, $7.5\times10^5$ cells were incubated for 2 h in 100 μl of assay medium containing 200 μM of coelenterazine at room temperature in the dark, washed three times in assay medium, resuspended at $5\times10^5$ cells/mL, transferred to 1.5-ml tubes, and rotated overnight at room temperature. Cells were incubated with antibody (10-100 μg/mL of purified, or a 1:1 ratio of hybridoma supernatant to cells) for 5-30 min at 37° C. then washed once and resuspended in assay medium. The assay was performed as described above.

EGFP-Aequorin Expression Construct

To fuse aequorin to GFP we generated a construct containing the enhanced GFP (EGFP) gene fused to a 6 amino acid linker (SGGGSG), followed by the aequorin gene. EGFP was amplified by PCR from the pEGFP-C1 vector (BD Biosciences Clontech), removing the stop codon and adding the linker region to the 3' end of the gene:

```
Sense primer:
                                          (SEQ ID NO: 12)
5'-GCCACCATGGTGAGCAAGGGC-3'

Anti-sense primer:
                                          (SEQ ID NO: 15)
5'-CCTGATCCACCGCCAGACTTGTACAGCTCGTCC-3'.
```

EGFP contains a double-amino-acid substitution (F64L and S65T) and shows enhanced fluorescence intensity compared to GFP. The aequorin gene was amplified from pCMV Aequorin construct, adding the linker region to the 5' end of the gene: Sense primer: 5'-CTGGCGGTGGATCAGGAAT-GACCAGCGAACAATA-3' (SEQ ID NO: 22); Anti-sense primer: 5'-TTAGGGGACAGCTCCA-3' (SEQ ID NO 19). The EGFP and aequorin genes were then linked together by overlap extension PCR with the linker region serving as the overlap region. The fused genes were then cloned into pcDNA3.1-TOPO (Invitrogen) and the sequence confirmed.

Assays for Clinical Samples

Nasal secretions were collected using foam-tipped swabs (VWR Critical Swabs) then seeded with the indicated amount of *B. anthracis* spores and placed in a basket containing a 5-μm filter (Millipore Ultrafree-MC) with 400 μL of assay medium. The eluate was collected in a 1.5-mL microfuge tube with a 2-min centrifugation, a step that also serves to concentrate the spores to the bottom of the tube. After centrifugation, the basket and swab are removed and the assay performed in the same tube.

Human urine (3 mL), to which *C. trachomatis* EBs ($10^2$-$10^5$/mL, Biodesign International) had been added, was passed through a 5-μm syringe filter (Minisart). One half milliliter aliquots were centrifuged for 2 min in a 1.5-mL microfuge tube at 10,000 RCF, the supernatant was decanted and the residual allowed to wick away by placing the edge of the tube against a clean paper towel. The pellet was resuspended by vortexing, 0.5 mL of assay medium was added, and the sample centrifuged again for 2 min at 10,000 RCF. The CANARY assay was performed as described above.

One-half milliliter of whole blood was collected into a custom-made heparinized plasma separation tube and centrifuged for 90 sec at 3500 RCF. The pathogen-containing plasma, with recovered volumes ranging from 50 to 250 μL, was collected into an assay tube by inversion. Fifty microliters of the plasma was mixed with 0.5 mL of assay medium and treated as described above in CANARY assay. To dilute the activator present in human plasma, 450 µL was added to 50 µL of plasma. To remove the activator by adsorption, 50 µL of plasma was incubated with 50 µL ($2\times10^5$ cells) of the parental B-cell line, M12g3R, for 10 min at room temperature. The cells were sedimented with centrifugation at 1500 RCF for 1 min to pellet cells, the plasma transferred to a clean tube and centrifuged at maximum speed for 2 min.

To construct the device for intracellular pathogens in blood, 200 µL of FICOLL™ HYPAQUE™ solution is placed in the bottom of a Capiject blood collection tube (T-M, Terumo Medical Corp.). The polyester gel from a CPT (Becton Dickinson Co.) is placed on top of the FICOLL. In order for proper separation of the blood cells to occur the whole blood must be diluted at least 6:1 with phosphate buffered saline (PBS); therefore 100 µL of PBS is placed over the gel. Heparinized whole blood (600 µL) is placed into the tube, the tube is inverted to mix the blood with the PBS and the device is centrifuged for 90 sec at 3500 RCF. The red plug in the top of the device is replaced with an assay tube and the plasma and white blood cells are collected in the assay tube by inversion. Liberation of intracellular pathogens is achieved by adding 600 µL M-Per cell-lysing reagent (Pierce Biotechnology, Inc.) to the assay tube and incubating at room temperature for 5 min with periodic vortexing. The sample is centrifuged at 18,000 RCF for 1 min, the supernatant replaced with 500 µL of assay medium, mixed by vortexing, and the centrifugation repeated. The sample is analyzed for the presence of pathogen as described above.

*Chlamydia* Validation

The following organisms were tested for cross reactivity with the *C. trachomatis* cell line: *Pseudomonas aeruginosa, Streptococcus pyogenes, Enterococcus faecalis, Neisseria gonorrhoeae, Branhamella catarrhalis, Salmonella enteritidis, Escherichia coli, Klebsiella pneumoniae, Proteus mirabilis, Acinetobacter baumanii, Staphylococcus epidermidis, Streptococcus pneumoniae, Staphylococcus aureus, Candida albicans, Corynebacterium minutissimum, Lactobacillus acidophilus, Streptococcus agalactiae, Staphylococcus saprophyticus, Streptococcus* group D, *Streptococcus mutans, Garderella vaginalis, Gemella morbillorium*. Serovars of *C. trachomatis* were obtained from Biodesign International.

Background

CANARY utilizes B cells that have been genetically engineered to produce aequorin, a calcium-sensitive bioluminescent protein originally found in the *Aequorea victoria* jellyfish. The system works as follows: (1) B cells can be exposed to suspected bioagents or other pathogens from an air sample, blood sample, or other source. (2) B cells have antibodies specific for certain bioagents. If one of those agents is present in the sample, it will bind to the antibodies on the surface of the B cell. (3) Crosslinking of a B cell's antibodies by a bioagent triggers an intracellular enzymatic cascade that releases calcium inside the cell. (4) In the presence of calcium, the aequorin emits blue-green light at 469 nm. (5) Light from stimulated B cells can be detected using a photomultiplier tube or other photodetector.

We have genetically engineered B-cell lines that express both (1) antibodies specific for bacterial and viral pathogens, and (2) the aequorin protein. Functional aequorin consists of the protein apoaequorin and its substrate, coelenterazine, which is a chemical that can spontaneously cross the cell membrane and binds to apoaequorin. After binding calcium ions, aequorin undergoes a conformational change causing the oxidation of coelenterazine and the emission of light. Activated aequorin-containing B cells, made antigen specific by transfection with DNA expression vectors for recombinant antibodies, emit light when exposed to polyvalent antigen. When incorporated into an appropriate sensor format, these cells can be of tremendous benefit to medical diagnostics, detection of biological warfare agents, and monitoring of the quality of food, water, and air.

The B-cell detection system is intrinsically so fast (identification in <1 sec) that the primary delay in the assay is the time required to bring the pathogens in contact with the B cells. This problem is not trivial, as the pathogens and B cells are essentially microscopic viscoelastic particles that tend to slide past each other in a fluid environment. We have solved this problem for bacteria and large viruses by using centrifugal force to drive the particles together. When the agent and B cells are simply placed together in suspension, the signal response is delayed in time and low in magnitude. When the agent and B cells are pelleted by a 5-sec spin, both the speed and magnitude of response improve. However, the greatest improvement in both speed and magnitude occurs when the agent is pre-pelleted, prior to addition of the B cells. The B cells are then driven into the pellet by an additional 5-sec spin.

Data was obtained for the bacterial pathogens *Francisella tularensis* and *Yersinia pestis* using this centrifugal format. These data collectively demonstrate excellent specificity as well as the best combination of speed and sensitivity (50 cfu in approximately 3 min) of any known pathogen identification method.

For larger viruses such as smallpox, which can be sedimented quickly at low speeds, the present centrifugation method works well. However, we have also engineered cell lines to produce antibodies specific for viruses such as FMD, Dengue, and VEE, which are too small to be concentrated under the same conditions. Although the LOD for small viruses is approximately 500,000 cfu in a 1-min assay, that number can be improved by as much as 100 fold with longer centrifugation or affinity purification.

CANARY B-Cell Sensor for Rapid, Sensitive Identification of Pathogens in Clinical Samples Introduction We describe a novel sensor that provides the best combination of speed and sensitivity yet demonstrated for any pathogen-identification technique. Our approach uses B lymphocytes, members of the immune system that have been optimized by nature to identify pathogens. We have engineered B-cell lines to express cytosolic aequorin, a calcium-sensitive bioluminescent protein, as well as membrane-bound antibodies specific for pathogens of interest. The crosslinking of membrane-bound antibodies by a polyvalent antigen induces a signal-transduction cascade that sequentially involves tyrosine kinases, phospholipase C, and inositol triphosphate ($IP_3$). $IP_3$ activates calcium channels, thereby increasing cytosolic calcium from both internal stores and the extracellular medium, which activates the aequorin, which emits light. This sensor, which we call CANARY, can detect <50 cfu of pathogen in <3 min, including the time required to concentrate the samples. In contrast, even state-of-the-art immunoassays take at least 15 min and have a much higher limit of detection, and while the PCR can be both highly specific and sensitive, most reports cite protocols that take >30 min. Although an ultrafast PCR with detection of 5 cfu in only 9 min has been reported, even when coupled with the most rapid sample-preparation technology the total assay requires 20-30 min to complete. Because of its unique combination of speed and sensitivity, CANARY could revolutionize pathogen identification in medical diagnostics, biowarfare defense, food and water-quality monitoring, and other applications.

We first developed a genetic-engineering system that allows efficient production of a variety of B-cell lines. We generated a parental cell line with stable expression of cytosolic aequorin from the M12g3R (IgM+) B-cell line, selecting the clone with the maximum emission of light upon crosslinking of the surface IgM. The M12g3R-aequorin cells are subsequently transfected with plasmids containing antibody light and heavy chain constant regions, into which we insert the variable regions specific for a particular target. Clones from the second transfection are selected based on their response to that target. In order to provide an idea of the range of agents that can be identified using CANARY, we have listed all of the 24 cell lines we have developed in the Table below.

| Detectable targets for CANARY cell lines | | |
|---|---|---|
| *Bacillus anthracis*, spores | *Bacillus subtilis* spores | *Potyvirus* |
| | *Salmonella* spp. | *Phytophthora* spp. |
| *Bacillus anthracis*, vegetative | *Shigella dysenteriae* | Rift Valley Fever virus |
| | *E. coli* O157:H7 | |
| *Francisella tularensis* | FMD virus | *Listeria* spp. |
| *Yersinia pestis* | Dengue virus | *Listeria monocytogenes* |
| *Vibrio cholerae* O139 | Orthopoxviruses (smallpox) | |
| *Vibrio cholerae* O1 | | VEE virus |
| *Brucella* spp. | *Ralstonia* spp. | Ovalbumin |
| *Chlamydia* spp. | | Botulinum toxin |

Results

The CANARY Assay

As little as 50 cfu of *Yersinia pestis*, the bacterium that causes the plague, is detected in less than 3-min total assay time. However, there is no response to relatively large numbers of an unrelated pathogen, *Francisella tularensis*. Furthermore, even an overwhelming amount of unrelated pathogen does not block the response to as few as 50 cfu of *Y. pestis*. In fact, for most bacteria or viruses large enough to be concentrated in a microcentrifuge, we have observed similar levels of sensitivity of ~50 cfu or pfu. When the sensitivity of the *Y. pestis*-specific cell line was tested repeatedly over several months, the CANARY sensor could detect 20 cfu 62% of the time (n=73), 50 cfu 79% of the time (n=38), 200 (n=74) and 2000 cfu (n=71) 99% of the time, and 20,000 cfu 100% of the time (n=66). A false-positive rate of only 0.4% (n=1288), combined with a level of sensitivity approaching that of PCR and an assay that can be performed in less than 3 min, makes CANARY one of the most promising pathogen-identification technologies currently in development.

Because the rate of diffusion determines the interactions between B cells and non-sedimentable targets, the sensitivity of CANARY for small viruses is higher than that for bacteria and large viruses. For example, B-cell lines specific for the A12 strain of foot-and-mouth disease virus (FMDV) produce an easily distinguishable signal when exposed to $7\times10^5$ plaque-forming units (pfu). Similarly, the sensitivity of the B-cell line specific for Venezuelan Equine Encephalitis (VEE) virus, tested with strain TC-83 that had been titered prior to inactivation, demonstrates a detectable signal from $5\times10^5$ pfu.

The specificity of CANARY is determined by the antibody the B cells express, and can be as broad or narrow as the antibodies that are available. For example, while the FMDV cell line responds to wild type A12 virus, no light is detected after the addition of an equivalent amount of the A12 variant strain (B2PD.3) that differs by three amino acids, a change that disrupts the antibody-epitope interaction. In contrast to the specificity of the FMDV cell lines, which react to only one strain of FMDV, the VEE B-cell line exhibits specificity similar to that of the parent monoclonal antibody, reacting with VEE strains representing subtypes IA (TC-83, TRD), IB (PTF-39), IC (P676), ID (3880), and IE (Mena II). The M12g3R parental line (control B cells) was also tested for reactivity with the different strains of VEE, and although they exhibit a nonspecific signal in the presence of the TC-83 and TRD antigen preparations (those isolated from suckling mouse brain but not from tissue culture), the signal produced by the specific B-cell line is clearly distinguishable from that of the control (>10-fold). We have also produced a VEE B-cell line from hybridoma 1A4D-1, which recognizes all but the Mena II strain listed above. Therefore, given suitable monoclonal antibodies, the specificity of the B-cell lines can be designed to have either a broad or narrow range of reactivity based on the antibodies that we choose to express. This greatly increases the flexibility of the system by designing it to distinguish organisms at the genus, species, or subspecies level, depending on the application.

Improvement in Sensitivity for Small Viruses

Several methods of small virus concentration and sedimentation have been tested for their ability to improve CANARY responses to these agents. Precipitation with methanol, TCA, or sodium phosphotungstate did not improve sensitivity, nor did absorption to nitrocellulose. Centrifugal concentrators from various vendors appeared to bind nonspecifically to the low concentrations of virus used in CANARY assays. Two methods have thus far shown good results: centrifugation and affinity purification.

Inactivated TC-83 VEE was used for all of the following virus concentration experiments. To generate physiologically relevant virus samples, VEE aggregates were removed by passage through 0.1-μm syringe filters. Samples were then centrifuged for different times and analyzed by CANARY. Centrifugation for 1 min sedimented little virus, 5 min gave intermediate results, and sedimentation approached completion in 10-30 min. This pattern was in much closer agreement with theoretical sedimentation rates for monomeric VEE, indicating that we have produced a test sample with similar sedimentation characteristics to those expected for real samples. This also demonstrates that centrifugation of monomeric VEE for 10-30 min in a microfuge increases the signal, and therefore the sensitivity.

Further experiments examined sonicating the aggregated material to improve monomeric virus recovery. The LOD was improved in sonicated samples (500,000 pfu*) compared to the untreated sample (50,000,000 pfu*), which reflects an increase in the quantity of monomeric virus present and able to pass through the 0.1-μm filter. The sample that was sonicated before filtering produced nearly 100 times more signal than the sample that was not sonicated. The sedimentation rate of the monomeric virus produced using sonication is also similar to the theoretical sedimentation rates, indicating that sonication did not fragment the virus to an extent detectable in these assays. Centrifugation can improve the sensitivity by a factor of 100.

A second effective method for improving CANARY sensitivity to small viruses is affinity purification. Monoclonal antibodies against VEE were conjugated to protein G-coated magnetic beads. This affinity resin was then incubated with media containing VEE, the resin washed to remove unbound virus, and CANARY cells used to detect the virus attached to the sedimented resin. Incubation of VEE with these affinity resins for as little as 15 min clearly increased the amplitude of the CANARY cell response, and improved the LOD by a factor of 10.

Both affinity purification and centrifugation methods result in improved CANARY responses to small virus. The method chosen will depend on the type of sample to be examined. Samples containing sedimentable or soluble interferents may be amenable to affinity purification of agents using magnetic beads. Samples containing soluble interferents or lacking interferents altogether may be assayed using centrifugation protocols.

Rapid Cell Engineering

Generation of pathogen-specific CANARY cells requires an available hybridoma cell line, involves several steps, and can take several months. There is a need to develop a universal cell line that can be used to generate new pathogen-specific cells in a rapid (<1 day) but specific manner, utilizing the CANARY platform. To address this issue, we explored using the Fc receptor as a possible "adaptor" molecule to attach pathogen-specific antibodies to CANARY cells. The Fc receptors are a family of membrane-expressed proteins that bind to antibodies or immune complexes. They are expressed on several hematopoietic cells including monocytes and macrophages. Several subclasses of Fc receptors exist including Fcγ Receptor I (FcγRI), a high-affinity binder of soluble antibody. FcγRI binds to the constant region (Fc portion) of Immunoglobulin G (IgG) leaving the antigen-binding region of the antibody free. Crosslinking of the antibody-bound receptor by specific antigen initiates a signaling pathway that stimulates calcium release.

The human macrophage cell line, U937, contains endogenous FCγR1 which can be upregulated upon treatment with IFNγ. Initial experiments demonstrate that U937 cells can be engineered to rapidly to respond to several different pathogens or simulants. U937 cells were treated for 24 h with IFNγ (200 ng/ml) to increase expression of endogenous FcγRI, and prepared for the CANARY assay. Then the cells were incubated with the following antibodies: mouse anti-*B. anthracis* spore, rabbit polyclonal anti-*B. anthracis* spore, mouse anti-*F. tularensis*, or mouse anti-*B. subtilis*. Cells were then used in the standard CANARY assay where they detected as few as 1000 cfu *B. anthracis* spores with the monoclonal antibody and 10,000 cfu spores with the rabbit polyclonal, as well as 10,000 cfu *F. tularensis* and 1,000 cfu *B. subtilis* spores. Although not as sensitive as the genetically engineered B cells, we have demonstrated the development of a rapidly engineered CANARY cell that requires days instead of months.

Multiplexed Assays

We have evaluated the feasibility of combining several different B-cell lines in a single assay. This would allow the detection of several agents with a single test, though it would not distinguish which agent is in the sample. Detection of 3 different agents with a single cell reagent was demonstrated where the limit of detection for *B. anthracis* was 50 cfu of B.a., *Y. pestis* was 50 cfu of Y.p., and *F. tularensis* was 500 cfu of F.t. At an optimized cell concentration and amount of 40 μL of $1.25 \times 10^5$ cells/mL, we were able to show that 4 cell lines can be combined without any loss in sensitivity.

A second method of multiplexing is cell lines that express more than one antibody and can respond to more than one agent. We have generated a cell line that expresses two antibodies, one specific for *B. anthracis* spores and the other for *Y. pestis*. This cell line was used to detect only 50 cfu of either *B. anthracis* spores or *Y. pestis*, demonstrating that we can create a cell line with multiple detection capabilities without any loss in sensitivity.

A third method that provides a multiplexed assay is CANARY cell lines that emit light of different wavelengths. In the jellyfish *Aequorea victoria* aequorin is naturally associated with green fluorescent protein (GFP). When the aequorin binds calcium and oxidizes coelenterazine it transfers its energy to GFP and stimulates the emission of green light (λmax, 509 nm). This naturally occurring chemiluminescence resonance energy transfer (CRET) activity can be reproduced in vitro by fusing the aequorin protein to GFP. GFP can be genetically modified to produce various fluorescent proteins including cyan fluorescent protein and yellow fluorescent protein. Fusion of aequorin to different GFP constructs can generate several aequorin proteins capable of producing light of different wavelengths. CANARY cells expressing these aequorin-GFP proteins provide a multiplexed assay, where detection of one or more wavelengths allows the identification of several pathogens in a single assay. This type of multiplexed assay has several advantages, including the identification of several pathogens in a single assay when the sample size is limited, the ability to test for multiple pathogens at one time when using a single channel sensor, and the potential to decrease false-positive rates in multi-channel sensors by increasing the number of replicates.

The EGFP-aequorin construct was transfected into M12g3R murine B cells and the clones were screened by response to anti-IgM stimulation. Positive clones were analyzed on a flow cytometer where cells expressing EGFP (λmax, 509 nm) can be detected in the FL1 channel, which measures light in the green spectrum from 515 to 545 nm. In order to further demonstrate that the cells expressing EGFP-aequorin are emitting a different wavelength of light than those expressing wild-type aequorin, we analyzed the light output with two photomultiplier tubes (PMTs) with different band-pass filters, 480 nm and 510 nm. The cells were stimulated with anti-IgM, and the light was measured simultaneously by both PMTs. Because the emission spectra of aequorin and the EGFP-aequorin overlap, the results are expressed as the ratio of green/blue light. The amount of green light emitted by the cells expressing EGFP-aequorin was significantly higher than that emitted by the cells expressing wild-type aequorin. Interestingly, unlike wild-type EGFP that fluoresces in the absence of any cofactor, the EGFP-aequorin required the presence of the aequorin cofactor, coelenterazine, before fluorescence was observed.

Development of Assays for Clinical Samples

There are many applications where a rapid pathogen-identification technique would be extremely valuable. For instance, a rapid test would ensure timely, accurate treatment of patients in the early stages of infection where immediate treatment is important, as in the case of inhalation anthrax. We therefore investigated the use of CANARY for detecting pathogens in clinically relevant samples. As few as 50 cfu of *B. anthracis* spores added to nasal swabs prior to sample preparation can be detected. In this protocol the swabs were placed in a basket containing a 5-μm filter with 400 μL of assay medium. The eluate was collected in a 1.5-mL microfuge tube with a 2-min centrifugation, a step that also serves to concentrate the spores to the bottom of the tube. After centrifugation, the basket and swab are removed and the assay performed in the same tube. The total assay time is less than 5 min, and thus, CANARY provides an excellent first screen for people who may have been exposed to aerosolized *B. anthracis* spores, thereby allowing immediate treatment.

Another example is the need for rapid point-of-care diagnostic tests to ensure treatment and control of diseases, such as those that are sexually transmitted, for which there is a high rate of medication noncompliance. *C. trachomatis* is a sexually transmitted disease that has a high prevalence, can cause pelvic inflammatory disease and fertility problems, and is underdiagnosed because of the high number of asymptomatic cases. Historically, the disease has been diagnosed from cervical or urethral smears with tests that require considerable time and expertise. Although the elementary bodies (EBs) of the organism can be found in the urine, a less invasive sample to collect, it is present in such low numbers that, until recently, the only tests sensitive enough to be effective are those that amplify nucleic acids. In a recent report, the concentration of *C. trachomatis* in urine from infected patients was determined to range from 30 to $2 \times 10^5$ EBs/mL using a quantitative ligase chain reaction, an assay that takes several hours to perform (Abbott). Due to the rapid performance of CANARY, we were able to demonstrate detection of 500 *C. trachomatis* EBs in urine in less than 5 min. Thus, CANARY is also useful as a rapid, sensitive assay for the diagnosis of *C. trachomatis* infections in a noninvasive test.

Whole blood is a difficult matrix to assay because of its opacity and the presence of both activators and inhibitors of the CANARY assay. The method we have developed relies on the use of plasma-separation tubes (PST) and differential centrifugation. This process uses a thixotropic gel with a density between that of plasma and blood cells, which forms a barrier between the plasma and cells during centrifugation. Any bacteria or viruses present in the blood remain in the plasma phase after centrifugation, which can then be harvested and tested in CANARY. Using a device assembled from commercial off-the-shelf ("COTS") parts, we have demonstrated the separation of whole blood samples in three rapid, simple steps. One-half milliliter of whole blood is collected into a heparinized plasma separation tube (step 1) and centrifuged for 90 sec (step 2). The separated pathogen-containing plasma, with recovered volume ranging from 50 to 250 µL, is collected into an assay tube by inversion (step 3). 50 µL of the plasma is mixed with 0.5 mL of assay medium (a process that reduces the effect of a CANARY cell activator that is present in plasma, as explained in more detail below) and the mixture is centrifuged to pellet the pathogen. The sample is then tested with pathogen-specific CANARY cells. The total time required from blood collection to pathogen detection is ~5 min. Using the PST method, the LOD is ~1000 cfu of live, avirulent *Y. pestis*/mL whole blood. By using 50 µL of the 200 µL of plasma recovered from 0.5 mL of whole blood, we detected as little as 125 cfu (assuming full recovery) per whole-blood sample. These results were consistent for each donor tested to date.

As mentioned previously, human plasma contains a B-cell activator that interferes with the CANARY assay, making it difficult to get a clear signal from low concentrations of agent that can be differentiated from the background. The signal produced by the activator peaks later than a pathogen-induced signal, and the amplitude of the signal is donor dependent, ranging from barely perceptible to several orders of magnitude. We have developed three sample-preparation methods that effectively remove the activator. Method 1 takes advantage of the fact that the activator is soluble and can therefore be removed by replacing the plasma with assay buffer. This technique is effective with bacteria and large viruses that can be sedimented by centrifugation before replacement, but is not useful with small viruses or soluble proteins. Method 2 involves diluting out the effect of the activator by adding an excess of CANARY assay medium to the plasma sample. This method is the most rapid and simple but needs further testing to ensure its effectiveness with a variety of blood samples, particularly those which contain a high-level activator. Method 3 utilizes a pretreatment of the plasma sample with B cells that function as an adsorbent for the activator.

In order to detect intracellular pathogens in white blood cells, a method was developed which incorporated modifications to the prototype device designed to detect pathogens in plasma. These modifications are based on a commercially available blood vacutainer tube, Cell Preparation Tube (CPT). This tube was designed to collect whole blood and separate mononuclear white blood cells by combining a polyester gel and a density-gradient cell-isolation medium in a single tube. Cell separation occurs during a single centrifugation step. The disadvantages of the commercial tube are that they require at least 6 mL of blood and a minimum of 15-min centrifugation. By incorporating the CPT gel and density-gradient medium into the custom-made processing device described above, the amount of blood is reduced to 0.5 mL and the centrifugation time is only 90 sec.

In order for proper separation of the blood cells to occur the whole blood should be diluted at least 6:1 with phosphate buffered saline (PBS); therefore 100 µL of PBS is placed over the gel. The device is now ready to process a blood sample. Heparinized whole blood (600 µL) is placed into the tube, the tube is inverted to mix the blood with the PBS. After a 90-sec centrifugation, the blood separates into its various components. The red plug in the top of the device is replaced with an assay tube and the plasma and white blood cells are collected in the assay tube by inversion.

Liberation of intracellular pathogens is achieved by adding M-Per cell-lysing reagent to the assay tube and incubating at room temperature for 5 min with periodic vortexing. The sample is centrifuged for 1 min to sediment the pathogen, the supernatant is replaced with 500 µL of assay medium, mixed by vortexing, and the centrifugation repeated. The total time from blood collection to agent detection is ~12 min. Detection of 1000 cfu of live *Y. pestis* per mL of whole blood (600 cfu/assay) was achieved. This method should work well for detection of intracellular pathogens that can be concentrated by low-speed centrifugation (i.e., bacteria and large viruses).

Validation

Validation was performed in which both cross reactivity and sensitivity using the *C. trachomatis* cell line was tested. Cross reactivity was observed with only 2 of the 22 types of bacteria tested, and only at very high concentrations ($10^7$/mL). While *Streptococcus pneumoniae* bacteria produce a positive reaction, it is only the monomeric polysaccharide of the bacteria that appears in the urine of a patient with pneumonia, and monomeric antigens do not stimulate the CANARY B cells. The other bacteria that cross reacted, *Gemella morbillorum*, is a normal intestinal organism that may contaminate a urine sample, but is unlikely to at such a high concentration. The sensitivity of the *C. trachomatis* cell line ranged from 10 to 150 EBs (10, 50, and 150 for serovars D, H, and K, respectively), depending on the serovar of *C. trachomatis* tested. However, since different lots gave slightly different results, the range of sensitivity may have been due to the accuracy of the quantitation and not differential response of the cell line. In either case, the LOD determined by the validation was in the range of 10's to 100's.

Conclusion

The CANARY B-cell-based biosensor exploits a highly evolved system for pathogen identification that provides several advantages over other identification technologies. With CANARY it is possible to provide identification in less than 5 min, and with those pathogens large enough to be concentrated in a microfuge, we have demonstrated a level of sensitivity that approaches PCR. In comparison, state-of-the-art immunoassays require at least 14 min and have a higher limit of detection ($6 \times 10^4$ cfu or $6 \times 10^6$ pfu). While PCR is extremely sensitive (1 to 5 cfu), highly specific, and has enjoyed technological breakthroughs that have reduced the time for amplification and signal detection, the assay takes at least 7 min (but typically 20-30 min), not including the time required to extract and purify the DNA. Applications that would benefit from such a technology include point-of-care diagnostics for illnesses where the return rate for treatment is low but the societal impact is high, such as sexually transmitted diseases. In addition, CANARY would be valuable for detection of agricultural pathogens at ports of entry, presymptomatic detection from nasal swabs in the aftermath of a biowarfare attack, or screening of perishable food supplies. In fact, CANARY is a rapid, sensitive method that can enable the detection and identification of highly infectious pathogens in any time-critical setting.

Dielectrophoresis for Concentration of Small Particles

Introduction: The CANARY assay can use centrifugation as a key step in colocalizing antigen-containing particles prior to introducing them to the B cells for recognition and signal generation. This approach has been highly successful in the rapid detection of bacterial and viral targets which have particle sizes of greater than 500 nm; however some viral targets, being much smaller, are more difficult to concentrate in this manner and can require more extensive centrifugation at very high speeds, and/or the addition of steps such as intermediate binding of the target particles to beads, to improve sedimentation of the composite particles. In order to determine centrifugation velocities required to sediment particles of a given size, we can use Stokes law of sedimentation (Equation 1) to calculate a particle's velocity in a fluid as a function of fluid viscosity and rotational parameters.

$$v_p = \frac{2}{9} r_p^2 \left( \frac{\rho_p - \rho_m}{\mu} \right) D \left( \frac{2\pi N}{60} \right)^2$$

$v_p$=particle velocity
$r_p$=particle radius
$\rho$=density
$\mu$=fluid viscosity
D=centrifugal radius
N=rotational speed As an example, using the current benchtop CANARY centrifuge having a maximum speed of 18,800 rpm, concentration of VEE viral particles (diameter 70 nm) through a typical sample volume of 50 μL in a microcentrifuge tube would take approximately 15 min. Using an ultracentrifuge with spin speeds of up to 100,000 rpm could reduce this sedimentation time to less than 1 min, but with the associated complexity in required equipment.

We have developed non-centrifuge-based methods for small-particle concentration, one being electrokinetic or electric-field-based methods. The most well-known of these techniques is electrophoresis, which has been used very successfully for many years to manipulate and separate charged particles and large molecules, including DNA and proteins, in liquids and gel-based media. It relies on the application of an electric field across the medium in which the particles reside; under the influence of this (constant) field, charged particles will migrate to one of the electrodes. The direction and rate of migration of the particles depends on their charge and size, as well as the properties of the medium, including its pH and ionic strength. Electrophoresis is a highly useful technique for the manipulation charged particles in a relatively imprecise manner. However, to concentrate particles to particular locations, and additionally these particles are not necessarily charged but are polarizable, then a technique called dielectrophoresis is used.

Dielectrophoresis—The Basics

The term dielectrophoresis (DEP) was first used by Pohl, who was able to induce movement and separation of multiple cell types by using a nonuniform electric field to generate a charge separation (polarization, creating a dipole) in uncharged particles. There are two DEP modes, positive and negative, as illustrated in FIG. 181; the mode is determined by the relative polarizability of the particle with respect to the surrounding medium. In both cases, the particle and the medium undergo a charge separation under an applied nonuniform electric field. If the particle is more polarizable than the medium, the net dipole results in the attraction of the particle towards the region of highest electric field; this is referred to as positive DEP. If the particle is less polarizable than the medium, then the fluid medium migrates towards the high field region, which pushes the particle towards the electric-field minimum; this is negative DEP.

Note that if the polarity of the electric field is switched, the induced charges and dipoles also switch polarities, so that the particle still moves in the same direction; this enables the use of alternating current (AC) fields to manipulate the particle. AC fields allow the exploitation of the polarizability of a particle which is frequency dependent; this means that the same particle can undergo either positive or negative DEP, depending on the frequency of the applied field. AC fields are also more desirable than DC because they do not result in significant net gas generation at the electrodes due to electrolysis. Generally, at low frequencies a particle will experience positive dielectrophoresis, since there is enough time in each cycle for the charges in the particle to separate with respect to the charges in the medium. At higher frequencies, charge distribution inside the particle cannot "keep up", and the particle becomes less polarizable with respect to the medium, putting it into the negative dielectrophoresis regime. Positive DEP can be used to concentrate particles at electrodes, and negative DEP to trap them in electric field "wells" away from electrodes. The frequency at which a particle switches from positive to negative DEP is called the crossover frequency.

Equation 2 shows the factors that influence the dielectrophoretic force ($F_{DEP}$); the force is proportional to the square of the applied voltage (V) and the cube of the particle radius (r), and inversely proportional to the electrode spacing (d). It is also a function of the relative permittivities of the particle ($\epsilon_p^*$) and the medium ($\epsilon_m^*$), both of which are frequency (ω) dependent, as indicated by their effect on the Clausius-Mossotti factor K(ω).

$$F_{DEP} = 2\pi r^3 \varepsilon_m Re[K(\omega)] \nabla E^2$$

$$\nabla E^2 \alpha \frac{V^2}{d^3}$$

$$K(\omega) = \frac{\varepsilon_p^* - \varepsilon_m^*}{\varepsilon_p^* + 2\varepsilon_m^*}$$

There are many demonstrations of the use of positive and negative DEP to manipulate and trap cells and larger (>1 μm) particles. More recently, with advances in fabrication methods that enable the formation of smaller-geometry electrodes, DEP has also been used to trap large viruses and even macromolecules such as proteins and DNA. We are using DEP to concentrate particles of less than 100 nm in diameter, a challenging problem as Equation 2 clearly indicates that as particle size decreases, there is a need to substantially increase the applied electric field (possibly generating electrolysis) and/or decrease the electrode spacing and geometry (which complicates fabrication processes).

Materials and Methods
Design of DEP Chip

A set of devices with various geometries of interdigitated electrodes were fabricated. Each device consisted of a set of platinum lines deposited on a square quartz chip with dimensions 25 mm×25 mm×0.5 mm, with the electrode pattern defined using a conventional liftoff process in which the negative image of the metal pattern is formed photolithographically using a photosensitive polymer, after which platinum is deposited using electron-beam evaporation and the excess platinum is removed by dissolving the underlying photopolymer (FIG. 182). FIG. 183 shows the basic electrode pattern and a completed device chip. In addition to the linear two-electrode pattern, a small number of spiral four-electrode structures were also fabricated; these may be used to achieve traveling-wave dielectrophoresis, in which four AC signals, separated equally in phase, are applied to the electrodes to step the particles along the structure to the center of the spiral.

Test Setup

Two setups were used to exercise the DEP chips, one in which the chips were held horizontally and the other in which they were held vertically. Note that although the simulations used a two-chip structure, initial experiments used a single set of electrodes only, to demonstrate attraction and repulsion of the test particles via positive and negative DEP respectively. In both the horizontal and the vertical configuration, the fluid channel was formed by sandwiching a 125-µm-thick silicone gasket between the electrode-containing chip and a plain quartz chip. The device was held in one of two types of jigs, and electrical access was obtained via copper alligator clips that contacted metal pads connected to the interdigitated electrodes on the electrode-containing chip.

Bead movement was generated by applying a square wave across the two electrodes, of amplitude 1-10 V (peak to peak) at a frequency of 1 Hz to 10 MHz, using a Hewlett Packard HP237 function generator. Test particles consisted of fluorescently tagged polystyrene beads (Bangs Laboratories, emission at 655 nm) of various diameters, suspended in distilled water. In the horizontal configuration, bead motion was observed in a static mode by filling the channel with beads suspended in fluid, applying the field, and imaging bead movement. In the vertical configuration, fluid flow was generated by applying a small amount of absorbent material at one end of the channel to act as a wick. Images of the particles were captured using a CCD camera attached to an Olympus BX60 fluorescence microscope equipped with a variety of fluorescence filter sets, and recorded on a DVD recorder.

Results

The goal of this effort was to show the ability to localize small particles using DEP. Therefore the devices were evaluated for this ability in either positive or negative DEP mode. At low frequencies the beads exhibited positive DEP, in which the beads localized to the electrodes; as the excitation frequency was increased, at some point the beads were released from the electrode surface and started to move away from the electrodes.

Using the horizontal configuration we were able to show attraction and repulsion of 2.7-µm and 0.3-µm-diameter beads using electrodes with 5-µm linewidths, but were unable to determine the repulsion distance due to the configuration of the test setup, in which the chips were held horizontally and observed from above. Subsequently fabricated devices containing electrodes with 2-µm linewidths were made and tested in the vertical configuration.

Conclusions

We were able to demonstrate both positive and negative dielectrophoretic movement of 300-nm and larger particles using interdigitated metal electrodes with linewidths of 2 µm. In the negative DEP regime, particles were repelled from the electrode plane to a distance of up to 20 µm. Negative DEP was also demonstrated using 50-nm particles, but with a repulsion distance of only 5 µm. The eventual goal of this effort was to concentrate particles smaller than 100 nm in diameter, and furthermore, to be able to repel them a suitable distance away from the driving electrodes to be able to separate the concentrated plane of particles from the remainder of the sample fluid. A repulsion distance of at least 100 µm would facilitate this separation in a microfluidic channel, but in our devices we were able to achieve a repulsion distance of less than 20 µm. If we look at the parameters governing the effective DEP force, we find that it scales as the inverse cube of the electrode linewidth. This indicates that a 10× reduction in the linewidth should give a 1000× increase in DEP force, and a corresponding increase in repulsion distance for a given driving voltage and particle diameter. Electrodes with 0.2-µm linewidths can be fabricated using the advanced photolithography systems, and these devices will enable concentration of 50-nm particles.

Toxin Detection with CANARY
Methods and Materials
GST-BoNT/A and E Hc Recombinant Expression and Purification cDNAs encoding BoNT/A Hc and BoNT/E Hc in plasmid pGEX-4T3. Plasmids were transfected into BL21 (DE3) pLys (Invitrogen) according to the manufacturer's instructions. Bacteria harboring plasmid were diluted from overnight cultures and grown to an OD600 of ~0.5, IPTG was added to a final concentration of 400 μM, and the incubation continued at 30° C. for 4 h. Bacteria were harvested, and each liter resuspended in 30 mL of BugBuster with 30 μL of benzonase nuclease (Novagen), and the tube rotated at RT for 20 min. The lysate was centrifuged at 21,000 RCF for 30 min at 4° C., the soluble protein decanted onto 3 mL of glutathione sepharose (Amersham Biosciences) equilibrated with PBS, 1 mM EDTA. The slurry was rotated at 4° C. for 2 h and poured onto a 20 mL disposable column (BioRad). The column was washed with PBS/EDTA, and recombinant protein eluted in 10-mM glutathione in 100-mM Tris, pH 8.0.

Nonmedical Matrices

1/7th volume of 7× HNa (560-mM NaCl, 1.4-M Hepes pH 7.9, and antibody-coated beads) was added to antigen-spiked solution. At the end of a 12-min binding step, 190 μL of assay medium was added, the tube was placed on the magnet for 30 sec, and the supernatant discarded. The beads were resuspended in 50 μL of assay medium, 20 μL of cells were added, the tube was spun for 5 sec to sediment the beads and CANARY cells, and light output monitored on a luminometer.

Antibody Production

Hybridomas were acclimatized to Hybridoma SFM media (Gibco)+1× nonessential amino acids (Gibco, 100-μM Na Pyruvate, and 200-μM L-glutamine). Some hybridomas required 10% serum initially, but all antibodies were ultimately produced in 0% serum containing media.

Antibody Purification

Hybridoma supernatants produced in serum-free media were centrifuged at 3700 RPM in clinical centrifuge, and the supernatant 0.2-micron filtered. 1 mL of PBS-equilibrated Protein G Sepharose 4 Fast Flow (GE Healthcare) was added to supernatant and rotated slowly either 3-4 h at RT or overnight at 4° C. Resin was poured into disposable column, washed with PBS, and 1 mL fractions eluted with 100 mM KPO4 pH 2.7 directly into 100 μL of 1 M Hepes pH 8.5. Buffer was exchanged to PBS using NAP-5 columns.

Crosslinking to Protein G Resin Beads (Dynal Dynabeads Protein G) were washed into 50 mM NaOAc, pH 5.0. The pH of the hybridoma supernatant was brought to about 5.0, BSA added to 0.1%, and to solution filtered through a 0.2-micron filter. 100 µL of beads were added to 10 mL of hybridoma supernatant, and the tube rotated for 1 hr at room temperature. The beads were washed into 0.2 M Na Borate, pH 8.0, and resuspended in 1 mL of borate containing 20-mM DMP. The tube was rotated at RT for 30 min, 250 µL of 1 M Tris, pH 8.0 was added, and incubated for 15 min. The beads were washed into PBS+ 0.05% triton X-100, and resuspended in 1 mL. About 0.4 µL of beads were used per CANARY assay for most experiments.

Biotin Crosslinking

Antibody was concentrated to ~1 mg/mL prior to conjugation using Nanosep 30K Omega centrifuge concentrators. Biotin (Sulfo-NHS-LC-LC-Biotin, Pierce) was resuspended in PBS to 10 mM. Biotin was added to a 20 fold molar excess over antibody (equilibrated in PBS) and incubated at RT for 30 min. Tris, pH 7.5 was added to 100 mM, and the buffer exchanged into PBS. Biotinylated antibodies were added to M-280 Dynabeads (Dynal) at sufficient concentration to saturate binding sites (20 µg of antibody per mg beads) and incubated at RT for 30 min. Beads were collected and washed and stored in PBS+0.05% Triton X-100. Typically the beads were diluted to one-tenth of their original stock concentration, and 0.4 µL of beads used per CANARY assay.

Introduction

CANARY has demonstrated exceptional performance in the detection of both viruses and bacteria. Detection of toxins presents a different problem. The difficulty with detecting toxins is that while an antibody expressed on the surface of B cells can bind to two toxin molecules, each toxin molecule can only bind to one antibody. This means that the antibodies will not be crosslinked by soluble, monomeric toxin, and consequently that the intracellular cascade leading to light emission from the CANARY cell will not be initiated.

An effective method to overcome this problem is to capture toxins on beads. These toxin-decorated beads can then crosslink multiple antibodies on the surface of CANARY cells and stimulate light emission. The use of capture-beads also facilitates the transfer of soluble protein toxin from cell-incompatible solutions (containing nonspecific stimulators or inhibitors of CANARY cells) into CANARY cell-compatible solutions. This important capability greatly expands the types of matrices in which CANARY can potentially be used to detect toxins.

Botulinum Toxin Detection

Toxin Forms: Several types of botulinum neurotoxin A (BoNT/A) antigen were used, depending on the purpose of the experiment and the maturity of the toxin assay.

GST fusion of BoNT/A heavy chain (BoNT/Hc) produced in *E. coli*. This recombinant protein was used for screening pools of CANARY cells for those expressing BoNT/A antibodies. The GST fusion allowed for facile attachment of the antigen to beads and screening of CANARY cells. Recombinant BoNT/E Hc was used as a control to demonstrate that responses from CANARY cells were specific to BoNT/A (the antibodies do not bind to BoNT/E). However, GST proteins have a propensity to dimerize in solution, and are therefore not a suitable target to demonstrate the ability of CANARY to detect monomeric proteins.

Commercial BoNT/Hc.

This nontoxic portion of BoNT/A is isolated from native toxin and must be captured from solution using an antibody against BoNT/A. This is a good model for detection of soluble protein, but the heavy chain portion of BoNT is not as stable as the holotoxin, and this instability made sensitivity measurements using this antigen difficult. Importantly, it also does not actually demonstrate the ability to detect active BoNT/A.

BoNT/A.

Most experiments were carried out using active BoNT/A purchased from a commercial source (Metabiologics).

BoNT/A Complex. BoNT/A as produced by *Clostridium botulinum* is complexed with a variety of other proteins. These associated proteins block binding of some antibodies, so it is necessary to demonstrate that the CANARY assay developed using these antibodies can detect not only BoNT/A but also BoNT/A Complex.

Antibodies

Most experiments used antibodies derived from hybridomas 6E10-10, 6C2-4. and 6B2-2. These antibodies bind to independent epitopes on BoNT/A. Most of the experiments described below used CANARY cells expressing the 6B2-2 antibody to detect BoNT/A antigen captured on 6E10-10 antibody bound to beads.

Additional experiments also used antibodies CR1, Raz, and S25, each of which bind to 3 separate epitopes on the BoNT/A protein. These antibodies were used to determine the effect of antibody affinity on CANARY assay sensitivity.

Beads:

Glutathione sepharose was used to capture recombinant BoNT/A Hc for presentation to CANARY cells for screening and initial testing. Protein G coated beads (sepharose or paramagnetic) were crosslinked to capture antibody and used to capture soluble BoNT/A products in solution for presentation to CANARY cells. Streptavidin-coated paramagnetic beads were coated with biotin-labeled antibody. These beads were more reproducible, and because they are paramagnetic, also allow sample preparation (toxin capture and bead washing) without requiring centrifugation.

Results: Experiments Using Stimulants for BoNT/A Toxin

The genes encoding antibodies to different epitopes on the BoNT/A Hc (6B2-2 and 6E10-10) were cloned and expressed in separate B cell lines to assess their function. Both resulting cell lines respond to the BoNT/A Hc-GST fusion protein bound to glutathione-sepharose beads. To test for CANARY cell function, the recombinant antigen was captured on glutathione beads, the beads washed in assay medium, and the capture antigen presented to CANARY cells expressing antibody 6E10-10. The 6B2-2 CANARY cell response could be partially abrogated by incubating the bead-bound BoNT/A Hc-GST with 6B2-2 antibody for 2.5 h or overnight. BoNT/E Hc-GST captured on glutathione beads does not stimulate the cells, demonstrating that the CANARY response is stimulated by interaction with antigen, and not nonspecifically by the beads or the toxin.

GST proteins dimerize in solution, and therefore cannot be used to demonstrate the ability of CANARY to detect soluble, monomeric protein. To show capture of soluble, monomeric antigen from solution, we used BoNT/A Hc purified from native BoNT/A (Metabiologics). The 6E10-10 antibody was conjugated to protein-G-labeled beads, and these beads were incubated with different concentrations of BoNT/A Hc. CANARY cells were added to the BoNT/A Hc-decorated beads, and the mixture centrifuged for 5 sec in order to co-sediment the beads and cells. The captured antigen effectively stimulated CANARY cells in a dose-specific manner, with an apparent sensitivity of 800 pg (80 ng/ml). The total assay time for this experiment was <5 min, including bead binding, cell addition, and light output measurement.

However, BoNT/A Hc aggregated during storage, making accurate measurements of assay sensitivity difficult. Unfrozen BoNT/A Hc produced a higher response than BoNT/A Hc that had been frozen. The supernatant of centrifuged, frozen-thawed BoNT/A Hc exhibited even less activity, indicating that aggregates had formed during the freeze-thaw process. In addition to the storage characteristics, lot-to-lot variability also affected our ability to accurately determine sensitivity. Since it is important to demonstrate that CANARY is capable of detecting soluble protein, we typically assayed BoNT/A Hc that has been stored frozen, and centrifuged upon thawing to remove aggregates.

Some solutions, such as orange juice or water, are incompatible with the CANARY assay, so it was necessary to exchange the original solution containing the toxin simulant with assay medium. In addition, some matrices were found to affect not only the cells, but also the capture of toxin by antibody-coated beads. For example, orange juice was problematic because of its low pH (pH=3.5). Our solution was to design a single buffering agent that, when added to a wide variety of solutions, normalized the pH and created some minimal salt concentration to allow specific capture of antigen. For these experiments, we created a concentrated buffer (7×HNa) to add to all liquids to raise the salt to at least 80 mM final, and to buffer the pH of acidic solutions like orange juice to about 6.5. The beads could be stored in this buffer, so the toxin assay still only required the addition of a single solution (7×HNa+capture beads) to the sample. The antibody-coated beads were incubated in solution for 12 min, washed with assay medium and used in the CANARY assay. The LOD for BoNT/A Hc in orange juice and PBS-Tx-100, defined as 3 fold over background, was 80 ng/ml. While the sensitivity of CANARY to BoNT/A Hc in orange juice and PBS/Tx-100 was comparable to the control, milk proved to be inhibitory (approximately 20% of control), indicating that the sample preparation would have to be altered to achieve ideal sensitivity in this matrix. Initial results indicate that increasing the salt concentration in milk may improve the sensitivity.

Several medically relevant matrices have also been tested and each required a specific sample preparation method. The procedure developed for assaying nasal samples had the samples collected on swabs, the stem of the swab was trimmed, and the swab end placed into a 5 micron filter basket fitted over an eppendorf tube. Assay medium containing BoNT/A Hc was added, and the assembly capped and centrifuged. The filtered eluate was collected in the eppendorf tube and assayed using the bead-capture procedure described above. The signals from actual and mock swabs with BoNT/Hc are very similar, indicating that no inhibitors are present in the nasal sample. The lack of a CANARY response to nasal swabs in the absence of antigen (nasal swab) shows that there are no nonspecific stimulators present in the nasal swab sample.

BoNT/A Toxin and CANARY Assay Sensitivity

To demonstrate that CANARY detects not only with BoNT/Hc toxin simulant, but also the active BoNT/A toxin, commercial BoNT/A was acquired and assayed using toxin captured with 6E10-10 beads and detected using 6B2-2 CANARY cells. The limit of detection in this assay was about 8 ng/ml or 80 pg of the toxin, which is an improvement of approximately 10 fold better than the LOD for BoNT/A Hc toxin simulant. Samples containing 16 pg of toxin (1.6 ng/ml) stimulate cells to about 3 fold over background, but with a kinetic profile that does not fit the current detection algorithm. This improvement in assay sensitivity indicates either that the active BoNT/A toxin remains soluble during storage, or that the antibodies bound better to the whole toxin than to the heavy chain.

Detection of BoNT/A toxin in actual samples was also demonstrated. The detection of BoNT/A toxin in urine was performed where the limit of detection was 16 ng/ml CANARY was also effective for the detection of BoNT/A in whole blood. BoNT/A was added to whole blood, and the blood briefly centrifuged through a polymer to facilitate separation of cells from soluble material. 6E10-10 beads were added to the resulting supernatant, incubated for 2 min, and assayed using 6B2-2 CANARY cells. As was observed when detecting toxin simulants in milk, the limit of detection for this assay, 16 ng/mL, is about 5 fold lower than the sensitivity seen using control medium.

It is possible that the high protein concentration in both of these matrices inhibited specific interactions between the bead-bound antibodies and the BoNT/A in solution. In an effort to improve the sensitivity in high protein solutions, the addition of salt and nonionic detergents was tested. Salt (NaCl), nonionic detergent (Tween-20 or Triton X-100) or combinations of the two were added to 48-ng/ml BoNT/A in plasma, and the results compared to the addition of water. The addition of Triton X-100 improved the signal, while addition of Tween did not. Addition of salt alone had a more dramatic effect, increasing the amplitude of the signal from 1700 RLU to about 4800 RLU. Addition of detergent to samples containing salt did not produce an additive effect. This indicates that addition of salt may have decreased nonspecific protein-protein interactions and increased the rate of BoNT/A binding to the antibody-coated beads.

Assay Optimization

The sensitivity of the BoNT/A assay would be expected to be dependent on the density of antigen on each bead which, in turn, is dependent on the number of beads used to capture the toxin in solution. Using a large number of beads ensures the maximum capture efficiency, but if the concentration of toxin is low the antigen present on each bead may be too sparse to elicit an effective cellular response. Therefore, a balance between bead number and antigen density on each bead must be struck. In order to optimize these parameters, a set of experiments was performed testing a variety of bead concentrations with different volumes of BoNT/A at 1.6 ng/mL. In one such experiment, different numbers of beads were added to each sample and were incubated for 2 min. When incubated in small volumes, large numbers of beads stimulated the cells less well than small numbers of beads. This would indicate that in samples containing low amounts of toxin, capturing with large numbers of beads results in too sparse a distribution of antigen to effectively stimulate the CANARY cells.

While extending the capture time significantly improves the LOD to 0.32 ng/ml of BoNT/A, we also observed that the effects of bead number became more pronounced. For example, with beads incubated overnight in 100 µl of BoNT/A at 0.32 ng/ml, decreasing the number of beads from 300,000 to 3,000 improved the signal. Fewer beads means each bead will have more toxin, improving the signal as the number of beads decreases.

The combination of biotinylating the antibody, improving binding and washing conditions, and optimizing bead number led to improved sensitivity of 16 pg (1.6 ng/ml) in a 6-min assay. Sixteen picograms of toxin represents about 0.000029 (1/34,370) of the LD50 by inhalation for a 55-kg (120 lb) person. This is about 0.00023×LD50 by injection, and 0.00000029×LD50 by ingestion. At this level of sensitivity the assay could detect about 1 LD50 present in 34 liters of fluid.

Results for Real Toxin: BoNT/A

BoNT/A spiked into urine could be detected, although the signal amplitude was somewhat reduced compared to controls. (FIG. 158) In this experiment no pretreatment was used, and the 6E10-10 coated beads were added directly to urine spiked with BoNT/A. The limit of detection for BoNT/A in urine was 16 ng/ml, compared to 3.2 ng/ml for toxin diluted directly into assay medium in parallel experiments.

CANARY was also effective for BoNT/A screening in whole blood using the sample preparation procedure described elsewhere (FIG. 159). Whole blood was spiked with BoNT/A, and the blood briefly centrifuged through a polymer to facilitate separation of cells from soluble material. 6E10-10 antibody-coated beads were added to the resulting supernatant, incubated for 2 minutes, and assayed using 6B2-2 CANARY cells. The limit of detection for this assay is 16 ng/ml, about 5 fold lower than the sensitivity seen using control medium. This sample preparation method resulted in a significant improvement over previous assays on plasma prepared by centrifugation in the absence of polymer.

In both milk and serum, the limit of detection for toxin by the CANARY assay was about 5-fold higher than controls. It is possible that this was because the high protein concentration in both of these matrices inhibited specific interactions between the bead-bound antibodies and the BoNT/A in solution. In an effort to improve the sensitivity in high protein solutions, the addition of salt and nonionic detergents was tested (FIG. 160). Salt (NaCl), nonionic detergent (Tween-20 or Triton X-100) or combinations of the two were added to 48 ng/ml BoNT/A in plasma, and the results compared to the addition of water. The addition of Triton X-100 improved the signal, while addition of Tween did not. Addition of salt alone had a more dramatic effect, increasing the amplitude of the signal from 1700 RLU to about 4800 RLU. Addition of detergent to samples containing salt did not produce an additive effect. This indicates that addition of salt may have decreased nonspecific protein-protein interactions, and increased the rate of BoNT/A binding to the antibody-coated beads.

We have shown that CANARY can effectively detect active BoNT/A, but if the toxin is isolated from certain strains of *Clostridium botulinum*, the toxin will be complexed with additional proteins, creating an antigenically different target, BoNT/A Complex. Importantly, CANARY detected BoNT/A Complex with the same response levels as BoNT/A (FIG. 161). Equimolar amounts of BoNT/A and BoNT/A Complex (5 fmoles of each) were added to 6E10-10 coated beads, and the captured toxin detected using 6B2-2 cells. The CANARY response was identical to both preparations, indicating that the epitopes on the BoNT/A bound by these antibodies were not blocked by the BoNT/A Complex proteins.

We have chosen to focus on developing an assay that is very fast. Longer incubations are of interest in determining the limits of the assay, but not for diagnostic or detection purposes. We found that biotinylating the capture antibody and attaching it to streptavidin beads was easier and gave marginally better results. The combination of biotinylating the antibody, improving binding and washing conditions, and optimizing bead number led to improved sensitivity over a period of time. In an assay on 10 µl of suspect solution spiked with BoNT/A, the sensitivity of the is 16 pg (1.6 ng/ml) (FIG. 162). The entire assay, including addition of the beads, binding for 2 minutes, magnetic capture and bead washing, cell addition and light output measurement takes about 6 minutes.

Summary

In summary, we have developed an assay for Botulinum toxin using antibody-coated beads to capture soluble toxin. These toxin-decorated beads are used to present immobilized toxin to CANARY cells. Importantly, the beads also facilitate the transfer of toxin from any variety of cell-incompatible matrices into assay media. This allows detection of toxin in blood, urine, nasal swabs, orange juice, milk, water, and PBS-Triton. Some matrices cause decreased responses in the CANARY assay, particularly those that contain high concentrations of protein (plasma and milk). This inhibition can be partially overcome by adding salt to decrease nonspecific protein interactions. The assay has been optimized for speed, and can detect 16 pg (1.6 ng/ml) BoNT/A in 6 min. Sensitivity would seem to be dependent on the affinity of the capture antibody, but the use of higher-affinity antibodies does not improve the limit of detection. Increasing the incubation time of the bead-capture step does result in better sensitivity (less than 0.32 ng/ml. Even in difficult matrices the assay can detect a fraction of an LD50 in 6 min.

Hardware Development for CANARY

Materials and Methods

Magnetic Agent Bead and Magnetic B-Cell Bead Assay

B-cell binding beads: Dynabeads® Mouse Pan B (B220) Catalog Number 114-41D were used without further modification.

Agent-binding beads: Dynabeads® M-280 Tosylactivated Catalog Number 142-03 were functionalized with capture antibodies according to the manufacturer's recommendations.

Assay procedure: Incubate magnetic beads (Dynal/cat. no. 142-03) coated with agent antibodies in 1.5-ml tube with sample for 5 min at room temperature. Pull captured agent and bead down to bottom of tube with a magnet. Add B-cell magnetic beads (Dynal/cat. no. 114-41D) to tube and pull them down to bottom of tube using a 10-sec exposure to a strong rare-earth magnet. Place tube in a luminometer and read signal.

Lateral Flow Strips

Materials:

Sample pads: Millipore glass fiber pads G041/GFCP1 030 00. Wick pads: Millipore cellulose absorbent sample pads C082/CFSP1 730 00

Capture membrane: Pall 0.45-µm GH polypro membrane (cat. no. GHP4550001/Pall)

Methods

Assemble the lateral flow strips as follows. Place a 0.25-in.×0.25-in. Millipore wick pad onto packing tape. Apply 0.4-in.×0.1-in. Pall 0.45-µm GH polypro membrane on top of wick pad so that ⅓ of membrane is on top of wick pad. Apply 0.25-in.×0.5-in. glass fiber filter to Pall GH polypro membrane.

Single-Channel Sensor Development

Described herein are improved single-channel hardware capable of performing optimal CANARY assays. We pursued two parallel paths: (1) Development of custom design concepts for a single unit capable of spinning and analyzing the CANARY samples, and (2) examining COTS luminometers and minicentrifuges that could be modified, or preferably used without modification, to perform single CANARY assays. The outcome of that process was the identification of inexpensive COTS hardware that improved CANARY assay procedures and performance. The optimum hardware combination consisted of the Berthold Detection Systems FB12 luminometer used in conjunction with a VWR minicentrifuge fitted with a custom rotor to enable spinning of up to eight CANARY samples in the optimum configuration.

The procedure for using the single-channel sensor begins with a ~2-min pre-spin at >6000 RCF in a conventional swing-bucket microcentrifuge, if available, or in the VWR minicentrifuge. A drop of B cells was added to the sample, placed in the minicentrifuge and spun for 5 sec. There is sufficient time before the signal peaks to transfer the sample to the luminometer for signal readout and CANARY identification. The entire CANARY test procedure can be completed in 3 min enabling this single-channel CANARY sensor operated by a single user to process up to 25 samples per hour with parallel sample pre-spins.

16-Channel Sensor Development

In its simplest form, a CANARY measurement consists of preparing a sample in a transparent tube, introducing an aliquot of specially prepared B cells into the tube, driving the B cells to the bottom of the tube using a quick centrifugal spin, and measuring the light output from the tube with a photon-counting sensor. In the laboratory, most CANARY measurements have been made sequentially, one sample at a time; in the automated BAWS/CANARY bioaerosol identification sensor, four samples are measured simultaneously, each sample having its own light-gathering channel. Each light-gathering channel typically consists of a photon sensor, high-voltage power supply, a pulse-discrimination circuit, and possibly a digital counter. The former system requires more time, while the latter requires more complex (and expensive) hardware.

A new approach that reduced the time to measure multiple samples (while keeping the hardware requirements minimal) was successfully tested. A sensor testbed was fabricated that allows the simultaneous measurement of up to 16 samples using a single light-gathering channel. The sensor consisted of a rotor holding 16 1.5-ml tubes horizontally, equally distributed about its circumference, and driven by a variable speed motor about a vertical axis. A single fixed photon-detecting element (in this case, a PMT) was positioned in the plane of the rotor just beyond the path of the tubes during rotation. In this way, each of the tubes was sequentially and repetitively brought into close proximity to the PMT, allowing its light output to be sampled on each pass.

Additionally, an optical switch consisting of an optical source (an infrared LED) and a detector (a phototransistor) was used to control the counting of detected photons and the reorganization of the data into 16 fields, each associated with a specific sample.

A single measurement consists of: 1. Preparing 16 samples (and/or controls) in individual 1.5-ml tubes; 2. Introducing an aliquot of B cells into each of the tubes; 3. Installing the tubes into the rotor situated in a dark box; 4. Localizing the B cells at the bottom of the tubes using a brief (5 sec) centrifugal spin at high RCF (~2000 g); 5. Reducing the rotor speed to 60 rpm for the duration of the measurement (1-2 min), each tube being sampled once every second; 6. Generating a time series of photon counts for each sample for display and/or input to a computer algorithm for evaluation.

Tests were run analyzing the signal collection characteristics from assays read while spinning to determine how fully the 16-place rotor in the testbed could be populated before signals began to overlap. With the rotor fully populated, all of the samples produced signals with signal to noise ratios comparable to those observed in the single-channel sensor, and no observable crosstalk of emitted light between channels was observed if sufficient baffling was provided to limit the transmitted angles for the light. An example of the data from the 16-channel testbed shows an LOD comparable to that of the single-tube method. While this sensor measures 16 samples as designed, larger sample numbers are possible, though physical size and the statistics of sampling will ultimately dictate practical limits.

The rotary format was incorporated into the design for the portable 16-channel prototype sensor. The primary goal of the design was to incorporate the hardware necessary for spinning and readout of CANARY assays into a small, self-contained portable unit less than 12 inches in the longest dimension. Additionally, provision was made to ensure that power consumption was low enough to enable inclusion of a battery into the enclosure for battery-powered operation. These goals were accomplished by building the sensor components into a small COTS transportation case that was water and light tight, and by using a smaller motor and controller that was capable of spinning the rotor using a 24-V DC power source.

Handheld Sensor Development: Simplified Assay Development

A compact handheld sensor targeted at clinical, point-of-care, and forward-deployed applications is of particular interest. We have focused on characterizing the performance of alternative assay procedures that can reduce or eliminate the requirement for centrifugation steps since they are currently the primary driver of energy consumption and instrument complexity. We experimentally evaluated a number of approaches toward assay formats that employ reduced centrifugation requirements, microfluidic channels, lateral-flow assemblies, filtration, or magnetic bead capture. Of these approaches, reduction of the centrifugation requirements, use of lateral-flow assemblies, and magnetic bead capture are described in more detail below.

Standard format with reduced centrifugation steps. Signals in response to high concentrations of agent have been observed without centrifugation steps, so in order to characterize the performance tradeoffs that would result, we performed a series of experiments using different centrifugation permutations. Experiments indicate that reducing the centrifugation and assay times (from ~3 min per assay to ~1 min per assay) will reduce the sensitivity by approximately one order of magnitude.

Lateral-Flow Formats.

We have characterized CANARY assay performance in devices that layer wicking and filter materials to accomplish sample fluid transport and antigen localization without centrifugation. The basic construction of the device as well as pictures demonstrating its ability to localize spore-sized particles are shown in FIGS. 184 and 185. FIG. 186 shows the resulting CANARY signals for both standard centrifuge assays and lateral-flow assays using the same agent and cell samples.

Dual-Magnetic-Bead Assay.

Figure 187B:
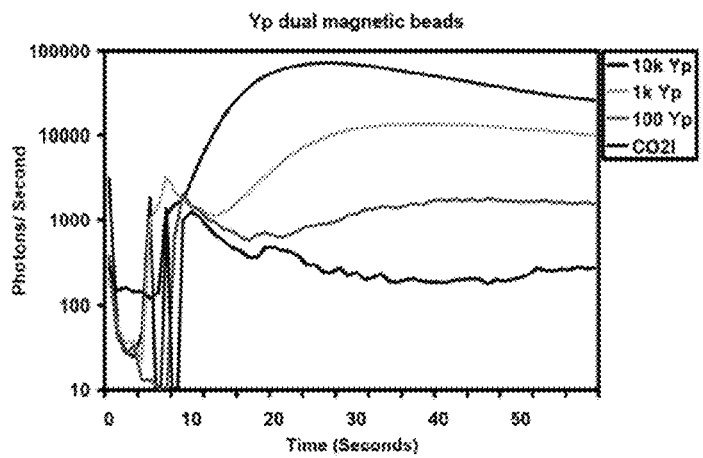

We have characterized an assay that takes advantage of two sets of magnetic beads. One set is specific for the CANARY B cells, while the other set is specific for a particular agent. In FIG. 187, a standard CANARY assay was run alongside a dual-bead assay using the same B cells and agent dilution series. Magnetic beads specific for *Y. pestis* were mixed with a dilution series of *Y. pestis* agent for 5 min. After 5 min the magnetic beads were pulled to the bottom of the assay tube along with any bound *Y. pestis*, and the supernatant was removed. Magnetically labeled B cells were then added to the sample and pulled down to the bottom of the tube. Localizing agent and B cells with magnetic beads has thus far proven to provide similar sensitivity to that of centrifugation.

Handheld Sensor Hardware Development

Handheld sensor hardware development began with the design of a cartridge capable of a single CANARY assay that can be performed without centrifugation. The cartridge was designed to contain a swab that has a small but powerful magnet in its tip, as well as a capsule of B cells that are attached to magnetic beads (FIG. 188). After using the swab to sample a surface, it would be introduced to the capsule containing the B cells, and the magnet would draw the bead-bound cells to the antigen on the surface of the swab. Then the entire cartridge would be slid into a specially adapted, battery-powered luminometer to record the light emission. This handheld sensor could be used in the field to determine exposure of a person or surface to a specific pathogen. The rationale for this design was based on several factors. We have demonstrated the ability to replace centrifugation with magnetic beads by using a magnet to draw bead-bound B cells to the antigen in a liquid sample (that was prepared by centrifugation). We have also shown that B cells can be packaged in capsules, as they would be in the cartridge, and either refrigerated for weeks or held at room temperature for 48 h without losing sensitivity. Finally, although magnets can have adverse effects on the function of a photomultiplier tube, we have been able to show that the distance between the magnetic swab and the photomultiplier tube in the luminometer can be controlled to prevent these adverse effects. Initial experiments have shown that bead-bound B cells, drawn to a spherical neodymium magnet in the absence of antigen, give off a transient light signal. This is most likely due to mechanical stress on the cells. Several possible remedies were identified including: use of weaker magnets (neodymium magnets are very strong); "tuned" magnets (a magnetic material at the tip of the swab, magnetized by a neodymium magnet mounted further away in the body of the swab); and a retractable magnet (which can be withdrawn immediately after the B cells have been attracted to the swab surface).

The complexity of magnetic manipulation and processing was removed from the consumable where it would drive up the cost of operation. Shifting the components required for magnetic sample and cell manipulations into the handheld readout device adds little to the overall cost of the device. Furthermore this approach enables the assays to be performed in COTS microcentrifuge tubes and ensures maximum sensitivity and reliability. Based on these advantages, the a handheld luminometer with features enabling onboard magnetic assay manipulation was developed. The optical sensor and supporting electronics are based on those found in a commercially available luminometer made by Berthold Detection Systems, the same manufacturer that produces the COTS luminometer that was incorporated into the single-channel CANARY sensor. The design that resulted is shown in FIG. 189. The completed sensor based on this design is shown in FIG. 190.

The handheld CANARY sensor (FIG. 190) features a PMT oriented with the photocathode<1 mm from the bottom of the assay tube, a readout screen with touch pad, a rechargeable battery pack, and a sliding sample door. The sample door contains a rare-earth magnet positioned so that insertion of a tube as shown in FIG. 189 results in co-localization of the captured target and magnetically labeled B cells. The assay procedure begins with the addition of magnetic beads to the sample, followed by mixing and incubation for 5 min. The sample/bead suspension is then placed in the magnetic tube holder on the door for 1 min to localize the captured target at the bottom of the tube. The sample that has been depleted of target is removed and replaced with assay buffer containing B cells, and the tube is returned to the magnetic holder. After 5 sec the tube is placed into the read position on the door, the door is closed, and the PMT signals are recorded.

Thus, we have developed a system for producing genetically engineered B cells that serve as sensors for the rapid identification of pathogens and toxins. The assays we have developed using these cells demonstrate the best combination of speed and sensitivity known (<50 particles of killed *Y. pestis* in <3 min, with a false-alarm rate of 0.4% with laboratory samples), and because the B cells are self-replicating, the cost of the materials is very low. In addition to the 24 genetically engineered B-cell lines we have generated, including Rift Valley Fever, Dengue viruses, and others of significance to clinical diagnostics, we have produced a CANARY cell line whose specificity can be engineered in days instead of months. We have developed 5-min assays for clinically relevant samples, demonstrating detection of 50 cfu of *B. anthracis* spores from nasal swabs, 500 *C. trachomatis* EBs in urine, and 1000 cfu of *Y. pestis*/mL of whole blood. We have also demonstrated that CANARY assays can be multiplexed by combining up to three cell lines in a single assay, or by engineering cells that respond to more than one pathogen. Alternatively, we have shown the production of B cells that emit different wavelengths of light, enabling a single assay that can distinguish between two or more pathogens.

We have extended the capabilities of CANARY to include protein toxins, demonstrating detection of as little as 16 pg (1.6 ng/ml) of Botulinum toxin A in a 6-min assay. Sixteen picograms of toxin represents about 0.000029 (1/34,370) of the LD50 by inhalation for a 55-kg (120 lb) person. This is about 0.00023×LD50 by injection, and 0.00000029×LD50 by ingestion. At this level of sensitivity the assay could detect about 1 LD50 present in 34 liters of fluid. It is unclear whether this sensitivity would be sufficient for diagnosis of BoNT/A using serum samples from patients (published data on serum concentrations are lacking), but it would certainly be an excellent screening method for food contamination, aerosolized material, or inhalation exposure (nasal swabs).

Although the CANARY assay can be performed in a single-channel format using several pieces of COTS equipment, we have developed a 16-channel sensor with an integrated spin motor and PMT that can process approximately 100 samples/hour while maintaining the optimum LOD of 50 cfu/pfu of bacteria or large viruses. We have also developed a handheld sensor that utilizes a noncentrifugal, dual-magnetic approach.

The CANARY B-cell-based biosensor exploits a highly evolved system for pathogen identification that provides several advantages over other identification technologies. With CANARY it is possible to provide identification in approximately 5 min, including sample preparation, and with those pathogens large enough to be concentrated in a microfuge, we have demonstrated a level of sensitivity that approaches PCR. In comparison, state-of-the-art immunoassays require at least 14 min and have a higher limit of detection (6×□$10^4$ cfu or 6×□$10^6$ pfu). While PCR is extremely sensitive (1 to 5 cfu), highly specific, and has enjoyed technological breakthroughs that have reduced the time for amplification and signal detection, the assay takes at least 7 min (typically 20-30 min), not including the time required to extract and purify the DNA. Applications that would benefit from a technology such as CANARY include point-of-care diagnostics for illnesses where the return rate for treatment is low but the societal impact is high, such as sexually transmitted diseases. In addition, CANARY would be valuable for pre-symptomatic detection from nasal swabs in the aftermath of a biowarfare attack, detection of agricultural pathogens at ports of entry, or screening of perishable food supplies. In fact, CANARY is a rapid, sensitive method that can enable the detection and identification of highly infectious pathogens in any time-critical setting.

Cell Engineering and Assay Method Examples

A. Cell Engineering Methods

M12g3R cells were maintained at 37° C. in a humidified atmosphere of 5% $CO_2$ in RPMI 1640 supplemented with 10% fetal bovine serum, 1 mM sodium pyruvate, 2 mM L-glutamine, 100 μM nonessential amino acids, 50 μM 2-mercaptoethanol, 50 μg/ml streptomycin, and 50 U/ml penicillin, 250 ng/ml amphotericin B (Life Technologies). Cells were transfected with pCMV.AEQ.IRES.NEO via electroporation (270 V, 950 μF) and selected in 1 mg/ml G418 for two weeks. G418-resistant clones were screened for response to anti-IgM. Those clones with the greatest increase in photon emission upon crosslinking of the surface IgM were used in subsequent transfections to generate B cell lines specific for particular pathogens. Surface expression of antibodies with engineered specificity is accomplished by co-transfection (via electroporation) with expression vectors for light and heavy chains, as well as with one that encodes a gene conferring resistance to puromycin. Puromycin-resistant pools and clones were selected on the basis of their response to antigen. The light chain expression vector, VKExpress, contains the constant region for the human kappa gene downstream of a multiple cloning site (MCS), under control of the human elongation factor-1α (EF-1α) promoter. The heavy chain vector was generated by modifying pDisplay (Invitrogen), retaining the cytomegalovirus (CMV) promoter and leader sequence, but replacing the platelet-derived growth factor (PDGF) receptor transmembrane domain with the gene for the membrane-bound constant region of murine IgM and removing both tags on either side of the MCS. The appropriate restriction sites are added to the antibody variable regions using PCR and the sequence of all PCR products is confirmed before cloning into the expression construct. The variable regions used to produce the recombinant antibody were cloned either from cDNA or from hybridomas using Reverse-Transcription (RT) with random oligonucleotide primers and PCR. RNA was extracted with Trizol reagent (Life Technologies), according to the manufacturers recommendations, and first strand synthesis performed using the Retroscript kit (Ambion). PCR was accomplished using sets of primers designed to anneal to the leader sequences of either light or heavy chains [S. T. Jones and M. M. Bendig, Bio/Technology 9, 88 (1991)] at the 5' end, and the constant regions of murine Kappa or IgG2 at the 3' end.

B. Bioluminescent B Cell Response to FMDV

The M12g3R B cell line, stably transfected with the pCMV.AEQ.IRES.NEO plasmid and expression vectors for a recombinant antibody that recognizes the A12 strain of FMDV, was prepared for the luminesence assay as follows: Cells were thawed on Day 1. Preparation of the cells 24 hours post-thaw is critical for maximum activity and reliability. The freeze/thaw step increases the response of the B cells by as much as 100 fold. On Day 2, $10^6$ cells were incubated at room temperature for 2 hours in assay medium [$CO_2$—Independent medium, 10% FBS, 50-μg/ml streptomycin, and 50-U/mil penicillin, 250 ng/ml amphotericin B (Life Technologies)] with 50-μM coelenterazine (Molecular Probes, Eugene, Oreg.) covered with foil, washed twice, and resuspended in assay medium at a final concentration of $5\times10^5$ cells/ml. Cells were left rotating overnight at room temperature in 1.5 ml microcentrifuge tubes and assayed 15-20 hours later. For the assay, 25 μl of cells was mixed with antigen (5 μl of the wt A12pRMC35 strain at $1.4\times10^8$ pfu/ml, 10 μl of the A12 variant, B2PD.3, at $7.5\times10^7$ pfu/ml) and the response measured in a luminometer (Lumat LB 9507, Perkin Elmer).

C. Bioluminescent Assay with Bacteria and Large Viruses

The sensor device and methods can be used for the rapid detection of bacterial, as well as viral pathogens. Cell lines were engineered to respond to the bacterium, *Francisella tularensis*, the etiological agent of tularemia. However, when assayed using the same protocol as with the FMD and VEE viruses, the signal is slow and almost indistinguishable from background, indicative of low interaction rates between the B cells and antigen (0s pre-spin/0s spin). Previous experiments performed with antigen-bead simulants have indicated that sensitivity and speed could be augmented by concentration of antigen and B cells (data not shown), so the luminometer was re-configured to include a centrifuge positioned above the photomultiplier tube (PMT). When the agent and cells are mixed together, then concentrated by centrifugation for 5 seconds, the signal is improved and the response faster (0s pre-spin/5s spin). Optimal results are observed when the slower-sedimenting *F. tularensis* is centrifuged prior to the addition of the cells (60s pre-spin/5s spin). This format ensures that a large number of cells come into physical contact with antigen within a short time frame, thereby providing a major improvement in sensitivity and speed. After additional optimization of the assay protocol, we can now detect as little as 60 colony-forming units (cfu) of *F. tularensis* in less than 3 minutes, including the time it takes to pre-spin the agent, but see no response to inactivated *Yersinia pestis*, the bacterium that causes the plague. This limit of detection has been confirmed with two other sources of inactivated *F. tularensis*, and one different strain (data not shown). Furthermore, the sensor device exhibits a wide range of sensitivity, detecting concentrations ranging over 7 orders of magnitude.

B cells were prepared as described above. 50 μl containing the indicated amounts of *Y. pestis* or *F. tularensis* were centrifuged for 60 s at 6500×g, then 20 μl of cells were added and spun an additional 5 s in the centrifuge luminometer. Photons were detected with a Hamamatsu HC-125 photomultiplier tube and the signal monitored with a Stanford Research Systems SR400Gated Photon Counter.

Nucleic Acid Detection Example

Characterization of Emittor Cells Expressing Digoxigenin Antibody

Figure 26A:
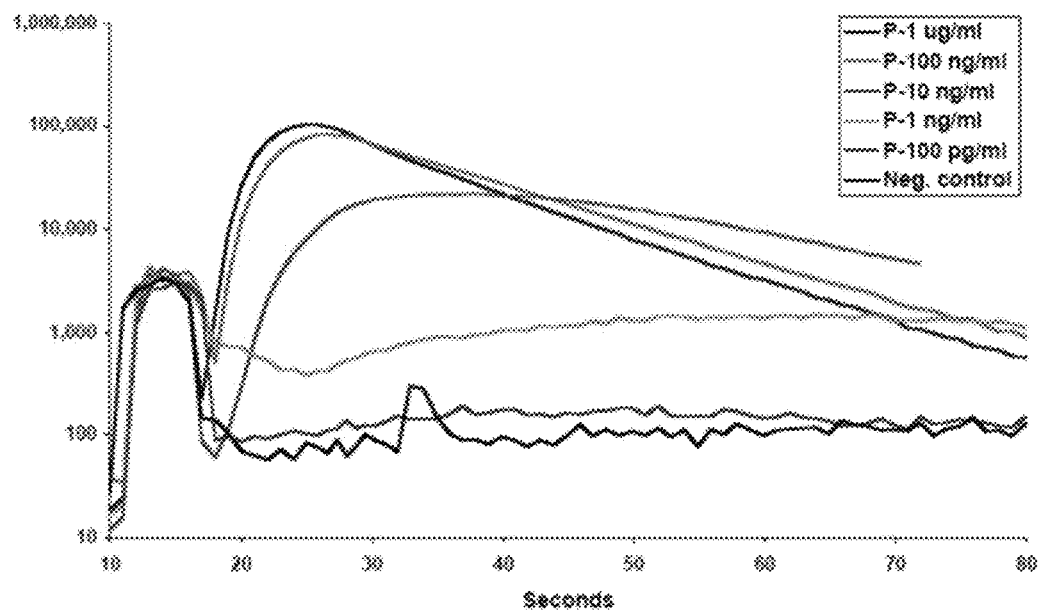
FIGS. 26A-C are graphs. CANARY cells (emittor cells) expressing antibodies against digoxigenin can be stimulated by digoxigenin-labeled DNA. Emittor cells expressing antibody against digoxigenin were added to centrifuge tubes containing 50 µl of the indicated concentration of digoxigenin-labeled DNA standards. The tube was centrifuged briefly to pellet the cells at the bottom of the tube, nearest the PMT, and photon emission as a function of time recorded. Three different types of digoxigenin-labeled DNA were used to stimulate the cells, and each was successful with a different degree of sensitivity.
Figure 26B:
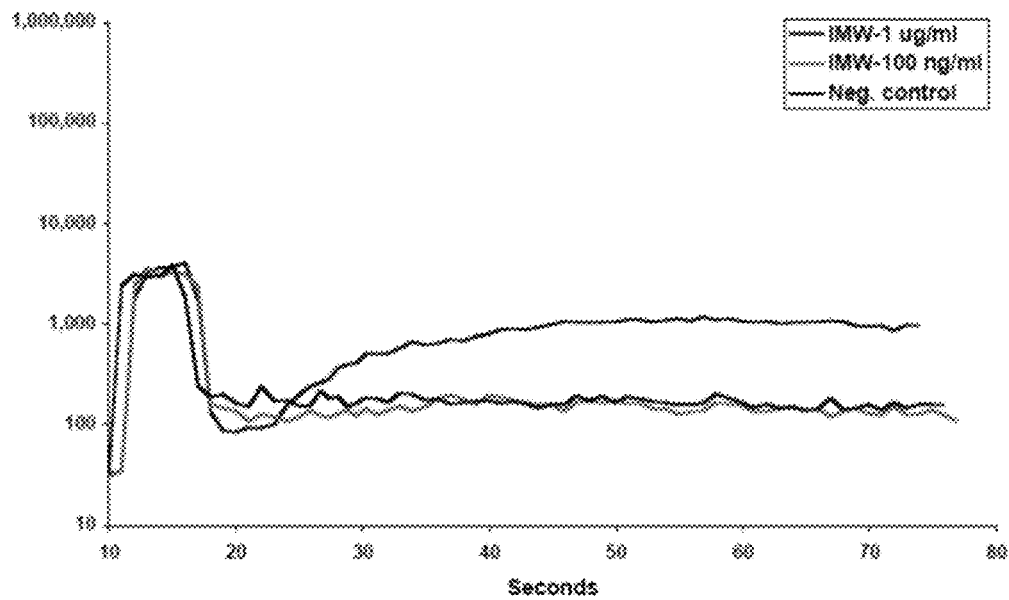
Figure 26C:
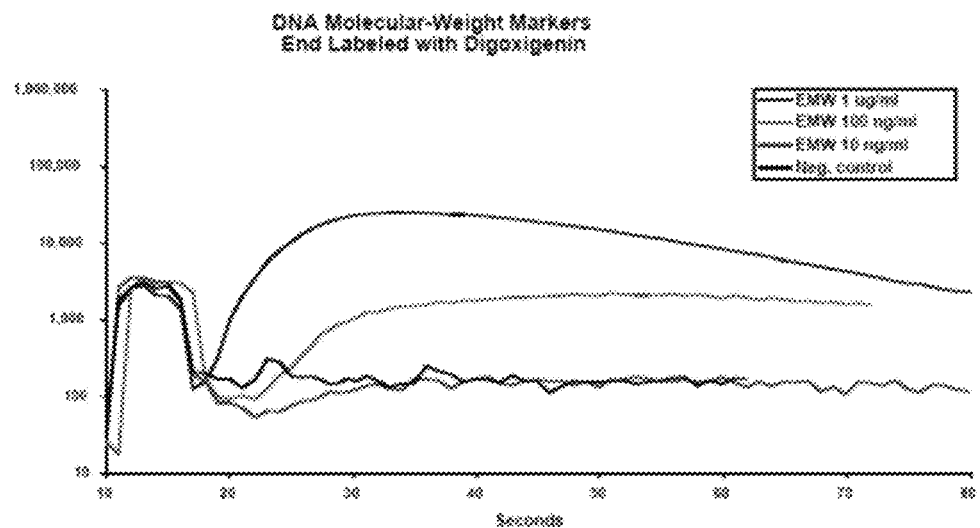

Plasmids encoding an antibody (Daugherty et al. (1998) Protein Engineering 11 (9): 825-832) against digoxigenin were introduced into emittor cells, and these cells were screened using protein (BSA) chemically conjugated to digoxigenin (Dig-BSA). Twelve independent pools were selected resulting in 12-24 independent cell lines. The first experiment tested whether these cells could detect digoxigenin antigens crosslinked by DNA (Dig-DNA). Three types of commercial Dig-DNA have been tested for reactivity with Dig antibody expressing CANARY cells (FIGS. 26A-C): plasmid DNA with a digoxigenin attached every 20 base pairs (FIG. 26A); DNA molecular-weight markers with digoxigenin attached every 200 bases (FIG. 26B); and DNA molecular-weight markers with one digoxigenin attached to each end (FIG. 26C). Each of these standards stimulated the emittor cells to a varying degree, with the most sensitive response being to the Dig-labeled plasmid DNA. The fact that antigens spaced an average of 20 bases apart stimulate the cells 100 fold more (on a per digoxigenin basis, not on a per microgram of DNA basis) than antigens spaced 200 bases apart is an indication that 200 bases is too great of a distance to stimulate an ideal response. In order to stimulate an intracellular cascade resulting in calcium release and aequorin light production, adjacent antibodies must be immobilized near enough to each other to initiate the reaction inside the cell.

Figure 27A:
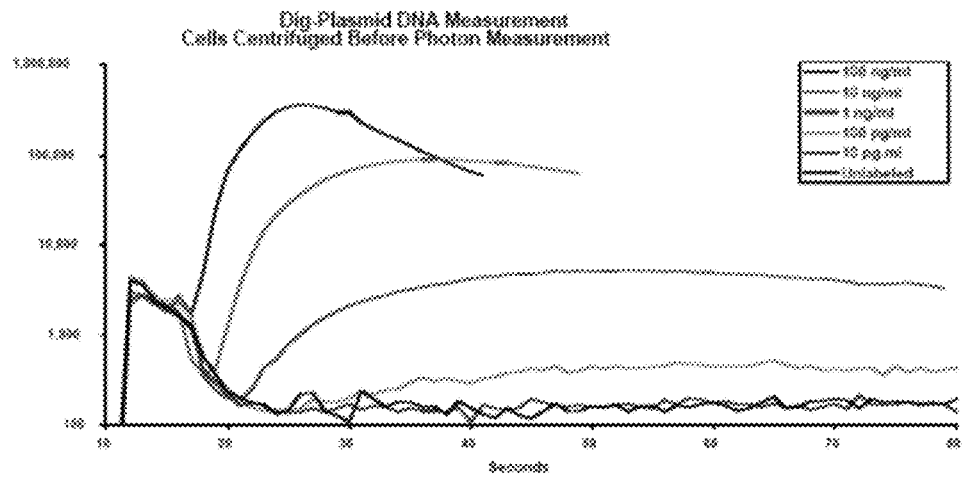
FIGS. 27A-B are graphs. Centrifugation of cells may decrease sensitivity to soluble antigen. Emittor cells expressing antibody against digoxigenin were added to centrifuge tubes containing 50 µl of the indicated concentration of digoxigenin-labeled plasmid DNA.
Figure 27B:
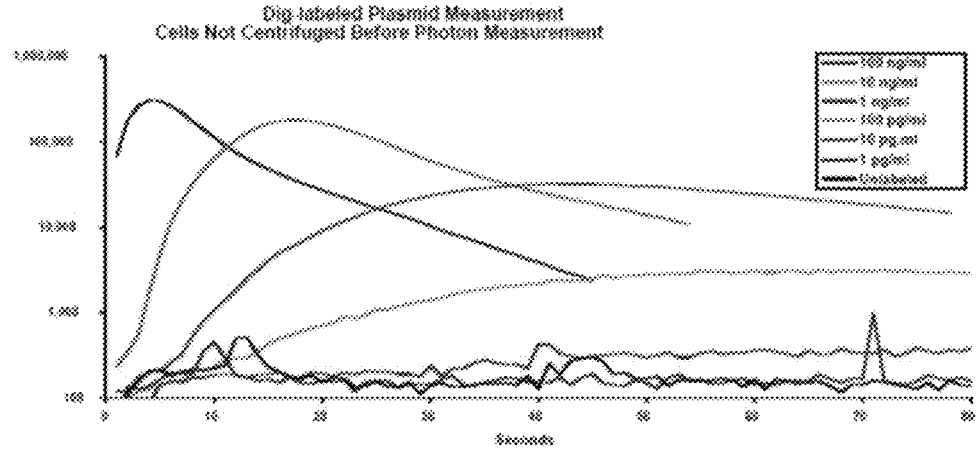

It was also noted that centrifugation just before measurement of light output, which is routine in the detection of both soluble and insoluble antigens using traditional CANARY, may actually decrease the sensitivity of CANARY against the soluble Dig-DNA antigen. In the experiment shown (FIGS. 27A and 27B), centrifuging the cells through the DNA solution appears to decrease the limit of detection by nearly a factor of 10. This result may reflect differences between detection of DNA and detection of other nonsedimentable antigens.

Detection of Hybridized Oligonucleotide Probes Using Emittor Cells

This assay was designed to detect hybridization of digoxigenin-labeled (Dig-labeled) probes to target DNA. The target DNA for these experiments was derived from the phagemid pBluescript II. This 3100 base pair-long circular phagemid can be induced to make double-stranded DNA (dsDNA) or either of the two single strands of DNA (ssDNA). These two ssDNA strands are termed the (+) strand or the (−) strand. Ten Dig-labeled oligonucleotide probes that bind specifically to the (+) strand were designed:

| Oligo number | DNA Sequence | Phagemid base position | Tm |
|---|---|---|---|
| 1 | GCAACGTTGTTGCCATT (SEQ ID NO: 1) | 2269-2285 | 56.0 |
| 2 | TACAGGCATCGTGGTGT (SEQ ID NO: 2) | 2288-2304 | 53.3 |
| 3 | GCTCGTCGTTTGGTATGG (SEQ ID NO: 3) | 2309-2326 | 57.3 |
| 4 | TCATTCAGCTCCGGTTC (SEQ ID NO: 4) | 2328-2344 | 55.0 |
| 5 | ACGATCAAGGCGAGTTAC (SEQ ID NO: 5) | 2348-2365 | 53.1 |
| 6 | GATCCCCATGTTGTGC (SEQ ID NO: 6) | 2368-2384 | 57.7 |
| 7 | AAAGCGGTTAGCTCCTTC (SEQ ID NO: 7) | 2388-2405 | 54.3 |
| 8 | TCCTCCGATCGTTGTCA (SEQ ID NO: 8) | 2408-2424 | 56.5 |
| 9 | GTAAGTTGGCCGCAGTG (SEQ ID NO: 9) | 2428-2444 | 55.7 |
| 10 | TCACTCATGGTTATGGCA (SEQ ID NO: 10) | 2448-2465 | 53.5 |
| NEG3 | CCATACCAAACGACGAGC (SEQ ID NO: 11) | 2326-2309 | 57.3 |

Oligonucleotides are numbered in the order of their location along the pBluescript phagemid DNA. Shown for each is the DNA sequence of the oligonucleotide, the position of that sequence on the phagemid, and the melting temperature (Tm) of that oligonucleotide (an approximation of the binding affinity). The small range in Tm's for these oligonucleotides indicate that they each have similar binding characteristics.

Each of these oligonucleotides has a digoxigenin (Dig) molecule attached to the first residue, and each have comparable target DNA binding characteristics as reflected by their similar calculated melting temperatures (Tm). Hybridization of this set of 10-digoxigenin-labeled oligonucleotides to the (+) strand of the target DNA yields a 200 base stretch of double-stranded DNA with one Dig molecule every 20 bases. The remaining 2900 bases of the plasmid remain single stranded. This collection of immobilized digoxigenin antigens crosslink digoxigenin antibodies on the surface of emittor cells and stimulate light production.

Figure 28:
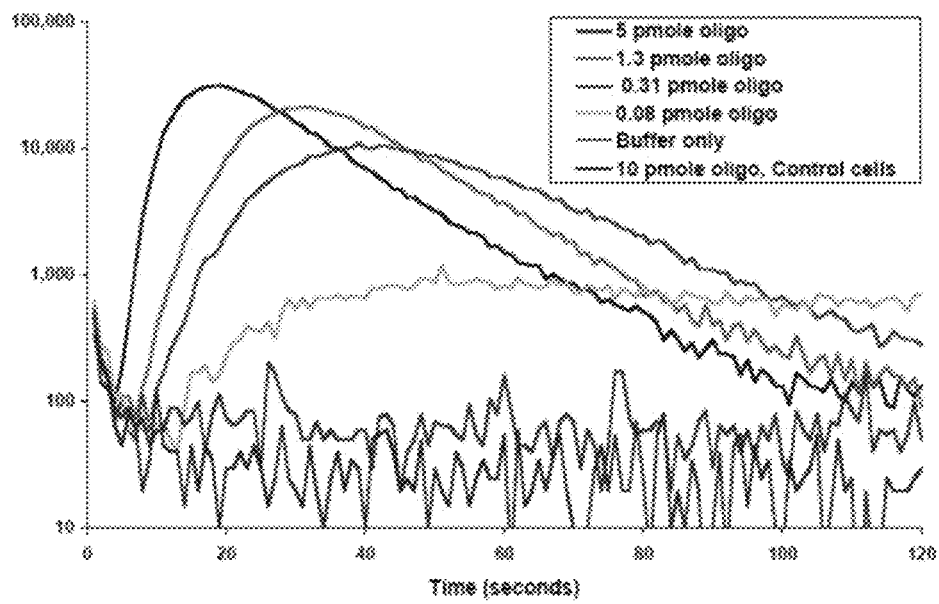
FIG. 28 is a graph. Two complementary Dig-labeled oligonucleotides (Oligo "3" and Oligo "NEG 3") were allowed to hybridize under experimental conditions. The sample was diluted 1:10 with CO2I media to a total volume of 100 µl, 20 µl of cells were added, and light emission measured. Dig cells express the Dig antibody, while control cells do not.

The 11th oligonucleotide (NEG 3) is a control. NEG 3 was designed to bind directly to oligonucleotide number 3, producing a short piece of dsDNA 20 nucleotides long with a single Dig on each end. Emittor cells expressing a digoxigenin antibody were capable of detecting 80 femptomoles of input oligonucleotide (FIG. 28). This control demonstrated that the hybridization conditions chosen were at least sufficient to support binding of two oligonucleotides within this Tm range. More importantly, this control demonstrated that the binding between 20 bases of complementary DNA is sufficiently strong to crosslink antibodies and elicit a signal from the emittor cell.

Figure 29:
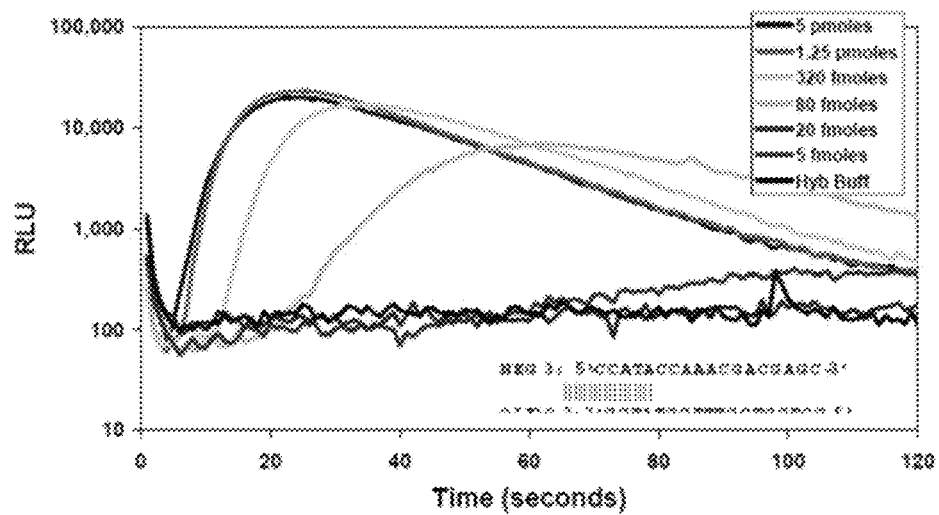
FIG. 29 is a graph. Rapid hybridization of Digoxigenin labeled, ssDNA oligonucleotides. The indicated amount of oligonucleotide "NEG3" was added to 8 μl of hybridization solution (50 mM NaCl, 40 mM Tris pH 7.5). 1 μl of "oligo 3" was added, followed immediately by 90 μl of CO2I medium and 20:1 of Dig CANARY cells. The tube flicked to mix, quickly placed into the luminometer and light output monitored. The total time between addition of the second oligonucleotide and placement in the luminometer ("0" on the x axis) was approximately 15 seconds.

Oligonucleotide-oligonucleotide hybridization occurs extremely quickly (FIG. 29). Oligonucleotide NEG3 was added to hybridization solution, followed by Oligo3. The solution was immediately diluted in medium, the emittor cells added, and the reaction place in the luminometer (elapsed time from addition of oligo 3 was 15 seconds). This abbreviated hybridization protocol did not drastically affect the sensitivity of the assay (compare FIG. 29 to FIG. 28).

Figure 30:
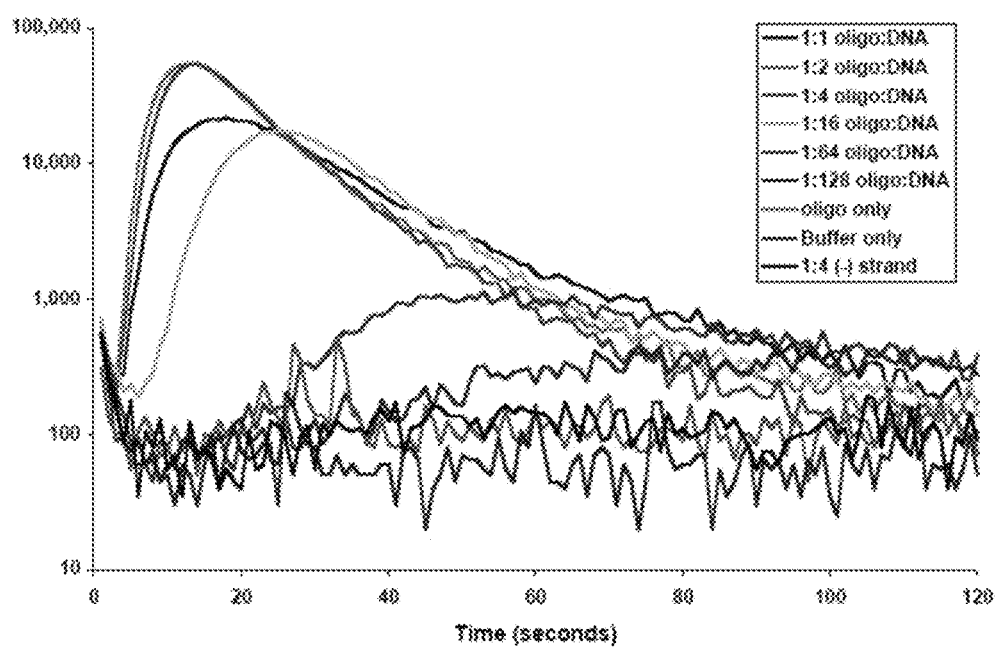
FIG. 30 is a graph. Single stranded DNA was generated from the pBluescript phagemid, and hybridized to all 10 Dig-labeled oligonucleotides. After hybridization the reaction was diluted to 100 μl in CO2I, 20 μl of Dig cells were added, and light emission was measured. The molar ratio indicated in the legend is that of oligonucleotide to target ssDNA. The ideal ratio in this experiments appears to be between 1:2 and 1:4.
Figure 31:
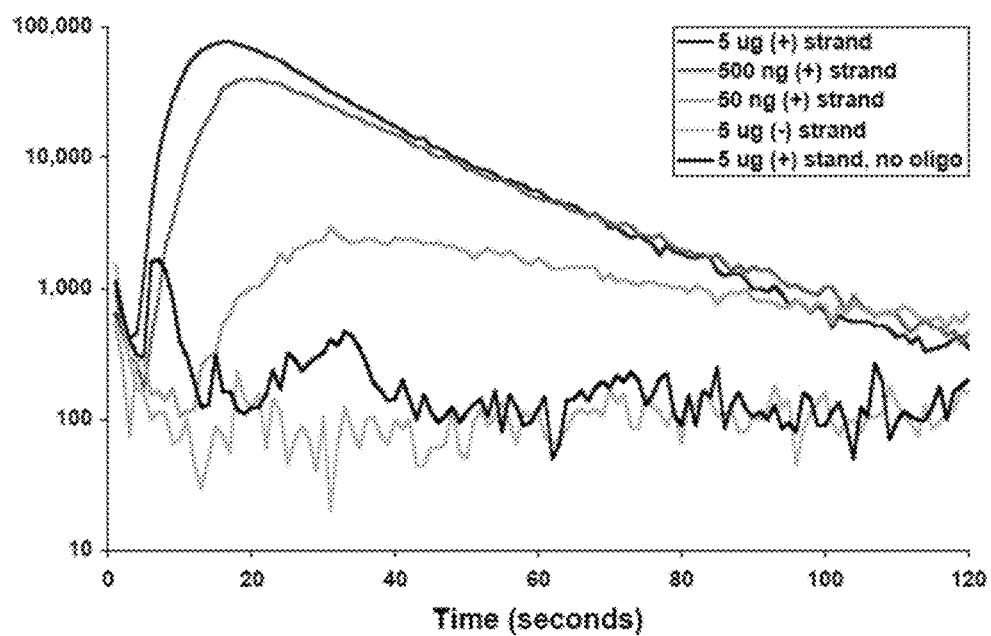
FIG. 31 is a graph. Sequence-specific detection of single-stranded DNA. Ten digoxigenin-labeled oligonucleotide probes complementary to the (+) strand of phagemid pBluescript were hybridized to the indicated amount of single-stranded phagemid DNA. Emittor cells expressing antibody to digoxigenin were added, and light output from the cells monitored on a photomultiplier tube. Only the (+) strand of the phagemid was detected, indicating that the identification is sequence specific. In the absence of oligonucleotide probe, single-stranded DNA did not stimulate the cells. The limit of detection in this experiment was 50 ng.

Next, multiple Dig-labeled oligonucleotides were hybridized to single-stranded DNA target. This complex was tested for its ability to stimulate emittor cells. FIG. 30 shows a series of hybridizations of different concentrations of the Dig-oligonucleotide probe set to a given amount of ssDNA. The ratio of ssDNA:oligonucleotide probe giving the best signal in this experiment was between 1:2 and 1:4. At higher concentrations of probe, the unbound Dig-labeled oligonucleotide appeared to inhibit signaling. In these experiments 0.63 pmoles of oligonucleotide worked well under many of the conditions tested. A dose-response curve gives a limit of detection for single stranded DNA of approximately 50 ng, or about 50 fmoles (FIG. 31). It is important to note that (−) strand DNA was not detected in either of these experiments, indicating hybridization of the Dig-labeled oligonucleotides and subsequent signaling from the emittor cells is dependent on the sequence of the target DNA.

Figure 32A:
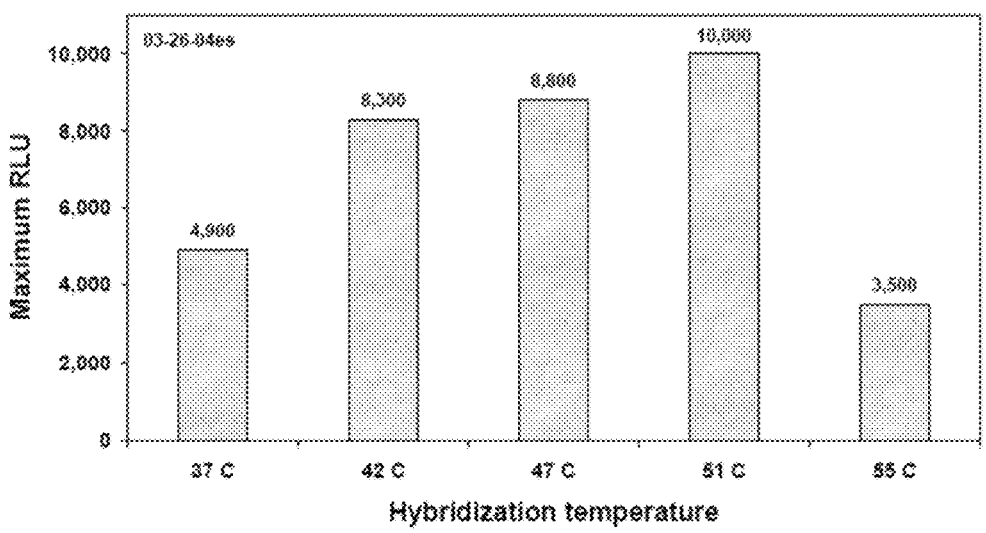
FIG. 32A. Hybridization in PBS shows maximum signal with hybridization at 51EC, but similar signals from samples hybridized at 47° C. and 42° C.
Figure 32B:
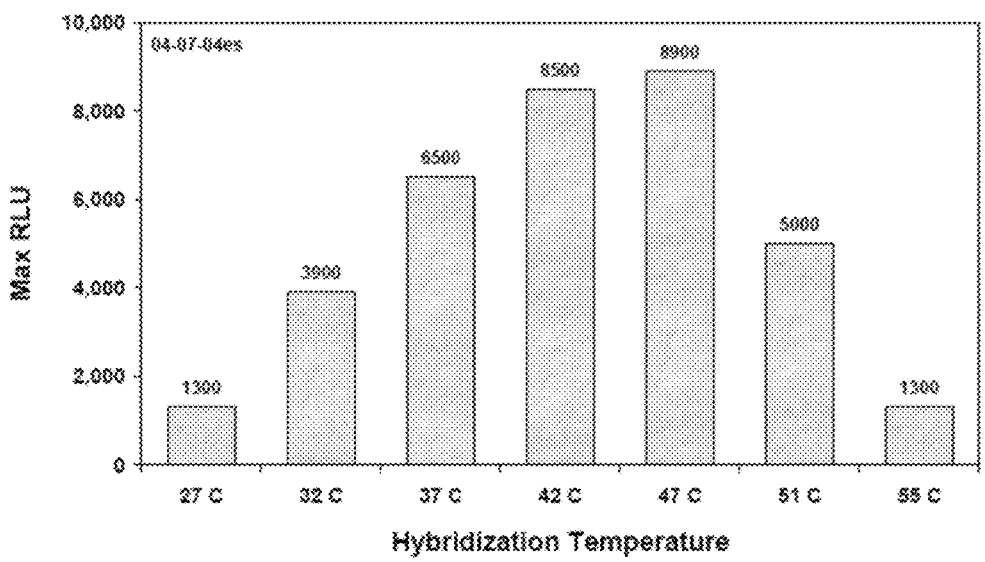
FIG. 32B. Hybridization at 42° C. displays an increase in the signal from experiments using lower concentrations of oligonucleotide probe, such that 0.16 pmoles of oligonucleotide works nearly as well as 0.63 pmoles, and the signal from 0.04 pmoles was doubled.

Temperature and buffer constituents affect hybridization of Dig-oligos to target NA. Hybridization at between 47° C. and 51° C. in either PBS (FIG. 32A) or TBS (FIG. 32B) gave the highest response. Hybridizations performed at higher or lower temperatures decreases the amplitude of the signal. Changes in the buffer constituents will obviously affect the ideal hybridization temperature.

Target DNA Capture

Figure 33:
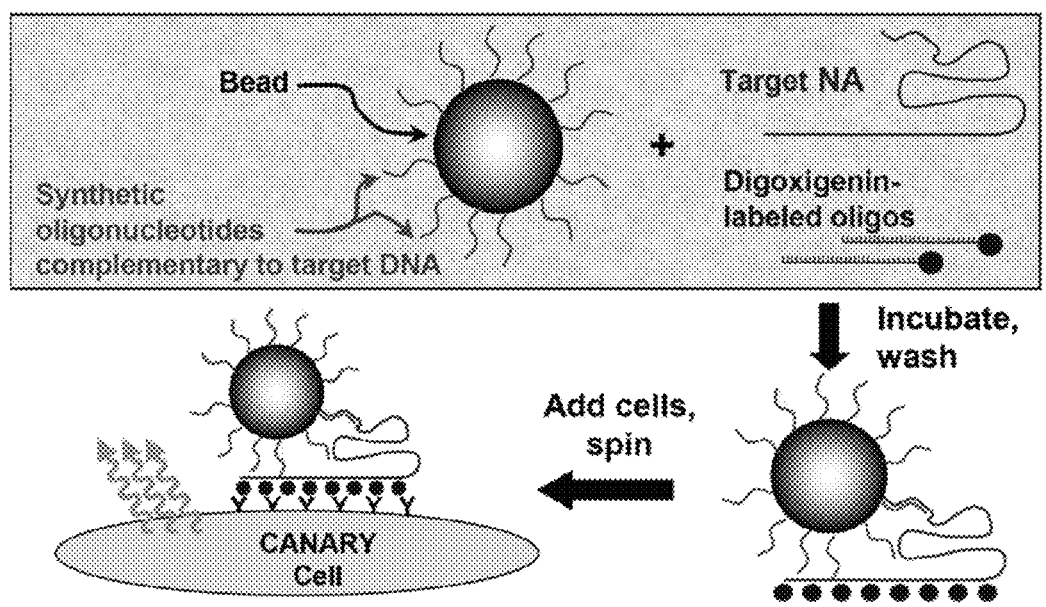
FIG. 33 is a schematic of the strategy for sedimentation of DNA. Capture oligonucleotides are attached to the surface of a sedimentable particle. These oligonucleotides bind to a region separate from that to which the Dig-oligonucleotides bind. Target NA bind to the capture oligonucleotides, and digoxigenin labeled oligonucleotides bind to the target. The entire complex is sedimented by centrifugation (or magnetic field), and detected by emittor cells expressing antibody against Digoxigenin.
Figure 34:
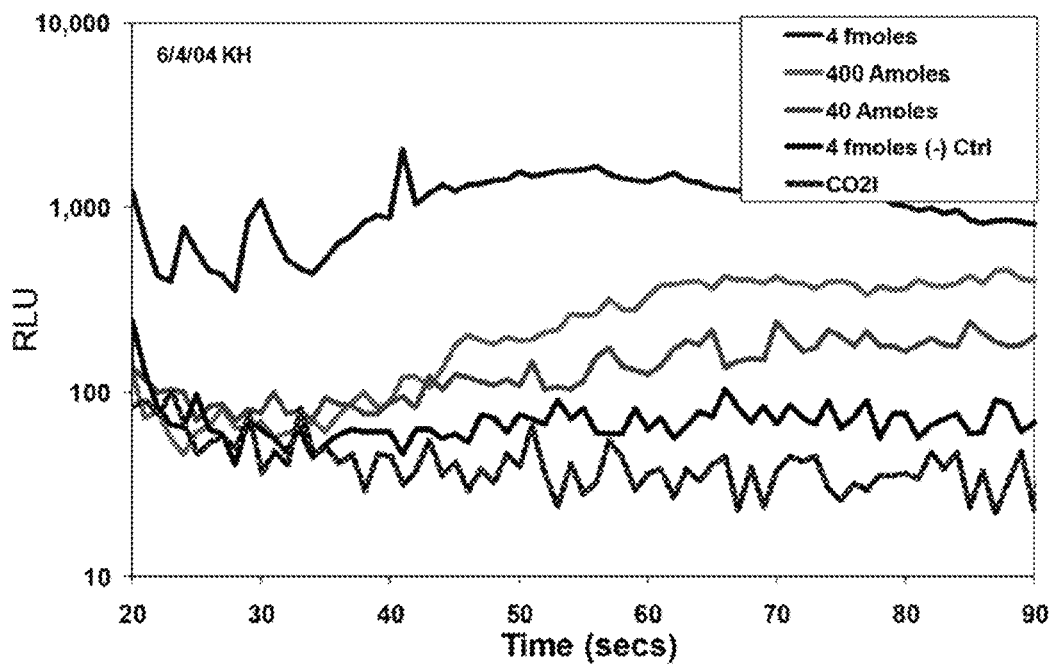
FIG. 34 is a graph. Sedimentation of target DNA improves sensitivity. Streptavidin-conjugated beads were saturated with biotin labeled capture oligonucleotide, and excess oligonucleotide removed by washing. pBluescript ssDNA (+strand) was incubated with the beads for 5 min at 47° C. and washed. Dig labeled detection oligonucleotides were added, hybridized for 20 min at 47° C., and excess removed by washing. Beads were resuspended in 200 ul CO2I, and 40 ul used in each assay.
Figure 35:
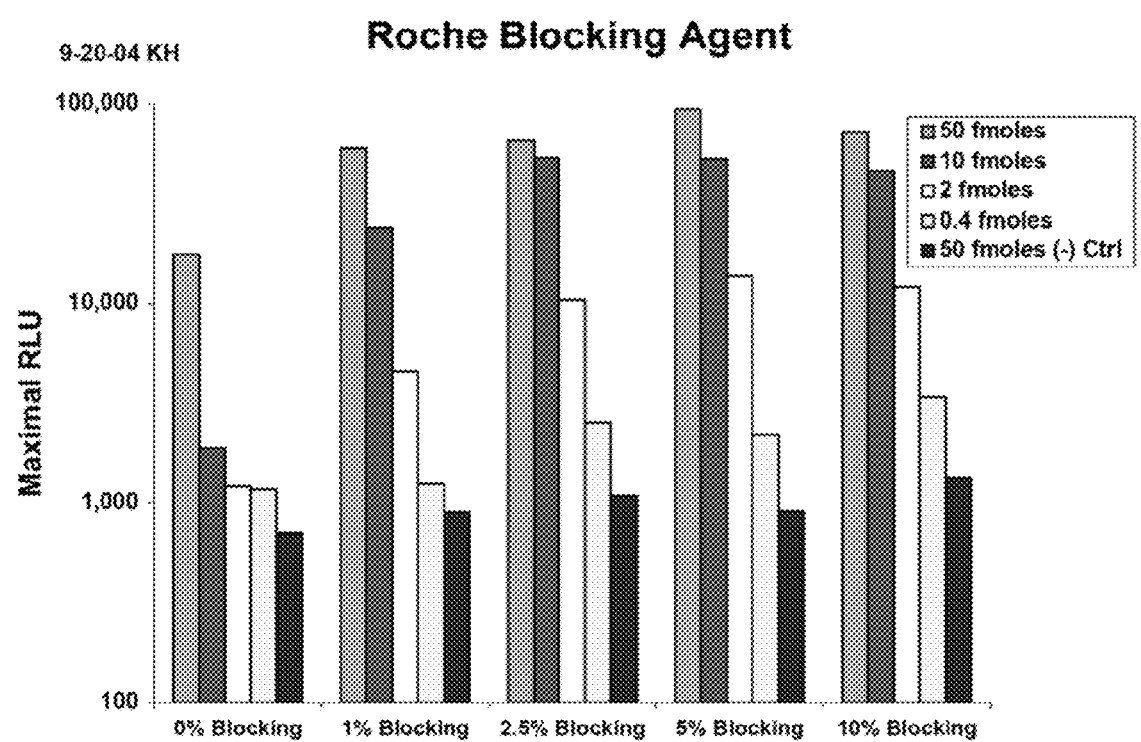
FIG. 35 is a bar chart. pBS phagemid ssDNA was incubated with biotin-labeled oligonucleotide bound to streptavidin-coated polystyrene beads and digoxigenin-labeled oligonucleotides for 20 minutes at 47° C. in the indicated concentrations of blocking reagent. The bead bound, digoxigenin labeled target was washed 3 times in TBS (50 mM Tris, 130 mM NaCl) at room temperature. Beads were resuspended in CO2I medium, emittor cells added, and the reaction spun and light output monitored in a luminometer.

Biotin-labeled oligonucleotides have been bound to the surface of streptavidin-coated magnetic and nonmagnetic beads. These "capture" oligos are designed to bind to the target DNA in a position well removed from the location of the Dig-labeled oligonucleotides. Binding the target NA to a sedimentable support will allow for more extensive washing of the DNA before addition of emittor cells, and improve the sensitivity of the assay. One strategy for sedimentation of target NA is shown in FIG. 33. In this scheme, a biotin-labeled capture oligonucleotide is attached either streptavidin-coated polystyrene or magnetic beads. Digoxigenin-labeled oligonucleotides are hybridized to the target, and the complex sedimented by centrifugation or application of a magnetic field. The emittor cells are then resuspended and sedimented with the beads, and the reaction tube placed in a luminometer. The effects of sedimentation on detection of target DNA is shown in FIG. 34. In this case, the LOD is improved to the high attomole range as compared to typical results in which the DNA is not sedimented. The addition of a commercial blocking reagent (Roche Applied Science Cat. #1 096 176) improves signal further. FIG. 35 shows the result of addition of different concentrations of blocking agent during the hybridization/capture step. In this experiment, addition of between 1% and 10% blocking reagent improved the signal to background ratio at all concentrations of target tested.

Fc Receptor Emittor Cells

The Fc receptors are a family of membrane-expressed proteins that bind to antibodies or immune complexes. They are expressed on several hematopoietic cells including monocytes and macrophages. Several subclasses of Fc receptors exist including Fc gamma Receptor I (FcγRI), a high-affinity binder of soluble antibody. FcγRI binds to the constant region (Fc portion) of Immunoglobulin G (IgG) leaving the antigen-binding region of the antibody free. Crosslinking of the antibody-bound receptor by specific antigen initiates a signaling pathway that stimulates calcium release.

The human macrophage cell line, U937, contains endogenous FCγR1. Treatment of these cells with IFNγ increases the expression of the FcγRI, as seen in FIG. 36A. U937 cells transfected with the aequorin expression plasmid produce functional aequorin as demonstrated by treating these cells with the calcium ionophore ionomycin. This causes a rapid and transient rise in calcium that stimulates the aequorin to emit light, as seen in FIG. 36B. U937 cells were then tested to determine if the aequorin would be stimulated by the calcium rise initiated by crosslinking of the Fc receptors. U937 cells were incubated with human IgG for 15 min at room temperature. The cells were washed to remove unbound IgG and treated with goat anti-human IgG. A rapid rise in calcium was observed, as shown in FIG. 36C.

Experiments demonstrated that U937 cells can be "engineered" rapidly to respond to several different pathogens or simulants. U937 cells were treated for 24 h with IFN (200 ng/ml) to increase expression of endogenous FcγRI, and prepared for the emittor cell assay. The cells were incubated with the following antibodies: mouse anti-*B. anthracis* spore (FIG. 37A), rabbit polyclonal anti-*B. anthracis* spore (FIG. 37B), mouse anti-*F. tularensis* (FIG. 37C), or mouse anti-*B. subtilis* (FIG. 37D). Cells were then used in the standard assay where they detected as few as 1000 cfu *B. anthracis* spores with the monoclonal antibody and 10,000 cfu spores with the rabbit polyclonal, as well as 10,000 cfu *F. tularensis* and 1,000 cfu *B. subtilis* spores.

The next set of experiments demonstrated that the specificity of the assay is determined by the antibody that is used. U937 cells were incubated with mouse anti-*F. tularensis* antibodies and were tested for their response to 105 cfu of *B. anthracis* spores. As shown in FIG. 38A, the cells did not respond to *B. anthracis* but did to 106 cfu of *F. tularensis*. Alternatively, cells loaded with mouse anti-*B. anthracis* spore antibodies did not respond to *F. tularensis* but did to 106 cfu of *B. anthracis* spores, as shown in FIG. 38B. Furthermore, the cells did not show any response to the 106 cfu of *F. tularensis* in the absence of anti-*F. tularensis* antibody, as seen in FIG. 38C.

Canary: Radiological Detection

The CANARY instrument can also be used to detect radiological materials. Radiological measurements can be made by adding scintillation fluid instead of B cells, and measuring light emitted from the scintillation fluid in response to radioactive decay. CANARY hardware has been shown to detect signal from alpha, beta, and gamma sources, and these measurements compare favorably to those made using a laboratory-based scintillation counter (FIG. 163). In this experiment, equal amounts of various types of emitters were added to commercial, aqueous scintillation fluid. The tube was shaken to mix, and placed in either a commercial scintillation counter or the normal benchtop CANARY luminometer. Light output was monitored on the same laptop computer using the same software as a normal CANARY assay. The responses of CANARY hardware was very similar to the response of the commercial scintillation counter.

This capability (plus that of chemical and explosive detection) makes CANARY sensors very broadly useful, as one sensor can be made that can detect all chemical, biological, radiological, nuclear, and explosive (CBRNE) materials in a variety of matrices (air, liquid, surface wipes, powders, etc.). See FIG. 163. Equal amounts of various radiological materials covering all three emitter types (alpha, beta, and gamma) were analyzed. The response of CANARY compares favorably to a commercial, laboratory-based instrument.

Additional Methods for Detecting Chemicals and Explosives

Background: Periplasmic Binding Proteins

The chemicals used for chemical warfare agents and/or explosives (also referred to herein as "CWA/E") are too small for CANARY to detect by direct antibody binding. However, bacteria are well equipped to detect and identify nutrients, many of which are small chemicals in the size range of CWA/E. CANARY can exploit a part of the bacterial nutrient detection pathway, and be modified to detect CWA/E.

Bacteria are motile organisms, and as such actively move toward nutrients. In order to determine the location of nutrients, bacteria use periplasmic binding proteins (PBPs) to monitor their environment. This PBP family has many members, each one of which binds to a specific nutrient. Using X-ray crystallography, researchers have shown that the protein resembles a Venus' Flytrap, consisting of 2 lobes connected by a hinge. Nutrients bind in the mouth formed between the 2 lobes, and in response to nutrient binding in the "mouth" of the protein, the protein closes (more accurately, its equilibrium state changes so that it is predominantly in the closed conformation in the presence of chemical target). This dramatic shape change is used to direct bacterial movement toward nutrients.

These and other structural studies indicate that PBPs use relatively few amino acids to actually bind to their target. Through computational design, one can predict how to mutate these amino acids so that a PBP will bind to a chemical completely different from its original target, such as the explosive TNT, the soman simulant PMPA (pinacolyl methylphosphonic acid), and the neurotransmitter serotonin (Allert et al., *Proc. Natl. Acad. Sci. USA* 101: 7907-7912 (2004); Looger et al., Computational design of receptor and sensor proteins with novel functions. *Nature* 423:185-190 (2003)). Large amounts of these mutant PBPs have been produced in bacteria, and shown to bind tightly and specifically to their new targets.

Using standard techniques, production of a high affinity CWA/E binding protein can be designed. If necessary, the design can start with several different parent PBPs, computationally designing all of them to bind to a given target, and testing the resulting affinities of each. For example, 3 different PBPs were selected as starting points to develop a binding protein for TNT: arabinose-binding protein (ABP), histidine-binding protein (HBP), and ribose-binding protein (RBP).

Published reports show that monoclonal antibodies can be readily made against the closed (target-bound) form of HBP (Wolf et al., *J. Biol. Chem.* 269: 23051-23058 (1994); Wolf et al., *J. Biol. Chem.* 271: 21243-21250 (1996)). These antibodies bound much faster to the HBP in the presence of histidine, when the protein would be predominantly in the closed conformation. In essence, then, the rate of antibody binding to the HBP protein is a measure of the target (histidine) concentration.

All PBPs undergo a large conformational change between the open and closed forms. Therefore, antibodies can be generated against the closed conformation of each PBP. Note also that the amino acids that are mutated to change the specificity of a given PBP are limited to the binding pocket. Thus, it is to be expected that a single antibody against the closed form of RBP, for instance, will also bind to the closed forms of the RBP mutants that bind to TNT or PMPA. The TNT-binding mutant could be put in "Channel 1" of the sensor, and the PMPA-binding mutant in "Channel 2", but a single CANARY cell line that reacts against the closed form of RBP can be used to detect target binding in both channels 1 and 2. The identity of the target chemical will be known because a different, target-specific PBP is used in each channel of the sensor. This means that the sensor should require far fewer CANARY cell lines than the number of chemicals that it can identify, greatly simplifying development of reagents for additional CWA/E.

Chemical Detection by CANARY Using Computationally Designed PBPs by Combining Individual Elements:

(1) Periplasmic binding proteins have been computationally designed that bind to a variety of chemicals. These proteins have been produced in bacteria, isolated, and their affinities to novel targets, including TNT and PMPA, measured. (2) These PBPs undergo conformation changes in the presence of ligand that can be measured using antibodies specific for the closed conformation. (3) CANARY has demonstrated the capability to use antibody binding to detect protein at attomole levels. Therefore, the CANARY assay can be adapted to detect PBPs in the closed conformation (see FIG. 164). This closed conformation will indicate the presence of CWA/E.

In detecting chemicals or explosives in the air, there are at least 2 possible methods for vapor sampling. The first is impingement, in which air is bubbled through liquid, capturing vapors and particulates. This is a time-tested method for air sampling. An alternate collection strategy is Solid phase extraction (SPE) or solid phase microextraction (SPME). This technique traps vapors directly from air onto dry, functionalized resins. Typically, these resins are eluted using heat or organic solvents.

16 Channel Sensor Example

A new approach that reduces the time to measure multiple samples (while keeping the hardware requirements minimal) has been successfully tested. An experimental sensor has been designed that allows the simultaneous measurement of 16 samples using a single light-gathering channel. The sensor consists of a rotor holding sixteen 1.5-ml tubes horizontally, equally distributed about its circumference, and driven by a variable speed motor about a vertical axis (FIG. 39). A single fixed photon-detecting element (in this case, a PMT) is positioned in the plane of the rotor just beyond the path of the tubes during rotation. In this way, each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

A single measurement consists of:
1. Preparing 16 samples (and/or controls) in individual 1.5-ml tubes;
2. Introducing an aliquot of emittor cells into each of the tubes;
3. Installing the tubes into the rotor situated in a dark box;
4. Localizing the emittor cells at the bottom of the tubes using a brief (5 sec) centrifugal spin at high RCF (2000 g);
5. Reducing the rotor speed to 60 rpm for the duration of the measurement (1-2 min), each tube being sampled once every second; and
6. Generating a time series of photon counts for each sample for display and/or input to a computer algorithm for evaluation.

Figure 41:
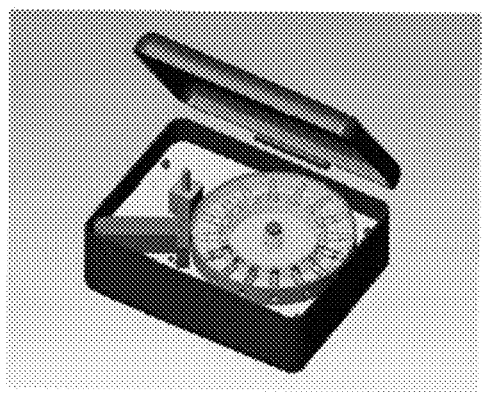
FIG. 41 is an illustration of a portable 16-channel-sensor design.

An example of the data from a 16-channel measurement, seen in FIG. 40, shows an LOD comparable to that of the single tube method. While this 16 channel sensor will measure 16 samples as designed, larger sample numbers are possible by increasing the number of channels, though physical size and the statistics of sampling will ultimately dictate practical limits. Similarly, smaller sample numbers are possible by decreasing either the number of samples loaded onto a sensor, or by reducing the number of channels on the sensor. A CAD drawing of the 16-channel portable sensor design is shown in FIG. 41.

A further implementation of this 16-channel design is referred to as a TCAN sensor. The TCAN (Triggered-CANARY) biosensor is an automated biosensor which combines both aerosol collection and B-cell liquid delivery into an integrated radial disc format. The TCAN CANARY disc (CD) (FIG. 42) interfaces with a manifold assembly which splits an air flow into separate channels. The aerosol collection assembly (FIG. 43) uses dry impaction techniques to then localize particles from the air flow into the bottom of clear plastic tubes.

After impaction of aerosol particles, the CD interfaces with the manifold assembly to actuate valves located in the disc. The disc is rapidly spun, which in turn causes the emittor cell liquid to deliver to individual tubes using centrifugal force (FIG. 44). An optical detector is then used to identify potential bioagents based on the photon output emittor cells interacting with the aerosol particles. This process of aerosol collection and emittor cell delivery can be repeated several times in one disc. This feature allows multiple CANARY assays to be performed after several trigger events without changing the CD.

Aerosol-Collection Techniques

Dry aerosol-collection technologies specifically tailored for the CANARY sensor have been developed to take full advantage of the potential speed of CANARY. Unlike many other air-collection systems that require wetting agents and complicated fluidics, the dry-impaction system collects particles directly from the air onto a dry surface thereby eliminating almost all consumables from the process. In addition to the low material consumption of this impaction system, it does not suffer from the low-temperature freeze-out experienced by liquid-based collection systems.

This simple collection method separates more dense pathogen particles from the airstream by exploiting the relatively high momentum of particles to force them to impact on a dry surface where a fraction of the impacted particles are bound non-specifically and retained. The basic concept and one of our collector prototypes are shown in FIG. 23.

An ideal aerosol impactor shows little or no collection of very small particles (which can follow the diverted air stream), almost 100% collection of large particles (whose momentum takes them out of the air stream), and a smooth transition in efficiency of capture for particle sizes between these extremes. Impactors are typically characterized by the particle size at which 50% collection efficiency occurs. FIG. 165 shows that for this prototype tube impactor, 50% collection efficiency ($D_{50}$) occurred at approximately 1-μm diameter at a flow rate of 5 liters per minute. Collection of larger total numbers of particles was accomplished easily by increasing the sampling rate or sampling time to increase the total volume of air sampled.

CANARY sensors have been used to identify bioagents collected using dry impaction without further processing since this method localizes bioagents to the tube surface, eliminating the need to pre-spin the sample for maximum performance. This allowed the CANARY assay protocol for dry sample identification to be much faster and simpler to perform (and automate) than the protocol used for liquid samples. Identification of dry samples also has the potential to provide improved overall sensitivity to small viruses and other pathogens that are not readily sedimentable in the liquid assay since all collected particles will be adhered to the bottom of the tube during impaction regardless of the size of the individual pathogens incorporated in the aerosol particle.

Proof of Concept for Integrating Dry-Impaction with CANARY

To demonstrate the efficacy of the dry-impaction collection technique for the CANARY sensor application, individual *Bacillus subtilis* spores were aerosolized with a Collison nebulizer and collected in the prototype shown above for 30 seconds at 5 liters per minute. The B cells were added directly to the sample-containing tube, placed in the portable CANARY apparatus, spun for 5 seconds, and the light signal quantified by PMT. The results are displayed in FIG. 166 and show that the direct-impaction technique yields a B-cell response that is similar in kinetics to the pre-spun liquid samples with no need for sample preparation before analysis.

With an overall response time as short as 1 minute in this proof-of-concept experiment (30 second collection followed by peak photon intensity less than 30 seconds of analysis time) CANARY demonstrated the potential to increase combined speed and sensitivity for bioaerosol identification by more than an order of magnitude compared to all other automated bioaerosol identification sensors. This dramatic performance improvement enables CANARY sensors to fill a long-standing technology gap in sensor performance prevented sensitive detection within ~3 minutes that is needed to warn and protect populations from exposure to threatening bioaerosols. CANARY sensors provided the first (and still the only) demonstration of the potential for detect-to-warn (also known as detect-to-protect) biodefense capability in a biological identification sensor. This unique demonstration of potential motivated the rapid development of automated bioaerosol sensors to enable the technology to leave the laboratory and operate in realistic environments to establish the real-world utility of CANARY.

Automated Canary Bioaerosol Sensor Development

To demonstrate detect-to-warn capability in bioaerosol defense applications, the CANARY identification technology was seamlessly integrated with the dry aerosol collection architecture in two first-generation sensors, BCAN and TCAN. The BCAN sensor was designed to provide 30 automated sampling and analysis cycles prior to reloading with sensitivity sufficient to detect low-concentration treats and was extensively tested in a variety of environments to establish ROC curves characterizing CANARY performance and false positive rates in a variety of realistic environments. The good performance characteristics demonstrated by the BCAN sensor provided the foundation that motivated development of TCAN under a separate program to demonstrate a simplified CANARY sensor tailored to meet the less demanding requirements anticipated for indoor bioaerosol monitoring.

BCAN Sensor Development and Testing

The first step toward developing any automated CANARY sensor based on the proof of concept results was to design a reliable way to combine the dry collection with a spin-enhanced CANARY assay. Furthermore, since fluidics systems are not needed in this architecture for liquid collection reagent delivery (as they are in all other bioaerosol identification sensors) we focused our design efforts on cell droplet storage and delivery without fluidics mechanisms. This unique approach of combining reagentless aerosol collection with a cell-based biosensor in an automated format enables complete elimination of a core system that accounts for much of the high cost, increased size and complexity, and reduced reliability of other bioaerosol identification sensor platforms. The ultimate solution implemented for the BCAN sensor utilizes simple carriers incorporating appropriate aerosol collection features and individual aliquots of B cells stored in COTS capsules that release their contents automatically during a brief spin after collection. The key details of this design are outlined in FIG. 167.

Each BCAN carrier contained 4 parallel mechanisms (or channels) that provide the four core functions necessary for CANARY analysis: Cell storage, aerosol sampling, cell delivery, and signal transmission to PMTs. The BCAN testbed contained and automatically processed up to 25 of these carriers between reloading. Speed and sensitivity characteristics for BCAN were established using Collison nebulizer-generated *Bacillus subtilis* spore aerosols as a simulant for anthrax and other bioaerosols and demonstrated that this first sensor could provide >96% probability of identification for bioaerosols at concentrations of ≥100 agent containing particles per lither of air (ACPLA) with a 3 minute total response time that includes automated aerosol collection and analysis. Furthermore, this sensor was operated in a variety of indoor and outdoor locations.

Over 13,000 tests were completed in 9 different locations spanning a wide range of background conditions and the results established that the frequency of anomalous positive signals (false positives) given by this sensor in realistic environments was similar to the frequency of false positives observed in the laboratory. These results together demonstrated the utility of this first sensor for fast, sensitive bioaerosol identification in less than 3 minutes. Furthermore it was demonstrated that the collection time needed for positive identification of a bioaerosol was proportional to the concentration of bioaerosol present so that total response times of less than 90 seconds were possible for sufficiently high concentrations of bioaerosol. No other antibody- or nucleic acid-based sensor platform has demonstrated this speed of response in an automated bioaerosol sensor.

An increase in the number of tests can be achieved by placing multiple B-cell lines or individual B-cell lines expressing multiple antibodies in an individual tube, or channel. Such a system utilizing cell-line or antibody combinations minimizes hardware complexity (and size) and can detect $2^n-1$ agents independently (where n is the number of channels) for a single-agent attack scenario. The practical limit of CANARY assays using multiple cell types per channel is reached with mixtures of three different B-cell lines. As more than three cell types per tube are used, the signal strength at low concentrations of target falls below the detection threshold as the probability of correct target-B cell interactions diminishes. In addition to expanding the number of agents that can be identified for a given number of channels, introducing test redundancy using this approach has been used to eliminate uncorrelated false positives (tests where not all of the simultaneous tests for a given agent give positive results) and reduce the false positive rate significantly.

An extensive set of measurements and fieldings demonstrated BCAN's capability to identify bioaerosols at biologically relevant concentrations in as little as 90 seconds. This response time is an order of magnitude faster than any other integrated bioaerosol identification sensor and is the only demonstration of speed consistent with the needs of detect-to-protect operation for biological defense. Perhaps even more importantly, the low false positive rates established for CANARY testing in real-world situations (between 0.2% and 0.3% for single tests, and 0.1% or less for 2-fold or greater redundancy while maintaining ≥96% probability of identification) shows that this capability can be practically implemented into systems demanding low false-alarm rates and superior speed for bioaerosol ID. While the BCAN was designed to be a powerful demonstration testbed, other sensor architectures offer potential advantages for customized applications. Motivated by the early successes of BCAN, TCAN sensor development was begun as a parallel sensor development effort to establish CANARY performance for building protection using a customized sensor design.

TCAN Sensor Development and Testing

The TCAN is a CANARY based biosensor developed as a simple, cost-effective means for real-time monitoring of bioaerosols in indoor building environments.

This particular sensor was designed to combine both aerosol collection and B-cell delivery into an integrated radial disc format. The disc is designed to interface with a manifold which separates particulate laden airflow into four separate channels. Inertial impaction techniques are then used to localize these particles into the bottom of clear disposable tubes.

After collection of aerosol particles, valves located within the disc are opened, and the disc is rapidly spun at 2000 RPM for 5 seconds. This spin step quickly drives the B-cell liquid into contact with the collected particles using centripetal force. A single photomultiplier tube (PMT) is then used to identify potential bioagents based on the photon output of B-cells interacting with the aerosol particles as the disc rotates. This process of aerosol collection and B-cell delivery can be repeated several times, allowing multiple CANARY assays to be performed in a single disc.

This CANARY sensor can deliver high confidence identification of suspect particles in less than 3 minutes.

Panther Sensor Development and Testing

Building on the successes and lessons of the two first-generation automated CANARY sensors, we have incorporated CANARY technology into a flexible bioaerosol sensor platform called PANTHER (Pathogen Analyzer for Threatening Environmental Releases). The core functions of aerosol collection and CANARY analysis were designed into a simple disk with 16 channels that forms the core of the second-generation PANTHER family of mission-specific bioaerosol identification sensors. The ultimate PANTHER sensors are intended for use individually or in networks to provide site/building protection, emergency response, rapid screening, and environmental monitoring. High-confidence identification of very low concentration bioaerosols in less than 2 minutes has been demonstrated using the first PANTHER sensor, a portable unit referred to as the CUB, that is 37 lb., ~1 ft$^3$, and can ultimately be made for less than \$20K. The design tested is simple and reliable: It has no fluidics, no liquid consumables, minimal moving parts, loads like a CD player, and automatically collects and analyzes the sample.

The CUB sensor was an outgrowth of a project initially focusing on the development of a CANARY-based sensor that could perform all of the automated collection and analysis functions of the current bioaerosol sensor fielded by the US military—The Joint Point Biological Detection System, or JBPDS. The PANTHER disk was designed to be the core of this sensor and enable 16 simultaneous tests to be performed on a single aerosol. The development of CUB followed that initial design effort and demonstrated the opposite end of the sensor complexity and capability spectrum: A small, inexpensive, portable sensor that could automatically process a single PANTHER disk. The resulting CUB sensor has been designed, fabricated, and tested. Preliminary results have demonstrated that the CUB offers improved speed and sensitivity, detection of spore aerosols at concentrations below 10 ACPLA and response times less than 2 minutes including collection and identification, in a much smaller and less expensive sensor. Additional environmental testing in the same environments used to characterize the BCAN bioaerosol sensor have demonstrated that the PANTHER CUB also has a very low false positive rate in realistic environments.

Panther Cub Disk Design and Function

Figure 173B:
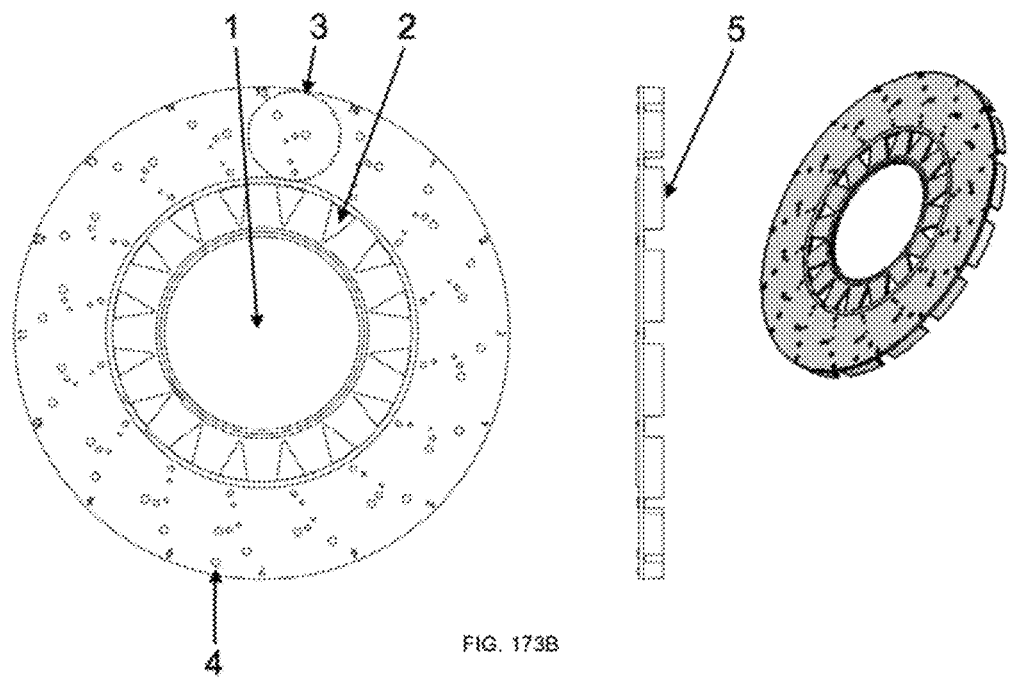

The disk used in PANTHER sensors performs two primary functions: 1) It provides specific geometries that enable it to collect aerosol particles out of air being drawn through the disk and deposit them in a focused location suitable for direct analysis using CANARY; and 2) It stores the CANARY B cells in sealed reservoirs that allow the reagent to be dispensed onto the collected aerosol particles without manual manipulation. Two parts, a carrier body and a lid, were designed to be injection moldable and amenable to ultrasonic welding to form the completed disk that is 120 mm in diameter and 6 mm tall with approximately uniform wall thicknesses of 1 mm (FIG. 173). The preferred polymer for the disk is polypropylene homopolymer because of it has demonstrated superior compatibility with B cells for long-term storage, but any other polymer with sufficient transparency (for signal transmission from the B cells to the light sensing element) and B-cell compatibility would also be suitable.

The carrier body has a continuous bottom with vertical walls oriented to form a plurality related feature sets in the welded disk for aerosol acceleration and collection and for liquid reagent storage and delivery that are arrayed radially about the central axis. These features can be identical or they can be tailored individually to enable a range of collector and assay functions to be provided by a single disk. An inner set of walls, FIG. 173A-feature 1, directs and accelerates the airflow toward slits in the outer perimeter of the disk with widths and spacings from the outer wall that can be tailored to provide for efficient collection of aerosol particles at variety of flow rates using principles well established in the literature (give references). An outer set of walls, FIG. 173A-feature 2, form a continuous perimeter around the edge of the disk and provide individual particle collection sites with defined geometries that help collect the particles accelerated by the inner set of walls onto a plurality of sites with localized areas demonstrating increased particle density. Another set of walls positioned between walls A and B, FIG. 173A-feature 3, create a plurality of compartments in the welded disk that can contain liquid reagents and other materials that provide for their release and distribution onto the collected particles during a subsequent spin or spins. The walls can be designed so that a single spin delivers stored CANARY cells from all compartments or so that multiple spins can deliver the contents of individual compartments or subsets of compartments on demand.

The lid has the form of is a 1 mm thick disk with two key sets of features. The first set of features comprises a variety of perforations to allow introduction of liquid reagents (FIG. 173B—feature 3) and aerosol samples (FIG. 173B—feature 1 inlet, and FIG. 173B-feature 2 outlets) into the assembled disk, and provides an indexing feature (J FIG. 173B—feature-4) that can be detected by an optical sensor to detect disk orientation during readout. The second set of features comprises raised structures on both sides that enable the lid to provide baffles that reduce carryover of light between adjacent channels in the disk (FIG. 173B-feature-5) (when the polymer used to form the disk contains a suitable pigment to make it opaque), provide features to enhance the ultrasonic welding of the disk halves and 3) reduce the contact area required to form a air seal with the manifold that delivers aerosol to the disk and removes depleted air after particle collection in the disk (circular rings just inside and outside the air outlets).

FIG. 174 illustrates how features A and B in the welded disk work together to direct aerosol flow and particle collection. Applying a partial vacuum using one or more suitable blowers or pumps to the array of triangular openings on the disk lid between the two circular ridges draws aerosol to be sampled into the disk through the large central opening. The air is distributed into a plurality of channels and flows radially outward as that channel tapers down to accelerate the aerosol as it nears the perimeter of the disk. The airflow is then forced to make a sharp turn at the outer perimeter of the disk before being drawn out through the triangular openings. The momentum of the aerosol particles entrained in the air sample prevents the particles from turning with the air, and they instead impact the inner surface of the disk at focused points that can be tailored by adjusting the geometry of the outer wall of the disk. A significant fraction of particles in the size range of interest (typically between 1 and 25 µm) adhere to the surface where they impact and are retained for subsequent CANARY analysis. The distribution of collection in the disk was characterized using fluorescent 1 µm spherical polystyrene particles. These particles were aerosolized then air was drawn through the disk at a rate of 30 L/min/channel and the resulting distribution of particles was visualized under ultraviolet illumination. This demonstrated that the distribution of collected particles could be tailored so that the particles collected into two dense lines with positions determined by the location of wall segment intersections on the collection surface. When the intersections are positioned to be at the maximum radius of the disk this results in reliable co-localization of the collected particles and the delivered CANARY cells for optical signal stimulation and detection.

Adjusting the flow rate through the nozzle can enable the size range of particles collected in this disk design to be adjusted as needed. FIG. 175 illustrates the relationship between the flow rate and the size of particles that are effectively transported through the disk and directed to impact onto the collection surface. At high flow rates (e.g. 30 L/min) particles>1 µm in diameter have sufficient momentum to contact the collection surface, however, the practical upper size limit for this flow rate is 8 µm because particles≥8 µm in diameter have too much momentum to make the initial 90° turn that occurs as the aerosol turns from the central inlet into the radial air channels that are in the plane of the disk. Reducing the airflow gradually increases the cutoff diameter for particles that have sufficient momentum to impact the surface but also enables larger particles to make the initial turn into the disk and expands the overall size range of particles that can be collected at the analysis location. For example lowering the flow rate to 4 L/min adjusts the size range of collected particles to between 2.5 µm and 25 µm, allowing much larger aerosol particles to be collected and analyzed.

FIG. 176 illustrates how features C in the welded disk work together to provide for storage and release of liquid reagents. The walls in the reagent storage zones are oriented to form a pocket that has an opening facing the outer radius of the disk and so that appropriately positioned holes in the lid provide access and vent ports into this pocket for loading 1) a viscous plug to block the opening to the rest of the disk, followed by 2) addition of the liquid reagent (e.g. B cells) through the loading port while the air escapes through the vent hole. The addition of a short wall protruding into the reagent storage zone that separates the loading port from the vent port ensures complete filling of the pocket during loading. Once the loading of the viscous plug and liquid reagent is complete the access holes are covered using an adhesive tape to seal the liquid into a pocket that remains air and liquid-tight until release is desired. To release the liquid reagent the disk is spun to a sufficient RPM (typically 4,000 rpm) so that the radial acceleration forces are sufficient to displace the viscous plug from its position thereby opening the pocket toward the outside of the disk and enabling the liquid to flow to the outer radius of the disk and cover the collected aerosol particles. For liquids containing B cells the 5 second spin that is used to dispense the liquid reagent is also sufficient to sediment the suspended B cells onto the outer wall of the disk and co-localize them where the aerosol particles were collected.

Following delivery of the B cells and any other liquid reagents, the spin is slowed down (typically to between 30 and 120 rpm) to enable a single photon-sensing element (e.g. a photomultiplier tube (PMT), a channel photomultiplier (CPM) or other photon counting device) to record sequentially the level of light emission from each channel as it passes in front of the photon sensor. The disk continues to rotate while the light output is monitored for up to 2 minutes then the data is processed and stored by the sensor used to process the disk or by an attached computer Panther Sensor Description The overall view of a compact sensor that has been built to automatically process the CANARY disks is shown in FIG. 177. The sensor body is 12" H×12" W×14" D, weighs approximately 37 lbs. and has all of the necessary components and controls to automatically collect and analyze aerosol samples using a single manually-loaded CANARY disk. Disk loading is accomplished by opening a drawer (FIG. 177—feature 1), placing the disk on a platform, and closing the drawer. When the sensor receives a signal to collect and analyze a sample, the sensor begins to pull air in via the inlet port (FIG. 177—feature 2), directing it through the disk, and then exhausting the particle-depleted air through the outlet port (FIG. 177—feature 3). Following aerosol collection for a time determined either by a pre-set parameter or by a signal received from an external controller, the sensor spins the disk at a speed sufficient to deliver the CANARY reagents (typically 4000 rpm) and begin the analysis phase. During the analysis the spin is slowed down to enable the photon emission to be measured for each individual channel in the disk as it spins in front of a single photon counting module.

The following core components (illustrated in FIG. 178) were assembled into the first sensor and are sufficient to perform all of the collection and analysis functions and enabled the performance described below. The CANARY disk (FIG. 178—feature 4) was placed onto the motor assembly (brushless DC motor Faulhaber part#3564K012BK1155, FIG. 178—feature 5) and the door was then closed to load the disk into the custom light-tight box (FIG. 178—feature 7). Two Ametek blowers (part#150193, FIG. 178—feature 1)

were connected to a custom manifold (FIG. 178—feature 6) that provided the interface with the CANARY disk and separated and directed the inlet and outlet flows as they entered and exited the disk. When the blowers turned on the disk was automatically lifted into place under the manifold and the vacuum from the blowers held it in place and provided sufficient sealing force to ensure proper aerosol flow through the disk. After the blowers turned off the disk dropped down automatically onto the motor assembly which spun the disk to 4000 rpm for 5 seconds to deliver the cells then slowed the spin to 60 rpm. That speed was maintained for 2 minutes while the channel photomultiplier module (Perkin Elmer part# MCP 1984, FIG. 178—feature 2) measured the light output from each individual channel. This entire process was controlled by an onboard computer (PC 104 from Diamond Systems-part# ATH660-128 with a custom interface board, FIG. 178—feature 3).

Panther Sensor Performance Demonstrations

To establish sensor sensitivity, test aerosols were produced by Collision nebulization of dilutions of a concentrated stock solution of *Bacillus subtilis* spores, sampled for 1 minute and analyzed using cells specific for the spores in the CUB. Approximate ACPLA levels produced by each dilution are shown in the legend of FIG. 179. The 1:8000 dilution generated a number of particles per liter that was indistinguishable from the chamber background produced when DI water was added to the nebulizer, but based on the general trend the concentration should be on the order of 5 spores per liter of air. Even at this extremely low concentration, a 1-minute sample at 30 L/min consistently produced an easily detectable signal with a peak intensity more than three times greater than the negative control.

The simulant identification data from the chamber studies was then combined with background measurements made in typical indoor environment over a 1-week period (>1000 tests) using cell lines specific for *Yersinia pestis*, and *Bacillus anthracis*. Analysis of the resulting data demonstrated that the PANTHER CUB sensor provides better than 95% probability of detection for concentrations≥50 ACPLA with a corresponding false alarm rate of ~0.1%. This performance provided a significant enhancement of capability compared to the first-generation BCAN and TCAN sensor performance and can be optimized further with additional hardware refinements and algorithm development.

Toxin Detection Example

Figure 48:
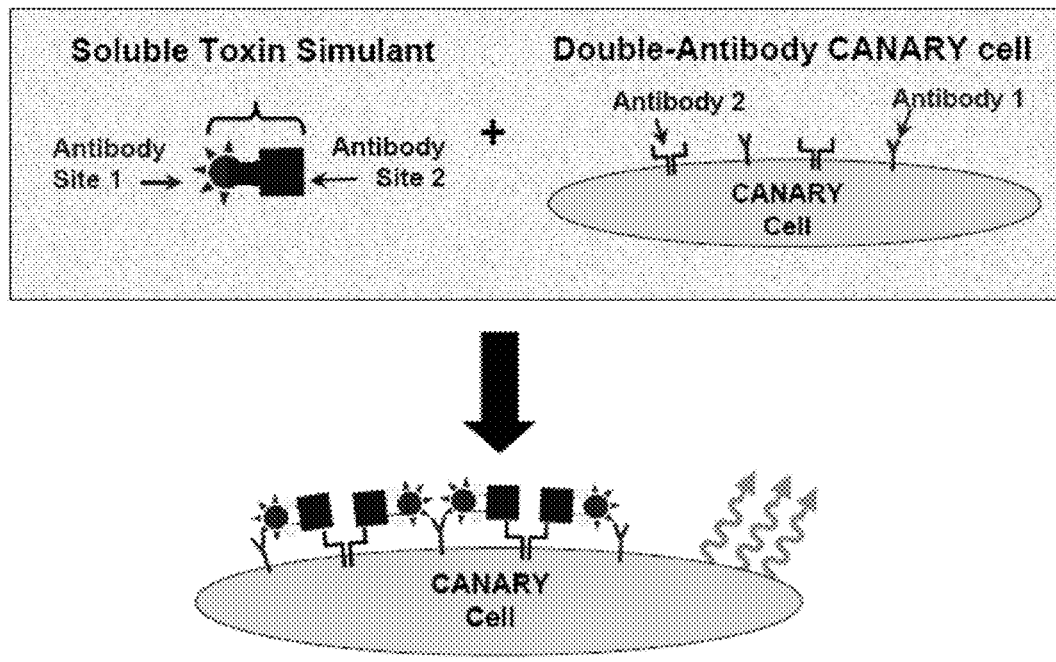
FIG. 48 is a schematic for the detection of soluble, monomeric antigens: strategy 1. A single emittor cell is engineered to express two different antibodies against two different epitopes on the same, monomeric antigen. The presence of antigen crosslinks the antibodies, stimulating the emittor cell to emit light.

Detection of soluble proteins can be achieved using a variety of methods. For example, in one method, two antibodies can be expressed in the same emittor cell, wherein the two antibodies are each against a different epitope on the same molecule. The antibodies are then crosslinked by monomeric antigen (FIG. 48). It should be pointed out that the sorting of antibodies in the secretory pathway is idealized in the schematic of FIG. 48. In one example, the antibodies can be heterofunctional, i.e., one antibody can have two different functional antigen binding sites. In another example, each antibody has only one functional antigen binding site. This method depends on two factors: (1) multiple functional antibodies are expressed by the same emittor cell and (2) two, linked epitopes are sufficient to stimulate emittor cells (although more than one of these pairs may be required to stimulate a given cell).

Figure 49:
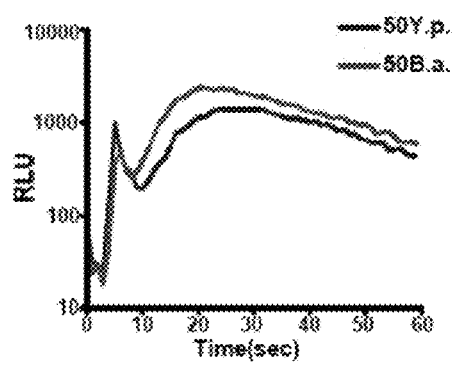
FIG. 49 is a graph depicting the results of a cell line expressing antibodies against both $B.$ $anthracis$ and $Y.$ $pestis$ which was challenged with each $B.$ $anthracis$ and $Y.$ $pestis.$ This clonal cell line can detect as few as 50 cfu of either $B.$ $anthracis$ and $Y.$ $pestis$, indicating that both antigen-binding sites from both antibodies are expressed and functional.

In one experiment, multiple, functional antibodies were expressed in the same emittor cell line (FIG. 49). A single cell line expressing antibodies against *Bacillus anthracis* and *Yersinia pestis* was generated. This clonal cell line reacts against both antigens with good sensitivity. It will be understood that two antibodies against two epitopes on the same soluble monomer can also be functionally expressed. Furthermore, two linked epitopes is sufficient to stimulate emittor cells.

Figure 50:
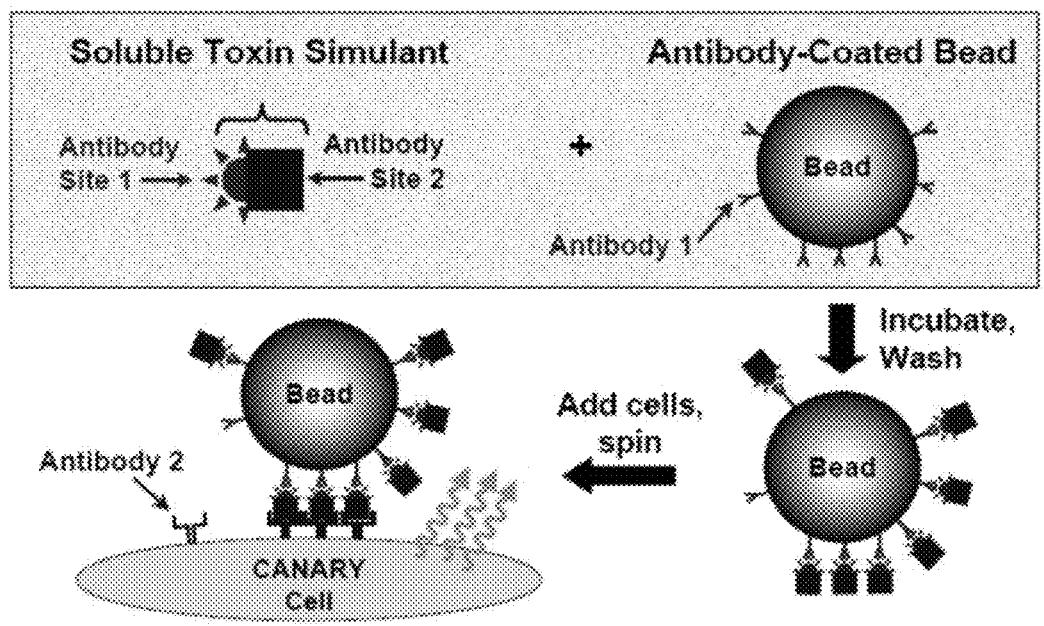
FIG. 50 is schematic of the strategy for detection of soluble proteins. An antigen composed of two or more epitopes is detected using two antibodies, one bound to beads (or any support that binds to multiple antibodies) and the second antibody is expressed by the emitter cell. The antigen is incubated with the antibody-coated bead, decorating its surface with multiple antigens. The bead is them presented to the emittor cell. Because the antigen is crosslinked by the bead, the emittor cell antibodies are crosslinked and light emission stimulated.

A second method for detecting soluble, monomeric antigens is to crosslink the soluble antigen to make it appear multivalent to the emittor cell (FIG. 50). This crosslinking can be done by attaching the protein to beads, either via tags, in the case of recombinant proteins, or via antibody, as has been demonstrated for botulinum toxin Hc fragment. There are a variety of other possible methods for effectively crosslinking the antigen, as will be understood by those of skill in the art, including precipitation of antigen with trichloroacetic acid (TCA), heat, or ethanol, and attachment of the antigen to a solid phase via ligands, antibodies, or chemical functional groups. This crosslinked monomer can then be detected using emittor cells expressing antibody that recognizes an epitope still available on the crosslinked antigen.

Figure 51:
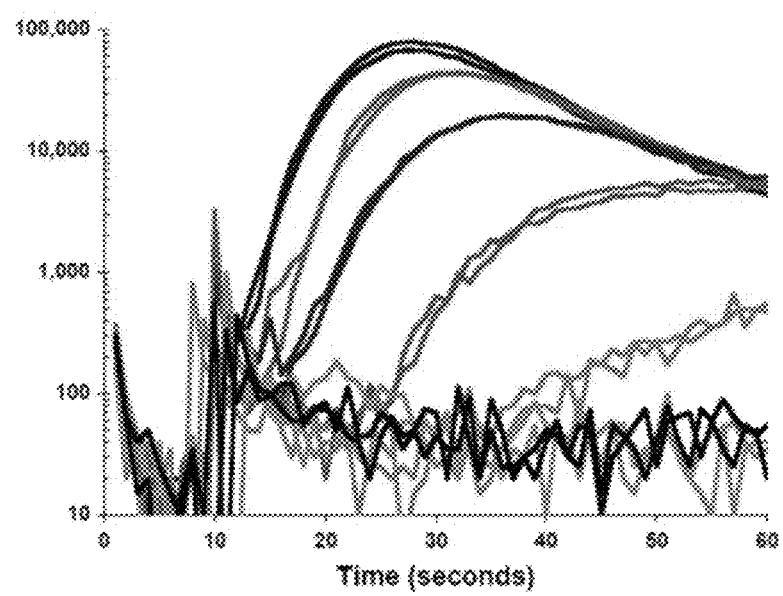
FIG. 51 is a graph depicting the results of antibody 6E10-10, crosslinked to Protein G magnetic beads, which was incubated with varying amounts of BoNT/A Hc for 3 hours at 4° C. Beads were washed with $CO_2I$ medium three times. Emittor cells expressing 6B2-2 antibody were added, the reaction was spun for 5 seconds, and the light output was monitored in a luminometer.

This second method has been demonstrated in practice, using the heavy chain of botulinum toxin type A (BoNT/A Hc) as the soluble, monomeric target protein (FIG. 51) and antibodies described in Pless et al., Infection and Immunity (2001) 570-574. Monoclonal antibody (6E10-10) against one epitope was crosslinked to protein G-coated beads. These beads were incubated with BoNT/A Hc for 3 hrs at 4° C., washed, and used to stimulate emittor cells expressing a second antibody (6B2-2) that recognizes a different BoNT/A Hc epitope. The BoNT/A Hc-decorated beads effectively stimulated the emittor cells, with an LOD of about 6 ng. Emittor cells expressing the same antibody as that used to bind the BoNT/A to the beads were not stimulated, indicating that the emittor reaction was not caused by aggregation of the target protein.

Chemical Detection Example

Figure 52:
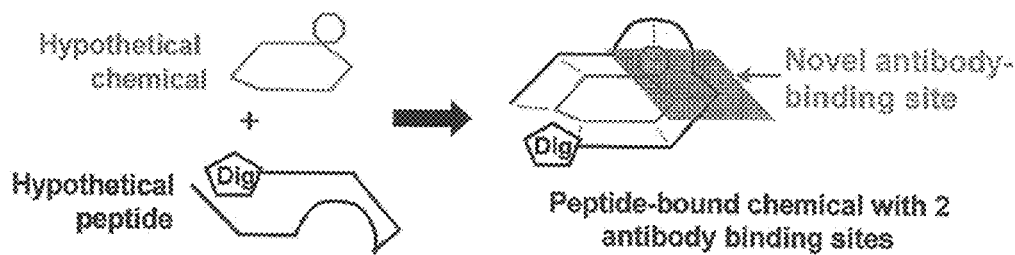
FIG. 52 is a schematic of the detection of a chemical. A peptide is isolated that binds specifically to the chemical of interest, and an antibody generated that binds specifically to the peptide-chemical complex. If the peptide-chemical only forms a single functional epitope, an additional epitope can be incorporated into the peptide. As shown, this epitope is a digoxigenin molecule, but any specific epitope would suffice. In the presence of chemical, the chemical-peptide complex would comprise two antibody-binding sites, and could be detected in a similar manner as protein toxins.

Chemical detection is of importance in both military and clinical settings. It is possible that some chemicals may have two epitopes to which antibodies can bind independently. In such cases the methods for chemical detection would be identical to that for toxins detection outlined above. In many cases, however, there will not be two independent epitopes on the chemical of interest. In such cases it will be necessary to modify the chemical such that it is capable of stimulating the emittor cell. Four of these modifications are outlined below.
1. Immobilize the chemical of interest on a solid support. Generate emittor cells expressing antibodies that recognize the portion of the chemical that remains available. When the density of the immobilized chemical on the solid support is high enough, antibodies on the emittor cell surface will be immobilized close enough to each other to stimulate the cell. This is analogous with the scheme for toxin detection shown in FIG. 50.
2. First, generate peptide(s) that bind specifically to the chemical. Next, generate antibodies that bind specifically to the chemical-peptide complex. If the chemical-peptide complex is composed of two or more epitopes, the complex can be detected by either of the two-antibody techniques outlined in the section on toxin detection. If the complex is only composed of one specific epitope, then an additional epitope, such as digoxigenin, can be added synthetically to the peptide (FIG. 52) The complex would then contain two antibody binding sites: (1) the epitope formed by the peptide-chemical complex and (2) the digoxigenin epitope. Only in the presence of chemical would both epitopes be present. These two epitopes can then be detected by either of the two-antibody techniques outlined in the section on toxin detection.

Figure 53:
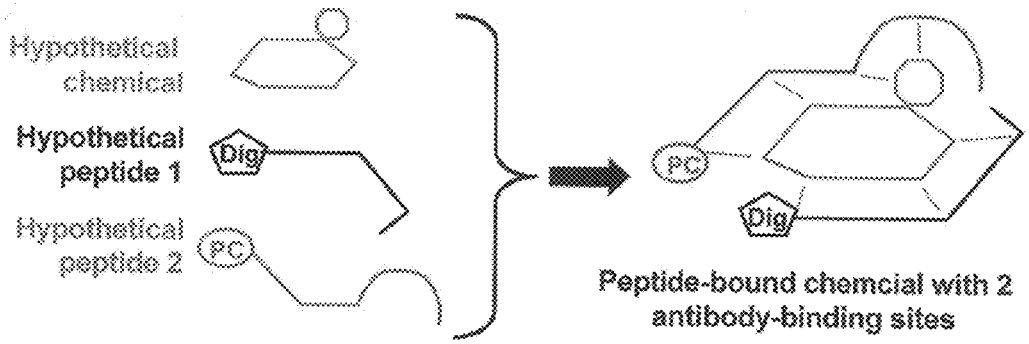
FIG. 53 is a schematic depicting an alternative method for detecting a chemical. Two peptides are isolated that bind in tandem to the chemical of interest. The binding of these peptides could be detected by generating antibodies against each peptide-chemical complex, or by tagging the peptides with antibody binding sites as shown.
Figure 54:
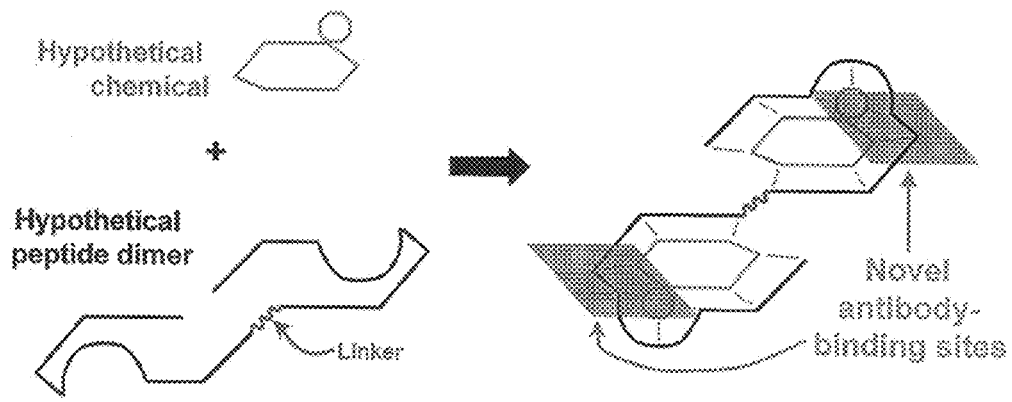
FIG. 54 is a schematic of another alternative method for detecting a chemical. A peptide that binds to two chemicals of interest is prepared which forms a chemical-peptide dimer complex. An antibody is prepared that binds specifically to the chemical-peptide dimer complex. The chemical-peptide dimer complex can contain two antibody binding sites sufficient to stimulate emitter cells to increase intracellular calcium, thereby resulting in photon emission by the emittor molecule.

3. Generate two peptides that specifically bind to the chemical (or to each other in the presence of the chemical). Each of these peptides can be synthetically tagged, such that only in the presence of chemical would two epitopes be bound to each other, and therefore detectable by the emittor cell (FIG. 53). Alternatively, one or more antibodies can be made against the peptide-chemical complex, and the presence of chemical detected as above using a combination of antibodies against the complex, or one antibody against the complex and one antibody against a peptide tag.

4. As above, generate peptide(s) that bind specifically to the chemical, and generate antibodies that specifically bind to the peptide-chemical complex. Dimerize the chemical-binding peptide, so that if the dimer binds to two chemicals, it will contain two antibody binding sites. This complex can be detected by emittor cells expressing an antibody against the chemical-peptide complex.

Peptides that bind to small molecules have been isolated from combinatorial libraries. These molecules include porphyrin (Nakamura et al., Biosensors and Bioelectronics 2001, 16: 1095-1100) tryptophan (Sugimoto et al., 1999, 677-678) and cadmium (Mejare et al., 1998, Protein Engineering 11(6): 489-494). However, the use of proteins in the place of peptides may yield higher affinity binders. Libraries have been constructed in which the binding sites have been combinatorially defined, and these can be used to isolate those binding to small molecules. Such a library using lipocalin as the starting protein has been used to isolate binders to digoxigenin variants (Schlehuber and Skerra, 2002, Biophysical Chemistry 96: 213-228). This approach can be used starting with any number of other proteins, but particularly those that might be expected to already have some binding activity with the chemical target (for example, acetylcholinesterase, in the case of VX and Sarin).

Further Examples 1

Nucleic Acid Detection

Figure 55:
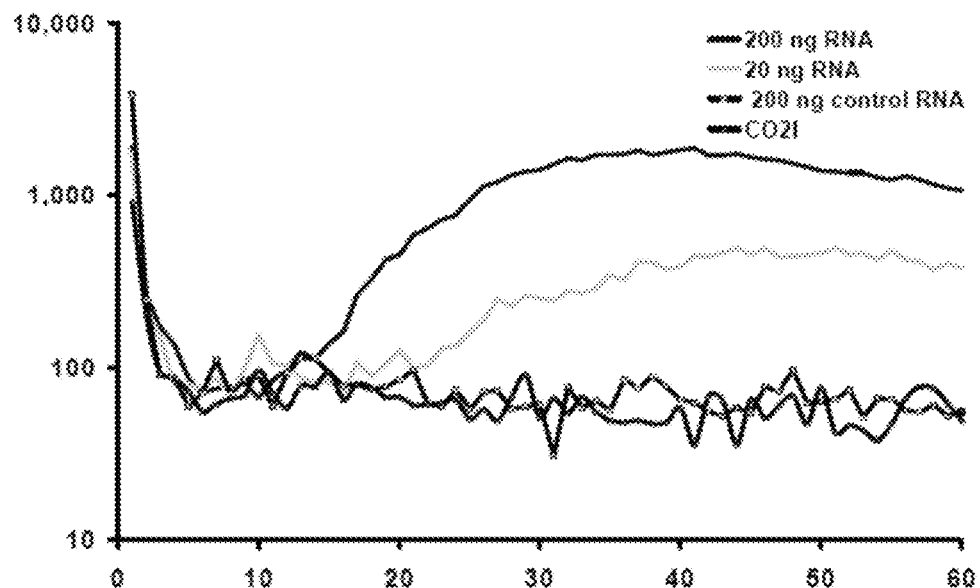
FIG. 55 is a graph. Digoxigenin labeled oligonucleotides were added to RNA in hybridization buffer (40 mM Tris, 130 mM NaCl, 10 mM DTT, RNasin Plus) and incubated for 2 minutes at 47° C. CO2I medium and cells were added, the tube was spun for 5 seconds, and light output monitored on a PMT. The limit of detection in this assay was 20 ng. Lack of response to the control RNA (opposite strand) indicates that the assay is sequence specific.

RNA detection is advantageous to DNA detection in several respects. First, the are more copies of a given RNA per cell (prokaryotic or eukaryotic) than copies of the genome, so the signal per cell is essentially amplified. Second, the presence of RNA is often used s a test of viability. Third, detection of RNA does not require denaturation of 2 complementary strands, as in the case of dsDNA. Experiments were performed in a manner similar to ssDNA detection, except an RNase inhibitor was added (RNasin Plus, Promega Corporation) (FIG. 55). Digoxigenin-labeled oligos were added to different concentrations of RNA, incubated at 47 C for 2 minutes. CANARY cells expressing antibody against digoxigenin were added, the tube spun for 5 sec, and light output monitored.

Alternate Protocols

CANARY can also detect nucleic acids by directly labeling the target. For example, by performing PCR in the presence of digoxigenin-labeled nucleotide, thus generating a PCR product with multiple antigens attached along its length. Likewise, rolling circle amplification can be used to incorporate label into target nucleic acid that can, in turn, be detected by CANARY. Ligase chain reaction and its derivatives essentially dimerize oligos, and CANARY can be used to monitor that dimerization if both oligos are labeled with one antigen each.

Toxin Detection

Figure 56:
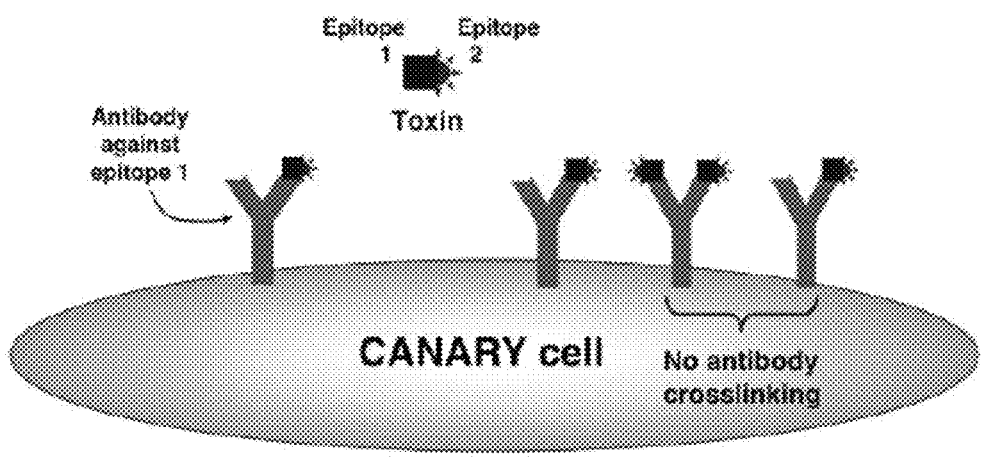
FIG. 56 is a schematic. Antigens, including toxins, may be comprised of 2 or more epitopes. A CANARY cell typically expresses a single antibody against the target epitope. In a worst case scenario the antigen may be present in monomeric form. While the antibody on the CANARY cell is capable of binding to the monomeric antigen, the antibodies are not crosslinked and no light is emitted.

CANARY in its basic form is incapable of detecting monomeric antigens (FIG. 56), because the antigens are incapable of crosslinking monoclonal antibodies: as described herein, the assay must be modified. Two general strategies are being used to detect toxin simulants using CANARY: (1) make the toxin antigen appear polyvalent to the CANARY cell or (2) make the antibody expressed by the CANARY cell polyclonal. For example, the protein antigen can appear polyvalent to the CANARY cell by adsorbing the antigen to beads, cells, or crosslinking the antigen with soluble antibody.

Initial experiments were carried out using a toxin simulant, botulinum neurotoxin Type A, heavy chain (BoNT/A Hc). The assay modification that has thus far given the best sensitivity and speed for toxin simulant detection by CANARY is to capture the simulant on antibody-coated magnetic beads, and detect the simulant-decorated bead using CANARY cells (FIG. 57). Three monoclonal antibodies that recognize non-overlapping epitopes on the BoNT/A Hc toxin simulant; 6E10-10, 6B2-2, and $6C_{2-4}$ (donated by Dr Bavari and Dr. Ludwig, USAMRIID) have been used. Soluble 6E10-10 antibody is conjugated to protein-G labeled magnetic beads, while the 6B2-2 antibody is expressed in CANARY cells. The 6E10-10 antibody-coated beads are incubated in solution spiked with BoNT/A Hc for 2 minutes, producing toxin simulant-decorated beads. CANARY cells are added, and the mixture spun for 5 seconds to pellet the beads and cells. These beads present the immobilized BoNT/A Hc to the CANARY cell, crosslinking the antibodies and stimulating light emission. This technique can detect 800 pg of BoNT/A Hc (80 ng/ml) in <5 minutes (FIG. 58).

Figures 59, 60:
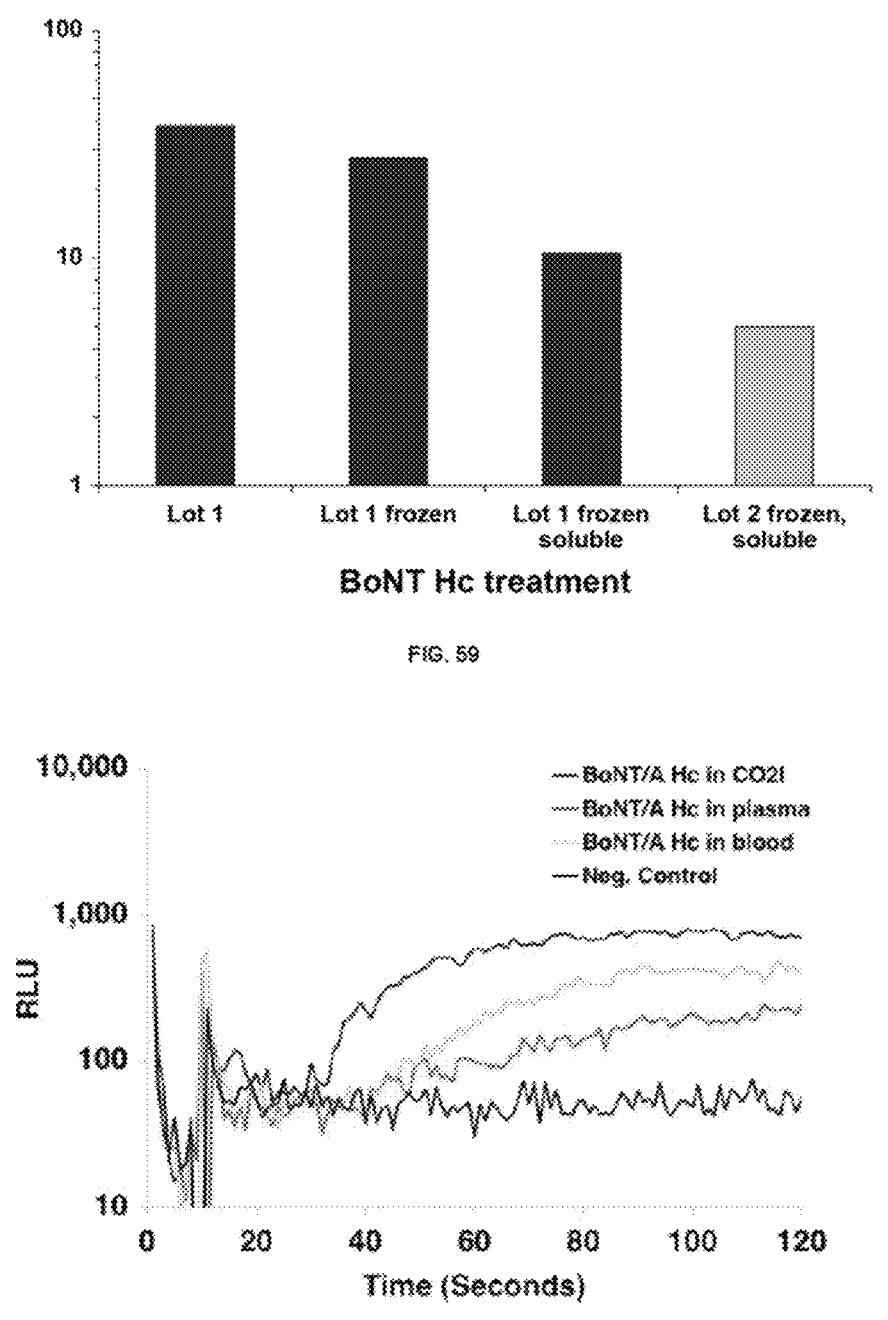

It should be noted that the sensitivity of the assay depends on the quality of the BoNT/A Hc. Lot-to-lot variability and storage characteristics of commercial BoNT/A Hc affect our apparent limit of detection (LOD). It is important in establishing the assay to demonstrate that CANARY is capable of detecting truly soluble protein. Fresh, unfrozen BoNT/A Hc gives a higher response (FIG. 59) than BoNT Hc that has been frozen (the suggested method for storage). Centrifugation of frozen-thawed BoNT Hc further decreases the reactivity, indicating that aggregates form during the freeze-thaw process. BoNT/A Hc used in these assays that has been stored frozen, is typically centrifuged upon thawing to remove aggregates. While this underrates the assay sensitivity, the interassay variation is decreased.

The bead-assay format is effective for soluble antigen screening in blood products (FIG. 60) using the whole blood preparation procedure described herein. Whole blood was spiked with BoNT/A heavy chain, and the blood briefly centrifuged through a polymer to facilitate separation of cells from soluble material. 6E10-10 antibody-coated beads were added to the resulting supernatant, and assayed using 6B2-2 CANARY cells. The sensitivity of the assay is similar to assays carried out in control medium, indicating that most interferents have been removed. Spiking plasma with an identical concentration of BoNT/A Hc after separation from blood cells gives a lower signal relative to samples in which the blood was spiked directly. This difference is probably an artifact of the blood sample preparation, not the presence of an additional CANARY inhibitor in the plasma.

BoNT/A Hc antigen spiked into urine can also be detected, although the signal amplitude is somewhat reduced. (FIG. 61) In this experiment no pretreatment was performed. 6E10-10 coated beads were added directly to urine samples, the beads washed into CO2I, and 6B2-2 CANARY cells added. Two of three spiked urine samples (blue lines) showed significant responses, while the third sample did not. It is not clear from this limited dataset why the third urine sample was negative, or why the signal amplitudes from samples in urine is lower than positive controls (gold lines).

The assay is also effective in detecting soluble antigen spiked into nasal swabs. To prepare samples for this assay, swabs are collected, the stem of the swab is trimmed and the swab end placed into a 5 micron filter basket fitted over an eppendorf tube (FIG. 62). Control or BoNT/A Hc-spiked CO2I medium is added, and the assembly capped and centrifuged. The filtered eluate, cleared of large particulates, is collected in the eppendorf and assayed using the normal bead procedure. The assay results for both actual and mock swabs spiked with BoNT/Hc are very similar, indicating that no inhibitors are present in the nasal sample (FIG. 63). The lack of a CANARY response to nasal swabs without spiked antigen (CO2I) shows that there are no nonspecific stimulators present in the nasal swab sample.

Figures 64, 65:
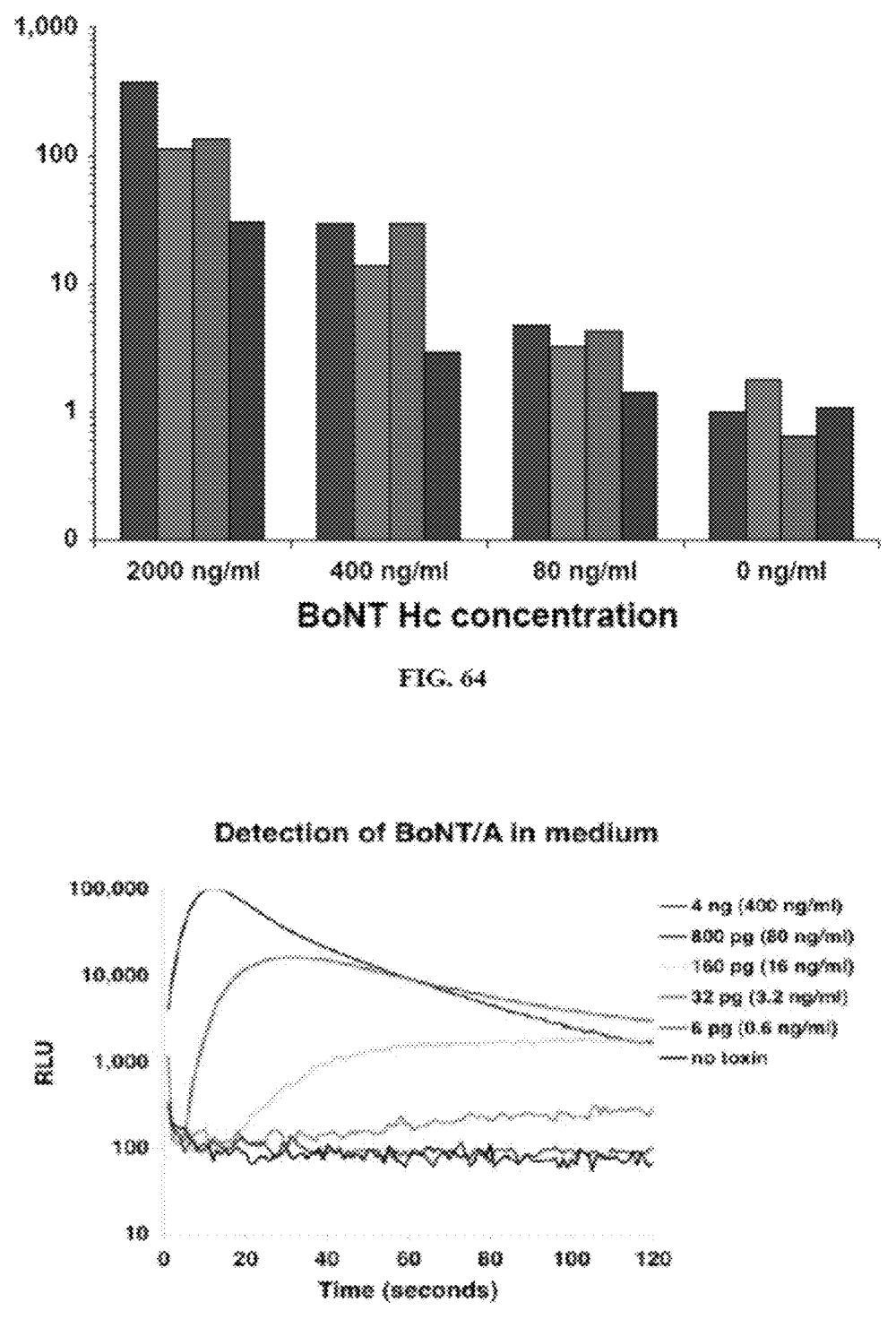

Many solutions, such as orange juice or PBS/Tx-100, stimulate CANARY cells nonspecifically, so it is necessary to exchange the original solution containing the toxin simulant for assay medium. In addition to crosslinking the target, the use of magnetic beads provides a simple method of exchanging the solution containing the simulant for cell compatible assay medium. In the survey of food matrices, orange juice stands out as having a potential pH problem (pH=3.5) and water as having a potential salt problem (none). Either of these characteristics could also affect the ability of antibody-coated beads to bind to the toxin simulant. For these experiments, 1/7th volume (1.4 microliters) of a solution containing 560 mM NaCl, 1.4 M Hepes pH 7.9 was added to all BoNT Hc-spiked matrices and antibody-coated beads. This brings the water matrix to a salt concentration of 80 mM final, the pH of orange juice to about 6.5, and simultaneously introduces the antibody-conjugated beads to initiate the binding step. At the end of a 12 minute binding step, 190 µl of assay medium is added, the tube is placed on the magnet for 30 seconds, and the supernatant discarded. The beads are resuspended in 50 µl of assay medium, 20 µl of cells are added, the tube is spun for 5 seconds to sediment the beads and CANARY cells, and light output monitored on a luminometer. (FIG. 64). In this graph, the values represent the peak light output normalized to background values (CANARY cells in assay medium with no antigen), so the red bar on the far right is set to one. All other bars are maximum responses relative to this control. The response of CANARY to BoNT/A Hc diluted into orange juice or PBS/Triton are very similar to BoNT Hc diluted into assay medium (positive control), with an LOD for in all 3 of these matrices of 80 ng/ml. Milk inhibits CANARY responses by more than 5 fold. A generalized CANARY sample preparation method can be applied to all liquid food matrices.

Figures 66, 67:
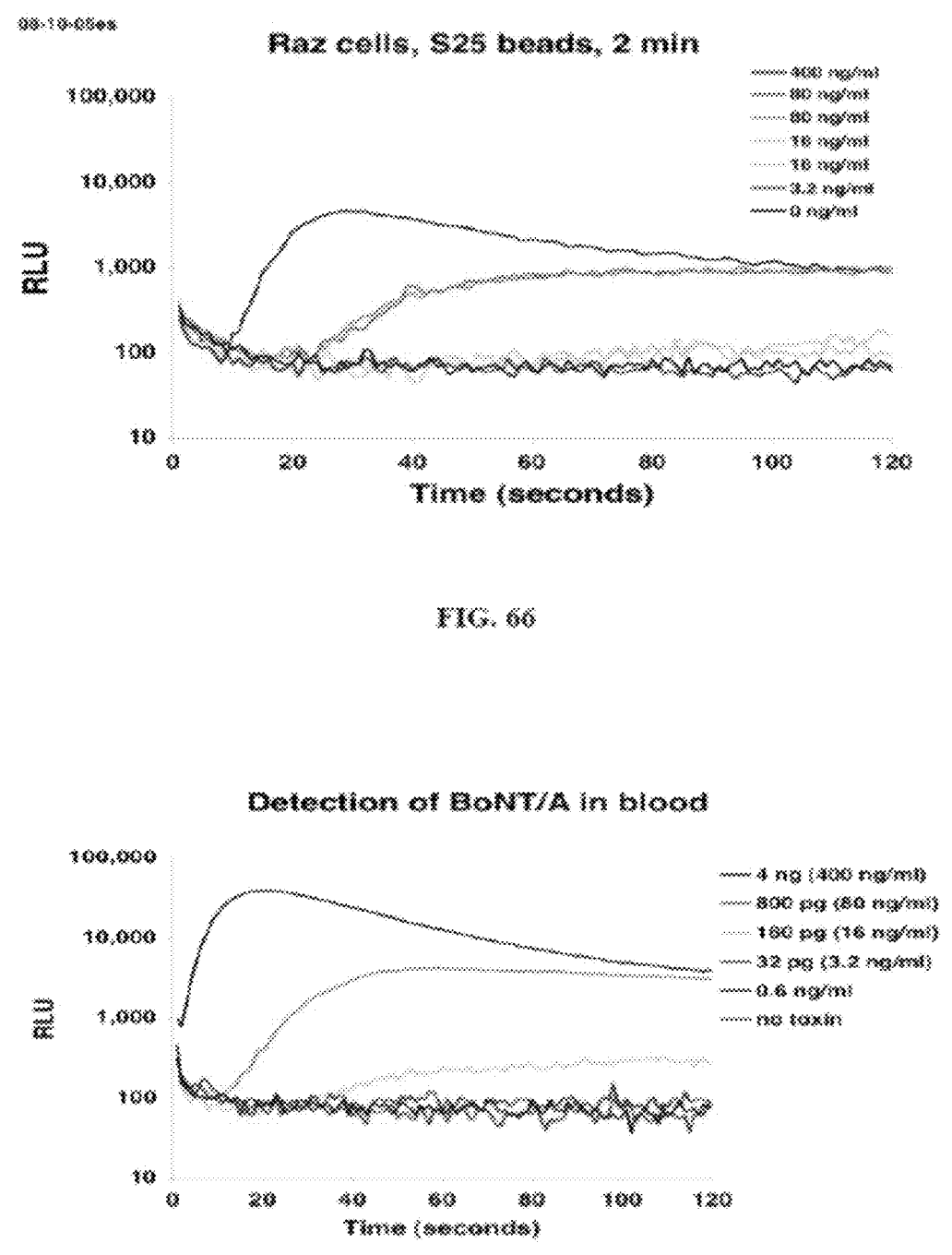

It is obviously critical to demonstrate that the assay works not only with toxin simulant, but also with the active BoNT/A toxin. Commercial BoNT/A was acquired and assayed using 6E10-10 beads and 6B2-2 CANARY cells (FIG. 65). The limit of detection of the assay to BoNT/A was about 3.2 ng/ml or 32 pg of the toxin. It is unclear whether this improvement in assay sensitivity is due to the stability of BoNT/A compared to the BoNT/A Hc, or if there is an antigenic difference between the 2 preparations. Similar types of BoNT/A detection results have been seen using an alternate set of antibodies against BoNT/A from Dr. James Marks at UCSF. The best combination of these antibodies thus far is bead-bound S25 antibody and CANARY cells expressing Raz antibody (FIG. 66). The reason for the lower sensitivity using this different antibody pairing is, at present, unclear.

CANARY can also detect BoNT/A spiked into whole blood (FIG. 67). Whole blood was spiked with various concentrations of BoNT/A, and plasma prepared as previously described. 6E10-10 antibody-coated beads were added to the plasma and incubated for 2 minutes. The beads were washed once in CO2I and assayed using CANARY cells expressing the 6B2-2 antibody. The limit of detection in serum drops by about 5 fold compared to control medium, to about 16 ng/ml (160 pg).

Alternate Bead Binding Chemistries

Figure 68:
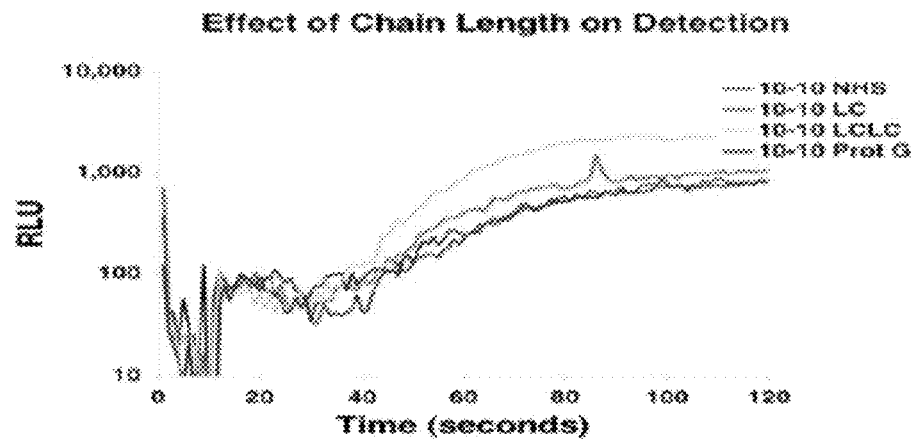
FIG. 68 is a graph. Streptavidin-coated beads were bound to 6E10-10 antibody that had been biotinylated with either sulfo-NHS-biotin, sulfo-NHS-LC-biotin or sulfo-NHS-LC-LC-biotin. Beads were added to solution containing 800 ng/ml BoNT/A Hc, and incubated for 2 minutes. 6B2-2 CANARY cells were added, the tube spun for 5 seconds, and light output monitored. Biotin attached by the longest spacer arm (LCLC) gave slightly better signal.
Figure 69:
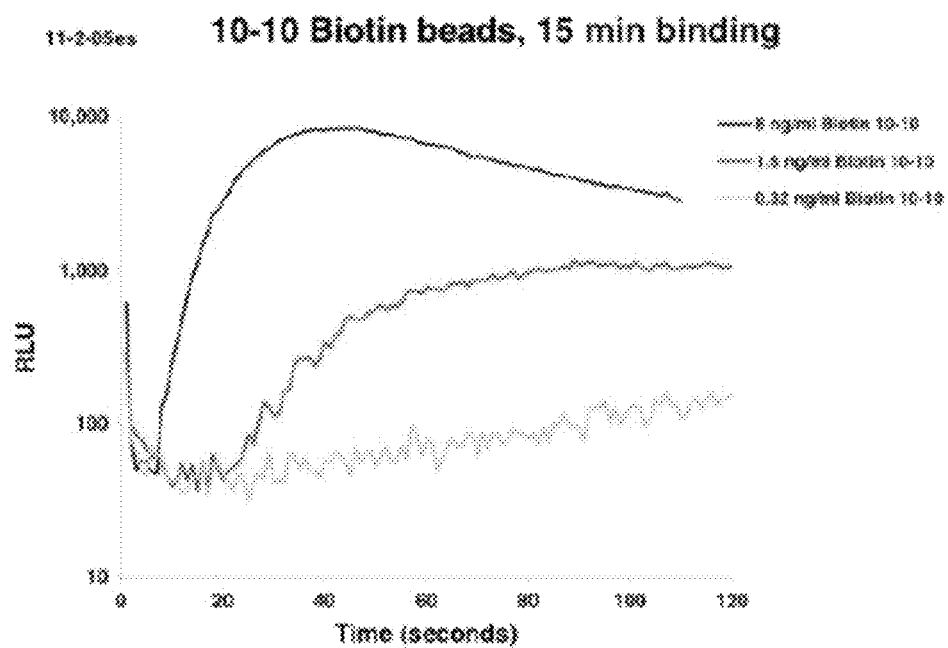
FIG. 69 is a graph. Biotinylated 6E10-10 antibody bound to streptavidin-coated beads were added to the indicated concentrations of BoNT/A and rotated for 15 minutes at room temperature. 6B2-2 CANARY cells were added, the tube spun for 5 seconds, and light output monitored on a PMT.
Figure 73:
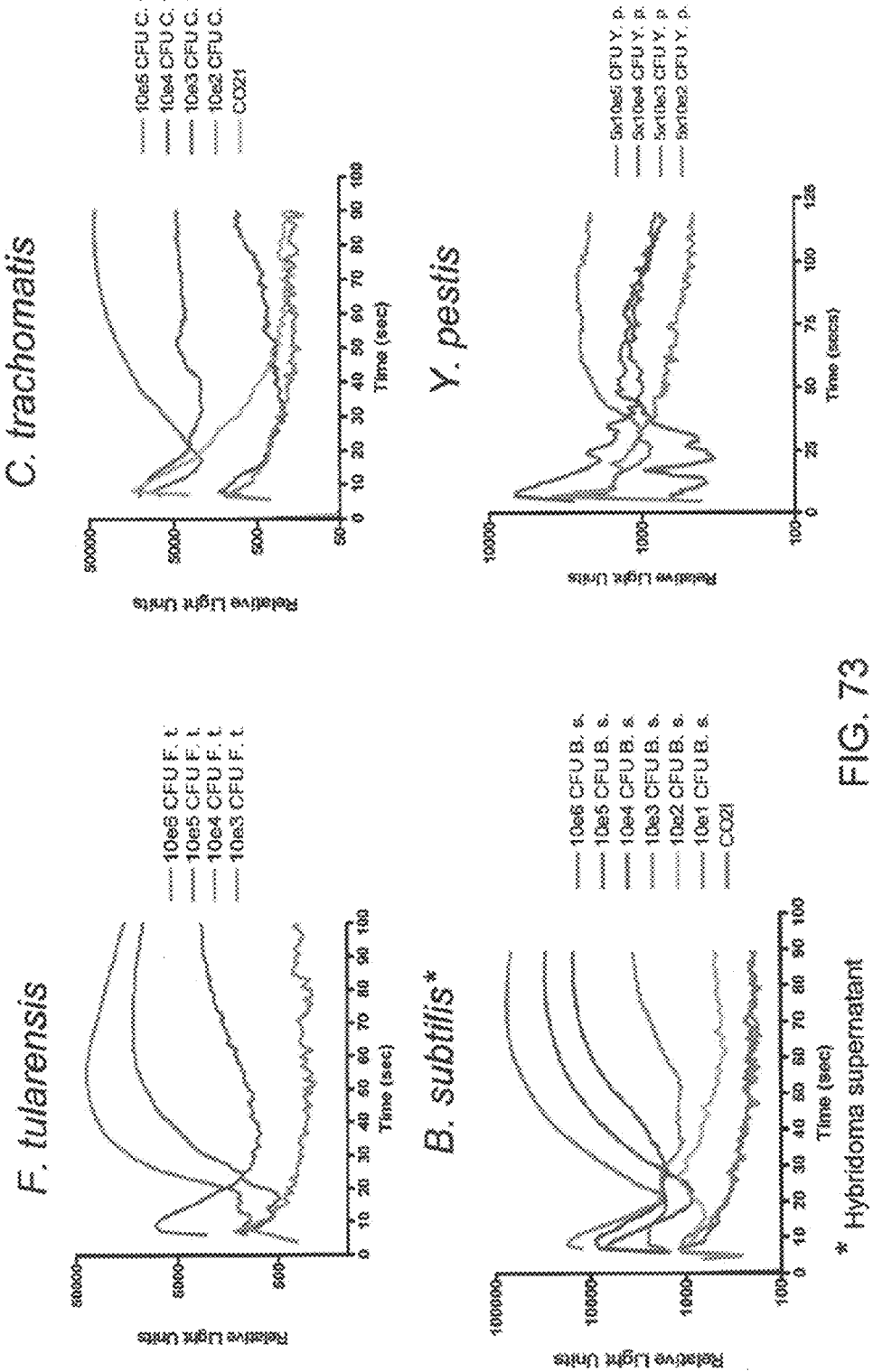
FIG. 73 is a series of graphs demonstrating U937 cells can be prepared to detect several different pathogens.
Figure 74:
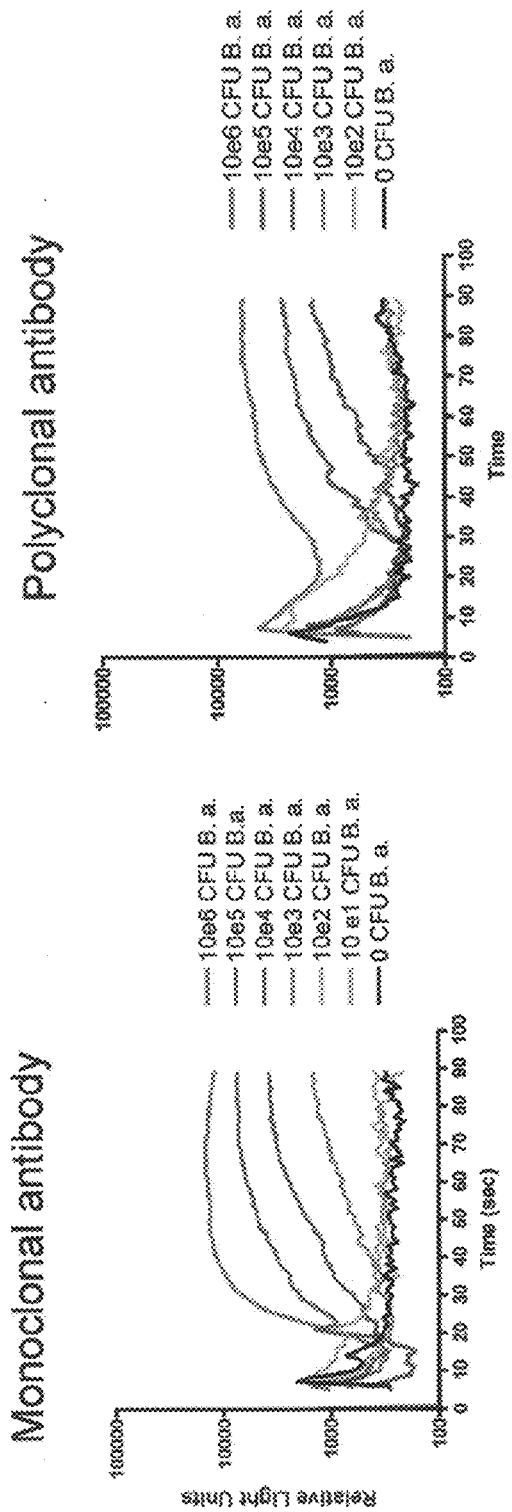
FIG. 74 is a pair of graphs demonstrating that U937 aequorin cells loaded with either monoclonal or polyclonal antibody can detect *B. anthracis* spore.
Figure 81:
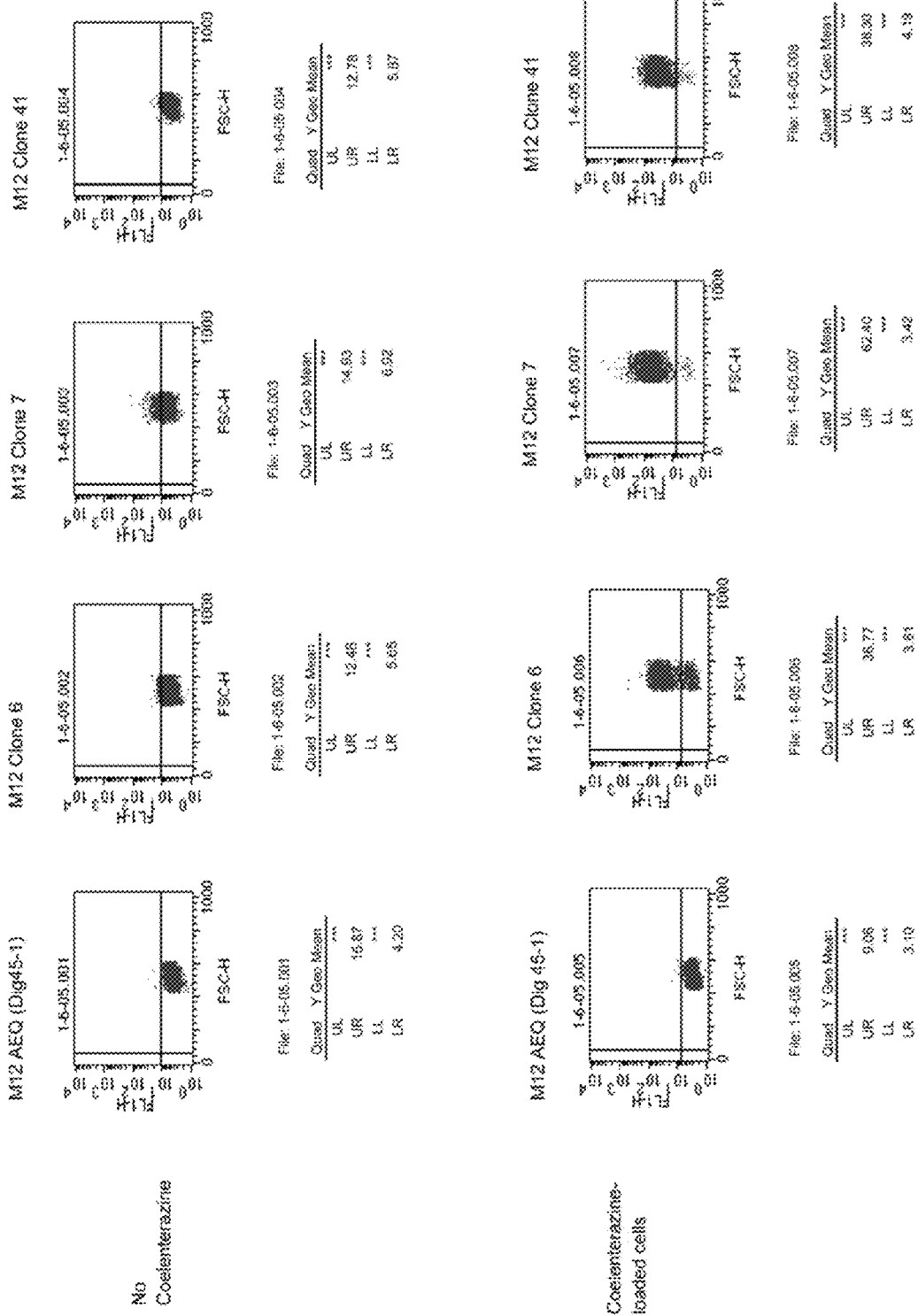
FIG. 81 is a series of FACS analysis graphs demonstrating detection of EGFP fluorescence of aequorin-GFP emittor molecule.
Figure 82:
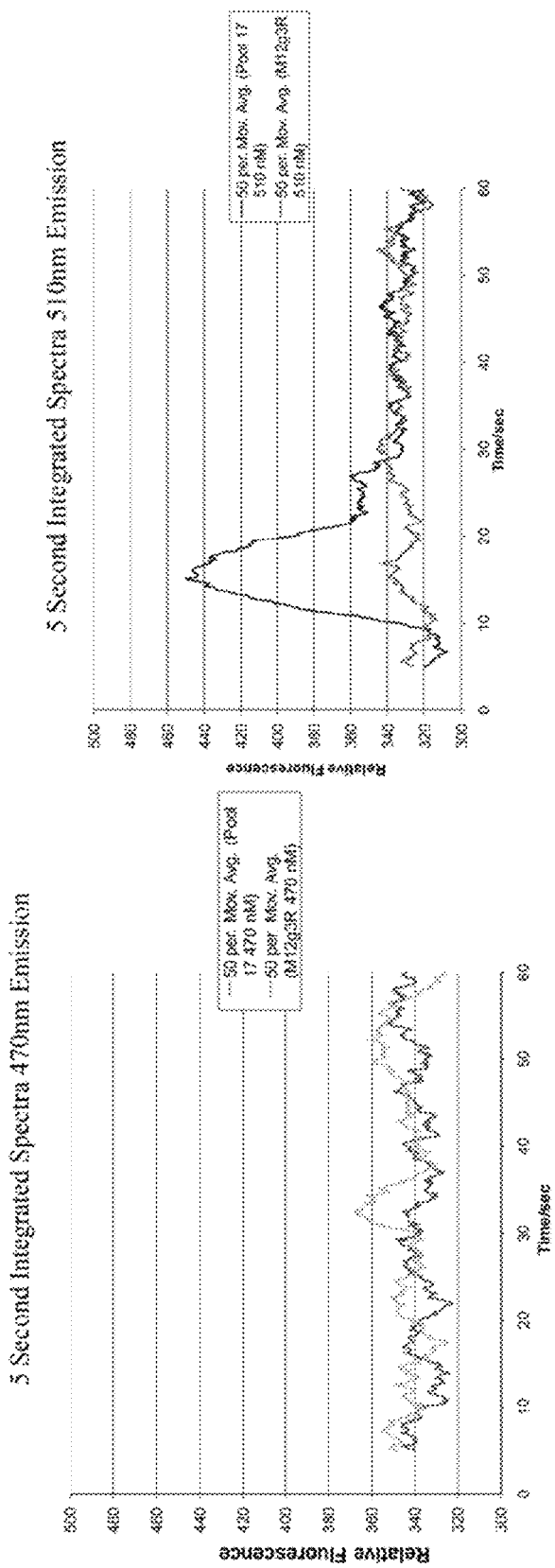
FIG. 82 is a pair of graphs demonstrating detection of aequorin-EGFP wavelength shift by spectrophotometer.
Figure 83:
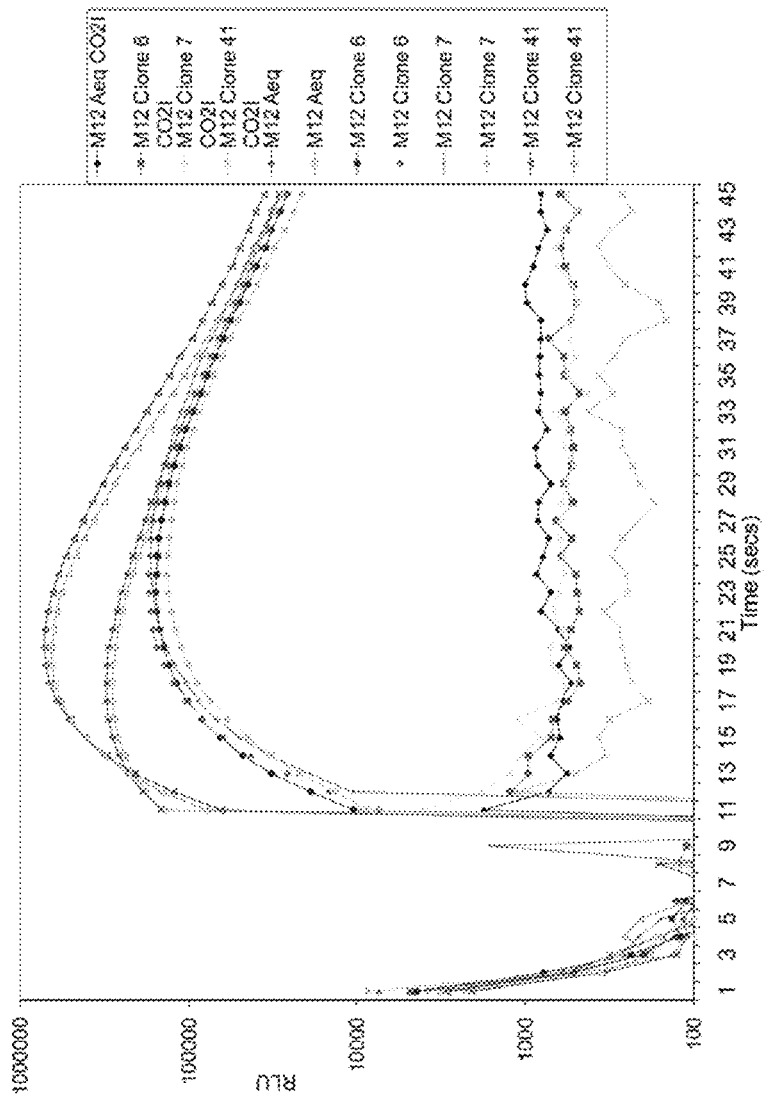
FIG. 83 is a graph demonstrating M12g3R EGFP-aequorin clones function similarly to M12g3R aequorin only cells.
Figure 84:
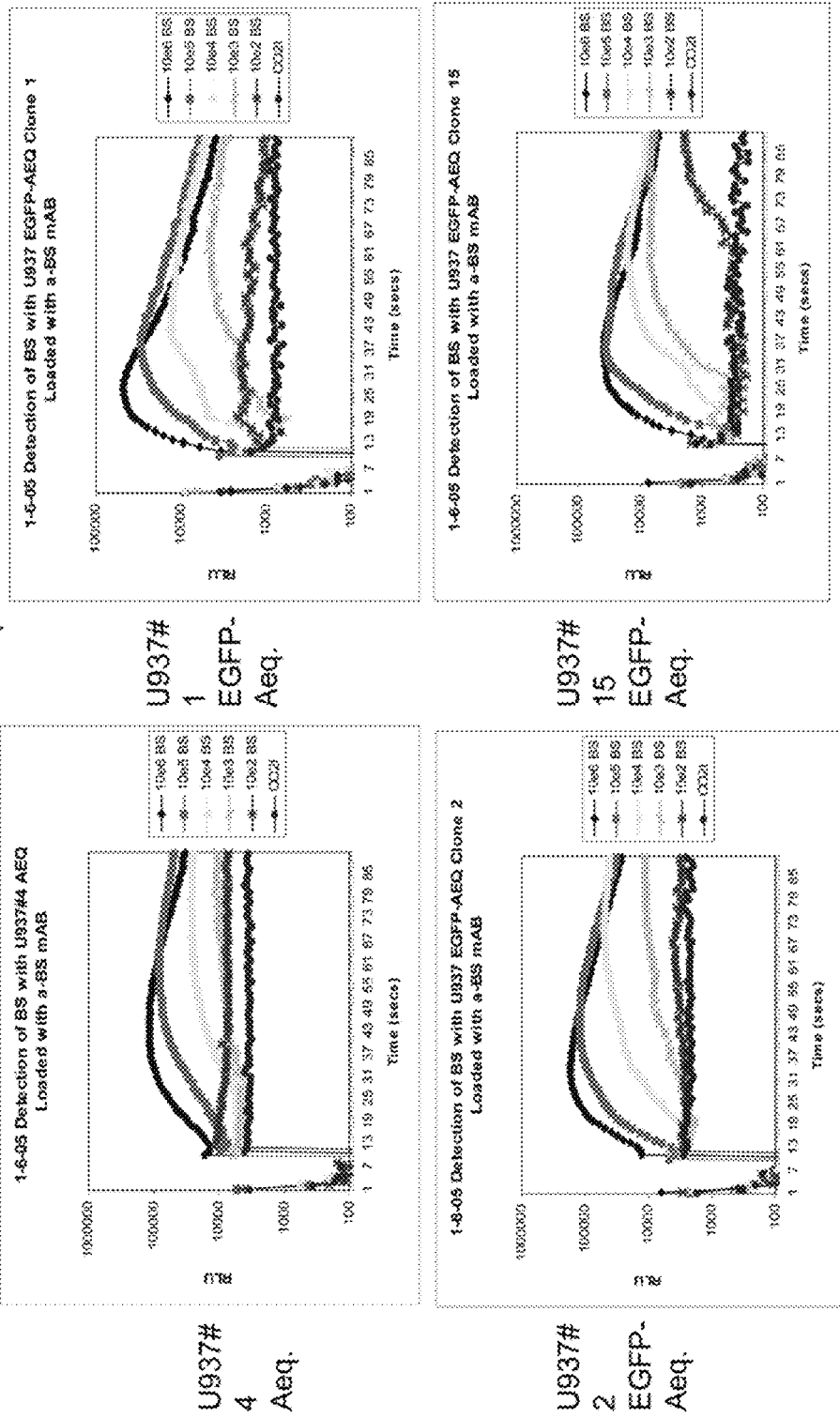
FIG. 84 is a series of graphs demonstrating spore detection by U937 aequorin and U937 EGFP-aequorin cells.
Figure 85:
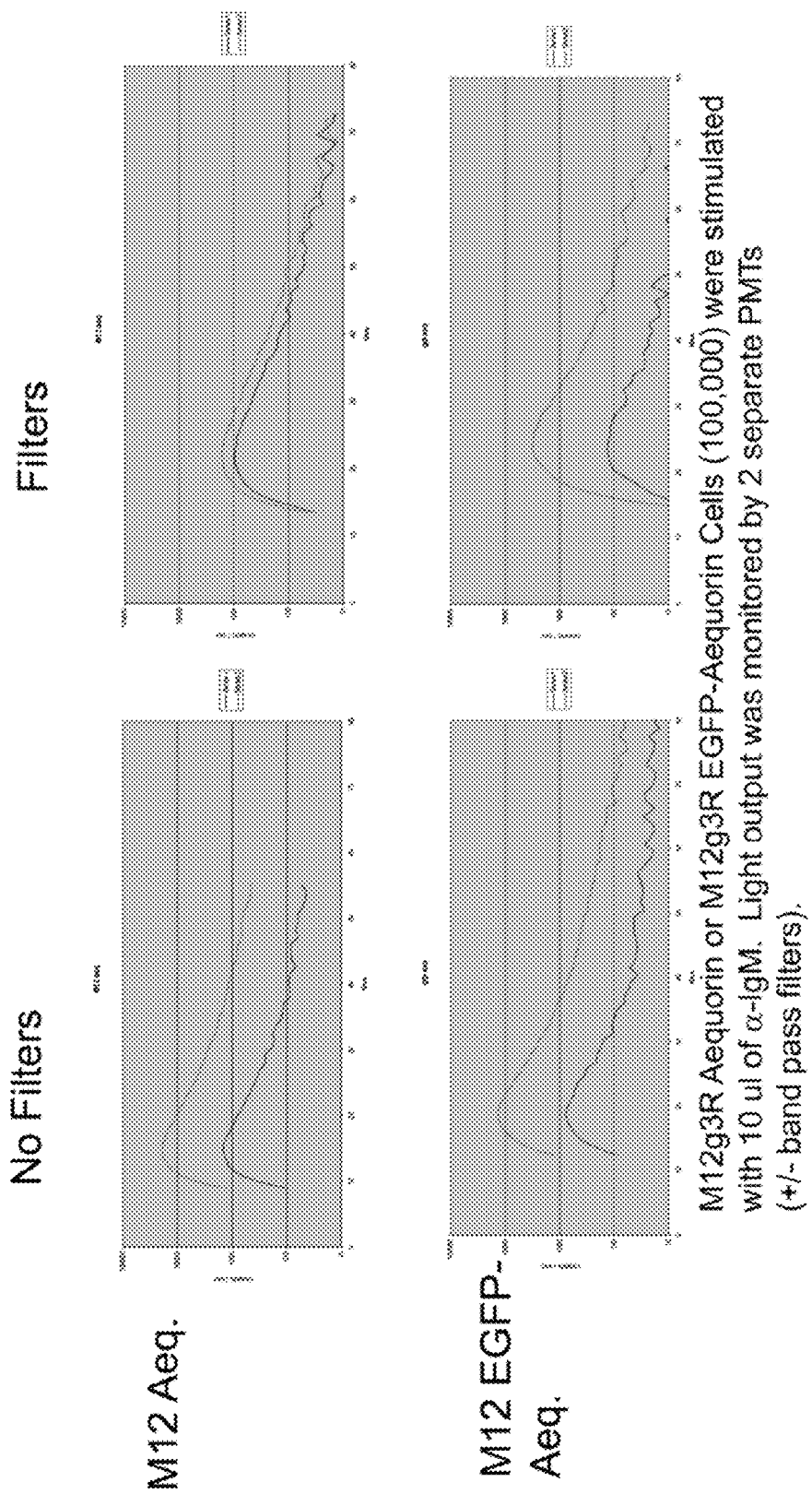
FIG. 85 is a series of graphs demonstrating fluorescence of stimulated CANARY cells.
Figure 89:
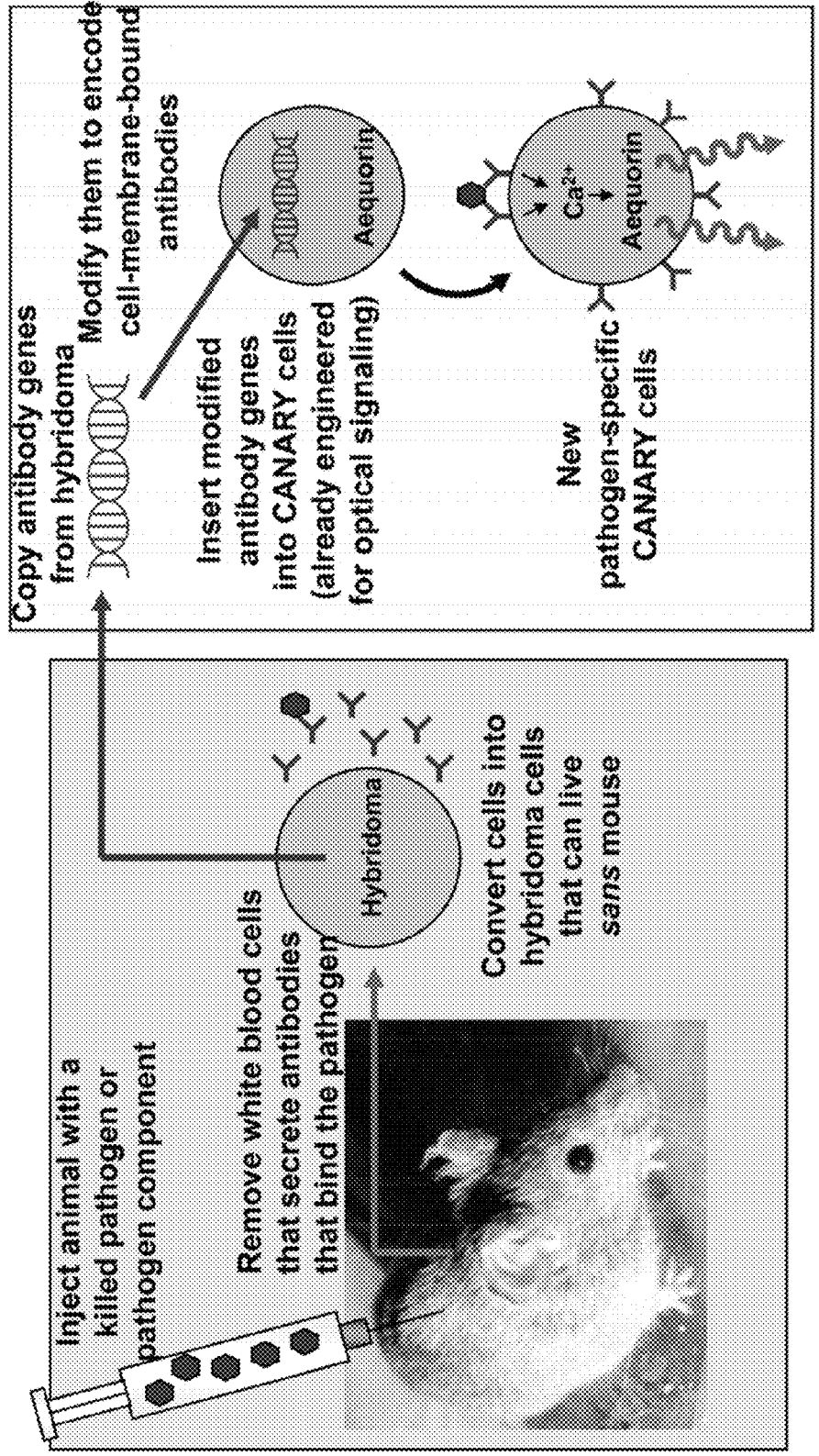
FIG. 89 is a schematic of producing pathogen-specific CANARY cells.
Figure 90:
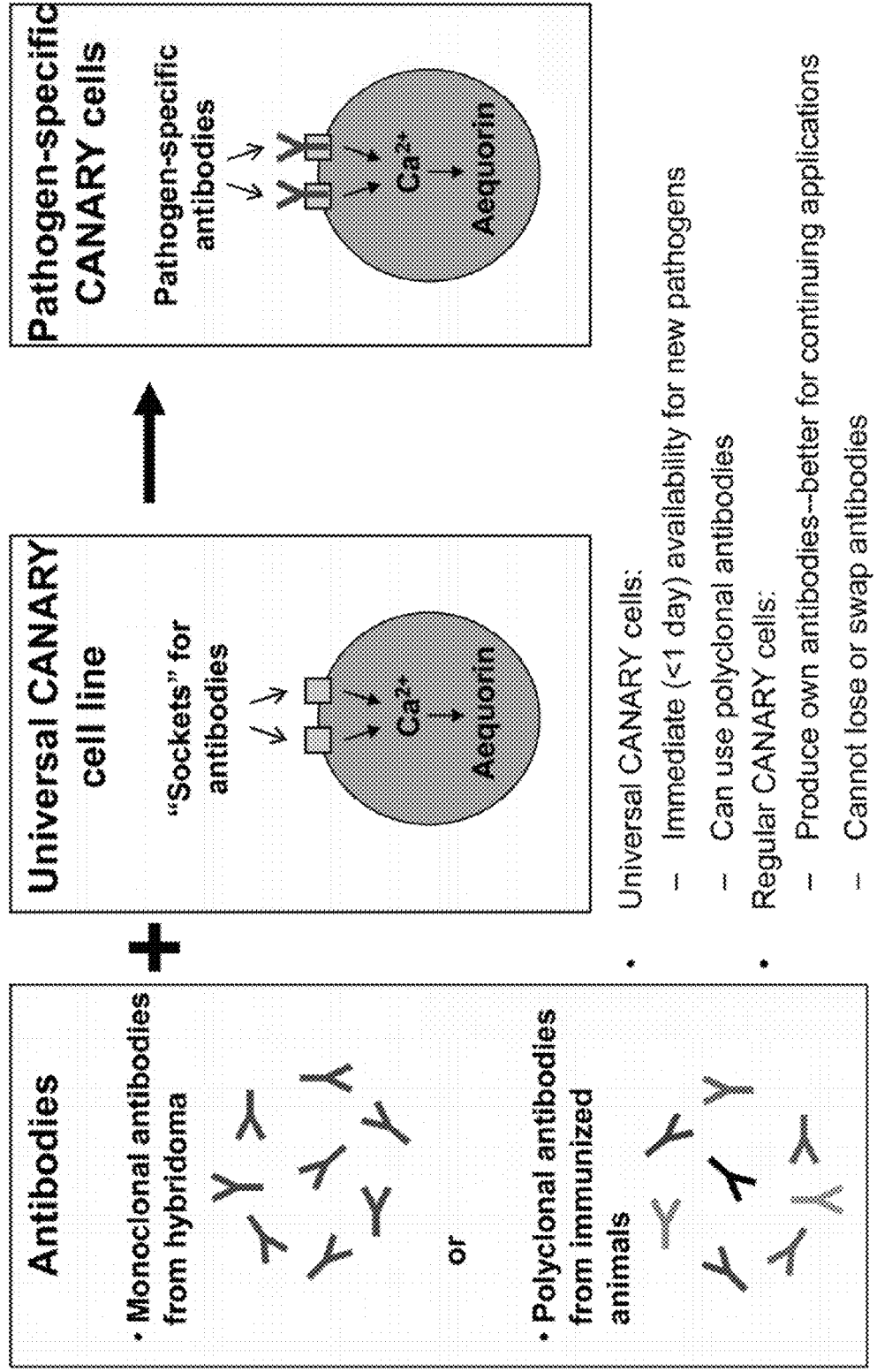
FIG. 90 is a schematic of universal CANARY cells.
Figure 92:
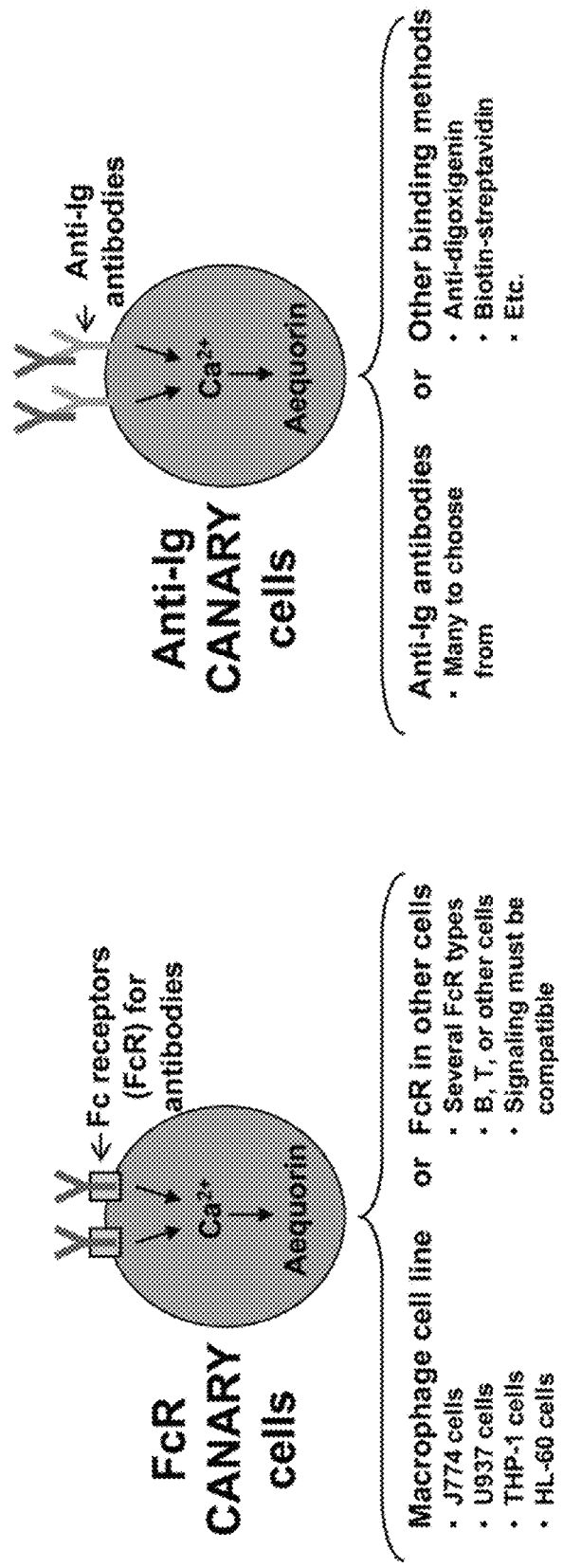
FIG. 92 is a schematic for producing universal CANARY cells.
Figure 94:
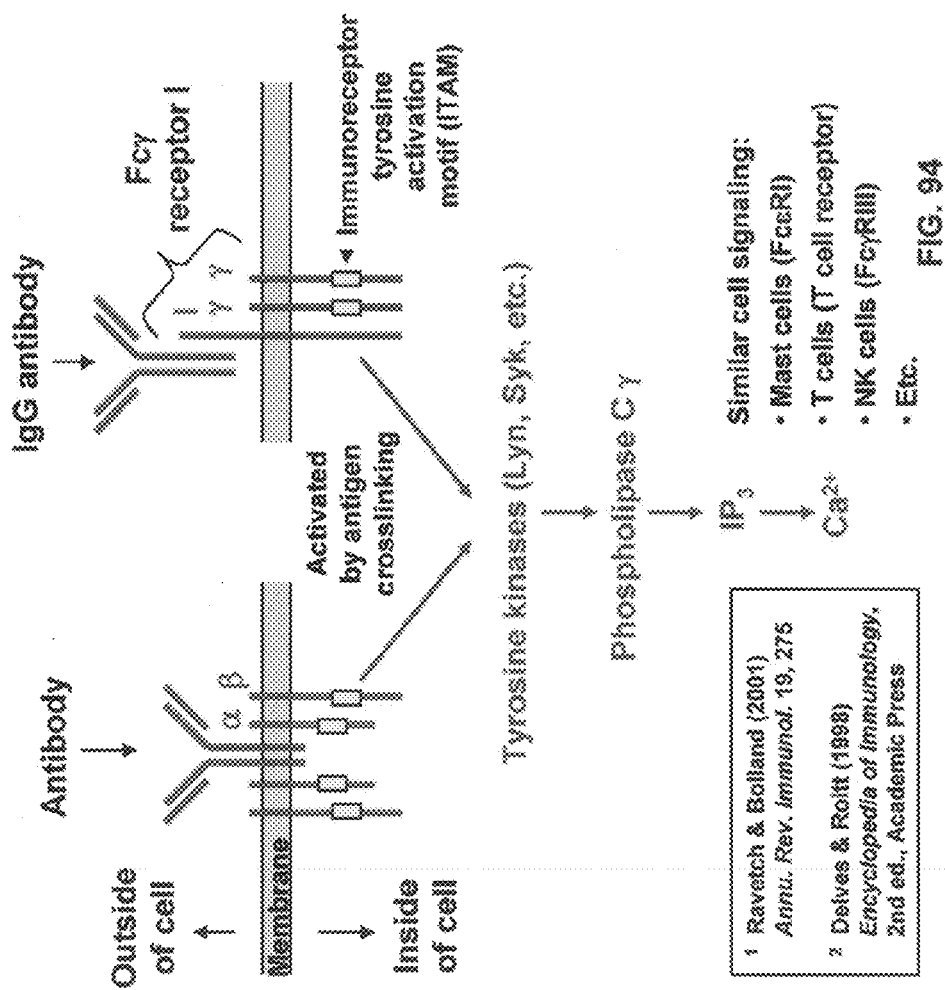
FIG. 94 is a schematic of Fc receptor signaling and production of a universal sensor cell.
Figure 95:
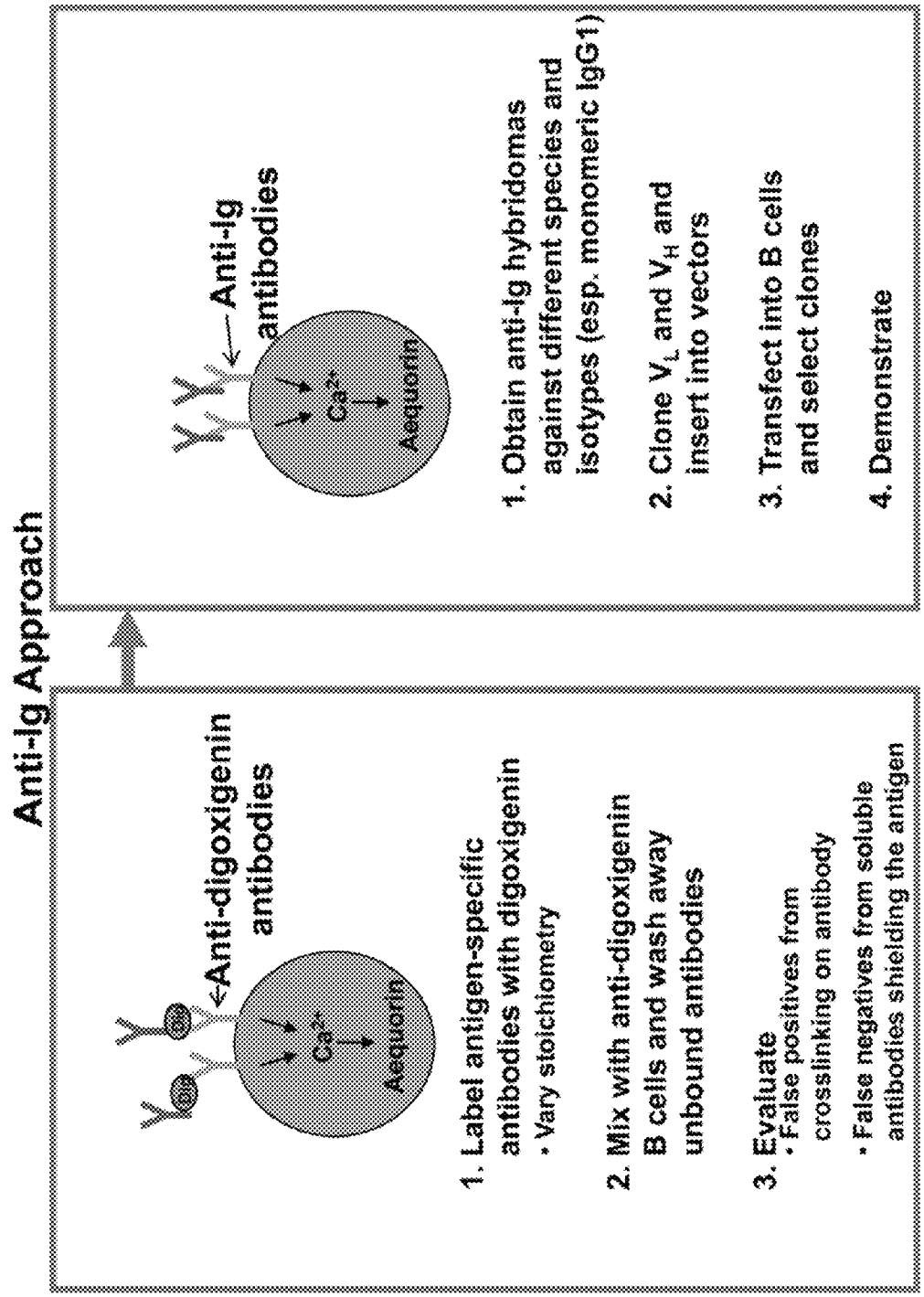
FIG. 95 is a schematic of an anti-Ig (anti-immunoglobulin) universal cell line.
Figure 96:
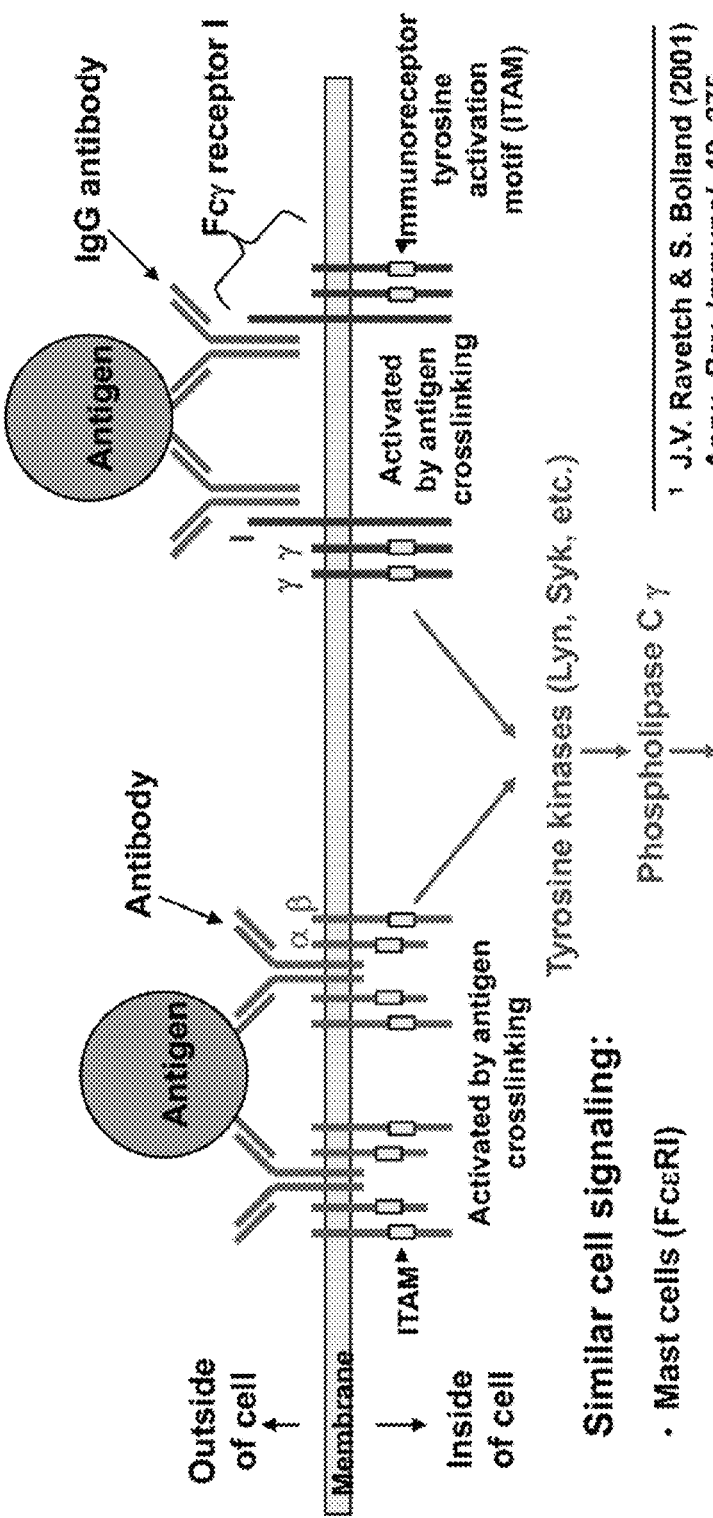
FIG. 96 is a comparison schematic.
Figure 98:
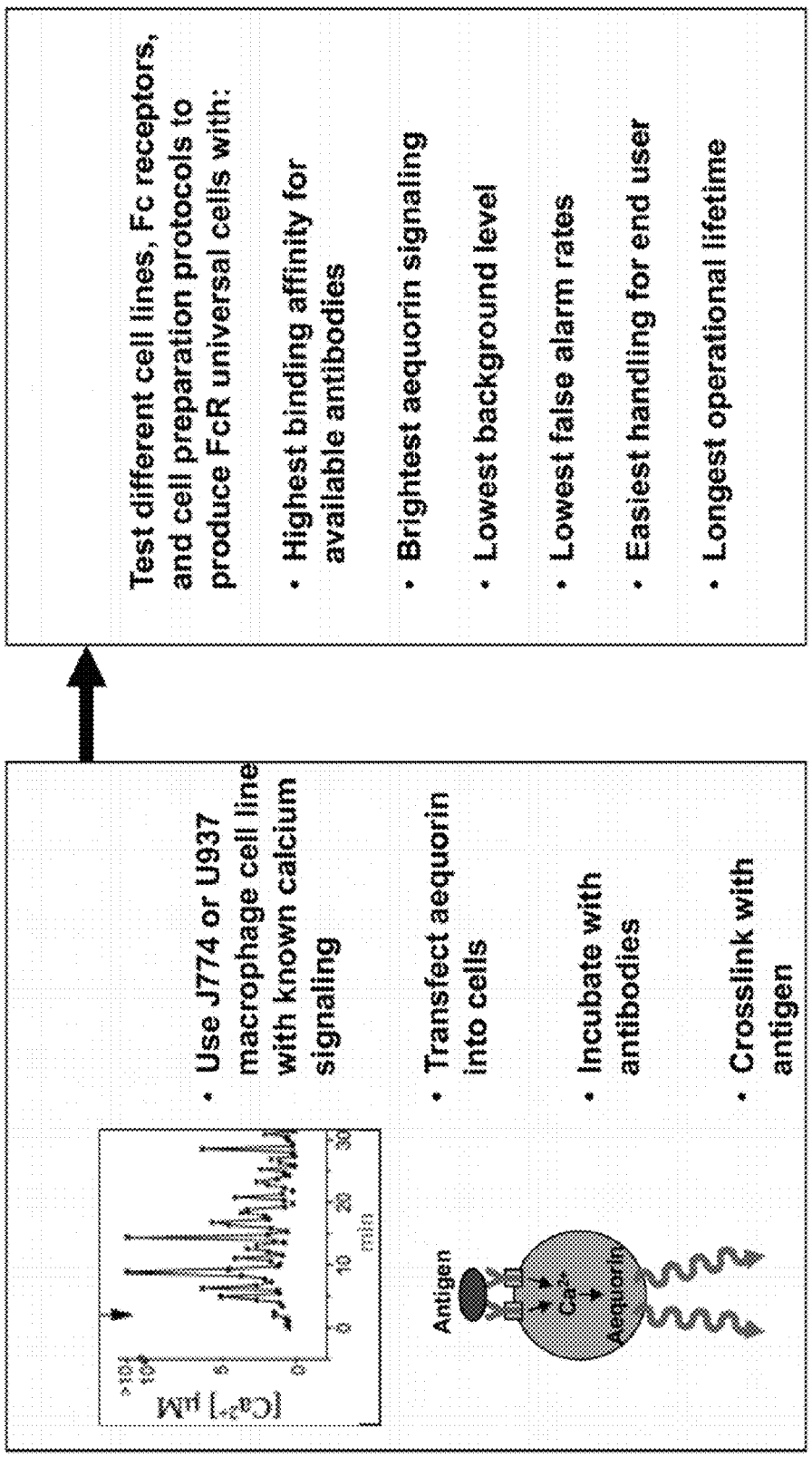
FIG. 98 is an outline of Fc receptor universal cells.
Figure 99:
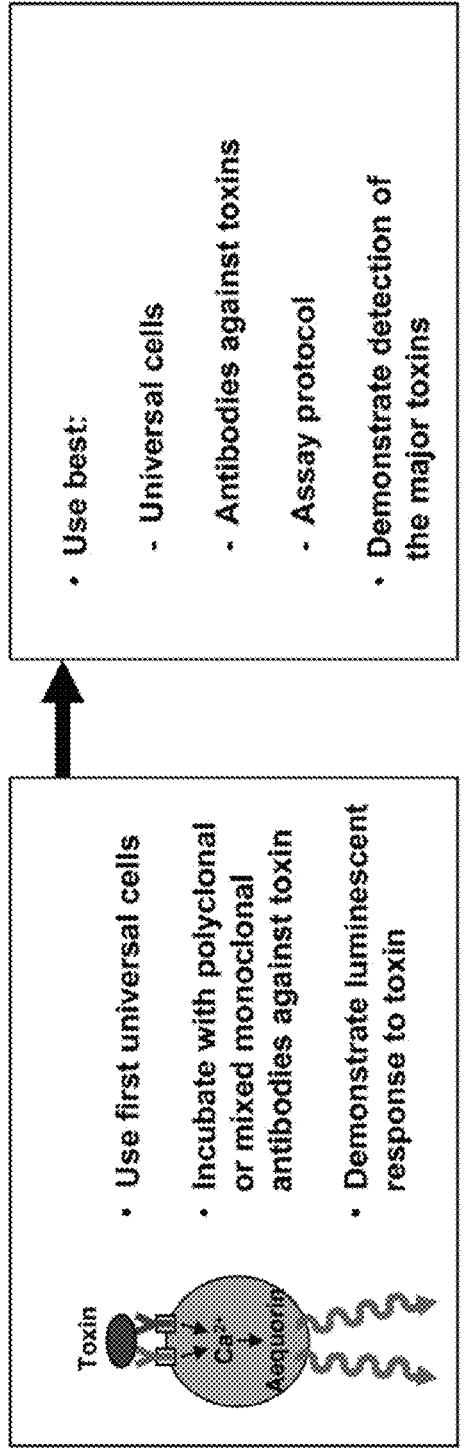
FIG. 99 is an outline of toxin detection embodiments.

Antibody-coated beads have also been made by biotinylating soluble antibody and attaching it to streptavidin-coated beads. Soluble antibody was crosslinked to biotin (Pierce Biotechnology Inc) according to manufacturer's instructions. This biotinylated antibody was bound to magnetic streptavidin-coated beads (Dynal, Dynabeads M-280). Initial experiments indicate that antibody conjugated to the sulfo-NHS-LC-LC-biotin gives slightly better signal than antibody conjugated to Sulfo-NHS-LC-biotin or sulfo-NHS-biotin. (FIG. 68). 6E10-10 beads produced in this way are capable of detecting soluble BoNT/A with similar sensitivity to protein G beads (FIG. 69). Multiple antibodies can be attached to the same beads using this technique, although to date the effects of binding multiple antibodies to the same beads has been marginal (FIG. 70).

Figures 70, 71:
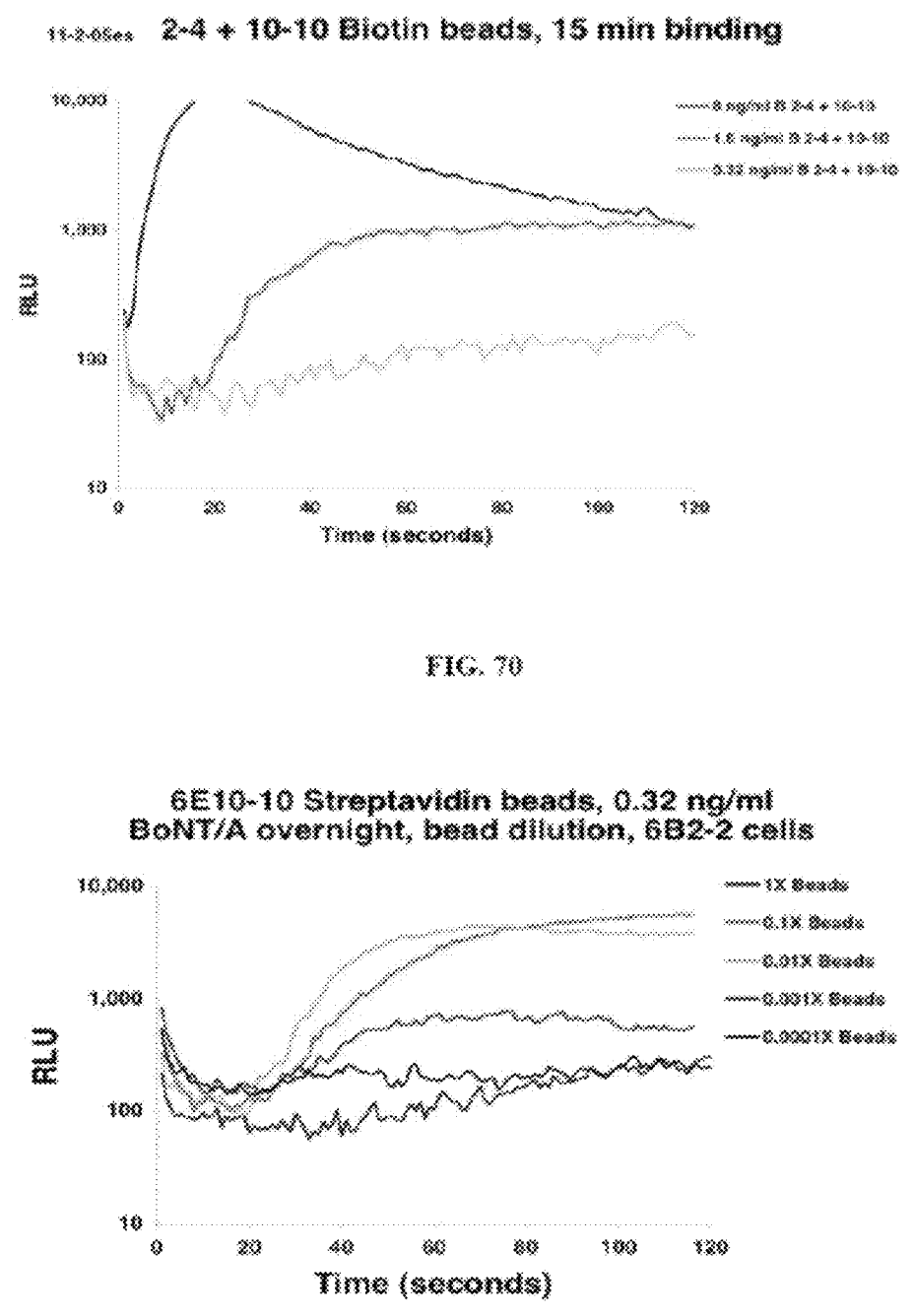

The combination of longer incubations with fewer beads does improve sensitivity (FIG. 71). Beads were diluted from their normal concentration (about 300,000 per assay) in a 10 fold series from 1× to 0.0001×. BoNT/A at 0.32 ng/ml was added, and incubated overnight. Poor signal was seen from samples containing the normal (1×) amount of beads, but samples with 0.1× and 0.01× beads gave robust signals. Similar improvements in sensitivity to BoNT/A are seen using protein G coated beads.

Additional Formats for Toxin Detection

Additional formats for CANARY detection of toxins have been envisioned, and feasibility experiments performed (see FIG. 72 for summary). Several of these variations are thematically similar to bead capture in that crosslinked antigen is presented to a CANARY cell expressing one monoclonal antibody. In approach 2, for example, the antibody-coated beads are replaced with CANARY cells, which are essentially live, antibody-coated beads. Two CANARY cell lines expressing antibodies against different epitopes on the same toxin are incubated in solution containing that toxin. One or both cells can have an emitter molecule. In some instances, both CANARY cells comprise an emitter molecule, wherein the emitter molecules are different in the different CANARY cells. In other instances, both CANARY cells comprise the same emitter molecule type. In the assay, both cells become decorated with toxin, but the cell is not stimulated because the toxin is monomeric. The cells are centrifuged to the bottom of the tube, where the 2 different CANARY cells present antigen to each other. This approach is effective than (LOD=50 ng or 1 µg/ml concentration), but less sensitive than toxin presentation on beads. It may be that fixation of one of the cells prior to decoration with toxin may better restrict the movement of antibodies in the membrane, and therefore better stimulate the opposing CANARY cell.

An alternative approach is to make a polyclonal CANARY cell (approach 4). Two different antibodies are expressed in a single CANARY cell line. Because these antibodies bind to different non-overlapping epitopes on the same toxin molecule, the CANARY cell can be stimulated directly be soluble antigen. Multiplexing studies have shown that a given CANARY cell line can express up to three different antibodies without affecting the sensitivity of the cell to antigen, implying that expression of 2 different antibodies against BoNT in the same CANARY cell line should not be a problem. This would simplify the assay because a bead addition step would not be necessary. However, sample preparation would require exchanging the solution containing the toxin for cell assay medium.

A final approach uses the same CANARY concept, but a different cell line. In this embodiment, a single cell line is generated that expresses the Fc receptor and aequorin. The Fc receptor binds to the Fc portion of antibodies, leaving the antigen-binding regions free to bind to target. Soluble antibody added to these cells produces a "new" cell line with the specificity of the added antibody in 10 minutes. Addition of antigen to these cells crosslinks the Fc receptors, stimulating light emission from aequorin. This approach works with both polyclonal and monoclonal antibody against *Bacillus anthracis*. For toxin detection, a polyclonal antibody against toxin (or 2 monoclonal antibodies against toxin) can be added to the cell, and the Fc receptors crosslinked by soluble antigen.

Alternative Protocols:

Further improvement may be found by the addition of a third, soluble antibody to the assay. Published data from Dr. J. D. Marks' laboratory (Nowakowski et al PNAS (2002) 99(17):11346-11350) shows that incubation of BoNT/A with one monoclonal antibody increases the apparent affinity of a second monoclonal antibody against a different epitope by about 100 fold. In this embodiment, a soluble antibody against a third epitope on the BoNT/A would be added with the antibody coated beads. Binding of the third antibody to BoNT/A would improve the kinetics of BoNT/A binding to the beads.

Alternatively, the biotinylated antibody need not be present on the beads when it is introduced into the assay. Soluble biotinylated antibody and streptavidin beads could be added separately. It could be that this will improve the binding of the antibody to the antigen, and the high affinity of the biotin-streptavidin interaction will quickly bind the antibody-antigen complex to the beads.

The use of protein G beads or streptavidin beads is one of convenience. Any support capable of crosslinking the antibodies can be used, such as dendrimers, tube surfaces, or membranes. Antibody could be labeled with anything that will attract it to a surface from which it will be able to present "polymerized" antigen.

Further Examples 2

Protocols for Assaying Plant Pathogens by CANARY

Plant tissue is a complex matrix which can adversely affect the CANARY assay by non-specifically inhibiting or activating the B cells. Therefore specific methods have been developed to process plant tissue to extract agents for detection by CANARY.

Bacterial Agents:

For plant bacterial pathogens which block the xylem, such as, but not limited to, *Ralstonia solanacearum*, the following method is employed to extract the agent.

Crown tissue is recovered by cutting the base of the plant stem at the soil line.
Compressed air, or any other method which will remove the excess soil is used to clean off the stem
A second cut is made ~1 cm from the base cut to yield a cross-sectional piece
Using a circular punch slightly smaller than the diameter of the stem, core the section to remove the outer layer (<1 mm thick)
Place the core into an appropriate-diameter tube containing 1 mL of distilled water or CANARY cell assay medium (CO2I) and soak for 5 minutes
Remove the core sample from the tube, vortex the liquid
Any portion or all of the sample can be assayed as follows:
Centrifuge sample at 10K-18K RCF for 2 minutes in swing-bucket microfuge
If distilled water was used for the extraction, aspirate the supernatant and discard, add 0.5 mL CO2I to the tube, vortex and centrifuge sample at1 OK-18K RCF for 2 minutes in swing-bucket microfuge
If CO2I was used for the extraction, no replacement step is required
Add 0.02 mL CANARY cells to assay tube, centrifuge for 5 seconds and read signal output in luminometer.

See FIG. 100. The graph demonstrates detection of 100 cfu/mL (5 cfu/CANARY test) of *Ralstonia solanacearum* in geranium extract utilizing the protocol listed above and pictured in FIG. 101.

*Ralstonia* spp.:

Relatively little sample prep is needed for *ralstonia*-infected tissue. Since the bacteria blocks the xylem (the vascular system of a plant), "bacterial streaming" (i.e. flow of the bacteria out of the cut end of a stem) results when the tissue sample is placed under water. This allows for recovery of ralstonia from infected tissue without having to grind the sample, thereby eliminating the need to extract the bacteria from potentially assay-interfering plant debris.

To test a plant sample, geranium in this case, the following procedure is performed. The crown, the area of the stem just above the soil, is sliced in cross-section and any residual soil is removed. A second cross-sectional cut is made ~1 cm above the first cut and a core sample just slightly smaller than the diameter of the stem is taken. This process leaves the xylem intact but removes the outer covering of the stem which interferes with the CANARY assay. The core sample is then placed into extraction medium for 5 minutes. Because the extraction phase takes place in CANARY assay medium, additional wash steps to make the sample compatible with CANARY are eliminated thereby shorting the processing time. We were able to detect *ralstonia* in seeded geranium extracts, at the same level of sensitivity as *ralstonia* in extraction medium alone (i.e. no plant tissue present), indicating that the presence of plant extract does not inhibit the *ralstonia*-specific CANARY signal.

A signal, clearly discernable from background (i.e. geranium extract without *ralstonia*) is apparent within 30 seconds from the time that the sample is put into the luminometer. The entire process, including sample prep, can be completed in less than 10 minutes. The assay is capable of detection of as few as 5 cfu *ralstonia* per CANARY test. Comparable results were obtained from the CANARY assay when eight different isolates of live *R. solanacearum* R1bv1 were tested.

Viral Agents:

The potyvirus group comprises the largest and economically the most important group of plant viruses. The broad spectrum-reacting monoclonal antibody, PTY1, which is expressed on CANARY B cells recognizes a cryptotope (an epitope found not on the virion surface but rather on coat protein subunits found within the intact virion). This presents special issues for CANARY which requires that the cryptotopes on the virus be exposed in order to be accessible to the B cells. The method described herein exposes the cryptotope by binding the potyvirus to pristine, 1-2 micron polystyrene beads. See FIG. 156. The technology also works with magnetic polystyrene beads. As the virus binds to the beads, it causes the virus coat to unwind and expose the epitope. The beads also provide a second advantage for the CANARY assay. The potyvirus is a long flexuous, filamentous particle (12×680-900 nm) which cannot be sedimented by quick, low speed centrifugation. By attaching the virus to beads which sediment very rapidly at a low spin speed or which can be concentrated with a magnet, the sensitivity of the CANARY assay for potyvirus is greatly increased. No special devices or equipment are needed to perform the sample prep/CANARY assay which incorporates the beads.

See FIG. 102. The graph shows detection of 5 ng/mL (0.05 ng/CANARY test) of BYMV, a potyvirus, using the bead attachment process described above. The method allows for collection-to-detection in under 7 minutes. Tests on six other strains of potyvirus resulted in similar limits of detection.

*Phytophthora* spp.:

Two B-cell lines to detect *phytophthora*, a fungal-like plant pathogen of considerable economic importance, were developed. The genes for the antibodies were extracted from hybridomas, PH 3812 and PH 4831, provided by Neogen Corporation. The antibodies recognize the mycelial portion of *Phytophthora* spp.

Sample prep for extraction of *phytophthora* is slightly more complicated than for the other two pathogens previously mentioned. Like tissue infected with potyvirus, it must be ground to liberate the organism. Although *phytophthora* is large enough to be sedimented by centrifugation, the plant debris co-sediments, interfering with the assay. In addition to the larger debris generated by macerating the plant tissue, abundant small particles (e.g. fines) also contaminate the sample and cannot be separated from the *phytophthora* by filtration without concomitant loss of the pathogen. The debris interferes with the CANARY assay by blocking light detection and in some instances causes a non-specific signal. We again took a bead-binding approach to sample prep for extraction of *phytophthora* from plant tissue. Unlike potyvirus, which has a natural affinity for polystyrene and binds very rapidly to it without any special treatment, *phytophthora* will not bind to an untreated bead surface. Therefore, *phytophthora* mycelia were captured by magnetic beads coated with a second *phytophthora*-specific antibody (i.e. recognizes a different epitope from the antibody expressed on the surface of the B cell) allowing the pathogen to be pulled away from the debris. Using a magnetic "pick-pen", the bead-bound *phytophthora* can be easily transferred to an assay tube and the CANARY assay can then be performed as indicated earlier. The rate-limiting step in sample prep is the 15 minutes required to achieve sufficient binding of the *phytophthora* to the antibody-coated beads.

Using this technique, we were able to demonstrate a dose dependent response to both live *Phytophthora infestans* and Phythophthora capsici mycelia, as well as detection of *Phytophthora infestans* in seeded potato tuber extract. LODs were not determined for the tests with *phytophthora*, since the antigen preps consisted of ground mycelia harvested from actively growing *phytophthora* cultures. 10-fold dilutions of the ground mycelia were tested until the signal returned to baseline (no *phytophthora*) levels.

Protocols for Assaying Blood-Borne Pathogens by CANARY

There are many parameters that influence CANARY's ability to detect blood-borne pathogens. As with other complex matrices, blood contains both activators and inhibitors of the CANARY assay. Light transmission is blocked because whole blood is opaque and pathogens can be either intracellular or in the fluid phase of a blood sample. Additionally, variability among samples from different donors has necessitated development of a universal sample preparation method that will work regardless of donor status. Described herein are method of whole blood sample preparation procedures and devices which overcome all of these issues and still allow for the detection of pathogens in blood without sacrificing either the speed or sensitivity of the CANARY assay.

The method uses a commercially available plasma-separation tubes (PST) and differential centrifugation. This process uses a thixotropic gel with a density between that of plasma and blood cells, which forms a barrier between the plasma and cells when the tube is centrifuged. The bacteria or viruses present in the blood, being of lesser density than the gel, remain in the plasma (fluid) phase during the centrifugation. The plasma can then be harvested and tested in CANARY.

Device and Protocol for CANARY Detection of Fluid-Phase Blood-Borne Pathogens:

A sample device (FIG. 103) has been assembled from modified commercial off the shelf (COTS) parts that enable the separation of whole blood samples in three rapid, simple steps. The device consists of a commercially available heparinized capillary PST blood collection tube. A threaded connecting collar is fitted over the cap of the PST tube, from which the top has been punched out. A stopper is then placed in the top half of the collar. One-half milliliter of whole blood is collected into a heparinized plasma separation tube (step 1) and centrifuged for 90 sec (step 2). The stopper is then replaced with a threaded 1.5 mL CANARY assay tube. The separated pathogen-containing plasma, with recovered volume ranging from 50 to 250 □L, is then collected into the assay tube by inversion (step 3). The plasma is mixed with 0.5 mL of assay medium (a process that reduces the effect of a CANARY cell activator that is present in plasma) and the mixture is centrifuged to pellet the pathogen. The sample is then tested with pathogen-specific CANARY cells as per the standard protocol. The total time required from blood collection to pathogen detection is approximately 5 min.

Using the simple three-step procedure detailed above, the limit of detection of *Yersinia pestis* in whole blood is 1000 cfu/mL (125 cfu/CANARY assay) with a total time from blood collection to agent detection/identification in approximately 5 minutes. See FIG. 103.

Device and Protocol for CANARY Detection of Intracellular Blood-Borne Pathogens:

Modifications to the device developed for isolation of fluid-phase pathogens allows for the recovery of white blood cells containing intracellular pathogens, plasma and fluid-phase pathogens all in one step. This is accomplished by incorporation of a white blood cells isolation medium (Ficol-Diatrizoate) into the device. There is currently no commercial device with this configuration that is built on such a small scale (i.e. capable of separating only 0.5 mL whole blood). Therefore the unit is assembled in its as follows.

Instead of a PST tube, an empty (no gel) capillary blood collection tube is used as the base tube. The following components in the order that they are listed are then added to the tube (Note: the amounts are highly relevant to the device functioning properly):

200 microliters Ficol-Diatrizoate (FD 5 millimeters Polyester gel 100 microliters Phosphate Buffered Saline (PBS)

500 microliters Whole heparanized or EDTA blood

See FIG. 104 for the tube configuration.

The tube configuration is identical to that described for fluid-phase separation and the same modifications are made to accommodate the threaded collar and assay tube described earlier. Once the blood is added to the tube and capped, the tube is inverted several times to mix the blood with the PBS and then centrifuged for 90 seconds. The lower diagram in FIG. 104 indicates the position of the components post-centrifugation.

The stopper is replaced with the CANARY assay tube and the cells, plasma and any free pathogens are collected by inversion of the device. Additional steps are useful at this point compared with the fluid-phase pathogen recovery assay. The pathogen-containing white blood cells should be lysed to allow release of agent so that it is accessible to the CANARY cells. First, the tube is centrifuged at 11000 RCF for 1 minute to pellet the white blood cells and any free (fluid-phase) pathogens. The liquid is discarded and a commercial lysing agent is added to the CANARY assay tube which is then vortexed to mix the cells with the lysing agent. The tube is incubated at room temperature for 5 minutes with occasional vortexing and then centrifuged again at 11000 RCF for 1 minute to pellet the pathogens. The lysing reagent above the pellet is discarded and 0.5 mL of CANARY assay medium is added to the tube which is again vortexed and centrifuged. The sample is now ready for the CANARY assay and follows the standard single sample assay format, i.e. add the B cells, centrifuge for 5 seconds and record light output in luminometer. The total time required for this assay from collection-to-detection is ~12 minutes.

The limit of detection for *Y. pestis* in spiked whole blood is 1000 cfu/mL when the blood sample is processed by the method described above to obtain intracellular pathogens (see FIG. 105).

Further Examples 3

CANARY B-Cell Impaction Techniques

The invention describes techniques for the efficient delivery of CANARY B-cells to wet or dry-impacted samples without centrifugation. These techniques should enable simpler, cheaper automated CANARY based on minimization of moving parts and time-partitioned photon readout.

Summary Technical Description

The device incorporates techniques using droplet impaction to maximize the rapid encounter between CANARY B-cells and the antigen-containing targets under investigation. Several variations are described (listed below) and relevant experimental and analytical techniques are described below.

Technique 1 "B cell Spray"
Technique 2 "CANARY Assay without Centrifuging"
Technique 3 "CANARY B cell Impaction"
Technique 4 "TCAN-3 B-cell delivery concept"
Technique 5 "Update on B-cell Impaction and CANARY"

The techniques described herein refer to either aerosolized antigen or droplets of antigen solution impinged onto a surface through an impactor during antigen collection. Subsequently, droplets of CANARY B-cells are aerosolized and impacted onto the same surface. The methods for impaction are either mechanical atomization and spraying onto the impacted antigen droplet from a fluid reservoir (Technique 1 through 3) or via the pressure differential created from a rapid puncture of a B-cell fluid reservoir (Technique 4). Technique 5 describes a series of experiments designed to verify the survivability of the B-cells during such aerosolization schemes. In all cases, the B-cells rapidly encounter the antigen on a transparent surface, beneath which is a photodetector or an optical waveguide to a photodetector. Upon binding of the B-cell antibodies to the impacted antigen, light is emitted and detected by the photodetector. The signal-to-noise ratio of the system can be improved by matching the optical waveguide geometry to the impaction nozzle geometry, which can be used to focus both the collected antigen as well as the atomized B-cell solution.

This device or the methods described herein can be used to conduct CANARY assays without centrifugation, thereby reducing the complexity of an automated identification instrument and potentially improving the performance. It uses aerosol impaction as part of a rapid immunoassay.

The CANARY assay is an extremely rapid immunoassay, with the primary time delay resulting from the current technique of centrifuging the B-cell solution in order to provoke binding to the antigen. This method not only introduces a time delay but, more significantly, requires greater device complexity (motors, engagement and disengagement mechanisms, position and velocity encoding, etc.) than the method proposed herein. The new technique uses aerosol impaction to bring the antibody and antigen into contact. The reduced complexity can also result in smaller, less expensive automated identification sensors than currently exist, thus enhancing their use as part of proliferated sensing systems.

This device can be used for the following: Biodefense detection/identification systems, either continuous monitoring or triggered; human health care—clinical disease and disease state characterization; environmental sampling and background flora characterization; food testing; animal health, as will be understood by a person of skill in the art.

Technique 1: B Cell Spray

Goal

The goal of this experiment was to determine if spraying B cells with an atomizer would be an alternate B cell delivery mechanism. Cell volume delivered, cell viability, and activity were measured.

Experimental Design

An alternate method of delivering a controlled volume of B cells was investigated. Sprayed B cell kinetics was investigated for liquid and dry samples, and was compared to samples tested with 20 ul B cells. These experiments were tested for cell counts, viability, activity reproducibility within a concentration, and background levels. The effect of spinning cells after delivery, and the typical cell volume sprayed was also tested.

B cells were loaded in a 3 ml atomizer Qosina spray bottle and used to deliver cells to samples containing Ba or Yp. To determine the volume of each spray, the spray bottle was filled with 2 ml CO2I and one spray was delivered to individual eppendorf tubes until the spray bottle was empty. The eppendorf tubes were centrifuged at 10,000 rpm for 30 seconds and volume was measured with a pipette. To measure cell counts, Ba B cells were loaded into spray bottle and sprayed into 5 individual eppendorf tubes. The eppendorf tubes were centrifuged at 10,000 rpm for 30 seconds and volume was measured with a pipette. 10 ul of cells were then loaded into hemocytometer for counting. Cell counts were compared to cells counted directly from original tube of cell preparation.

In order to measure B cell activity for liquid samples, 50 ul of samples were prepared with agent in 1.5 ml eppendorf tubes, and centrifuged at 10,000 rpm for 2 min. For dried samples, 5 ul of agent, diluted in water, was prepared in 1.5 ml eppendorf tubes, centrifuged at 10,000 rpm for 2 min, and allowed to dry overnight. 1 spray of B cells, typically with a volume of 34±8 ul/spray, was directly sprayed into tube. Samples were then spun in a mini-centrifuge for 5 seconds and read with a Berthold luminometer.

Results

Results indicate that each spray bottle can be loaded with 2 ml of B cells and can be sprayed 45-47 times. Each spray delivers 34±8 ul/spray (n=47). While cells counted directly from original tube average to $3.2 \times 10^5 \pm 8.0 \times 10^4$ cells/ml (n=5), sprayed cells showed a reduced average of $1.3 \times 10^5 \pm 2.9 \times 10^4$ cells/ml (n=5). Consequently, the number of cells/sample delivered resulted in 5392±954 (n=5) for sprayed cells and 5283±76 (n=5) for cells delivered with 20 ul pipette.

FIG. 106 is a graph of Ba Standard with 20 ul cell delivery. 50 ul of Ba samples prepared in CO2(I) media and tested with 20 ul B cells. Results indicate low background and an LOD of 50 cfu Ba (n=2).

FIG. 107 is a graph of Ba B cell spray. 50 ul of Ba samples prepared in CO2 (I) media and tested with varying number of B cell sprays. Results indicate increased background with 2 sprays compared to 20 ul cell delivery. Number of sprays did not affect peak intensity with 50,000 cfu Ba (n=1).

FIG. 108 is a graph of Ba Standard with 1-spray cell delivery. 50 ul of Ba samples prepared in CO2 (I) media and tested with one spray of B cells. Results indicate similar backgrounds with 20 ul cell delivery and LOD of 5,000 cfu. 50 and 500 cfu Ba showed 50% chance of detection (n=2).

FIG. 109 is a graph of Ba Standard: 500 cfu Ba detection with 20 ul B cells. 50 ul of Ba samples with 500 cfu Ba was prepared in CO2 (I) media and tested with 20 ul B cells. Results 100% detection of 500 cfu even with higher background than normally seen (n=3).

FIG. 110 is a graph of Ba B cell Spray: 500 cfu Ba detection with 1-spray B cells. 50 ul of Ba samples with 500 cfu Ba was prepared in CO2 (I) media and tested with 1 spray of B cells. Results indicate 50% detection of 500 cfu and a 2-3× higher background (n=14).

FIG. 111 is a graph of Ba B cell Spray: 500 cfu Ba detection with 1-spray B cells and no spin. 50 ul of Ba samples with 500 cfu Ba was prepared in CO2 (I) media and tested with 1 spray of B cells. Samples were not spun for 5 seconds before reading. Results indicate no cell to agent interaction resulting in 0% detection of 500 cfu Ba (n=3).

FIG. 112 is a graph of Yp B cell Spray: 500 cfu Yp detection with 20 ul B cells. 50 ul of Yp samples with 500 cfu Yp was prepared in CO2 (I) media and tested with 20 ul B cells. Results indicate a typical background and 100% detection of 500 cfu Yp (n=4).

FIG. 113 is a graph of Yp B cell Spray: 500 cfu Yp detection with 1-spray B cells. 50 ul of Yp samples with 500 cfu Yp was prepared in CO2 (I) media and tested with 1 spray of B cells. Results indicate a slightly increased background with 100% detection of 500 cfu Yp (n=8).

FIG. 114 is a graph of Yp Standard: 500 cfu Ba detection with 20 ul B cells. 50 ul of Yp samples with 500 cfu Yp was prepared in CO2 (I) media and tested with 20 ul B cells. Results 100% detection of 500 cfu with a typical background (n=7).

FIG. 115 is a graph of Yp B cell Spray: 500 cfu dried Yp detection with 20 ul B cells. 5 ul of Yp samples with 500 cfu Yp was prepared in dH2O, dried overnight, and tested with 20 ul B cells. Results indicate 100% detection of 500 cfu Yp (n=10).

FIG. 116 is a graph of Yp B cell Spray: 500 cfu dried Yp detection with 1-spray B cells. 5 ul of Yp samples with 500 cfu Yp was prepared in dH2O, dried overnight, and tested with 1-spray B cells. Results indicate a higher background, but 100% detection of 500 cfu Yp (n=10).

Conclusion:

Results indicated that spraying B cells is a suitable method for B cell delivery. Although the cell counts decreased with spraying, the larger volume allows for similar number of cells delivered per sample. Spraying Ba B cells continues to show detection capabilities with 50 and 500 cfu, but at 50% detection. It is possible that optimizing spraying conditions, possibly with a higher concentration of B cells or newer cells, this activity can be recovered. Ba B cell spraying experiments also indicates that the 5 second spin step is still required for appropriate B cell activity. Interestingly, Yp B cell spraying did not affect B cell activity as much as Ba detection. Background levels remained similar and 500 cfu Yp showed 100% detection. Effects of B cells were also tested on liquid and dried samples. First, detection of 500 cfu Yp in wet or dry formats did not change with 20 ul cell delivery. Although, backgrounds increased for sprayed cells compared to 20 ul cell delivery with dried Yp samples, detection of dry 500 cfu Yp remained to show 100% detection.

These results suggest the B cells may keep similar LODs after undergoing some pump delivery mechanisms and can withstand some of the pressures seen in capillary or small orifice environments. Sprayed B cell delivery may facilitate field experiments where the storing and delivery is in one piece and doesn't require pipettes.

Technique 2: Canary Assay without Centrifuging

The CANARY assay. CANARY is a fast and sensitive bio-assay. It uses modified lines of B-cells that fluoresce upon binding with antigens. Antigen cells are either centrifuged or impacted onto a surface. Then B-cells are centrifuged onto these cells and the fluorescence is measured by a luminometer. Several projects (for example BCAN and TCAN) are using CANARY for field detection of pathogens, combining aerosol collection and impaction with the CANARY assay.

Previous CANARY Systems.

In the current versions of the CANARY field detectors, cumbersome centrifuging equipment and delicate optical equipment are of necessity combined in a small space. This requirement plagues the design and construction of these detectors. Eliminating centrifuging reduces design costs, construction costs, and maintenance costs plus improves reliability. We describe an alternative technique using impaction.

Alternative Techniques to Impact B-Cells.

In order to avoid the expense and design complications due to centrifuging, several methods have been suggested as alternatives to move the B-cells to the binding surface. These include manipulation of magnetic beads inside the cells, thermophoresis, electrophoresis, and acoustic manipulation. Each of these methods requires the development and refinement of new technologies into the CANARY system.

Proposed Technique.

Described herein is a technique that uses CANARY technology applied in a novel manner, specifically the binding of B-cells to the antigens by impaction. This technique uses an impaction well similar to that used in BCAN or TCAN. The B-cell solution is sprayed through the antigen cell impaction nozzle. Because of their greater mass, even though the B-cells are in solution they still impact on the impaction surface. This is described in more detail in the next section. The spray is at same flow rate as used for the bioaerosol. Therefore, the same pump used for bioaerosol collection can drive the B-cell impaction.

Physics of B-Cell Impaction.

Impaction of a particle through liquid is similar to impaction of a particle through gas. When fluid streamlines change direction suddenly due to physical obstructions, sufficiently massive particles in the fluid cross the streamlines and collide with the obstruction. The unitless parameter describing the likelihood of collision is the Stokes number. It is the ratio of the stopping distance of a particle to the dimension of an obstacle. The Stokes number is approximately $$Stk \approx \frac{\tau U}{D},$$

where U is the fluid velocity moving towards the obstacle, D is the size of the obstacle and τ is the particle relaxation time. The relaxation time is a function of the particle diameter, particle density, and fluid viscosity. For fluid flowing out of a nozzle onto an impaction surface, D is the diameter of the nozzle.

The equation for the particle cut-off diameter at an impaction nozzle is $$d_{50} = \left(\frac{9\eta D^3 (Stk_{50})}{4\rho_p Q}\right)^{1/2},$$

where $Stk_{50}$ is a constant (~0.5), η is the fluid viscosity (0.01 P for water and 0.0002 P for air) and Q is the flow rate. For BCAN, Q is 2 lpm and D is 0.1 cm. Then the calculated $d_{50}$ for water is 6 microns and for air is 0.8 microns.

Therefore, the same impaction plumbing can be used both to impact a particle in air and to impact a B-cell in solution.

The new method has several advantages. The new technique eliminates the B-cell centrifuge step. The method is fast—it takes only seconds to impact the B-cells. There are no moving parts near the PMTs, which means that the PMTs will have a longer operating life and that they can be positioned for a more sensitive signal. This detector is inexpensive and rugged compared to a centrifuge-based detector. It is easy to build by modifying an existing BCAN or TCAN.

Technique 3: Canary B Cell Impaction

Goal:

To develop an alternate B cell delivery method for CANARY field devices that does not involve a centrifugation step.

Experimental Design

Earlier CANARY protocols require a 5 second centrifugation step at 500 g for B cell delivery. However, centrifuging samples limit the effectiveness of Canary field devices by setting severe design constraints on an automated system which includes delicate components such as B cells and PMTs. The new method described herein eliminates extra moving parts by impacting both agent and B cells, as impacted in a manner similar to the BCAN or TCAN systems. This differs from the current method in which only the agent is impacted. Consequently, the only moving part is a valve for atomizing the B cells, which is placed at some distance from the binding surface.

In the new method, droplets of B cells are dispersed into the impaction stream. Experiments in technique 1 "B cell spray" show that B cells survive at least some form of atomization. Calculations in technique 2 "Canary Assay without Centrifuging", show that B cells will impact through an aqueous solution moving at the flow rates used in the BCAN. Because the BCAN has an impaction cut-off of 1 micron, B cell droplets with diameters 10 micron and above will easily impact in the air flow provided by a BCAN pump using the same flow rates. As the droplet size is much smaller than the BCAN nozzle, losses at the nozzle will be negligible. Whether B cells survive impaction can only be determined experimentally.

The new spraying method removes moving parts for the three operations of agent impaction, B cell impaction and PMT measurement. Consequently, this simplifies the design requirements for the field device where the B cells can be stored in a single reservoir at a distance. A simple valve mechanism at the impactor is used because the airflow does not need to be separated from the B cell addition.

This technique requires a disperser capable of aerosolizing 10 or 20 micron droplets. Collison nebulizers, the laboratory standard disperser for bioaerosol has low efficiency for droplets greater than 5 microns. Two alternative atomizers have been considered. The first is a metered dose sprayer available from Qosina and developed for the cosmetics industry. ISome experiments indicate that particle sizes are 10 microns or greater and produces a pulse of aerosol. These sprayers cost $1 each. The other type of atomizer for these particle sizes is the ultrasonic atomizer used for continuous flows. Two companies producing ultrasonic atomizer systems are Sono-tek and Sonaer. These systems cost from $7.5 k to $15 k.

An experiment to test the Qosina atomizer with a BCAN prototype is setup as follows (see FIG. 117). The disk will be placed in an impaction rig, which was built for BCAN experiments. It consists of an impaction nozzle, a well holding the impaction disk, and an outlet barb. The barb will be connected through a tube to a rotometer, HEPA filter, and pump to operate near 5 lpm. A tube will connect the inlet of the rig to a tee, one end of which will be open to ambient air and the other to the Qosina atomizer, which will contain a solution of B cells. A PMT will be placed underneath the glass disk. Because the PMT is sensitive to light, the impaction rig and PMT will be placed in a darkbox. Dark tubing will connect the outlet to the rotometer and the inlet to the tee. During the test, agent simulant will be spotted onto the glass impaction disk and the disk placed in the rig. Next the pump will be turned on and B cells sprayed from the atomizer. At this point, if the B cells survive atomizing and impaction is sufficient quantity, a luminescence signal is expected from the PMT. A supporting test will be to impact B cells onto a disk free of agent, to test that the impaction alone does not cause the B cells to luminesce.

Technique 4: TCAN-3 B-Cell Delivery Concept

Goal:

Currently the TCAN-2 biosensor incorporates COTs trumpet valves to control the release and delivery of B cells. This trumpet valve is both expensive and bulky. Additionally, a spring inside the trumpet valve has to be removed prior to use to keep the valve open during the centrifugation step. This technique proposes an alternative scheme for B cell release and delivery based on a simple application of Bernoulli's principle.

Concept:

The proposed concept utilizes the aerosol collection pump to aspirate the B cells into the aerosol path from a liquid reservoir. This is accomplished by sealing the B cell reservoir with a foil seal that is closed during the aerosol collection. After aerosol collection, the seal is punctured, resulting in a pressure differential (ΔP) between the aerosol path and the reservoir.

This concept is based on the Bernoulli principle which states that the pressure of a fluid varies inversely with speed; therefore increases in air velocity will produce a decrease in pressure. The principles for this concept are identical to common atomizers. Most atomizers work by generating an air flow over a liquid reservoir. The fast moving air decreases the pressure at the inlet, aspirating the liquid into the air path based on the pressure differential.

Bernoulli's Principle:

$$\frac{P}{\rho} + \frac{1}{2}V^2 + gz = const.$$

P=pressure; ρ=density of fluid; V=velocity
g=gravitational acceleration; z=height Prior to puncturing the seal, the B cells should remain in the reservoir because the backend pressure ($P_2$) will equilibrate with the inlet pressure ($P_1$) based on the ideal gas law. Assuming that the temperature stays the same, as the fluid plug is pulled into the aerosol path the volume of air ($V_2$) will also increase resulting in a decrease in the backend pressure ($P_2$). The backend pressure will balance itself with the inlet pressure until the seal is broken. After the seal is broken the backend pressure will equilibrate with the surrounding atmospheric pressure.

Ideal Gas Law:

$$PV=nRT$$

Design Parameters:

There are several key experiments that need to be completed. Key design parameters include determining the ideal diameter and geometry of reservoir channel. This diameter will affect the surface tension at the liquid-gas interface. The pressure differential due to the surface tension in a capillary tube is as follows: (Surface tension=γ=0.073 N/m for water)

$$\Delta P = 2\gamma/radius$$

As the radius is decreased the pressure needed to aspirate the liquid from the reservoir is also increased.

Conclusions:

This method of B cell release and delivery will simplify the design of the CD currently being used in TCAN-2. This method could also decrease the cost and size of the CD, resulting in cheaper and easier to produce parts. This technique may also be applicable to non-centrifugal B cell delivery approaches also described herein.

Technique 5: Further Experiments on B-Cell Impaction and CANARY

The method described herein targets the B cells onto the antigen by impacting B cell droplets onto the antigen substrate. This is particularly suitable for CANARY dry impaction. B cells are placed in the same location as the antigen because they are placed by the same mechanism.

The excess stresses the B cells is subject to are those due to aerosolization. Specifically, stresses occur during aerosol transport, and aerosol impaction. During bioaerosol generation, cells may be subject to severe mechanical stresses and to charging. During the transport stage, the droplet may suffer from solvent evaporation and changes in solute concentration. These effects may lead to desiccation, oxygen toxicity and osmotic pressure imbalances. During the impaction stage, particles are once again subject to mechanical stresses. All of these effects may inactivate the B cell, preventing its use as an antigen detector.

B cells are not inactivated by aerosolization during FACS analysis, nor is cell viability affected. During FACS/flow cytometer analysis, FACS machines disperse cells one at a time into droplets (i.e., an aerosol) and the droplets are analyzed optically and then (optionally) collected into tubes for further study. B cells also survive for hours after impaction into dry tubes, even in the presence of ion chelators. Only 10% of cells are lost after one hour. Therefore sufficient B cells for CANARY detection will impact in less than one second.

Test Study

To further study the effect of aerosolization on B cells, an antigen can be placed at the bottom of a FACS sorter test tube. CANARY B cells can then be processed through the FACS machine. The test tube can then be analyzed in a luminometer for photon emission by the CANARY B cell. A negative control would omit the antigen in the tube. In addition, impaction of antigen and CANARY cells into a tube together can be tested.

Further Examples 4

16 Channel Sensor

Described herein is a refined and improved 16-channel sensor, that provides the same level of sensitivity as seen with a single-channel system (FIG. 121). This portable prototype is suitable for external validation and testing. Specifically, it allows the simultaneous measurement of 16 samples using a single light-gathering channel. The sensor consists of a rotor holding 16 assay tubes horizontally, equally distributed about its circumference, and driven by a variable-speed motor about a vertical axis. A single fixed photon-detecting element, in this case a PMT, is positioned in the plane of the rotor just beyond the path of the tubes during rotation. In this way, each of the tubes is sequentially and repetitively brought into close proximity to the PMT, allowing its light output to be sampled on each pass. Finally, an optical switch consisting of an optical source (an infrared LED) and a detector (a phototransistor) is used to control the counting of detected photons and the reorganization of the data into 16 fields, each associated with a specific sample.

A single measurement consists of

1. Preparing 16 samples (and/or controls) in individual assay tubes.
2. Introducing an aliquot of B cells into each of the tubes using any of a variety of methods including, but not limited to, manual transfer, automatic transfer, capsules, or blister-packages.
3. Loading the assay tubes into the rotor.
4. Localizing the B cells at the bottom of the tubes using a brief (5 sec) centrifugal spin at high relative centrifugal force (RCF) (2000 g)
5. Reducing the rotor speed to between 10 and 120 rpm for the duration of the measurement (1-2 min), each tube being sampled once per revolution.
6. Generating a time series of photon counts for each sample for display and/or input to a computer algorithm for evaluation.

Non-Centrifugal Assay Formats

Other assay formats that are compatible with a compact handheld sensor targeted at clinical, point-of-care, and forward-deployed applications are also described herein. In general, the goal during the exploration has been to identify formats that can simplify both the CANARY assay procedure and the hardware it requires, while maintaining as much of the speed and sensitivity as possible. Specifically, focus has been on characterizing the performance of alternative assay procedures that can reduce or eliminate the requirement for centrifugation steps since they are currently the primary driver of energy consumption and instrument complexity. A number of approaches have been experimentally evaluated toward assay formats that employ physical manipulation of surface-bound targets, microfluidic channels, wicking assemblies, filtration, or magnetic bead capture. The use of lateral-flow assemblies and magnetic bead capture, inter alia, are described in more detail below.

Physical Manipulation of Surface Bound Particle (a.k.a. 'Pinhead') Methods

This is a family of non-centrifugal methods for using CANARY B-cells inspired by (and originally tested using) common straight pins. In practice, the straight pin can be replaced by any suitable solid surface that satisfies 3 basic criteria: 1) the surface does not stimulate B-cell calcium fluxes, 2) the surface is capable of receiving and retaining/binding target in a way that that does not alter the ability of antibodies on the CANARY B-cells to bind the bound target, and 3) the surface is amenable to physical manipulation to bring it into contact with a layer of B cells (emittor cells) on the surface of a reaction vessel. Generally, particles to be tested can be collected onto the 'pinhead' from air or liquid samples by various means (FIG. 122) and subsequently presented to an aliquot of settled B cells (FIG. 123); if the collected sample includes the antigen to which those cell express antibodies, a weak light signal would be generated and collected by a sensitive luminometer.

In the centrifugal CANARY methods, particles (including bacteria, virus, or toxin) to be tested are localized at a sample site by either air impaction (as in the BCAN) or, in the case of liquid sample, by a long ($\geq 2$ min), hard ($\geq 10$ K RCF) centrifugal 'pre-spin'. (Either of these sample preparations effectively concentrates the particles in a small volume near the sample site.) CANARY B-cells are then introduced into the sample volume and, after a brief ($\approx 5$ sec), soft ($\approx 500$ RCF) cell-delivery spin, are driven to the sample site where they may encounter particles. Because of the short time it takes to move the B cells to the sample surface, these encounters happen over a short time window; the resulting luminous response from the B cells are synchronized creating a more clearly identifiable signal in the form of a recognizable pattern of detected photons.

Pinhead methods accomplish a similar concentration of particles and B cells on or near a surface: particles to be tested are collected onto a surface (the pinhead) by various means, and that surface is physically maneuvered to a previously arranged thin layer of B cells (gravitationally settled, prespun, or grown adherent to a surface). This again results in a synchronized stimulation of the B cells, resulting in a sufficiently strong signal.

The first experimental validation of these concepts consisted of drying a 2-µl samples containing known quantities of antigenic simulants onto pinheads and introducing these into settled (by centrifugation) aliquots of various lines of B cells (each 'line' being a clonal population of B cell expressing antibodies to a known agent or simulant). Strong response was observed when corresponding antigen and cell line were used, and no signal was observed in mismatched cases (FIG. 124 shows a typical dose response).

The second experimental validation consisted of electrostatic collection of Bs spores in a setup similar to FIG. 122(b). Using roughly similar concentrations of Bs spores in air, a fixed air-flow speed, and varying the collection time, a dose response was observed when the collection pins were introduced to tubes containing settled B cells which express antibodies to Bs (FIG. 125).

Dual-Magnetic-Bead Assay

Described herein is an assay that takes advantage of two sets of magnetic beads. One set is specific for the CANARY B cells, while the other set is specific for a particular agent. These agent specific beads could have either a general affinity for a particular agent class (e.g. gram+/−bacteria, viruses, proteins, DNA, etc.) (see for example, US2005/0118570 and U.S. patent Ser. No. 11/056,518, the teachings of all of which are incorporated herein by reference), or could have specific affinity for a single agent. In FIG. 127, a standard CANARY assay was run alongside a dual-bead assay. Magnetic beads specific for *Y. pestis* were mixed with a dilution series of *Y. pestis* agent for 5 min. After 5 min the magnetic beads were pulled to the bottom of the assay tube along with any bound *Y. pestis*, and the supernatant was removed. Magnetically labeled B cells were then added to the sample and pulled down to the bottom of the tube. Localizing agent and B cells with magnetic beads has thus far proven to provide similar sensitivity to that of centrifugation.

Wicking Formats

Described herein is a CANARY assay in devices that layer wicking and filter materials to accomplish sample fluid transport and antigen localization without centrifugation. The basic construction of the device and pictures demonstrating its ability to localize spore-sized particles are shown in FIGS. 128 and 129.

FIG. 130 shows the resulting CANARY signals for both standard centrifuge assays and lateral-flow assays using the same agent and cell samples. These and other experiments have shown that although B cells can be used in a lateral-flow assay, the signal-to-noise levels tend to be lower than a centrifugation assay, thus lowering the overall LOD. The reduced signal amplitude indicates that this format is less effective at either localizing antigen particles or synchronizing the presentation of the B cells as they reach the particles on the filter material, or both. Increased background levels are also observed. These vary in intensity with different wicking materials and flow rates, and are generally correlated with materials and flow rates that are expected to result in increased mechanical stress on the B cells due to increased surface adhesion and liquid shear forces. Possible remedies include using B cells selected for higher resistance to mechanical stress, using low levels of detergents to decrease system shear stress, decreasing the thickness and size of the capture zone to ensure all captured antigen can be seen by B cells, and decreasing sheer stress by reducing the length of the wick strip. The initial devices used a 0.2-µm filter for capture but can be combined with beads to capture particles smaller than 0.2 µm.

Further Examples 5

Automated CANARY Bioaerosol Sensor Embodiments

Described herein is the combination of aerosol collection by inertial impaction with CANARY identification in automated sensors to demonstrate collection and identification of airborne pathogen in as little as 90 seconds. The fastest response times currently reported for other automated bioaerosol collection and identification devices is >18 minutes, so this represents an improvement of more than one order of magnitude compared to the current state of the art. Two embodiments based on this design, the BCAN and TCAN sensors (FIG. 131) have previously been built and tested and described herein are the key materials, methods, and devices that are being incorporated into the next-generation of the CANARY technology which we call PANTHER (Pathogen Analyzer for Threatening Environmental Releases, FIG. 131).

Key details of the core technology are described in the related figures (FIGS. 131-137) and their legends and can be summarized as follows:

1) Air containing aerosol particles to be analyzed is pulled through a 4.75" diameter disk with features that direct and accelerate the airflow through 16 or more channels with geometries that cause the entrained aerosol particles to impact the surface of the disk in well-defined areas that are amenable to direct CANARY analysis.

2) CANARY B cells are stored on board in 16 or more individual aliquots that can be automatically released using a number of available mechanisms and delivered via a brief (less than 5 second) spin to each of the aerosol collection sites.

3) The spin forces contact between the CANARY B cells and the collected aerosol particles and light is emitted from any samples that contain the pathogen target of the CANARY B cells. The disk is transparent to the emitted wavelength of light in the reaction zones and the emitted light is collected and quantified using a photon-counting light detection device (e.g. a photomultiplier tube).

4) Multiple disks as described above are loaded into a device that provides for the storage, transport, processing, and analysis of the data. Operation of this instrument will provide pathogen collection and analysis that is capable of identification of airborne pathogens in as little as 90 seconds.

APPENDIX

Acronym/Symbol Definitions:
AC alternating current
AFB Air Force Base
ATP adenosine triphosphate
BAWS Biological Agent Warning Sensor
Bcl2l11 Bcl2-like 11
Bmf Bcl2 modifying factor
BoNT/A botulinum neurotoxin A
BoNT/A Hc botulinum neurotoxin A heavy chain
CANARY Cellular Analysis and Notification of Antigen Risks and Yields
CCD charge-coupled device
CDC Center for Disease Control
COTS commercial off-the-shelf
CPT cell preparation tube
CRET chemical resonance energy transfer
DC direct current
DEP dielectrophoresis
DMSO dimethylsulfoxide
DNA deoxyribonucleic acid
DoD Department of Defense
EBs elementary bodies
EGFP enhanced green fluorescent protein
FcγRI Fc gamma receptor I
FMD foot-and-mouth disease
GADD45β growth-arrest and DNA-damage-inducable beta
GFP green fluorescent protein
GST glutathione transferase
HA hemagglutinin
HBSS Hanks balanced saline solution
Hells helicase, lymphoid-specific
Hist1H1c Histonel H1c
HSF1 heat-shock factor 1
IFNγ interferon gamma
LD50 lethal dose 50%
LOD limit of detection
NiCd nickel-cadmium
PBS phosphate buffered saline
PCR polymerase chain reaction
Pdcd1lg1 programmed cell death 1 ligand 1
PMT photomultiplier tube
PST plasma-separation tube
RCF relative centrifugal force
RLU relative light unit
TCA trichloroacetic acid
Tx-100-Triton X-100
USAMRIID United States Army Medical Research Institute of Infectious Diseases
VEE Venezuelan equine encephalitis While this invention has been particularly shown and described with references to preferred embodiments thereof, it will be understood by those skilled in the art that various changes in form and details may be made therein without departing from the scope of the invention encompassed by the appended claims.

The relevant teachings of all the references, patents and patent applications cited herein are incorporated herein by reference in their entirety.

What is claimed is:

1. A method for detecting an antigen in a sample comprising:

a) spraying emitter cells onto a sample, wherein the emitter cell comprises a receptor and an emitter molecule that emits a photon in response to binding of a target antigen in the sample to the receptor;

b) detecting photon emission, wherein photon emission is indicative of the antigen in the sample.

2. The method of claim 1, wherein the emitter cells are sprayed onto the sample using an atomizer.

3. The method of claim 1, wherein the emitter cells are sprayed onto a liquid sample.

4. The method of claim 1, wherein the emitter cells are sprayed onto a solid surface comprising said sample.

5. The method of claim 1, wherein the emitter cells are sprayed onto a solid surface comprising a dried sample.

6. The method of claim 4, wherein the solid surface is a centrifuge tube.

* * * * *